(12) United States Patent
Dinsmore et al.

(10) Patent No.: US 10,059,705 B2
(45) Date of Patent: Aug. 28, 2018

(54) ACYCLIC CYANOETHYLPYRAZOLO PYRIDONES AS JANUS KINASE INHIBITORS

(71) Applicant: Merck Sharp & Dohme Corp., Rahway, NJ (US)

(72) Inventors: Christopher Dinsmore, Newton, MA (US); Peter Fuller, Ashland, MA (US); David Guerin, Natick, MA (US); Jason David Katz, Newton, MA (US); Christopher F. Thompson, Arlington, MA (US); Danielle Falcone, Brookline, MA (US); Wei Deng, Lexington, MA (US); Luis Torres, Norwood, MA (US); Hongbo Zeng, Westford, MA (US); Yunfeng Bai, Beijing (CN); Jianmin Fu, Beijing (CN); Norman Kong, Beijing (CN); Yumei Liu, Beijing (CN); Zhixiang Zheng, Beijing (CN); Mark E. Scott, Andover, MA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 97 days.

(21) Appl. No.: 14/778,055

(22) PCT Filed: Mar. 19, 2014

(86) PCT No.: PCT/CN2014/000299
§ 371 (c)(1),
(2) Date: Sep. 17, 2015

(87) PCT Pub. No.: WO2014/146493
PCT Pub. Date: Sep. 25, 2014

(65) Prior Publication Data
US 2016/0272634 A1    Sep. 22, 2016

Related U.S. Application Data

(60) Provisional application No. 61/803,241, filed on Mar. 19, 2013.

(51) Int. Cl.
*C07D 471/04* (2006.01)
*C07D 519/00* (2006.01)

(52) U.S. Cl.
CPC ......... *C07D 471/04* (2013.01); *C07D 519/00* (2013.01)

(58) Field of Classification Search
CPC .................................................. C07D 471/04
See application file for complete search history.

(56) References Cited

U.S. PATENT DOCUMENTS 9,371,320 B2 * 6/2016 Nara .................... C07D 471/04
2010/0105661 A1  4/2010 Shirakami
2012/0178740 A1  7/2012 Nielsen et al.

FOREIGN PATENT DOCUMENTS

| CN | 102574857 A | 7/2012 |
|---|---|---|
| EP | 2857400 | 4/2015 |
| WO | 2011112662 A1 | 9/2011 |
| WO | 2012127506 A1 | 9/2012 |
| WO | WO2013017479 | 2/2013 |
| WO | WO2013017480 | 2/2013 |
| WO | 2013180265 A1 | 5/2013 |

OTHER PUBLICATIONS

Ferreira "How many JAK inhibitors in myelofibrosis?" Best Practice & Research Clinical Haematology 27 (2014) 187-195.*
Johnson, et. al. "Relationships between drug activity in NCI preclinical in vitro and in vivo models and early clinical trials." British Journal of Cancer 2001, 84, 1424-1431.*
Ledford "US cancer institute overhauls cell lines" Nature Feb. 25, 2016 vol. 530 p. 391.*
Ocana, A. "Preclinical development of molecular targeted agents for cancer" Nat. Rev. Clin. Oncol. 2011, 8, 200-209.*
Sharma "Cell line-based platforms to evaluate the therapeutic efficacy of candidate anticancer agents" Nature Reviews Cancer Apr. 2010, vol. 10, 241-253.*
Damia "Contemporary pre-clinical development of anticancer agents—What are the optimal preclinical models?" EUROPEAN Journal of Cancer 2009, 45, 2768-2781.*
Georg Pilz, "Modern multiple sclerosis treatment—what is approved, what is on the horizon" Drug Discovery Today Dec. 2008 , vol. 13, Nos. 23/24 1013-1025.*
Chaichian "Targeted Therapies in Systemic Lupus Erythematosus: A State-of-the-Art Review" J Clin Cell Immunol 2013, S6, 1-8.*
Taylor "Filgotinib for the treatment of rheumatoid arthritis", Expert Opinion on Investigational Drugs, 2017, 26:10, 1181-1187.*
Bendele "Animal Models of Arthritis: Relevance to Human Disease" Toxicol Pathol 1999 27: 134-142.*
Garber "Pfizer's JAK inhibitor sails through phase 3 in rheumatoid arthritis" Nature Biotechnology 29 No. Jun. 6, 2011 467-468.*
Bendele "Animal models of rheumatoid arthritis" J Musculoskel Neuron Interact 2001; 1(4):377-385.*
PCTCN2014000299 Search Report dated Mar. 19, 2014.
Smyth, et al, Synthesis and reactivity of 3-amino-1H-pyrazolo[4,3-c]pyridin-4(5H)-ones: development of a novel kinase-focussed library, Tetrahedron, 2010, pp. 2843-2854, vol. 66.

* cited by examiner

*Primary Examiner* — David K O'Dell
(74) *Attorney, Agent, or Firm* — Patricia A. Shatynski; John C. Todaro

(57) ABSTRACT

The instant invention provides compounds of formula I which are JAK inhibitors, and as such are useful for the treatment of JAK-mediated diseases such as rheumatoid arthritis, asthma, COPD and cancer.

7 Claims, No Drawings

ACYCLIC CYANOETHYLPYRAZOLO PYRIDONES AS JANUS KINASE INHIBITORS

CROSS REFERENCE TO RELATED APPLICATIONS

This application is a U.S. National Phase application under 35 U.S.C. § 371 of PCT Application No. PCT/CN2014/000299, filed Mar. 19, 2014 which claims benefit under 35 U.S.C. § 199(e) of U.S. Provisional Application No. 61/803,241 filed on Mar. 19, 2013.

BACKGROUND OF THE INVENTION

Protein kinases are a group of enzymes that regulate the activity of their target proteins by the addition of phosphate groups to the protein substrate. Kinases play an essential role in many physiological processes including cell division, differentiation, cellular homeostasis and signal transduction. Kinases can be subdivided by their target into Serine/Threonine kinases and Tyrosine kinases. Tyrosine kinases are further subdivided into receptor tyrosine kinases and non-receptor tyrosine kinases. The mammalian Janus kinase (JAK) family members are non-receptor tyrosine kinases.

The JAK family has four members; JAK1, JAK2, JAK3 and TYK2. JAK1, JAK2 and TYK2 are universally expressed, whereas JAK3 expression is limited to hematopoetic cells. The JAK family is involved in intracellular signal transduction from >70 different cytokines. Cytokines bind to their cell surface receptors resulting in receptor dimerization and subsequent activation/phosphorylation of JAK tyrosine kinases. The JAKs are either constitutively associated with the receptor or are recruited upon cytokine binding. Specific tyrosine residues on the receptor are then phosphorylated by activated JAKs and serve as docking sites for STAT proteins. STATs are phosphorylated by JAKs, dimerize, then translocate to the nucleus where they bind specific DNA elements and activate gene transcription. JAK1 signals in conjunction with all JAK isoforms in a cytokine dependent manner.

JAKs are essential for multiple physiological functions. This has been demonstrated using genetically engineered mouse models that are deficient in specific JAKs. Jak1$^{-/-}$ mice die perinatally, while Jak2$^{-/-}$ mice have deficiencies in erythropoesis and die around day E12. Jak3$^{-/-}$ mice are viable, but have a SCID phenotype with deficiencies in T cells, B cells and NK cells. TYK2$^{-/-}$ mice exhibit features of hyper IgE syndrome. These phenotypes demonstrate the essential and non-redundant roles of JAK activity in vivo (K. Ghoreschi, A. Laurence, J. J. O'Shea, *Immunol. Rev.* 228, 273 (2009)).

Furthermore, mutations in the JAK enzymes have been associated with diseases in humans. Inactivating mutations in JAK3 (or the cognate common gamma chain cytokine receptor) cause a severe SCID phenotype (J. J. O'Shea, M. Pesu, D. C. Bork, P. S. Changelian, *Nat. Rev. Drug Discov.* 3, 555 (2004)). Deletions of TYK2 result in hyper IgG syndrome and increased infection risk (Y. Minegishi et al., *Immunity.* 25, 745 (2006)). No inactivating mutations have been reported for JAK1 or JAK2, consistent with the data from mice that demonstrates that JAK1 and JAK2 deficient mice are not viable. However, several mutations that result in constitutively active JAK2 have been identified, resulting in myeloproliferative diseases and confirming the central role of JAK2 in hematopoesis (O. bdel-Wahab, *Curr. Opin. Hematol.* 18, 117 (2011)). JAK2 is the sole JAK family member involved in signal transduction of the critical hematopoetic cytokines IL-3, GMCSF, EPO and TPO.

The wealth of mouse and human genetic data demonstrating a central role for JAK kinase activity in autoimmune disease, hematopoesis and oncology has been supported by the use of pan-JAK inhibitors in clinical trials for autoimmune diseases and neoplasms (See K. Ghoreschi, et al, *Immunol. Rev.* 228, 273 (2009), and A. Quintas-Cardama, H. Kantarjian, J. Cortes, S. Verstovsek, *Nat. Rev. Drug Discov.* 10, 127 (2011)).

A considerable body of literature has accumulated that link the Jak/STAT pathway to various diseases and disorders including hyperproliferative disorders and cancer such as leukemia and lymphomas, immunological and inflammatory disorders such as transplant rejection, asthma, chronic obstructive pulmonary disease, allergies, rheumatoid arthritis, type I diabetes, amyotropic lateral sclerosis and multiple sclerosis.

SUMMARY OF THE INVENTION

The present invention provides novel compounds which are inhibitors of JAKs. The invention also provides a method for the treatment and prevention of JAK-mediated diseases and disorders using the novel compounds, as well as pharmaceutical compositions containing the compounds.

DETAILED DESCRIPTION OF THE INVENTION

The present invention provides compounds of formula I or pharmaceutically acceptable salts, or stereoisomers thereof:

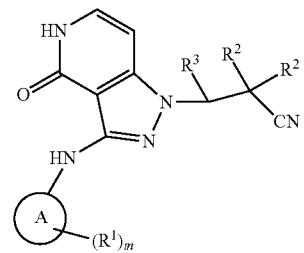

I

A is selected from aryl and heteroaryl;
m is 0, 1, 2, 3, or 4;
$R^2$ is independently selected from hydrogen and $C_{1-6}$ alkyl;
$R^3$ is selected from: hydrogen, halogen, $C_{1-6}$ alkyl, $C_{3-6}$ cycloalkyl, and ($C_{3-8}$)heterocycloalkyl;
wherein $R^2$ and $R^3$ are optionally, each independently substituted by 1, 2, or 3 $R^5$ substituents;
$R^5$ is independently selected from hydroxy, ($C_{1-6}$)alkyl, ($C_{1-6}$)alkoxy, ($C_{1-6}$ alkyl)OH, halogen, —$CO_2H$, —($C_{0-4}$)alkylCN, —O(C=O)$C_1$-$C_4$alkyl, $NO_2$, trifluoromethoxy, trifluoroethoxy, trifluoromethyl, trifluoroethyl, $C_{1-6}$ alkylsulfonyl, oxo (O=), aminosulfonyl, —$SO_2NH_2$, —$SO_2NH(C_{1-10}$ alkyl), —$SO_2N(C_{1-6}$ alkyl)$_2$, —$SO_2C_{1-6}$alkyl, —$SO_2CF_3$, —$SO_2CF_2H$, —$C_{1-6}$ alkylsulfinyl, —$O_{(0-1)}(C_{1-6})$haloalkyl, amino($C_{1-6}$alkyl)$_{0-2}$ and $NH_2$;
$R^1$ is selected from:
halogen,
Oxo (=O),
$C_{1-10}$ alkyl(oxy)$_{0-1}$(carbonyl)$_{0-1}$$C_{0-10}$ alkyl, $C_{1-10}$ heteroalkyl(oxy)$_{0-1}$(carbonyl)$_{0-1}C_{0-10}$ alkyl,
$C_{2-10}$ alkenyl(oxy)$_{0-1}$(carbonyl)$_{0-1}C_{0-10}$ alkyl,
aryl $C_{0-10}$ alkyl(oxy)$_{0-1}$(carbonyl)$_{0-1}C_{0-10}$ alkyl,
$C_{3-12}$ cycloalkyl $C_{0-10}$ alkyl(oxy)$_{0-1}$(carbonyl)$_{0-1}C_{0-10}$ alkyl,
heteroaryl $C_{0-10}$ alkyl(oxy)$_{0-1}$(carbonyl)$_{0-1}C_{0-10}$ alkyl,
$(C_{3-12})$heterocycloalkyl $C_{0-10}$ alkyl(oxy)$_{0-1}$(carbonyl)$_{0-1}C_{0-10}$ alkyl,
$C_{0-10}$ alkyl(oxy)$_{0-1}$(carbonyl)$_{0-1}$amino$C_{0-10}$ alkyl,
$(C_{1-10})$heteroalkyl(oxy)$_{0-1}$(carbonyl)$_{0-1}$amino$C_{0-10}$ alkyl,
$C_{3-12}$ cycloalkyl $C_{0-10}$ alkyl(oxy)$_{0-1}$(carbonyl)$_{0-1}$amino$C_{0-10}$ alkyl,
aryl $C_{0-10}$ alkyl(oxy)$_{0-1}$(carbonyl)$_{0-1}$amino$C_{0-10}$ alkyl,
heteroaryl $C_{0-10}$ alkyl(oxy)$_{0-1}$(carbonyl)$_{0-1}$amino$C_{0-10}$ alkyl,
$(C_{3-12})$heterocycloalkyl $C_{0-10}$ alkyl(oxy)$_{0-1}$(carbonyl)$_{0-1}$amino$C_{0-10}$ alkyl,
$C_{0-10}$ alkylamino (carbonyl)$_{0-1}C_{0-10}$ alkyl,
$(C_{1-10})$heteroalkylamino (carbonyl)$_{0-1}C_{0-10}$ alkyl,
$C_{3-12}$ cycloalkylamino (carbonyl)$_{0-1}C_{0-10}$ alkyl,
aryl $C_{0-10}$ alkylaminoamino (carbonyl)$_{0-1}C_{0-10}$ alkyl,
heteroaryl $C_{0-10}$ alkylamino(carbonyl)$_{0-1}C_{0-10}$ alkyl,
$(C_{3-12})$heterocycloalkylamino(carbonyl)$_{0-1}C_{0-10}$ alkyl,
$C_{1-10}$ alkylsulfonyl$C_{0-10}$ alkyl,
$C_{1-10}$ heteroalkylsulfonyl$C_{0-10}$ alkyl,
$(C_{3-12})$cycloalkyl$C_{0-10}$alkylsulfonyl$C_{0-10}$ alkyl,
$(C_{3-12})$cycloheteroalkyl$C_{0-10}$alkylsulfonyl$C_{0-10}$ alkyl,
heteroaryl$C_{0-10}$ alkylsulfonyl$C_{0-10}$ alkyl,
aryl$C_{0-10}$ alkylsulfonyl$C_{0-10}$ alkyl,
$C_{1-10}$ alkylsulfamoyl$C_{0-10}$ alkyl,
$C_{1-10}$ heteroalkylsulfamoyl$C_{0-10}$ alkyl,
$(C_{3-12})$cycloalkyl$C_{0-10}$ alkylsulfamoyl$C_{0-10}$ alkyl,
$(C_{3-12})$cycloheteroalkyl$C_{0-10}$alkylsulfamoyl$C_{0-10}$ alkyl,
heteroaryl$C_{0-10}$ alkylsulfamoyl$C_{0-10}$ alkyl,
aryl$C_{0-10}$ alkylsulfamoyl$C_{0-10}$ alkyl,
$(C_{0-10}$ alkyl$)_{1-2}$ amino,
—$CO_2(C_{0-10}$ alkyl),
—$(C_{0-10}$ alkyl)$CO_2H$,
—$SO_2NH_2$,
—$SO_2NH(C_{1-10}$ alkyl),
—$SO_2N(C_{1-10}$ alkyl$)_2$,
—$SO_2CF_3$,
—$SO_2CF_2H$,
$C_{1-10}$ alkylsulfinyl$C_{0-10}$ alkyl,
$C_{1-4}$ acylamino $C_{0-10}$ alkyl,
hydroxy,
—$(C_{1-10}$ alkyl)OH,
—$C_{0-10}$ alkylalkoxy,
cyano,
$(C_{1-6}$ alkyl)cyano, and
$C_{1-6}$ haloalkyl;
wherein $R^1$ is independently optionally substituted with 1, 2, 3, or 4 $R^4$ substituents and wherein two $R^1$ may optionally join together with the ring atoms to which they are attached to form a 3 to 6 membered ring; and
$R^4$ is independently selected from hydroxy, $(C_{1-6})$alkyl, $(C_{1-6})$alkoxy, $(C_{1-10}$ alkyl)OH, —$(C_{0-10}$alkyl)$CO_2H$, halogen, —$(C_{1-10}$ alkyl)OH, —$CO_2H$, $C_{1-10}$ alkyl (oxy)$_{0-1}$(carbonyl)$_{0-1}C_{0-10}$ alkyl, —$(C_{0-6})$alkylCN, —$C_{0-10}$ alkyl O(C=O)$C_1$-$C_6$ alkyl, $NO_2$, trifluoromethoxy, trifluoroethoxy, trifluoromethyl, trifluoroethyl, —N=C(O)O($C_{0-6}$)alkyl, —N($R^b$)—C(O)O($C_{0-6}$) alkyl, $C_{1-10}$ alkylsulfonyl, oxo (O=), aminosulfonyl, —$SO_2NH_2$, —$SO_2NH(C_{1-10}$ alkyl), —$SO_2N(C_{1-10}$ alkyl$)_2$, —$SO_2C_{1-6}$ alkyl, —$SO_2CF_3$, —$SO_2CF_2H$, —$C_{1-10}$ alkylsulfinyl, —$O_{(0-1)}(C_{1-10})$haloalkyl, amino $(C_{1-6}$alkyl$)_{0-2}$, $C_{3-12}$ cycloalkyl, $(C_{3-12})$cycloheteroalkyl, and $NH_2$, wherein $R^b$ is $C_{1-10}$ alkyl.

Representative compounds of the instant invention include, but are not limited to the following compounds and their pharmaceutically acceptable salts and stereoisomers thereof:

4-((1-(1-cyanopropan-2-yl)-4-oxo-4,5-dihydro-1H-pyrazolo[4,3-c]pyridin-3-yl)amino)-N,N-dimethylbenzenesulfonamide;

4-((1-(2-cyano-1-cyclopropylethyl)-4-oxo-4,5-dihydro-1H-pyrazolo[4,3-c]pyridin-3-yl)amino)-N,N-dimethylbenzenesulfonamide;

4-(1-((-2-cyano-1-(2,2-difluorocyclopropyl)ethyl)-4-oxo-4,5-dihydro-1H-pyrazolo [4,3-c]pyridin-3-yl)amino)-N,N-dimethylbenzenesulfonamide;

4-((1-(2-cyano-1-(2,2-dimethylcyclopropyl)ethyl)-4-oxo-4,5-dihydro-1H-pyrazolo [4,3-c]pyridin-3-yl)amino)-N,N-dimethylbenzenesulfonamide;

4-((1-(2-cyano-1-cyclobutylethyl)-4-oxo-4,5-dihydro-1H-pyrazolo[4,3-c]pyridin-3-yl)amino)-N,N-dimethylbenzenesulfonamide;

3-cyclobutyl-3-(4-oxo-3-((4-(pyrrolidin-1-ylsulfonyl)phenyl)amino)-4,5-dihydro-1H-pyrazolo[4,3-c]pyridin-1-yl) propanenitrile;

3-cyclopropyl-3-{3-[(4-fluorophenyl)amino]-4-oxo-4,5-dihydro-1H-pyrazolo[4,3-c]pyridin-1-yl}propanenitrile;

3-cyclopropyl-3-[4-oxo-3-({4-[(2,2,2-trifluoro-1-hydroxy-1-methylethyl]phenyl}amino) -4,5-dihydro-1H-pyrazolo [4,3-c]pyridin-1-yl]propanenitrile;

3-cyclopropyl-3-(3-{[1-hydroxy-1-(trifluoromethyl)-2,3-dihydro-1H-inden-5-yl]amino}-4-oxo -4,5-dihydro-1H-pyrazolo[4,3-c]pyridin-1-yl)propanenitrile;

3-cyclopropyl-3-{3-[(1,1-dioxido-2,3-dihydro-1-benzothiophen-5-yl) amino]-4-oxo-4,5-dihydro-1H-pyrazolo[4,3-c]pyridin-1-yl}propanenitrile;

3-{3-[(2-tert-butyl-1,1-dioxido-2,3-dihydro-1,2-benzisothiazol-5-yl) amino]-4-oxo-4,5-dihydro-1H-pyrazolo[4,3-c] pyridin-1-yl}-3-cyclopropylpropanenitrile;

4-({1-[2-cyano-1-cyclopropylethyl]-4-oxo-4,5-dihydro-1H-pyrazolo[4,3-c]pyridin-3-yl}amino)benzonitrile;

3-cyclopropyl-3-(4-oxo-3-{[4-(trifluoromethyl)phenyl] amino}-4,5-dihydro-1H-pyrazolo[4,3-c]pyridin-1-yl)propanenitrile;

3-cyclopropyl-3-(3-{[4-(methylsulfonyl)phenyl]amino}-4-oxo-4,5-dihydro-1H-pyrazolo[4,3-c]pyridin-1-yl)propanenitrile;

3-cyclopropyl-3-{4-oxo-3-[(3,4,5-trifluorophenyl)amino]-4,5-dihydro-1H-pyrazolo[4,3-c]pyridin-1-yl}propanenitrile;

3-cyclopropyl-3-{3-[(2-methyl-1,1-dioxido-2,3-dihydro-1,2-benzisothiazol-5-yl)amino]-4-oxo-4,5-dihydro-1H-pyrazolo[4,3-c]pyridin-1-yl}propanenitrile;

3-cyclopropyl-3-{3-[(2-fluoropyridin-4-yl)amino]-4-oxo-4,5-dihydro-1H-pyrazolo[4,3-c]pyridin-1-yl}propanenitrile;

3-cyclopropyl-3-{4-oxo-3-[(1-oxo-2,3-dihydro-1H-inden-5-yl)amino]-4,5-dihydro-1H-pyrazolo[4,3-c]pyridin-1-yl}propanenitrile;

3-cyclopropyl-3-[3-(2,3-dihydro-1-benzofuran-5-ylamino)-4-oxo-4,5-dihydro-1H-pyrazolo[4,3-c]pyridin-1-yl]propanenitrile;

3-[3-(1,3-benzodioxol-5-ylamino)-4-oxo-4,5-dihydro-1H-pyrazolo[4,3-c]pyridin-1-yl]-3-cyclopropylpropanenitrile;

3-cyclopropyl-3-[4-oxo-3-(quinolin-6-ylamino)-4,5-dihydro-1H-pyrazolo[4,3-c]pyridin-1-yl]propanenitrile;

3-cyclopropyl-3-(3-{[3-fluoro-4-(methylsulfonyl)phenyl] amino}-4-oxo-4,5-dihydro-1H-pyrazolo[4,3-c]pyridin-1-yl)propanenitrile;

3-cyclopropyl-3-[4-oxo-3-(quinoxalin-6-ylamino)-4,5-dihydro-1H-pyrazolo[4,3-c]pyridin-1-yl]propanenitrile;

3-{3-[(4-chlorophenyl)amino]-4-oxo-4,5-dihydro-1H-pyrazolo[4,3-c]pyridin-1-yl}-3-cyclopropylpropanenitrile;

cyclopropyl-3-[3-({4-[(1-methylethyl)sulfonyl] phenyl}amino]-4-oxo-4,5-dihydro-1H-pyrazolo[4,3-c]pyridin-1-yl]propanenitrile;

(3-{[4-(tert-butylsulfonyl)phenyl]amino}-4-oxo-4,5-dihydro-1H-pyrazolo[4,3-c]pyridin-1-yl)-3-cyclopropylpropanenitrile;

N-tert-butyl-4-{[(2-cyano-1-cyclopropylethyl)-4-oxo-4,5-dihydro-1H-pyrazolo[4,3-c]pyridin-3-yl] amino}benzenesulfonamide;

3-[3-({4-[1-amino-2,2,2-trifluoroethyl]phenyl}amino)-4-oxo-4,5-dihydro-1H-pyrazolo[4,3-c]pyridin-1-yl]-3-cyclopropylpropanenitrile;

4-({1-[2-cyano-1-cyclopropylethyl]-4-oxo-4,5-dihydro-1H-pyrazolo[4,3-c]pyridin-3-yl}amino)-N-ethyl-N-methylbenzenesulfonamide;

3-cyclopropyl-3-(4-oxo-3-{[4-(piperidin-1-ylsulfonyl)phenyl]amino}-4,5-dihydro-1H-pyrazolo[4,3-c]pyridin-1-yl)propanenitrile;

4-({1-[2-cyano-1-cyclopropylethyl]-4-oxo-4,5-dihydro-1H-pyrazolo[4,3-c]pyridin-3-yl}amino)-N-methyl-N-(1-methylethyl)benzenesulfonamide;

4-({1-[2-cyano-1-cyclopropylethyl]-4-oxo-4,5-dihydro-1H-pyrazolo[4,3-c]pyridin-3-yl}amino)-N-methylbenzenesulfonamide;

3-cyclopropyl-3-(4-oxo-3-{[4-(pyrrolidin-1-ylsulfonyl)phenyl]amino}-4,5-dihydro-1H-pyrazolo[4,3-c]pyridin-1-yl)propanenitrile;

4-({1-[2-cyano-1-cyclopropylethyl]-4-oxo-4,5-dihydro-1H-pyrazolo[4,3-c]pyridin-3-yl}amino)-N,N-diethylbenzenesulfonamide;

3-cyclopropyl-3-[3-({4-[(3,3-dimethylpiperidin-1-yl)sulfonyl]phenyl}amino)-4-oxo-4,5-dihydro-1H-pyrazolo[4,3-c]pyridin-1-yl]propanenitrile;

3-cyclopropyl-3-[3-({4-[(3,3-dimethylpyrrolidin-1-yl)sulfonyl]phenyl}amino)-4-oxo-4,5-dihydro-1H-pyrazolo[4,3-c]pyridin-1-yl]propanenitrile;

3-{3-[(2-tert-butyl-1-oxo-2,3-dihydro-1H-isoindol-5-yl)amino]-4-oxo-4,5-dihydro-1H-pyrazolo[4,3-c]pyridin-1-yl}-3-yclopropylpropanenitrile;

3-{3-[(2-cyclopentyl-1-oxo-2,3-dihydro-1H-isoindol-5-yl)amino]-4-oxo-4,5-dihydro-1H-pyrazolo[4,3-c]pyridin-1-yl}-3-cyclopropylpropanenitrile;

3-{3-[(2-cyclohexyl-1-oxo-2,3-dihydro-1H-isoindol-5-yl)amino]-4-oxo-4,5-dihydro-1H-pyrazolo [4,3-c]pyridin-1-yl}-3-cyclopropylpropanenitrile;

3-cyclopropyl-3-[3-({4-[(2,2-dimethylpiperidin-1-yl)sulfonyl]phenyl}amino)-4-oxo-4,5-dihydro-1H-pyrazolo[4,3-c]pyridin-1-yl]propanenitrile, tert-butyl 1-{[4-({1-[2-cyano-1-cyclopropylethyl]-4-oxo-4,5-dihydro-1H-pyrazolo[4,3-c]pyridin-3-yl}amino)phenyl]sulfonyl}piperidine-4-carboxylate, 3-cyclopropyl-3-{3-[(4-{[3-hydroxypyrrolidin-1-yl)sulfonyl}phenyl)amino]-4-oxo-4,5-dihydro-1H-pyrazolo[4,3-c]pyridin-1-yl}propanenitrile, tert-butyl 1-{[4-({1-[2-cyano-1-cyclopropylethyl]-4-oxo-4,5-dihydro-1H-pyrazolo[4,3-c]pyridin-3-yl}amino)phenyl]sulfonyl}-D-prolinate, 3-cyclopropyl-3-{4-oxo-3-[(4-{[3-(trifluoromethyl)pyrrolidin-1-yl]sulfonyl}phenyl)amino]-4,5-dihydro-1H-pyrazolo[4,3-c]pyridin-1-yl}propanenitrile;

3-cyclopropyl-3-{4-oxo-3-[(4-{[2-(trifluoromethyl)pyrrolidin-1-yl]sulfonyl}phenyl)amino]-4,5-dihydro-1H-pyrazolo[4,3-c]pyridin-1-yl}propanenitrile;

tert-butyl-1-{[4-({1-[2-cyano-1-cyclopropylethyl]-4-oxo-4,5-dihydro-1H-pyrazolo[4,3-c]pyridin-3-yl}amino) phenyl]sulfonyl}pyrrolidine-3-carboxylate;

3-cyclopropyl-3-[3-({4-[(2,2-dimethylpyrrolidin-1-yl)sulfonyl]phenyl}amino)-4-oxo-4,5-dihydro-1H-pyrazolo[4,3-c]pyridin-1-yl]propanenitrile;

3-cyclopropyl-3-{3-[(4-{[2-methylpyrrolidin-1-yl]sulfonyl}phenyl)amino]-4-oxo-4,5-dihydro-1H-pyrazolo[4,3-c]pyridin-1-yl}propanenitrile;

3-(3-{[4-(azetidin-1-ylsulfonyl)phenyl]amino}-4-oxo-4,5-dihydro-1H-pyrazolo[4,3-c]pyridin-1-yl)-3-cyclopropylpropanenitrile;

3-cyclopropyl-3-(3-{[4-(morpholin-4-ylsulfonyl)phenyl] amino}-4-oxo-4,5-dihydro-1H-pyrazolo[4,3-c]pyridin-1-yl)propanenitrile;

3-cyclopropyl-3-[3-({4-[(3,3-dimethylazetidin-1-yl)sulfonyl]phenyl}amino)-4-oxo-4,5-dihydro-1H-pyrazolo[4,3-c]pyridin-1-yl]propanenitrile;

3-cyclopropyl-3-[3-({4-[(3-methylazetidin-1-yl)sulfonyl] phenyl}amino)-4-oxo-4,5-dihydro-1H-pyrazolo[4,3-c]pyridin-1-yl]propanenitrile;

3-cyclopropyl-3-[3-({4-[(2,2-dimethylazetidin-1-yl)sulfonyl]phenyl}amino)-4-oxo-4,5-dihydro-1H-pyrazolo[4,3-c]pyridin-1-yl]propanenitrile;

3-cyclopropyl-3-[3-({4-[(3-hydroxy-3-methylazetidin-1-yl)sulfonyl]phenyl}amino) -4-oxo-4,5-dihydro-1H-pyrazolo[4,3-c]pyridin-1-yl]propanenitrile;

3-cyclopropyl-3-[3-({4-[(3-hydroxyazetidin-1-yl)sulfonyl] phenyl}amino) -4-oxo-4,5-dihydro-1H-pyrazolo[4,3-c]pyridin-1-yl]propanenitrile;

3-cyclopropyl-3-[3-({4-[(3,3-dimethylmorpholin-4-yl)sulfonyl]phenyl}amino) -4-oxo-4,5-dihydro-1H-pyrazolo[4,3-c]pyridin-1-yl]propanenitrile;

3-cyclopropyl-3-[3-({4-[(2,2-dimethylmorpholin-4-yl)sulfonyl]phenyl}amino) -4-oxo-4,5-dihydro-1H-pyrazolo[4,3-c]pyridin-1-yl]propanenitrile;

3-cyclopropyl-3-{3-[(4-{[3-methylmorpholin-4-yl] sulfonyl}phenyl) amino]-4-oxo-4,5-dihydro-1H-pyrazolo[4,3-c]pyridin-1-yl}propanenitrile;

3-cyclopropyl-3-{3-[(4-{[3-hydroxy-3-(trifluoromethyl) pyrrolidin-1-yl]sulfonyl}phenyl)amino]-4-oxo-4,5-dihydro-1H-pyrazolo[4,3-c]pyridin-1-yl}propanenitrile;

3-cyclopropyl-3-[3-({4-[hexahydrocyclopenta[b][1,4]oxazin-4(4aH)-ylsulfonyl]phenyl}amino) -4-oxo-4,5-dihydro-1H-pyrazolo[4,3-c]pyridin-1-yl]propanenitrile;

3-cyclopropyl-3-{3-[(4-{[2,6-dimethylmorpholin-4-yl] sulfonyl}phenyl) amino]-4-oxo-4,5-dihydro-1H-pyrazolo[4,3-c]pyridin-1-yl}propanenitrile;

3-cyclopropyl-3-{3-[(4-{[2-methylmorpholin-4-yl] sulfonyl}phenyl) amino]-4-oxo-4,5-dihydro-1H-pyrazolo[4,3-c]pyridin-1-yl}propanenitrile;

3-cyclopropyl-3-{3-[(4-{[2-methylazetidin-1-yl] sulfonyl}phenyl) amino]-4-oxo-4,5-dihydro-1H-pyrazolo[4,3-c]pyridin-1-yl}propanenitrile;

3-cyclopropyl-3-[3-({4-[(3-methoxyazetidin-1-yl)sulfonyl] phenyl}amino) -4-oxo-4,5-dihydro-1H-pyrazolo[4,3-c]pyridin-1-yl]propanenitrile;

3-cyclopropyl-3-[3-({4-[(3-fluoroazetidin-1-yl)sulfonyl] phenyl}amino) -4-oxo-4,5-dihydro-1H-pyrazolo[4,3-c]pyridin-1-yl]propanenitrile;

3-cyclopropyl-3-[3-({3-methyl-4-[2,2,2-trifluoro-1-hydroxy-1-methylethyl]phenyl}amino) -4-oxo-4,5-dihydro-1H-pyrazolo[4,3-c]pyridin-1-yl]propanenitrile;

3-cyclopropyl-3-[3-({4-[1-hydroxy-1-(trifluoromethyl) propyl]phenyl}amino)-4-oxo-4,5-dihydro-1H-pyrazolo[4,3-c]pyridin-1-yl]propanenitrile;

tert-butyl 2-(4-((1-(2-cyano-1-cyclopropylethyl)-4-oxo-4,5-dihydro-1H-pyrazolo[4,3-c]pyridin-3-yl)amino)-N-methylphenylsulfonamido)-2-methylpropanoate;

3-cyclopropyl-3-(4-oxo-3-((1-oxo-2-(2,2,2-trifluoroethyl) isoindolin-5-yl)amino)-4,5-dihydro-1H-pyrazolo[4,3-c]pyridin-1-yl)propanenitrile;

ethyl 2-(4-((1-(2-cyano-1-cyclopropylethyl) -4-oxo-4,5-dihydro-1H-pyrazolo[4,3-c]pyridin-3-yl)amino)-N-methylphenylsulfonamido)-2-methylpropanoate;

tert-butyl 2-(5-((1-(2-cyano-1-cyclopropylethyl)-4-oxo-4,5-dihydro-1H -pyrazolo[4,3-c]pyridin-3-yl)amino)-1-oxoisoindolin-2-yl)-2-methylpropanoate;

4-({1-[2-cyano-1-cyclopropylethyl]-4-oxo-4,5-dihydro-1H-pyrazolo[4,3-c]pyridin-3-yl}amino)-N,N,2-trimethylbenzenesulfonamide;

3-cyclopropyl-3-(3-{[3-methyl-4-(pyrrolidin-1-ylsulfonyl) phenyl]amino}-4-oxo-4,5-dihydro-1H-pyrazolo[4,3-c] pyridin-1-yl)propanenitrile;

3-cyclopropyl-3-(3-{[4-(5,5-dimethyl-3-oxo-2-oxabicyclo [2.2.2]oct-1-yl) phenyl]amino}-4-oxo-4,5-dihydro-1H-pyrazolo[4,3-c]pyridin-1-yl)propanenitrile;

3-cyclopropyl-3-[3-({4-[-1-(dimethylamino)-2,2,2-trifluoroethyl]-3-methylphenyl}amino)-4-oxo-4,5-dihydro-1H-pyrazolo[4,3-c]pyridin-1-yl]propanenitrile;

3-cyclopropyl-3-[3-({4-[(1-methylcyclopropyl)sulfonyl] phenyl}amino) -4-oxo-4,5-dihydro-1H-pyrazolo[4,3-c] pyridin-1-yl]propanenitrile;

3-[3-({4-[1-(tert-butylamino)-2,2,2-trifluoroethyl] phenyl}amino) -4-oxo-4,5-dihydro-1H-pyrazolo[4,3-c] pyridin-1-yl]-3-cyclopropylpropanenitrile;

3-cyclopropyl-3-[4-oxo-3-({4-[2,2,2-trifluoro-1-pyrrolidin-1-ylethyl]phenyl}amino)-4,5-dihydro-1H-pyrazolo[4,3-c]pyridin-1-yl]propanenitrile;

3-cyclopropyl-3-{4-oxo-3-[(4-{2,2,2-trifluoro-1-[(1-methylethyl) amino]ethyl}phenyl)amino]-4,5-dihydro-1H-pyrazolo[4,3-c]pyridin-1-yl}propanenitrile;

3-[3-({4-[1-azetidin-1-yl-2,2,2-trifluoroethyl] phenyl}amino) -4-oxo-4,5-dihydro-1H-pyrazolo[4,3-c] pyridin-1-yl]-3-cyclopropylpropanenitrile;

3-cyclopropyl-3-[3-({4-[1-(ethylamino)-2,2,2-trifluoroethyl]phenyl}amino) -4-oxo-4,5-dihydro-1H-pyrazolo[4,3-c]pyridin-1-yl]propanenitrile;

tert-butyl 4-(5-((1-(2-cyano-1-cyclopropylethyl)-4-oxo-4,5-dihydro-1H-pyrazolo[4,3-c]pyridin-3-yl)amino)-1-oxoisoindolin-2-yl)cyclohexanecarboxylate;

2-(5-((1-(2-cyano-1-cyclopropylethyl)-4-oxo-4,5-dihydro-1H-pyrazolo[4,3-c]pyridin-3-yl)amino)-1-oxoisoindolin-2-yl)-2-methylpropanoic acid;

ethyl 3-(4-((1-2-cyano-1-cyclopropylethyl)-4-oxo-4,5-dihydro-1H-pyrazolo [4,3-c]pyridin-3-yl)amino)phenyl)-4,4,4-trifluoro-3-hydroxy-2,2-dimethylbutanoate;

isopropyl 3-(4-((1-(2-cyano-1-cyclopropylethyl)-4-oxo-4,5-dihydro-1H-pyrazolo[4,3-c]pyridin-3-yl)amino)phenyl)-4,4,4-trifluoro-3-hydroxy-2,2-dimethylbutanoate;

3-cyclopropyl-3-(3-(1-hydroxy-2,2-dimethyl-1-(trifluoromethyl) -2,3-dihydro-1H-inden-5-yl)amino)-4-oxo-4,5-dihydro-1H-pyrazolo[4,3-c]pyridin-1-yl)propanenitrile;

3-cyclopropyl-3-(4-oxo-3-((4-(1-(trifluoromethyl)cyclopropyl)phenyl)amino) -4,5-dihydro-1H-pyrazolo[4,3-c]pyridin-1-yl)propanenitrile;

3-cyclopropyl-3-(3-((4-(1-(2-methoxyethyl)-1H-pyrazol-3-yl)phenyl)amino) -4-oxo-4,5-dihydro-1H-pyrazolo[4,3-c] pyridin-1-yl)propanenitrile;

3-(3-((3-chloro-4-(1-methyl-1H-pyrazol-3-yl)phenyl) amino) -4-oxo-4,5-dihydro-1H-pyrazolo[4,3-c]pyridin-1-yl)-3-cyclopropylpropanenitrile;

3-(3-((3-chloro-4-(1-(2-cyanoethyl)-1H-pyrazol-3-yl)phenyl) amino)-4-oxo-4,5-dihydro-1H-pyrazolo[4,3-c]pyridin-1-yl)-3-cyclopropylpropanenitrile;

ethyl 1-(4-((1-(2-cyano-1-cyclopropylethyl)-4-oxo-4,5-dihydro-1H-pyrazolo[4,3-c]pyridin-3-yl)amino)-2-methylphenyl)-1H-pyrazole-4-carboxylate;

isopropyl 6-((1-(2-cyano-1-cyclopropylethyl)-4-oxo-4,5-dihydro-1H-pyrazolo[4,3-c]pyridin-3-yl)amino)quinoline-2-carboxylate;

3-cyclopropyl-3-(3-((2-methylbenzo[d]thiazol-6-yl)amino) -4-oxo-4,5-dihydro-1H-pyrazolo[4,3-c]pyridin-1-yl)propanenitrile;

3-cyclopropyl-3-(3-((4-(oxazol-2-yl)phenyl)amino) -4-oxo-4,5-dihydro-1H-pyrazolo[4,3-c]pyridin-1-yl)propanenitrile;

3-cyclopropyl-3-(3-((3,3-dimethyl-2-oxoindolin-6-yl) amino)-4-oxo-4,5-dihydro-1H-pyrazolo[4,3-c]pyridin-1-yl)propanenitrile;

3-cyclopropyl-3-(3-((4-(1,1-dioxidothiomorpholine-4-carbonyl)-3-methylphenyl) amino)-4-oxo-4,5-dihydro-1H-pyrazolo[4,3-c]pyridin-1-yl)propanenitrile;

4-((1-(2-cyano-1-cyclopropylethyl)-4-oxo-4,5-dihydro-1H-pyrazolo[4,3-c]pyridin-3-yl)amino)benzoic acid;

4-((1-(2-cyano-1-cyclopropylethyl)-4-oxo-4,5-dihydro-1H-pyrazolo [4,3-c]pyridin-3-yl)amino)-N-(methylsulfonyl) benzamide;

3-cyclopropyl-3-(3-((2-morpholinoquinolin-6-yl)amino)-4-oxo-4,5-dihydro-1H-pyrazolo [4,3-c]pyridin-1-yl)propanenitrile;

3-cyclopropyl-3-(3-((2-(2,5-dimethylmorpholino) quinolin-6-yl)amino)-4-oxo-4,5-dihydro-1H-pyrazolo[4,3-c]pyridin-1-yl)propanenitrile;

3-cyclopropyl-3-(4-oxo-3-((4-1,1,1-trifluoro-2-methoxypropan-2-yl)phenyl) amino)-4,5-dihydro-1H-pyrazolo[4,3-c]pyridin-1-yl)propanenitrile;

3-cyclopropyl-3-(3-((4-(3-ethylmorpholine-4-carbonyl)-3-methylphenyl) amino)-4-oxo-4,5-dihydro-1H-pyrazolo [4,3-c]pyridin-1-yl)propanenitrile;

3-cyclopropyl-3-(3-((4-(3-isopropylmorpholine-4-carbonyl)-3-methylphenyl) amino)-4-oxo-4,5-dihydro-1H-pyrazolo[4,3-c]pyridin-1-yl)propanenitrile;

3-cyclopropyl-3-(3-((3-methyl-4-(2-methyl-1-(2H-1,2,3-triazol-2-yl) propyl)phenyl)amino)-4-oxo-4,5-dihydro-1H-pyrazolo[4,3-c]pyridin-1-yl)propanenitrile;

3-(3-((2-benzyl-1,1-dioxido-2,3-dihydrobenzo[d]isothiazol-5-yl) amino)-4-oxo-4,5-dihydro-1H-pyrazolo[4,3-c]pyridin-1-yl)-3-cyclopropylpropanenitrile;

3-Cyclopropyl-3-(3-((3-methyl-4-(2-methyl-1-(1H-1,2,3-triazol-1-yl) propyl)phenyl)amino)-4-oxo-4,5-dihydro-1H-pyrazolo[4,3-c]pyridin-1-yl)propanenitrile;

3-cyclopropyl-3-(3-((3-methyl-4-(2,2,2-trifluoro-1-hydroxyethyl)phenyl) amino)-4-oxo-4,5-dihydro-1H-pyrazolo[4,3-c]pyridin-1-yl)propanenitrile;

3-(3-((4-(cyclopentyl(2H-1,2,3-triazol-2-yl)methyl)-3-methylphenyl) amino)-4-oxo-4,5-dihydro-1H-pyrazolo [4,3-c]pyridin-1-yl)-3-cyclopropylpropanenitrile;

3-(3-((4-(1-amino-2,2,2-trifluoroethyl)-3-methylphenyl) amino)-4-oxo-4,5-dihydro-1H-pyrazolo[4,3-c]pyridin-1-yl)-3-cyclopropylpropanenitrile;

3-(3-((2-cyclohexyl-1,1-dioxido-2,3-dihydrobenzo[d]isothiazol-5-yl) amino)-4-oxo-4,5-dihydro-1H-pyrazolo[4,3-c] pyridin-1-yl)-3-cyclopropylpropanenitrile;

3-cyclopropyl-3-(3-((2-(1-methylcyclohexyl)-1,1-dioxido-2,3-dihydrobenzo[d]isothiazol-5-yl)amino)-4-oxo-4,5-dihydro-1H-pyrazolo[4,3-c]pyridin-1-yl)propanenitrile;

3-cyclopropyl-3-(3-((3-hydroxy-2,2-dimethyl-1,1-dioxido-2,3-dihydrobenzo[b]thiophen-5-yl)amino)-4-oxo-4,5-dihydro-1H-pyrazolo[4,3-c]pyridin-1-yl)propanenitrile;

3-cyclopropyl-3-(3-((3-hydroxy-1,1-dioxido-3H-spiro[benzo[b]thiophene-2,1'-cyclohexan]-5-yl)amino)-4-oxo-4,5-dihydro-1H-pyrazolo[4,3-c]pyridin-1-yl)propanenitrile;

3-cyclopropyl-3-(4-oxo-3-((4-(2-(trifluoromethyl)pyrrolidin-2-yl)phenyl)amino)-4,5-dihydro-1H-pyrazolo[4,3-c]pyridin-1-yl)propanenitrile;

3-(3-((4-(2-azaspiro[3.3]heptan-2-ylsulfonyl)-3-methylphenyl)amino)-4-oxo-4,5-dihydro-1H-pyrazolo[4,3-c]pyridin-1-yl)-3-cyclopropylpropanenitrile;

3-cyclopropyl-3-(3-((1,1-dioxido-3H-spiro[benzo[b]thiophene-2,1'-cyclopentan]-5-yl)amino)-4-oxo-4,5-dihydro-1H-pyrazolo[4,3-c]pyridin-1-yl)propanenitrile;

3-cyclopropyl-3-(3-((1,1-dioxido-3H-spiro[benzo[b]thiophene-2,1'-cyclohexan]-5-yl)amino)-4-oxo-4,5-dihydro-1H-pyrazolo[4,3-c]pyridin-1-yl)propanenitrile;

3-cyclopropyl-3-(3-((2,2-dimethyl-1,1-dioxido-2,3-dihydrobenzo[b]thiophen-5-yl)amino)-4-oxo-4,5-dihydro-1H-pyrazolo[4,3-c]pyridin-1-yl)propanenitrile;

3-cyclopropyl-3-(3-((3-hydroxy-2-methyl-1,1-dioxido-2,3-dihydrobenzo[b]thiophen-5-yl)amino)-4-oxo-4,5-dihydro-1H-pyrazolo[4,3-c]pyridin-1-yl)propanenitrile;

3-cyclopropyl-3-(3-((2-methyl-1,1-dioxido-2,3-dihydrobenzo[b]thiophen-5-yl)amino)-4-oxo-4,5-dihydro-1H-pyrazolo[4,3-c]pyridin-1-yl)propanenitrile;

3-cyclopropyl-3-(3-((3-methyl-4-(2-(trifluoromethyl)pyrrolidin-2-yl)phenyl)amino)-4-oxo-4,5-dihydro-1H-pyrazolo[4,3-c]pyridin-1-yl)propanenitrile;

3-cyclopropyl-3-(4-oxo-3-((1-oxo-2-(1-(trifluoromethyl)cyclohexyl)isoindolin-5-yl)amino)-4,5-dihydro-1H-pyrazolo[4,3-c]pyridin-1-yl)propanenitrile;

3-cyclopropyl-3-(3-((2-(4-methyltetrahydro-2H-pyran-4-yl)-1,1-dioxido-2,3-dihydrobenzo[d]isothiazol-5-yl)amino)-4-oxo-4,5-dihydro-1H-pyrazolo[4,3-c]pyridin-1-yl)propanenitrile;

3-cyclopropyl-3-(3-((4-(1-methyl-2-(trifluoromethyl)pyrrolidin-2-yl)phenyl)amino)-4-oxo-4,5-dihydro-1H-pyrazolo[4,3-c]pyridin-1-yl)propanenitrile;

4-((1-(2-cyano-1-cyclopropylethyl)-4-oxo-4,5-dihydro-1H-pyrazolo[4,3-c]pyridin-3-yl)amino)-N, 2-dimethyl-N-(tetrahydro-2H-pyran-4-yl)benzamide;

3-cyclopropyl-3-(3-((3-fluoro-4-(2,2,2-trifluoro-1-(isopropylamino)ethyl)phenyl)amino)-4-oxo-4,5-dihydro-1H-pyrazolo[4,3-c]pyridin-1-yl)propanenitrile;

3-cyclopropyl-3-(3-((4-(1-(ethylamino)-2,2,2-trifluoroethyl)-3-fluorophenyl)amino)-4-oxo-4,5-dihydro-1H-pyrazolo[4,3-c]pyridin-1-yl)propanenitrile;

3-(3-((4-(1-(tert-butylamino)-2,2,2-trifluoroethyl)-3-fluorophenyl)amino)-4-oxo-4,5-dihydro-1H-pyrazolo[4,3-c]pyridin-1-yl)-3-cyclopropylpropanenitrile;

3-cyclopropyl-3-(4-oxo-3-((4-(2-(trifluoromethyl)tetrahydrofuran-2-yl)phenyl)amino)-4,5-dihydro-1H-pyrazolo[4,3-c]pyridin-1-yl)propanenitrile;

3-cyclopropyl-3-(3-((2-hydroxy-2-(trifluoromethyl)-2,3-dihydro-1H-inden-5-yl)amino)-4-oxo-4,5-dihydro-1H-pyrazolo[4,3-c]pyridin-1-yl)propanenitrile;

3-cyclopropyl-3-(3-((3-fluoro-4-(2,2,2-trifluoro-1-hydroxyethyl)phenyl)amino)-4-oxo-4,5-dihydro-1H-pyrazolo[4,3-c]pyridin-1-yl)propanenitrile;

3-(3-((3-chloro-4-(2,2,2-trifluoro-1-hydroxyethyl)phenyl)amino)-4-oxo-4,5-dihydro-1H-pyrazolo[4,3-c]pyridin-1-yl)-3-cyclopropylpropanenitrile;

3-cyclopropyl-3-(3-((2-hydroxy-2-methyl-2,3-dihydro-1H-inden-5-yl)amino)-4-oxo-4,5-dihydro-1H-pyrazolo[4,3-c]pyridin-1-yl)propanenitrile;

3-(3-((4-(1-(tert-butylamino)-2,2,2-trifluoroethyl)-3-chlorophenyl)amino)-4-oxo-4,5-dihydro-1H-pyrazolo[4,3-c]pyridin-1-yl)-3-cyclopropylpropanenitrile;

3-cyclopropyl-3-(4-oxo-3-((4-(2-(trifluoromethyl)piperidin-2-yl)phenyl)amino)-4,5-dihydro-1H-pyrazolo[4,3-c]pyridin-1-yl)propanenitrile;

methyl-2-(4-((1-(2-cyano-1-cyclopropylethyl)-4-oxo-4,5-dihydro-1H-pyrazolo[4,3-c]pyridin-3-yl)amino)phenyl)-2-(trifluoromethyl)pyrrolidine-1-carboxylate;

3-cyclopropyl-3-(3-((2-(4,4-difluoro-1-methylcyclohexyl)-1,1-dioxido-2,3-dihydrobenzo[d]isothiazol-5-yl)amino)-4-oxo-4,5-dihydro-1H-pyrazolo[4,3-c]pyridin-1-yl)propanenitrile;

3-cyclopropyl-3-(4-oxo-3-((4-(2,2,2-trifluoro-1-hydroxy-1-(pyridin-2-yl)ethyl)phenyl)amino)-4,5-dihydro-1H-pyrazolo[4,3-c]pyridin-1-yl)propanenitrile;

3-cyclopropyl-3-(4-oxo-3-((4-(2,2,2-trifluoro-1-hydroxy-1-(pyridin-4-yl)ethyl)phenyl)amino)-4,5-dihydro-1H-pyrazolo[4,3-c]pyridin-1-yl)propanenitrile;

3-cyclopropyl-3-(4-oxo-3-((4-(2,2,2-trifluoro-1-thiomorpholinoethyl)phenyl)amino)-4,5-dihydro-1H-pyrazolo[4,3-c]pyridin-1-yl)propanenitrile;

4-((1-(2-cyano-1-cyclopropylethyl)-4-oxo-4,5-dihydro-1H-pyrazolo[4,3-c]pyridin-3-yl)amino)-N, 2-dimethyl-N-(2,2,2-trifluoroethyl)benzamide;

4-((1-(2-cyano-1-cyclopropylethyl)-4-oxo-4,5-dihydro-1H-pyrazolo[4,3-c]pyridin-3-yl)amino)-N-ethyl-2-methyl-N-(2,2,2-trifluoroethyl)benzamide;

4-((1-(2-cyano-1-cyclopropylethyl)-4-oxo-4,5-dihydro-1H-pyrazolo[4,3-c]pyridin-3-yl)amino)-N-(2-(dimethylamino)ethyl)-2-methyl-N-(2,2,2-trifluoroethyl)benzamide;

3-cyclopropyl-3-(3-((3-methyl-4-(thiomorpholine-4-carbonyl)phenyl)amino)-4-oxo-4,5-dihydro-1H-pyrazolo[4,3-c]pyridin-1-yl)propanenitrile;

3-cyclopropyl-3-(3-((3-methyl-4-(4-methylpiperazine-1-carbonyl)phenyl)amino)-4-oxo-4,5-dihydro-1H-pyrazolo[4,3-c]pyridin-1-yl)propanenitrile;

3-cyclopropyl-3-(3-((3-methyl-4-(2-(trifluoromethyl)pyrrolidine-1-carbonyl)phenyl)amino)-4-oxo-4,5-dihydro-1H-pyrazolo[4,3-c]pyridin-1-yl)propanenitrile;

4-((1-(2-cyano-1-cyclopropylethyl)-4-oxo-4,5-dihydro-1H-pyrazolo[4,3-c]pyridin-3-yl)amino)-N, 2-dimethyl-N-(1-methylpiperidin-4-yl)benzamide;

4-((1-(2-cyano-1-cyclopropylethyl)-4-oxo-4,5-dihydro-1H-pyrazolo[4,3-c]pyridin-3-yl)amino)-N-ethyl-N, 2-dimethylbenzamide;

3-cyclopropyl-3-(3-((3-methyl-4-(morpholine-4-carbonyl)phenyl)amino)-4-oxo-4,5-dihydro-1H-pyrazolo[4,3-c]pyridin-1-yl)propanenitrile;

3-cyclopropyl-3-(3-((4-(3,3-dimethylpyrrolidine-1-carbonyl)-3-methylphenyl)amino)-4-oxo-4,5-dihydro-1H-pyrazolo[4,3-c]pyridin-1-yl)propanenitrile;

3-cyclopropyl-3-(3-((4-(3,3-dimethylazetidine-1-carbonyl)-3-methylphenyl)amino)-4-oxo-4,5-dihydro-1H-pyrazolo[4,3-c]pyridin-1-yl)propanenitrile;

3-cyclopropyl-3-(3-((4-(2,2-dimethylmorpholine-4-carbonyl)-3-methylphenyl)amino)-4-oxo-4,5-dihydro-1H-pyrazolo[4,3-c]pyridin-1-yl)propanenitrile;

3-cyclopropyl-3-(3-((4-(2,5-dimethylpyrrolidine-1-carbonyl)-3-methylphenyl)amino)-4-oxo-4,5-dihydro-1H-pyrazolo[4,3-c]pyridin-1-yl)propanenitrile;
3-cyclopropyl-3-(3-((4-(3-fluoropyrrolidine-1-carbonyl)-3-methylphenyl)amino)-4-oxo-4,5-dihydro-1H-pyrazolo[4,3-c]pyridin-1-yl)propanenitrile;
3-cyclopropyl-3-(3-((3-methyl-4-(2-methylpiperidine-1-carbonyl)phenyl)amino)-4-oxo-4,5-dihydro-1H-pyrazolo[4,3-c]pyridin-1-yl)propanenitrile;
3-cyclopropyl-3-(3-((3-methyl-4-(2-methylpiperidine-1-carbonyl)phenyl)amino)-4-oxo-4,5-dihydro-1H-pyrazolo[4,3-c]pyridin-1-yl)propanenitrile;
3-cyclopropyl-3-(3-((4-(4,4-difluoropiperidine-1-carbonyl)-3-methylphenyl)amino)-4-oxo-4,5-dihydro-1H-pyrazolo[4,3-c]pyridin-1-yl)propanenitrile;
3-cyclopropyl-3-(3-((4-(4-hydroxy-4-methylpiperidine-1-carbonyl)-3-methylphenyl)amino)-4-oxo-4,5-dihydro-1H-pyrazolo[4,3-c]pyridin-1-yl)propanenitrile;
3-cyclopropyl-3-(3-((4-(4-methoxypiperidine-1-carbonyl)-3-methylphenyl)amino)-4-oxo-4,5-dihydro-1H-pyrazolo[4,3-c]pyridin-1-yl)propanenitrile;
3-cyclopropyl-3-(3-((4-(4-(2-hydroxypropan-2-yl)piperidine-1-carbonyl)-3-methylphenyl)amino)-4-oxo-4,5-dihydro-1H-pyrazolo[4,3-c]pyridin-1-yl)propanenitrile;
4-((1-(2-cyano-1-cyclopropylethyl)-4-oxo-4,5-dihydro-1H-pyrazolo[4,3-c]pyridin-3-yl)amino)-N-(3-hydroxy-3-methylbutyl)-N,2-dimethylbenzamide;
3-(3-((4-(azepane-1-carbonyl)-3-methylphenyl)amino)-4-oxo-4,5-dihydro-1H-pyrazolo[4,3-c]pyridin-1-yl)-3-cyclopropylpropanenitrile;
3-cyclopropyl-3-(3-((4-(3-fluoroazetidine-1-carbonyl)-3-methylphenyl)amino)-4-oxo-4,5-dihydro-1H-pyrazolo[4,3-c]pyridin-1-yl)propanenitrile;
3-cyclopropyl-3-(3-((4-(3-methoxyazetidine-1-carbonyl)-3-methylphenyl)amino)-4-oxo-4,5-dihydro-1H-pyrazolo[4,3-c]pyridin-1-yl)propanenitrile;
3-(3-((4-(8-oxa-3-azabicyclo[3.2.1]octane-3-carbonyl)-3-methylphenyl)amino)-4-oxo-4,5-dihydro-1H-pyrazolo[4,3-c]pyridin-1-yl)-3-cyclopropylpropanenitrile;
4-((1-(2-cyano-1-cyclopropylethyl)-4-oxo-4,5-dihydro-1H-pyrazolo[4,3-c]pyridin-3-yl)amino)-N-cyclohexyl-N,2-dimethylbenzamide;
tert-butyl(1-(4-((1-(2-cyano-1-cyclopropylethyl)-4-oxo-4,5-dihydro-1H-pyrazolo[4,3-c]pyridin -3-yl)amino)-2-methylbenzoyl)piperidin-4-yl)(methyl)carbamate;
3-(3-((4-fluorophenyl)amino)-4-oxo-4,5-dihydro-1H-pyrazolo[4,3-c]pyridine-1-yl)butanenitrile;
3-[4-oxo-3-({4-[(2,2,2-trifluoro-1-hydroxy-1-methylethyl]phenyl}amino)-4,5-dihydro-1H-pyrazolo [4,3-c]pyridin-1-yl]butanenitrile;
3-(3-{[1-hydroxy-1-(trifluoromethyl)-2,3-dihydro-1H-inden-5-yl]amino}-4-oxo-4,5-dihydro-1H-pyrazolo [4,3-c]pyridin-1-yl)butanenitrile;
3-{3-[(1,1-dioxido-2,3-dihydro-1-benzothiophen-5-yl)amino]-4-oxo-4,5-dihydro-1H-pyrazolo [4,3-c]pyridin-1-yl}butanenitrile;
4-({1-[2-cyano-1-methylethyl]-4-oxo-4,5-dihydro-1H-pyrazolo[4,3-c]pyridin-3-yl}amino)benzonitrile;
3-(4-oxo-3-{[4-(trifluoromethyl)phenyl]amino}-4,5-dihydro-1H-pyrazolo[4,3-c]pyridin-1-yl)butanenitrile;
3-(3-{[4-(methylsulfonyl)phenyl]amino}-4-oxo-4,5-dihydro-1H-pyrazolo[4,3-c]pyridin-1-yl)butanenitrile;
3-{4-oxo-3-[(3,4,5-trifluorophenyl)amino]-4,5-dihydro-1H-pyrazolo[4,3-c]pyridin-1-yl}butanenitrile;
3-{3-[(2-methyl-1,1-dioxido-2,3-dihydro-1,2-benzisothiazol-5-yl)amino]-4-oxo-4,5-dihydro-1H-pyrazolo [4,3-c]pyridin-1-yl}butanenitrile;

3-{3-[(2-fluoropyridin-4-yl)amino]-4-oxo-4,5-dihydro-1H-pyrazolo[4,3-c]pyridin-1-yl}butanenitrile;
3-{4-oxo-3-[(1-oxo-2,3-dihydro-1H-inden-5-yl)amino]-4,5-dihydro-1H-pyrazolo[4,3-c]pyridin -1-yl}butanenitrile;
3-[3-(2,3-dihydro-1-benzofuran-5-ylamino)-4-oxo-4,5-dihydro-1H-pyrazolo[4,3-c]pyridin-1-yl]butanenitrile;
3-[3-(1,3-benzodioxol-5-ylamino)-4-oxo-4,5-dihydro-1H-pyrazolo[4,3-c]pyridin-1-yl]butanenitrile;
3-[4-oxo-3-(quinolin-6-ylamino)-4,5-dihydro-1H-pyrazolo [4,3-c]pyridin-1-yl]butanenitrile;
3-(3-{[3-fluoro-4-(methylsulfonyl)phenyl]amino}-4-oxo-4,5-dihydro-1H-pyrazolo[4,3-c]pyridin-1-yl)butanenitrile;
3-[4-oxo-3-(quinoxalin-6-ylamino)-4,5-dihydro-1H-pyrazolo[4,3-c]pyridin-1-yl]butanenitrile;
3-{3-[(4-chlorophenyl)amino]-4-oxo-4,5-dihydro-1H-pyrazolo[4,3-c]pyridin-1-yl}butanenitrile;
N-tert-butyl-4-({1-[2-cyano-1-methylethyl]-4-oxo-4,5-dihydro-1H-pyrazolo[4,3-c]pyridin-3-yl}amino)benzenesulfonamide;
3-{3-[(2-tert-butyl-1,1-dioxido-2,3-dihydro-1,2-benzisothiazol-5-yl)amino]-4-oxo-4,5-dihydro -1H-pyrazolo[4,3-c]pyridin-1-yl}butanenitrile;
methyl 3-((4-(azetidin-1-ylsulfonyl)phenyl)amino)-1-(2-cyano-1-cyclopropylethyl)-4-oxo-4,5-dihydro-1H-pyrazolo[4,3-c]pyridine-7-carboxylate;
3-(3-((4-(azetidin-1-ylsulfonyl)phenyl)amino)-7-(hydroxymethyl)-4-oxo-4,5-dihydro-1H-pyrazolo[4,3-c]pyridin-1-yl)-3-cyclopropylpropanenitrile;
3-cyclopropyl-3-(3-((1,1-dioxido-3H-spiro[benzo[b]thiophene-2,1'-cyclohexan]-5-yl)amino)-4-oxo-4,5-dihydro-1H-pyrazolo[4,3-c]pyridin-1-yl)propanenitrile;
3-cyclopropyl-3-(3-((1,1-dioxido-3H-spiro[benzo[b]thiophene-2,1'-cyclopentan]-5-yl)amino)-4-oxo-4,5-dihydro-1H-pyrazolo[4,3-c]pyridin-1-yl)propanenitrile; and
3-cyclopropyl-3-(3-((2,3-dimethyl-1,1-dioxido-2,3-dihydrobenzo[b]thiophen-5-yl)amino)-4-oxo -4,5-dihydro-1H-pyrazolo[4,3-c]pyridin-1-yl)propanenitrile.

The invention also encompasses pharmaceutical compositions containing a compound of formula I, and methods for treatment or prevention of JAK mediated diseases using compounds of formula I.

The invention is described using the following definitions unless otherwise indicated.

As used herein except where noted, "alkyl" is intended to include both branched- and straight-chain saturated aliphatic hydrocarbon groups, including all isomers, having the specified number of carbon atoms. Commonly used abbreviations for alkyl groups are used throughout the specification, e.g. methyl may be represented by "Me" or $CH_3$, ethyl may be represented by "Et" or $CH_2CH_3$, propyl may be represented by "Pr" or $CH_2CH_2CH_3$, butyl may be represented by "Bu" or $CH_2CH_2CH_2CH_3$, etc. "$C_{1-6}$ alkyl" (or "$C_1$-$C_6$ alkyl") for example, means linear or branched chain alkyl groups, including all isomers, having the specified number of carbon atoms. $C_{1-6}$ alkyl includes all of the hexyl alkyl and pentyl alkyl isomers as well as n-, iso-, sec- and t-butyl, n- and isopropyl, ethyl and methyl. "$C_{1-4}$ alkyl" means n-, iso-, sec- and t-butyl, n- and isopropyl, ethyl and methyl.

The term "alkylene" refers to both branched- and straight-chain saturated aliphatic hydrocarbon groups, including all isomers, having the specified number of carbons, and having two terminal end chain attachments. For illustration, the term "unsubstituted A-$C_4$alkylene-B" represents A-$CH_2$—$CH_2$—$CH_2$—$CH_2$—B.

The term "alkoxy" represents a linear or branched alkyl group of indicated number of carbon atoms attached through an oxygen bridge.

"Acyl" means a —C(O)R radical Where R is optionally substituted alkyl, alkenyl, cycloalkyl, heterocycloalkyl, aryl heteroaryl, etc.

"Acylamino" means a —NRR' radical where R is H, OH, or alkoxy and R' is acyl, as defined herein.

The term "alkyl" refers to an aliphatic hydrocarbon group which may be straight or branched and having the indicated number of carbon atoms. Non-limiting examples of alkyl groups include methyl, ethyl, propyl, isopropyl, butyl, s- and t-butyl, pentyl, hexyl, and the like.

The term "heteroalkyl" refers to an alkyl group where 1, 2, or 3 of the carbon atoms is substituted by a heteroatom independently chosen from N, O, or S.

"Alkenyl" refers to an aliphatic hydrocarbon group containing at least one carbon-carbon double bond and which may be straight or branched and having the indicated number of carbon atoms. Preferably alkenyl contains one carbon to carbon double bond, and up to four nonaromatic carbon-carbon double bonds may be present. Examples of alkenyl groups include ethenyl, propenyl, n-butenyl, 2-methyl-1-butenyl, 3-methylbut-2-enyl, n-pentenyl, octenyl and decenyl.

"Alkynyl" refers to an aliphatic hydrocarbon group containing at least one carbon-carbon triple bond and which may be straight or branched and having the indicated number of carbon atoms. Non-limiting examples of suitable alkynyl groups include ethynyl, propynyl, 2-butynyl and 3-methylbutynyl.

"Alkoxy" refers to an alkyl-O— group in which the alkyl group is as described above. $C_{1-6}$alkoxy, for example, includes methoxy, ethoxy, propoxy, isopropoxy, and the like.

"Alkoxyalkyl" refers to an alkyl group as described above in which one or more (in particular 1 to 3) hydrogen atoms have been replaced by alkoxy groups. Examples include $CH_2OCH_3$, $CH_2CH_2OCH_3$ and $CH(OCH_3)CH_3$.

"Aminoalkyl" refers to an alkyl group as described above in which one hydrogen atom has been replaced by an amino, monoalkylamino or dialkylamino group. Examples include $CH_2NH_2$, $CH_2CH_2NHCH_3$ and $CH(N(CH_3)_2)CH_3$.

The term "$C_0$" as employed in expressions such as "$C_{0-6}$ alkyl" means a direct covalent bond; or when the term appears at the terminus of a substituent, $C_{0-6}$ alkyl means hydrogen or $C_{1-6}$alkyl. Similarly, when an integer defining the presence of a certain number of atoms in a group is equal to zero, it means that the atoms adjacent thereto are connected directly by a bond. For example, in the structure

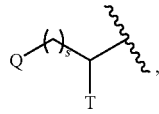

wherein s is an integer equal to zero, 1 or 2, the structure is

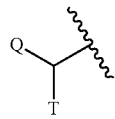

when s is zero.

The term "$C_{3-8}$ cycloalkyl" (or "$C_3$-$C_8$ cycloalkyl") means a cyclic ring of an alkane having three to eight total carbon atoms (i.e., cyclopropyl, cyclobutyl, cyclopentyl, cyclohexyl, cycloheptyl, or cyclooctyl). The terms "$C_{3-7}$ cycloalkyl", "$C_{3-6}$ cycloalkyl", "$C_{5-7}$ cycloalkyl" and the like have analogous meanings.

The term "halogen" (or "halo") refers to fluorine, chlorine, bromine and iodine (alternatively referred to as fluoro (F), chloro (Cl), bromo (Br), and iodo (I)).

The term "aryl" refers to aromatic mono- and polycarbocyclic ring systems, wherein the individual carbocyclic rings in the polyring systems are fused or attached to each other via a single bond. Suitable aryl groups include phenyl, naphthyl, 2,3-dihydro-1H-indenyl, and biphenyl.

The term "carbocycle" (and variations thereof such as "carbocyclic" or "carbocyclyl") as used herein, unless otherwise indicated, refers to (i) a $C_3$ to $C_8$ monocyclic, saturated or unsaturated ring or (ii) a $C_7$ to $C_{12}$ bicyclic saturated or unsaturated ring system. Each ring in (ii) is either independent of, or fused to, the other ring, and each ring is saturated or unsaturated. The carbocycle may be attached to the rest of the molecule at any carbon atom which results in a stable compound. The fused bicyclic carbocycles are a subset of the carbocycles; i.e., the term "fused bicyclic carbocycle" generally refers to a $C_7$ to $C_{10}$ bicyclic ring system in which each ring is saturated or unsaturated and two adjacent carbon atoms are shared by each of the rings in the ring system. A fused bicyclic carbocycle in which one ring is saturated and the other is saturated is a saturated bicyclic ring system. A fused bicyclic carbocycle in which one ring is benzene and the other is saturated is an unsaturated bicyclic ring system. A fused bicyclic carbocycle in which one ring is benzene and the other is unsaturated is an unsaturated ring system. Saturated carbocyclic rings are also referred to as cycloalkyl rings, e.g., cyclopropyl, cyclobutyl, etc. Unless otherwise noted, carbocycle is unsubstituted or substituted with $C_{1-6}$ alkyl, $C_{1-6}$ alkenyl, $C_{1-6}$ alkynyl, aryl, halogen, $NH_2$ or OH. A subset of the fused bicyclic unsaturated carbocycles are those bicyclic carbocycles in which one ring is a benzene ring and the other ring is saturated or unsaturated, with attachment via any carbon atom that results in a stable compound. Representative examples of this subset include the following:

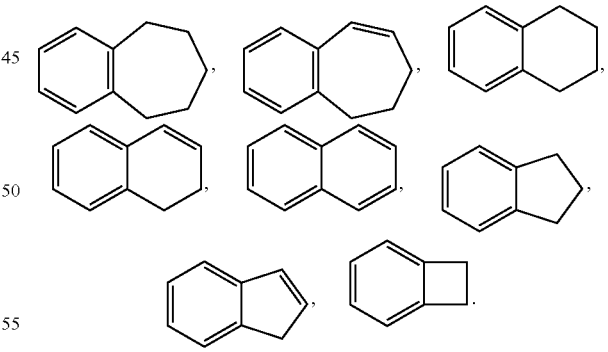

"Cyanoalkyl" refers to an alkyl group as described above in which one hydrogen atom has been replaced by a cyano group. Examples include $CH_2CN$, $CH_2CH_2CN$ and $CH(CN)CH_3$.

"Cycloalkyl" means a carbocyclic ring system having 3 to 12 ring carbon atoms; said ring system may be (a) a monocyclic saturated carbocycle optionally fused to a benzene or a partially unsaturated carbocycle, or (b) a bicyclic saturated carbocycle. For a bicyclic system, within either (a) or (b), the rings are fused across two adjacent ring carbon atoms (e.g., decalin), at one ring carbon atom (e.g., spiro [2.2]pentane), or are bridged groups (e.g., norbornane). Additional examples within the above meaning include, but are not limited to, cyclopropane, cyclobutane, cyclopentane, cyclohexane, perhydroindan, decalin, spiro[4.5]decane, bicyclo[2.2.2]octane, and the like.

"Haloalkyl" refers to an alkyl group as described above wherein one or more (in particular 1 to 5) hydrogen atoms have been replaced by halogen atoms, with up to complete substitution of all hydrogen atoms with halo groups. $C_{1-6}$haloalkyl, for example, includes —$CF_3$, —$CF_2CF_3$, $CHFCH_3$, and the like.

"Heterocycle", "heterocyclic" or "heterocyclyl" represents a monocyclic or bicyclic 3-12 membered ring system in which at least one ring is non-aromatic (saturated or partially unsaturated) and containing at least one heteroatom selected from O, S and N. In a bicyclic ring system, the second ring may be a heteroaryl, heterocycle or a saturated, partially unsaturated or aromatic carbocycle, and the point (s) of attachment to the rest of the molecule may be on either ring. For a bicyclic system, the rings may be fused across two adjacent ring atoms (e.g., quinoline), at one ring carbon atom (e.g., azaspiro[3.3]heptane), or are bridged groups (e.g. 2-oxabicyclo[2.2.2]octane). "Heterocyclyl" therefore includes heteroaryls, as well as dihydro and tetrahydro analogs thereof. Attachment of a heterocyclyl substituent can occur via a carbon atom or via a heteroatom.

Examples of heterocycles (heterocyclyl) include, but are not limited to, azetidinyl, pyrrolidinyl, piperidinyl, piperazinyl, morpholinyl, thiamorpholinyl, tetrahydrofuranyl, dihydrofuranyl, tetrahydrothienyl, tetrahydropyranyl, dihydropyranyl, dihydroimidazolyl, dihydroindolyl, 1,2,3,4-tetrahydroisoquinolinyl, 5,6,7,8-tetrahydroimidazo[1,2-a]pyrazine, 2,3-dihydrobenzofuranyl, benzo-1,4-dioxanyl, benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridinyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, aziridinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof.

Saturated heterocyclics form a subset of the heterocycles; i.e., the terms "saturated heterocyclic and ($C_{3-12}$)heterocloalkyl" generally refers to a heterocycle as defined above in which the entire ring system (whether mono- or polycyclic) is saturated. The term "saturated heterocyclic ring" refers to a 4- to 8-membered saturated monocyclic ring or a stable 7- to 12-membered bicyclic ring system which consists of carbon atoms and one or more heteroatoms selected from N, O and S. Representative examples include piperidinyl, piperazinyl, azepanyl, pyrrolidinyl, pyrazolidinyl, imidazolidinyl, oxazolidinyl, isoxazolidinyl, morpholinyl, 2-oxabicyclo[2.2.2]octyl, 8-oxa-3-azabicyclo[3.2.1]octane, thiomorpholinyl, thiazolidinyl, isothiazolidinyl, and tetrahydrofuryl (or tetrahydrofuranyl)

Heteroaromatics form another subset of the heterocycles; i.e., the term "heteroaromatic" (alternatively "heteroaryl") generally refers to a heterocycle as defined above in which the entire ring system (whether mono- or poly-cyclic) is an aromatic ring system. The term "heteroaromatic ring" refers a 5- or 6-membered monocyclic aromatic ring or a 7- to 12-membered bicyclic which consists of carbon atoms and one or more heteroatoms selected from N, O and S. For a bicyclic heteroaryl only one of the rings need to be heteroaromatic, the second ring may be a heteroaromatic or an aromatic, saturated, or partially unsatuated carbocycle, and the point(s) of attachment to the rest of the molecule may be on either ring. In the case of substituted heteroaryl rings containing at least one nitrogen atom (e.g., pyridine), such substitutions can be those resulting in N-oxide formation. Examples of heteroaryl include, but are not limited to, furanyl, thienyl (or thiophenyl), pyrrolyl, imidazolyl, pyrazolyl, oxazolyl, thiazolyl, isoxazolyl, isothiazolyl, triazolyl, oxadiazolyl, thiadiazolyl, tetrazolyl, pyridyl, pyrimidinyl, pyrazinyl, pyridazinyl, triazinyl, quinolinyl, isoquinolinyl, naphthyridinyl, benzothienyl, benzofuranyl, benzimidazole, benzpyrazolyl, indolyl, isoindolyl, indolizinyl, indazolyl, purinyl, quinolizinyl, phthalazinyl, quinoxalinyl, quinazolinyl, benzoxazolyl, benzisoxazolyl, 5,6,7,8-tetrahydroquinolinyl, imidazo[1,2-a]pyridinyl, imidazo[1,2-a]-pyrimidinyl, 5,6-dihydropyrrolo[1,2-b]pyrazolyl, pyrrolo[3,2-c]pyridinyl, pyrrolo[2,3-b]pyridinyl, thieno[2,3-b]pyrrolyl, furopyridine and thienopyridine.

Representative examples of bicyclic heterocycles include benzotriazolyl, indolyl, isoindolyl, indazolyl, indolinyl, isoindolinyl, quinoxalinyl, quinazolinyl, cinnolinyl, chromanyl, isochromanyl, tetrahydroquinolinyl, quinolinyl, tetrahydroisoauinolinyl, isoauinolinyl, 2,3-dihydrobenzofuranyl, 2,3-dihydrobenzo-1,4-dioxinyl

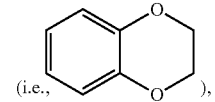

(i.e., ), imidazo(2,1-b)(1,3)thiazole,

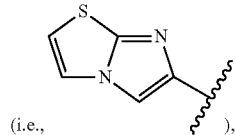 [SMILES: *c1cn2ccsc2n1]

(i.e., ), and benzo-1,3-dioxolyl

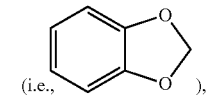

(i.e., ),

In certain contexts herein,

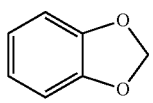

is alternatively referred to as phenyl having as a substituent methylenedioxy attached to two adjacent carbon atoms.

Non-limiting examples of substituted heteroaryls include: isoindolinone, isoindolin-1-one, 2,3-dihydro-1H-pyrazolo[4,3-c]pyridin-4(5H)-one, 2,3,4,5-tetrahydrobenzo[d]isothiazole 1,1-dioxide, and 2,3,4,5-tetrahydrobenzo[b]thiophene 1,1-dioxide.

"Hydroxyalkyl" refers to an alkyl group as described above in which one or more (in particular 1 to 3) hydrogen atoms have been replaced by hydroxy groups. Examples include $CH_2OH$, $CH_2CHOH$ and $CHOHCH_3$.

"Alkylene," "alkenylene," "alkynylene," "cycloalkylene," "arylene," "heteroarylene," and "heterocyclylene" refer to a divalent radical obtained by the removal of one hydrogen atom from an alkyl, alkenyl, alkynyl, cycloalkyl, aryl, heteroaryl, and heterocyclyl group, respectively, each of which is as defined above.

Unless expressly stated to the contrary, an "unsaturated" ring is a partially or fully unsaturated ring. For example, an "unsaturated monocyclic $C_6$ carbocycle" refers to cyclohexene, cyclohexadiene, and benzene.

Unless expressly stated to the contrary, all ranges cited herein are inclusive. For example, a heterocycle described as containing from "1 to 4 heteroatoms" means the heterocycle can contain 1, 2, 3 or 4 heteroatoms.

When any variable occurs more than one time in any constituent or in any formula depicting and describing compounds of the invention, its definition on each occurrence is independent of its definition at every other occurrence. Also, combinations of substituents and/or variables are permissible only if such combinations result in stable compounds.

The term "sulfamoyl" is a suffix to denote radicals derived from sulfamide such as $-SO_2NH_2$, and $-SO_2N(RR^1)$.

The term "substituted" (e.g., as in "aryl which is optionally substituted with one or more substituents . . . ") includes mono- and poly-substitution by a named substituent to the extent such single and multiple substitution (including multiple substitution at the same site) is chemically allowed.

The term "oxy" means an oxygen (O) atom. The term "thio" means a sulfur (S) atom. The term "oxo" means "=O". The term "carbonyl" means "C=O."

When any variable (e.g., $R^2$, $R^3$, etc.) occurs more than one time in any substituent or in formula I its definition in each occurrence is independent of its definition at every other occurrence. Also, combinations of substituents and/or variables are permissible only if such combinations result in stable compounds.

Under standard nomenclature used throughout this disclosure, the terminal portion of the designated side chain is described first, followed by the adjacent functionality toward the point of attachment. For example, a $C_{1-5}$ alkylcarbonylamino $C_{1-6}$ alkyl substituent is equivalent to

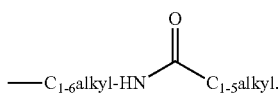

In choosing compounds of the present invention, one of ordinary skill in the art will recognize that the various substituents, i.e. $R^1$, $R^2$, $R^3$, etc., are to be chosen in conformity with well-known principles of chemical structure connectivity.

Lines drawn into the ring systems from substituents indicate that the indicated bond can be attached to any of the substitutable ring atoms. If the ring system is polycyclic, it is intended that the bond be attached to any of the suitable carbon atoms on the proximal ring only.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups can be on the same carbon or on different carbons, so long as a stable structure results. The phrase "optionally substituted with one or more substituents" should be taken to be equivalent to the phrase "optionally substituted with at least one substituent" and in such cases one embodiment will have from zero to three substituents.

Structural representations of compounds having substituents terminating with a methyl group may display the terminal methyl group either using the characters "$CH_3$", e.g. "$-CH_3$," or using a straight line representing the presence of the methyl group, e.g. "-", i.e.,

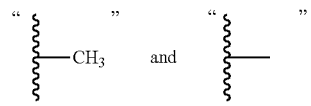

have equivalent meanings.

For variable definitions containing terms having repeated terms, e.g., $(CR^iR^j)_r$, where r is the integer 2, $R^i$ is a defined variable, and $R^j$ is a defined variable, the value of $R^i$ may differ in each instance in which it occurs, and the value of $R^j$ may differ in each instance in which it occurs. For example, if $R^i$ and $R^j$ are independently selected from the group consisting of methyl, ethyl, propyl and butyl, then $(CR^iR^j)_2$ can be

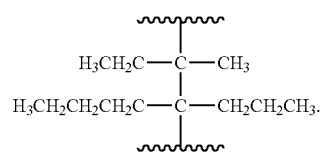

"Patient" includes both human and animals.

"Mammal" means humans and other mammalian animals.

"Therapeutically effective amount" means that amount of a drug or pharmaceutical agent that will elicit the biological or medical response of a tissue, a system, animal or human that is being sought by a researcher, veterinarian, medical doctor or other clinician.

The term "treatment" or "treating" includes alleviating, ameliorating, relieving or otherwise reducing the signs and symptoms associated with a disease or disorder.

The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of formula I, and pharmaceutically acceptable excipients.

The term "optionally substituted" means "unsubstituted or substituted," and therefore, the generic structural formulas described herein encompasses compounds containing the specified optional substituent as well as compounds that do not contain the optional substituent.

Each variable is independently defined each time it occurs within the generic structural formula definitions. For example, when there is more than one substituent for aryl/heteroaryl, each substituent is independently selected at each occurrence, and each substituent can be the same or different from the other(s). As another example, for the group —(CR$^3$R$^3$)$_2$—, each occurrence of the two R$^3$ groups may be the same or different. As used herein, unless explicitly stated to the contrary, each reference to a specific compound of the present invention or a generic formula of compounds of the present invention is intended to include the compound(s) as well as pharmaceutically acceptable salts thereof.

In one embodiment of the invention, A is selected from phenyl, pyridinyl, 2,3-dihydrobenzo[d]thiazolyl, dihydroisoindolyl, dihydrobenzisothiazolyl, dihydroindenyl, 2,3-dihydrobenzofuranyl, 2,3-dihydro-IH-indenyl, dihydrobenzofuranyl, 1-oxo-2,3-dihydro-IH-indenyl, benzo[d]dioxolyl, quinolinyl, quinoxalinyl, benzothiophenyl, 1,3-benzo[d]dioxolyl, isoindolyl, isoindolinyl, dihydro[b]thiophenyl,

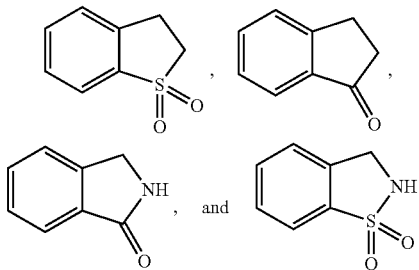

In one embodiment of the invention, A is selected from phenyl, pyridinyl, 2,3-dihydrobenzo[d]thiazolyl, dihydroindenyl, dihydrobenzofuranyl, 2,3-dihydro-IH-indenyl, 2,3-dihydrobenzofuranyl, benzo[d]dioxolyl, 1,3-benzo[d]dioxolyl quinolinyl quinoxalinyl, benzothiophenyl, isoindolinyl, dihydro[b]thiophenyl,

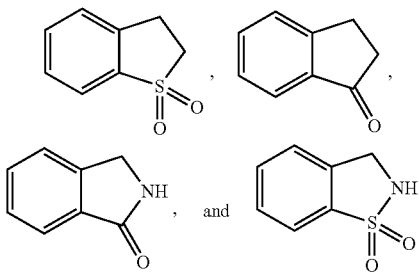

In yet another embodiment of the invention, A is selected from phenyl, pyridinyl, 2,3-dihydrobenzo[d]thiazolyl, 2,3-dihydro-IH-indenyl, 2,3-dihydrobenzofuranyl, 1,3-benzo[d]dioxolyl, quinolinyl, quinoxalinyl, isoindolinyl,

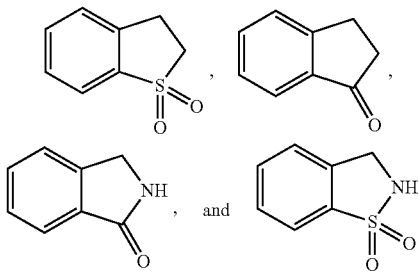

In one variant of the invention A is selected from phenyl and 2,3-dihydro-1H-indenyl. In a variant of this embodiment, A is phenyl.

In another embodiment, A is selected from quinolinyl, pyridinyl, and quinoxalinyl.

In yet another embodiment, A is selected from 2,3-dihydrobenzo[d]thiazolyl, 1,3-benzo[d]dioxolyl, and 2,3-dihydrobenzofuranyl. In another embodiment of the invention, A is selected from isoindolinyl,

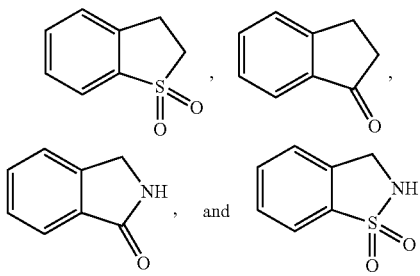

In one embodiment of the invention, m is 1, 2, 3, or 4. In another embodiment, m is 1, 2, or 3. In another embodiment of the invention, m is 0.

In one embodiment of the invention, R$^2$ is independently selected from hydrogen, methyl, ethyl, propyl, isopropyl, butyl, and tert-butyl, wherein R$^2$ is optionally, independently substituted by 1, 2, or 3 R$^5$ substituents. In a variant of this embodiment, R$^2$ is hydrogen.

In one embodiment of the present invention, R$^3$ is selected from: hydrogen, halogen, methyl, ethyl, propyl, isopropyl, butyl, and tert-butyl, cyclopropyl, cyclobutyl and cyclopentyl, wherein R$^3$ is optionally substituted by 1, 2, or 3 R$^5$ substituents. In a variant of this embodiment, R$^3$ is methyl or cyclopropyl, wherein R$^3$ is optionally substituted by 1, 2, or 3 R$^5$ substituents. In another variant of this embodiment, R$^3$ is hydrogen, methyl, cyclobutyl, or cyclopropyl, wherein R$^3$ is optionally substituted by 1, 2, or 3 R$^5$ substituents.

In one embodiment of the invention, R$^5$ is independently selected from hydroxy, (C$_{1-6}$)alkyl, (C$_{1-6}$)alkoxy, (C$_{1-6}$ alkyl)OH, halogen, —CO$_2$H, trifluoromethoxy, trifluoroethoxy, trifluoromethyl, NH$_2$, trifluoroethyl, oxo (O=), —SO$_2$NH$_2$, —SO$_2$C$_{1-6}$alkyl, and —SO$_2$CF$_3$. In a variant of this embodiment, R$^5$ is independently selected from (C$_{1-6}$)alkyl, and halogen, such as for example, methyl and fluoro.

In one embodiment of the invention, R$^1$ is selected from: halogen, Oxo (=O), C$_{1-10}$alkyl(oxy)$_{0-1}$(carbonyl)$_{0-1}$C$_{0-10}$ alkyl, $C_{1-10}$ heteroalkyl$(oxy)_{0-1}$(carbonyl)$_{0-1}C_{0-10}$ alkyl, aryl $C_{0-10}$ alkyl$(oxy)_{0-1}$(carbonyl)$_{0-1}C_{0-10}$ alkyl, $C_{3-12}$ cycloalkyl $C_{0-10}$ alkyl$(oxy)_{0-1}$(carbonyl)$_{0-1}C_{0-10}$ alkyl, heteroaryl $C_{0-10}$ alkyl$(oxy)_{0-1}$(carbonyl)$_{0-1}C_{0-10}$ alkyl, $(C_{3-12})$heterocycloalkyl $C_{0-10}$ alkyl$(oxy)_{0-1}$(carbonyl)$_{0-1}C_{0-10}$ alkyl, $C_{0-10}$ alkyl$(oxy)_{0-1}$(carbonyl)$_{0-1}$amino$C_{0-10}$ alkyl, $(C_{1-10})$heteroalkyl$(oxy)_{0-1}$(carbonyl)$_{0-1}$amino$C_{0-10}$ alkyl, $C_{3-12}$ cycloalkyl $C_{0-10}$ alkyl$(oxy)_{0-1}$(carbonyl)$_{0-1}$amino$C_{0-10}$ alkyl, aryl $C_{0-10}$ alkyl$(oxy)_{0-1}$(carbonyl)$_{0-1}$amino$C_{0-10}$ alkyl, heteroaryl $C_{0-10}$ alkyl$(oxy)_{0-1}$(carbonyl)$_{0-1}$amino$C_{0-10}$ alkyl, $(C_{3-12})$heterocycloalkyl $C_{0-10}$ alkyl$(oxy)_{0-1}$(carbonyl)$_{0-1}$amino$C_{0-10}$ alkyl, $C_{0-10}$ alkylamino (carbonyl)$_{0-1}C_{0-10}$ alkyl, $(C_{1-10})$heteroalkylamino(carbonyl)$_{0-1}C_{0-10}$ alkyl, $C_{3-12}$ cycloalkylamino(carbonyl)$_{0-1}C_{0-10}$ alkyl, aryl $C_{0-10}$ alkylaminoamino(carbonyl)$_{0-1}C_{0-10}$ alkyl, heteroaryl $C_{0-10}$ alkylamino(carbonyl)$_{0-1}C_{0-10}$ alkyl, $(C_{3-12})$heterocycloalkyl amino(carbonyl)$_{0-1}C_{0-10}$ alkyl, $C_{0-10}$ alkylsulfonyl$C_{0-10}$ alkyl, $C_{1-10}$ heteroalkylsulfonyl$C_{0-10}$alkyl, $(C_{3-12})$cycloalkyl$C_{0-10}$alkylsulfonyl$C_{0-10}$ alkyl, $(C_{3-12})$cycloheteroalkyl$C_{0-10}$alkylsulfonyl$C_{0-10}$ alkyl, heteroaryl$C_{0-10}$ alkylsulfonyl$C_{0-10}$ alkyl, aryl$C_{0-10}$ alkylsulfonyl$C_{0-10}$ alkyl, $C_{1-10}$ alkylsulfamoyl$C_{0-10}$ alkyl, $C_{1-10}$ heteroalkylsulfamoyl$C_{0-10}$ alkyl, $(C_{3-12})$cycloalkyl$C_{0-10}$ alkylsulfamoyl$C_{0-10}$ alkyl, $(C_{3-12})$cycloheteroalkyl$C_{0-10}$alkylsulfamoyl$C_{0-10}$ alkyl, heteroaryl$C_{0-10}$ alkylsulfamoyl$C_{0-10}$ alkyl, aryl$C_{0-10}$ alkylsulfamoyl$C_{0-10}$ alkyl, $(C_{0-10}$ alkyl$)_{1-2}$ amino, —$(C_{0-10}$ alkyl$)$CO$_2$H, —SO$_2$N($C_{1-10}$ alkyl)$_2$, hydroxy, —($C_{1-10}$ alkyl)OH, cyano, and $C_{1-6}$haloalkyl; wherein $R^1$ is independently optionally substituted with 1, 2, 3, or 4 $R^4$ substituents and wherein two $R^1$ may optionally join together with the ring atoms to which they are attached to form a 3 to 6 membered ring.

In one embodiment of the invention, $R^1$ is selected from: halogen, Oxo (═O), $C_{1-10}$alkyl$(oxy)_{0-1}$(carbonyl)$_{0-1}C_{0-10}$ alkyl, $C_{1-10}$ heteroalkyl$(oxy)_{0-1}$(carbonyl)$_{0-1}C_{0-10}$ alkyl, aryl $C_{0-10}$ alkyl$(oxy)_{0-1}$(carbonyl)$_{0-1}C_{0-10}$ alkyl, $C_{3-12}$ cycloalkyl $C_{0-10}$ alkyl$(oxy)_{0-1}$(carbonyl)$_{0-1}C_{0-10}$ alkyl, heteroaryl $C_{0-10}$ alkyl$(oxy)_{0-1}$(carbonyl)$_{0-1}C_{0-10}$ alkyl, $(C_{3-12})$heterocycloalkyl $C_{0-10}$ alkyl$(oxy)_{0-1}$(carbonyl)$_{0-1}C_{0-10}$ alkyl, $C_{0-10}$ alkyl$(oxy)_{0-1}$(carbonyl)$_{0-1}$amino$C_{0-10}$ alkyl, $C_{3-12}$ cycloalkyl $C_{0-10}$ alkyl$(oxy)_{0-1}$(carbonyl)$_{0-1}$amino$C_{0-10}$alkyl, $C_{0-10}$ alkylamino$(oxy)_{0-1}$(carbonyl)$_{0-1}C_{0-10}$ alkyl, $(C_{1-10})$heteroalkylamino(carbonyl)$_{0-1}C_{0-10}$ alkyl, $(C_{3-12})$heterocycloalkylamino(carbonyl)$_{0-1}C_{0-10}$alkyl, $C_{0-10}$ alkylsulfonyl$C_{0-10}$ alkyl, $C_{1-10}$ heteroalkylsulfonyl$C_{0-10}$ alkyl, $(C_{3-12})$cycloalkyl$C_{0-10}$alkylsulfonyl$C_{0-10}$ alkyl, $(C_{3-12})$cycloheteroalkyl$C_{0-10}$alkylsulfonyl$C_{0-10}$ alkyl, $C_{1-10}$ alkylsulfamoyl$C_{0-10}$ alkyl, $(C_{3-12})$cycloheteroalkyl$C_{0-10}$alkylsulfamoyl$C_{0-10}$ alkyl, $(C_{0-10}$ alkyl$)_{1-2}$ amino, —$(C_{0-10}$ alkyl)CO$_2$H, —SO$_2$N($C_{1-10}$ alkyl)$_2$, hydroxy, —($C_{1-10}$ alkyl)OH, cyano, and $C_{1-6}$haloalkyl; wherein $R^1$ is independently optionally substituted with 1, 2, 3, or 4 $R^4$ substituents and wherein two $R^1$ may optionally join together with the ring atoms to which they are attached to form a 3 to 6 membered ring.

In one embodiment of the invention, $R^1$ is independently selected from: tert-butylsulfonyl, tert-butylsulfamoyl, amino, fluoro, methylsulfamoyl, dimethylsulfamoyl, tert-butyloxycarbonyl(methylethyl), diethylsulfamoyl, ethylsulfamoyl, pyrrolidinylsulfonyl, (methylethyl)sulfamoyl, methyl, tert-butylaminomethyl, methylaminocarbonyl, ethyl, propyl, piperidinylsulfonyl, thiomorpholinylcarbonyl, thiomorpholinylmethyl, piperazinylcarbonyl, pyrrolidinylcarbonyl, piperidinylcarbonyl, ethylaminocarbonyl, morpholinylcarbonyl, azetidinylcarbonyl, tert-butyl, cyclopentyl, cyclohexyl, benzyl, oxo, hydroxymethyl, triazolyl(2-methylpropyl), 8-oxa-3-azabicyclo[3.2.1]octanylcarbonyl, ethyloxycarbonyl, ethoxycarbonyl(dimethyleth-2yl), hydroxy, trifluoromethyl, azetidinylsulfonyl, cyclopropylsulfonyl, chloro, methylaminomethyl, pyrrolidinylmethyl, cyclopropyl, pyrazolyl, morpholinylsulfonyl, isopropylaminomethyl, isopropyloxycarbonyl, pyrrolidinyl, azaspiro[3.3]heptylsulfonyl, piperadinyl, methylsulfonyl, isopropylsulfonyl, isopropylsulfamoyl, tert-butylsulfonyl, tert-butyloxycarbonyl, hexahydrocyclopenta[b][1,4]oxazin-4(4aH)-ylsulfonyl, 2-oxabicyclo[2.2.2]octyl, azetidinylmethyl, methoxyethyl, methylamino, triazolylmethyl, aminomethyl, azaspiro[3.3]heptylcarbonyl, tetrahydrofuranyl, azetidinylcarbonyl, oxazolyl, carboxy, ethylaminomethyl, piperidinylaminocarbonyl, isopentylaminocarbonyl, azepanylcarbonyl, aminocarbonyl, morpholinyl, tetrahydro-2H-pyranyl, tetrahydropyranyl, isopropyl, sulfonyl, cyano, isopropylaminomethyl, ethylaminomethyl, tetrahydropyranylaminocarbonyl, trifluoroisopropyl, pyridinylmethyl, 2,2,2-trifluoro(methyl)ethyl, 2,2,2-trifluoroethyl, trifluoroethylaminocarbonyl, tert-butylaminomethyl, cyclohexylaminocarbonyl, isopropyloxycarbonyl(dimethyleth-2yl), wherein $R^1$ is independently optionally substituted with 1, 2, 3, or 4 $R^4$ substituents and wherein two $R^1$ may optionally join together with the ring atoms to which they are attached to form a 3 to 6 membered ring.

In one embodiment of the invention, $R^4$ is independently selected from hydroxy, $(C_{1-6})$alkyl, $(C_{1-6})$alkoxy, $(C_{1-10}$ alkyl)OH, halogen, —$(C_{1-10}$ alkyl)OH, —$(C_{0-10}$ alkyl)CO$_2$H, —CO$_2$H, $C_{1-10}$ alkyl$(oxy)_{0-1}$(carbonyl)$_{0-1}C_{0-10}$ alkyl, —$(C_{0-6})$alkylCN, —$C_{0-10}$ alkyl O(C═O)$C_1$-$C_6$ alkyl, NO$_2$, trifluoromethoxy, trifluoroethoxy, trifluoromethyl, trifluoroethyl, —N—C(O)O$(C_{0-6})$alkyl, —N($R^b$)—C(O)O$(C_{0-6})$alkyl, $C_{1-10}$ alkylsulfonyl, oxo (O═), aminosulfonyl, —SO$_2$NH$_2$, —SO$_2$NH($C_{1-10}$ alkyl), —SO$_2$N($C_{1-10}$ alkyl)$_2$, —SO$_2C_{1-6}$alkyl, —SO$_2$CF$_3$, —SO$_2$CF$_2$H, —$C_{1-10}$ alkylsulfinyl, —O$_{(0-1)}(C_{1-10})$haloalkyl, amino($C_{1-6}$alkyl)$_{0-2}$, $C_{3-12}$ cycloalkyl, $(C_{3-12})$cycloheteroalkyl, and NH$_2$, wherein $R^b$ is $C_{1-10}$ alkyl.

In a variant of this embodiment, $R^4$ is independently selected from hydroxy, $(C_{1-6})$alkyl, $(C_{1-6})$alkoxy, $(C_{1-10}$ alkyl)OH, halogen, —$(C_{1-10}$ alkyl)OH, —$(C_{0-10}$ alkyl)CO$_2$H, —CO$_2$H, $C_{1-10}$ alkyl$(oxy)_{0-1}$(carbonyl)$_{0-1}C_{0-10}$ alkyl, —$(C_{0-6})$alkylCN, —$C_{0-10}$ alkyl O(C═O)$C_1$-$C_6$ alkyl, trifluoromethoxy, trifluoroethoxy, trifluoromethyl, trifluoroethyl, —N—C(O)O$(C_{0-6})$alkyl, —N($R^b$)—C(O)O$(C_{0-6})$ alkyl, $C_{1-10}$ alkylsulfonyl, oxo (O═), aminosulfonyl, —SO$_2$NH$_2$, —SO$_2$NH($C_{1-10}$ alkyl), —SO$_2$N($C_{1-10}$ alkyl)$_2$, —SO$_2C_{1-6}$alkyl, —SO$_2$CF$_3$, —SO$_2$CF$_2$H, —$C_{1-10}$ alkylsulfinyl, —O$_{(0-1)}(C_{1-10})$haloalkyl, amino($C_{1-6}$alkyl)$_{0-2}$, $C_{3-12}$ cycloalkyl, $(C_{3-12})$cycloheteroalkyl, and NH$_2$, wherein $R^b$ is $C_{1-10}$ alkyl.

In an embodiment, $R^4$ is independently selected from: trifluoromethyl, tert-butyloxycarbonylisopropyl, ethyloxycarbonylisopropyl, fluoro, hydroxy, methyl, ethyl, 2,2,2-trifluoroethyl, dimethylamino, tert-butyloxycarbonyl, carboxyisoproyl, amino, cyclopentyl, methoxyethyl, cyanoethyl, ethyloxycarbonyl, oxo, methoxy, hydoxyisopropyl, tert-butyloxycarbonyl(methyl)amino, methylsulfonyl, isopropyl, tert-butyl, tert-butylamino, isopropyloxycarbonyl, isopropylamino, methoxycarbonyl, and carboxy.

One embodiment of the invention include the following compounds and their pharmaceutically acceptable salts and stereoisomers thereof:

4-((1-(1-cyanopropan-2-yl)-4-oxo-4,5-dihydro-1H-pyrazolo[4,3-c]pyridin-3-yl)amino)-N,N-dimethylbenzenesulfonamide;

4-((1-(2-cyano-1-cyclopropylethyl)-4-oxo-4,5-dihydro-1H-pyrazolo[4,3-c]pyridin-3-yl)amino)-N,N-dimethylbenzenesulfonamide;

3-cyclopropyl-3-{3-[(4-fluorophenyl)amino]-4-oxo-4,5-dihydro-1H-pyrazolo[4,3-c]pyridin-1-yl}propanenitrile;

3-cyclopropyl-3-[4-oxo-3-({4-[2,2,2-trifluoro-1-hydroxy-1-methylethyl]phenyl}amino)-4,5-dihydro-1H-pyrazolo[4,3-c]pyridin-1-yl]propanenitrile;

3-cyclopropyl-3-(3-{[1-hydroxy-1-(trifluoromethyl)-2,3-dihydro-1H-inden-5-yl]amino}-4-oxo-4,5-dihydro-1H-pyrazolo[4,3-c]pyridin-1-yl)propanenitrile;

3-cyclopropyl-3-{3-[(1,1-dioxido-2,3-dihydro-1-benzothiophen-5-yl)amino]-4-oxo-4,5-dihydro -1H-pyrazolo[4,3-c]pyridin-1-yl}propanenitrile;

3-{3-[(2-tert-butyl-1,1-dioxido-2,3-dihydro-1,2-benzisothiazol-5-yl)amino]-4-oxo-4,5-dihydro -1H-pyrazolo[4,3-c]pyridin-1-yl}-3-cyclopropylpropanenitrile;

4-({1-[2-cyano-1-cyclopropylethyl]-4-oxo-4,5-dihydro-1H-pyrazolo[4,3-c]pyridin-3-yl}amino)benzonitrile;

3-cyclopropyl-3-(4-oxo-3-{[4-(trifluoromethyl)phenyl]amino}-4,5-dihydro-1H-pyrazolo[4,3-c]pyridin-1-yl)propanenitrile;

3-cyclopropyl-3-(3-{[4-(methylsulfonyl)phenyl]amino}-4-oxo-4,5-dihydro-1H-pyrazolo[4,3-c]pyridin-1-yl)propanenitrile;

3-cyclopropyl-3-{4-oxo-3-[(3,4,5-trifluorophenyl)amino]-4,5-dihydro-1H-pyrazolo[4,3-c]pyridin-1-yl}propanenitrile;

3-cyclopropyl-3-{3-[(2-methyl-1,1-dioxido-2,3-dihydro-1,2-benzisothiazol-5-yl)amino]-4-oxo-4,5-dihydro-1H-pyrazolo[4,3-c]pyridin-1-yl}propanenitrile;

3-cyclopropyl-3-{3-[(2-fluoropyridin-4-yl)amino]-4-oxo-4,5-dihydro-1H-pyrazolo[4,3-c]pyridin-1-yl}propanenitrile;

3-cyclopropyl-3-{4-oxo-3-[(1-oxo-2,3-dihydro-1H-inden-5-yl)amino]-4,5-dihydro-1H-pyrazolo [4,3-c]pyridin-1-yl}propanenitrile;

3-cyclopropyl-3-[3-(2,3-dihydro-1-benzofuran-5-ylamino)-4-oxo-4,5-dihydro-1H-pyrazolo[4,3-c]pyridin-1-yl]propanenitrile;

3-[3-(1,3-benzodioxol-5-ylamino)-4-oxo-4,5-dihydro-1H-pyrazolo[4,3-c]pyridin-1-yl]-3-cyclopropylpropanenitrile;

3-cyclopropyl-3-[4-oxo-3-(quinolin-6-ylamino)-4,5-dihydro-1H-pyrazolo[4,3-c]pyridin-1-yl]propanenitrile;

3-cyclopropyl-3-(3-{[3-fluoro-4-(methylsulfonyl)phenyl]amino}-4-oxo-4,5-dihydro-1H-pyrazolo[4,3-c]pyridin-1-yl)propanenitrile;

3-cyclopropyl-3-[4-oxo-3-(quinoxalin-6-ylamino)-4,5-dihydro-1H-pyrazolo[4,3-c]pyridin-1-yl]propanenitrile;

3-{3-[(4-chlorophenyl)amino]-4-oxo-4,5-dihydro-1H-pyrazolo[4,3-c]pyridin-1-yl}-3-cyclopropylpropanenitrile;

cyclopropyl-3-[3-({4-[(1-methylethyl)sulfonyl]phenyl}amino)-4-oxo-4,5-dihydro-1H-pyrazolo[4,3-c]pyridin-1-yl]propanenitrile;

(3-{[4-(tert-butylsulfonyl)phenyl]amino}-4-oxo-4,5-dihydro-1H-pyrazolo[4,3-c]pyridin-1-yl)-3-cyclopropylpropanenitrile;

N-tert-butyl-4-{[(2-cyano-1-cyclopropylethyl)-4-oxo-4,5-dihydro-1H-pyrazolo[4,3-c]pyridin-3-yl]amino}benzenesulfonamide;

3-(3-((4-fluorophenyl)amino)-4-oxo-4,5-dihydro-1H-pyrazolo[4,3-c]pyridine-1-yl)butanenitrile;

3-[4-oxo-3-({4-[2,2,2-trifluoro-1-hydroxy-1-methylethyl]phenyl}amino)-4,5-dihydro-1H-pyrazolo[4,3-c]pyridin-1-yl]butanenitrile;

3-(3-{[1-hydroxy-1-(trifluoromethyl)-2,3-dihydro-1H-inden-5-yl]amino}-4-oxo-4,5-dihydro-1H-pyrazolo[4,3-c]pyridin-1-yl)butanenitrile;

3-{3-[(1,1-dioxido-2,3-dihydro-1-benzothiophen-5-yl)amino]-4-oxo-4,5-dihydro-1H-pyrazolo[4,3-c]pyridin-1-yl}butanenitrile;

3-{3-[(1,1-dioxido-1-benzothiophen-5-yl)amino]-4-oxo-4,5-dihydro-1H-pyrazolo[4,3-c]pyridin-1-yl}butanenitrile;

4-({1-[2-cyano-1-methylethyl]-4-oxo-4,5-dihydro-1H-pyrazolo[4,3-c]pyridin-3-yl}amino)benzonitrile;

3-(4-oxo-3-{[4-(trifluoromethyl)phenyl]amino}-4,5-dihydro-1H-pyrazolo[4,3-c]pyridin-1-yl)butanenitrile;

3-(3-{[4-(methylsulfonyl)phenyl]amino}-4-oxo-4,5-dihydro-1H-pyrazolo[4,3-c]pyridin-1-yl)butanenitrile;

3-{4-oxo-3-[(3,4,5-trifluorophenyl)amino]-4,5-dihydro-1H-pyrazolo[4,3-c]pyridin-1-yl}butanenitrile;

3-{3-[(2-methyl-1,1-dioxido-2,3-dihydro-1,2-benzisothiazol-5-yl)amino]-4-oxo-4,5-dihydro-1H-pyrazolo[4,3-c]pyridin-1-yl}butanenitrile;

3-{3-[(2-fluoropyridin-4-yl)amino]-4-oxo-4,5-dihydro-1H-pyrazolo[4,3-c]pyridin-1-yl}butanenitrile;

3-{4-oxo-3-[(1-oxo-2,3-dihydro-1H-inden-5-yl)amino]-4,5-dihydro-1H-pyrazolo[4,3-c]pyridin-1-yl}butanenitrile;

3-[3-(2,3-dihydro-1-benzofuran-5-ylamino)-4-oxo-4,5-dihydro-1H-pyrazolo[4,3-c]pyridin-1-yl]butanenitrile;

3-[3-(1,3-benzodioxol-5-ylamino)-4-oxo-4,5-dihydro-1H-pyrazolo[4,3-c]pyridin-1-yl]butanenitrile;

3-[4-oxo-3-(quinolin-6-ylamino)-4,5-dihydro-1H-pyrazolo[4,3-c]pyridin-1-yl]butanenitrile;

3-(3-{[3-fluoro-4-(methylsulfonyl)phenyl]amino}-4-oxo-4,5-dihydro-1H-pyrazolo[4,3-c]pyridin-1-yl)butanenitrile;

3-[4-oxo-3-(quinoxalin-6-ylamino)-4,5-dihydro-1H-pyrazolo[4,3-c]pyridin-1-yl]butanenitrile;

3-{3-[(4-chlorophenyl)amino]-4-oxo-4,5-dihydro-1H-pyrazolo[4,3-c]pyridin-1-yl}butanenitrile;

N-tert-butyl-4-({1-[2-cyano-1-methylethyl]-4-oxo-4,5-dihydro-1H-pyrazolo[4,3-c]pyridin-3-yl}amino)benzenesulfonamide; and 3-{3-[(2-tert-butyl-1,1-dioxido-2,3-dihydro-1,2-benzisothiazol-5-yl)amino]-4-oxo-4,5-dihydro-1H-pyrazolo[4,3-c]pyridin-1-yl}butanenitrile.

Optical Isomers-Diastereomers-Geometric Isomers-Tautomers

Compounds of formula I contain one or more asymmetric centers and can thus occur as racemates and racemic mixtures, single enantiomers, diastereomeric mixtures and individual diastereomers. The present invention is meant to comprehend all such isomeric forms of the compounds of formula I, either as single species or mixtures thereof.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form known as keto-enol tautomers. The individual tautomers as well as mixture thereof are encompassed with compounds of formula I.

Specific embodiments of the present invention include a compound which is selected from the group consisting of the subject compounds of the Examples herein or a pharmaceutically acceptable salt thereof.

The compounds of the present invention may contain one or more asymmetric centers and can thus occur as "stereoisomers" including racemates and racemic mixtures, enantiomeric mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the scope of this invention. The present invention is meant to comprehend all such isomeric forms of these compounds. When bonds to the chiral carbon are depicted as straight lines in the Formulas of the invention, it is understood that both the (R) and (S) configurations of the chiral carbon, and hence both enantiomers and mixtures thereof, are embraced within the Formula. For example, Formula I shows the structure of the class of compounds without specific stereochemistry. When the compounds of the present invention contain one chiral center, the term "stereoisomer" includes both enantiomers and mixtures of enantiomers, such as the specific 50:50 mixture referred to as racemic mixtures.

The compounds of Formula (I) may contain asymmetric or chiral centers, and, therefore, exist in different stereoisomeric forms. It is intended that all stereoisomeric forms of the compounds of Formula (I) as well as mixtures thereof, including racemic mixtures, form part of the present invention. In addition, the present invention embraces all geometric and positional isomers. For example, if a compound of Formula (I) incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I) may be atropisomers (e.g., substituted biaryls) and are considered as part of this invention. Enantiomers can also be separated by use of chiral HPLC column.

It is also possible that the compounds of Formula (I) may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of Formula (I) incorporates a double bond or a fused ring, both the cis- and trans-forms, as well as mixtures, are embraced within the scope of the invention. Also, for example, all keto-enol and imine-enamine forms of the compounds are included in the invention.) Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

In the present application when a particular stereomeric compound is named using an "and" in the stereomeric designation, the "and" indicates a racemic mixture of the enantiomers. That is, the individual enantiomers were not individually isolated.

When the stereomeric nomenclature includes "or", for example, (3R or S)-3-{3-[(1,1-dioxido-2,3-dihydro-1-benzothiophen-5-yl)amino]-4-oxo-4,5-dihydro-1H-pyrazolo[4,3-c]pyridin-1-yl}butanenitrile, the "or" indicates that chiral resolution of racemate into individual enantiomers was accomplished but the actual optical activity of the specific enantiomer was not necessarily determined.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art. Alternatively, any enantiomer of a compound can be obtained by stereoselective synthesis using optically pure starting materials or reagents of known configuration by methods well known in the art.

Salts

The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, 1-hydroxy-2-naphthoic acid (xinafoate) and the like. Particularly preferred are citric, hydrobromic, hydrochloric, maleic, phosphoric, sulfuric, and tartaric acids.

It will be understood that, unless otherwise specified, references to the compound of formula I subsets thereof, embodiments thereof, as well as specific compounds are meant to also include the pharmaceutically acceptable salts and stereoisomers thereof.

Furthermore, some of the crystalline forms for compounds of the present invention may exist as polymorphs and as such all forms are intended to be included in the present invention In addition, some of the compounds of the instant invention may form solvates with water (hydrates) or common organic solvents. Such solvates are encompassed within the scope of this invention.

Labelled Compounds

In the compounds of generic Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

Utilities

Compound of formula I or its pharmaceutically acceptable salts and pharmaceutical compositions can be used to treat or prevent a variety of conditions or diseases mediated by Janus kinases, in particular diseases or conditions that can be ameliorated by the inhibition of a Janus kinase such as JAK1, JAK2, JAK3 or TYK2. Such conditions and diseases include, but are not limited to: (1) arthritis, including rheumatoid arthritis, juvenile arthritis, and psoriatic arthritis; (2) asthma and other obstructive airways diseases, including chronic asthma, late asthma, airway hyper-responsiveness, bronchitis, bronchial asthma, allergic asthma, intrinsic asthma, extrinsic asthma, dust asthma, recurrent airway obstruction, and chronic obstruction pulmonary disease including emphysema; (3) autoimmune diseases or disorders, including those designated as single organ or single cell-type autoimmune disorders, for example Hashimoto's thyroiditis, autoimmune hemolytic anemia, autoimmune atrophic gastritis of pernicious anemia, autoimmune encephalomyelitis, autoimmune orchitis, Goodpasture's disease, autoimmune thrombocytopenia, sympathetic ophthalmia, myasthenia gravis, Graves' disease, primary biliary cirrhosis, chronic aggressive hepatitis, ulcerative colitis and membranous glomerulopathy, those designated as involving systemic autoimmune disorder, for example systemic lupus erythematosis, rheumatoid arthritis, Sjogren's syndrome, Reiter's syndrome, polymyositis-dermatomyositis, systemic sclerosis, polyarteritis nodosa, multiple sclerosis and bullous pemphigoid, and additional autoimmune diseases, which can be B-cell (humoral) based or T-cell based, including Cogan's syndrome, ankylosing spondylitis, Wegener's granulomatosis, autoimmune alopecia, Type I or juvenile onset diabetes, and thyroiditis; (4) cancers or tumors, including alimentary/gastrointestinal tract cancer, colon cancer, liver cancer, skin cancer including mast cell tumor and squamous cell carcinoma, breast and mammary cancer, ovarian cancer, prostate cancer, lymphoma, leukemia, including acute myelogenous leukemia and chronic myelogenous leukemia, kidney cancer, lung cancer, muscle cancer, bone cancer, bladder cancer, brain cancer, melanoma including oral and metastatic melanoma, Kaposi's sarcoma, myelomas including multiple myeloma, myeloproliferative disorders, proliferative diabetic retinopathy, and angiogenic-associated disorders including solid tumors; (5) diabetes, including Type I diabetes and complications from diabetes; (6) eye diseases, disorders or conditions including autoimmune diseases of the eye, keratoconjunctivitis, vernal conjunctivitis, uveitis including uveitis associated with Behcet's disease and lens-induced uveitis, keratitis, herpetic keratitis, conical keratitis, corneal epithelial dystrophy, keratoleukoma, ocular premphigus, Mooren's ulcer, scleritis, Grave's ophthalmopathy, Vogt-Koyanagi-Harada syndrome, keratoconjunctivitis sicca (dry eye), phlyctenule, iridocyclitis, sarcoidosis, endocrine ophthalmopathy, sympathetic ophthalmitis, allergic conjunctivitis, and ocular neovascularization; (7) intestinal inflammations, allergies or conditions including Crohn's disease and/or ulcerative colitis, inflammatory bowel disease, coeliac diseases, proctitis, eosinophilic gastroenteritis, and mastocytosis; (8) neurodegenerative diseases including motor neuron disease, Alzheimer's disease, Parkinson's disease, amyotrophic lateral sclerosis, Huntington's disease, cerebral ischemia, or neurodegenerative disease caused by traumatic injury, strike, glutamate neurotoxicity or hypoxia; ischemic/reperfusion injury in stroke, myocardial ischemica, renal ischemia, heart attacks, cardiac hypertrophy, atherosclerosis and arteriosclerosis, organ hypoxia, and platelet aggregation; (9) skin diseases, conditions or disorders including atopic dermatitis, eczema, psoriasis, scleroderma, pruritus and other pruritic conditions; (10) allergic reactions including anaphylaxis, allergic rhinitis, allergic dermatitis, allergic urticaria, angioedema, allergic asthma, or allergic reaction to insect bites, food, drugs, or pollen; (11) transplant rejection, including pancreas islet transplant rejection, bone marrow transplant rejection, graft-versus-host disease, organ and cell transplant rejection such as bone marrow, cartilage, cornea, heart, intervertebral disc, islet, kidney, limb, liver, lung, muscle, myoblast, nerve, pancreas, skin, small intestine, or trachea, and xeno transplantation.

Accordingly, another aspect of the present invention provides a method for the treatment or prevention of a JAK-mediated disease or disorder comprising administering to a mammal in need thereof a therapeutically effective amount of a compound of formula I. In one embodiment such diseases include asthma and rheumatoid arthritis.

Another aspect of the present invention provides for the use of a compound of formula I in the manufacture of a medicament for the treatment or prevention of a JAK-mediated diseases or disorder.

One aspect of the invention is the use of a compound of Formula I or a pharmaceutically acceptable salt or a stereoisomer thereof in the manufacture of a medicament for the treatment of a disease or a disorder ameliorated by selective inhibition of Janus kinases JAK1 and JAK2.

Another aspect of the invention is the use of a compound of Formula I or a pharmaceutically acceptable salt or a stereoisomer thereof and a second active agent in the manufacture of a medicament for the treatment of a disease or a disorder ameliorated by selective inhibition of Janus kinases JAK1 and JAK2.

Dose Ranges

The magnitude of prophylactic or therapeutic dose of a compound of formula I will, of course, vary with the nature and the severity of the condition to be treated and with the particular compound of formula I and its route of administration. It will also vary according to a variety of factors including the age, weight, general health, sex, diet, time of administration, rate of excretion, drug combination and response of the individual patient. In general, the daily dose from about 0.001 mg to about 100 mg per kg body weight of a mammal, preferably 0.01 mg to about 10 mg per kg. On the other hand, it may be necessary to use dosages outside these limits in some cases.

The amount of active ingredient that may be combined with the carrier materials to produce a single dosage form will vary depending upon the host treated and the particular mode of administration. For example, a formulation intended for the oral administration of humans may contain from 0.05 mg to 5 g, of active agent compounded with an appropriate and convenient amount of carrier material which may vary from about 5 to about 99.95 percent of the total composition. In some cases, the dosage unit forms may contain from about 0.05 to about 3 g of active ingredient. Dosage unit forms will generally contain between from about 0.1 mg to about 0.4 g of an active ingredient, typically 0.1 mg, 0.2 mg, 0.3 mg, 0.4 mg, 0.5 mg, 1 mg, 2 mg, 5 mg, 10 mg, 25 mg, 50 mg, 100 mg, 200 mg, or 400 mg.

Pharmaceutical Compositions

Another aspect of the present invention provides pharmaceutical compositions comprising a compound of formula I with a pharmaceutically acceptable carrier. For the treatment of any of the prostanoid mediated diseases compounds of formula I may be administered orally, by inhalation spray, topically, parenterally or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle, sheep, dogs, cats, etc., the compound of the invention is effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and U.S. Pat. No. 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water-miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropyl methylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example *arachis* oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of an oil-in-water emulsion. The oily phase may be a vegetable oil, for example olive oil or *arachis* oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. Cosolvents such as ethanol, propylene glycol or polyethylene glycols may also be used. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Dosage forms for inhaled administration may conveniently be formulated as aerosols or dry powders. For compositions suitable and/or adapted for inhaled administration, it is preferred that the active substance is in a particle-size-reduced form, and more preferably the size-reduced form is obtained or obtainable by micronization.

In one embodiment the medicinal preparation is adapted for use with a pressurized metered dose inhaler (pMDI) which releases a metered dose of medicine upon each actuation. The formulation for pMDIs can be in the form of solutions or suspensions in halogenated hydrocarbon propellants. The type of propellant being used in pMDIs is being shifted to hydrofluoroalkanes (HFAs), also known as hydrofluorocarbons (HFCs). In particular, 1,1,1,2-tetrafluoroethane (HFA 134a) and 1,1,1,2,3,3,3-heptafluoropropane (HFA 227) are used in several currently marketed pharmaceutical inhalation products. The composition may include other pharmaceutically acceptable excipients for inhalation use such as ethanol, oleic acid, polyvinylpyrrolidone and the like.

Pressurized MDIs typically have two components. Firstly, there is a canister component in which the drug particles are stored under pressure in a suspension or solution form. Secondly, there is a receptacle component used to hold and actuate the canister. Typically, a canister will contain multiple doses of the formulation, although it is possible to have single dose canisters as well. The canister component typically includes a valve outlet from which the contents of the canister can be discharged. Aerosol medication is dispensed from the pMDI by applying a force on the canister component to push it into the receptacle component thereby opening the valve outlet and causing the medication particles to be conveyed from the valve outlet through the receptacle component and discharged from an outlet of the receptacle. Upon discharge from the canister, the medication particles are "atomized", forming an aerosol. It is intended that the patient coordinate the discharge of aerosolized medication with his or her inhalation, so that the medication particles are entrained in the patient's aspiratory flow and conveyed to the lungs. Typically, pMDIs use propellants to pressurize the contents of the canister and to propel the medication particles out of the outlet of the receptacle component. In pMDIs, the formulation is provided in a liquid or suspension form, and resides within the container along with the propellant. The propellant can take a variety of forms. For example, the propellant can comprise a compressed gas or liquefied gas.

In another embodiment the medicinal preparation is adapted for use with a dry powder inhaler (DPI). The inhalation composition suitable for use in DPIs typically comprises particles of the active ingredient and particles of a pharmaceutically acceptable carrier. The particle size of the active material may vary from about 0.1 µm to about 10 µm; however, for effective delivery to the distal lung, at least 95 percent of the active agent particles are 5 m or smaller. Each of the active agent can be present in a concentration of 0.01-99%. Typically however, each of the active agents is present in a concentration of about 0.05 to 50%, more typically about 0.2-20% of the total weight of the composition.

As noted above, in addition to the active ingredients, the inhalable powder preferably includes pharmaceutically acceptable carrier, which may be composed of any pharmacologically inert material or combination of materials which is acceptable for inhalation. Advantageously, the carrier particles are composed of one or more crystalline sugars; the carrier particles may be composed of one or more sugar alcohols or polyols. Preferably, the carrier particles are particles of dextrose or lactose, especially lactose. In embodiments of the present invention which utilize conventional dry powder inhalers, such as the Handihaler™, Rotohaler™, Diskhaler™, Twisthaler™ and Turbohaler™, the particle size of the carrier particles may range from about 10 microns to about 1000 microns. In certain of these embodiments, the particle size of the carrier particles may range from about 20 microns to about 120 microns. In certain other embodiments, the size of at least 90% by weight of the carrier particles is less than 1000 microns and preferably lies between 60 microns and 1000 microns. The relatively large size of these carrier particles gives good flow and entrainment characteristics. Where present, the amount of carrier particles will generally be up to 95%, for example, up to 90%, advantageously up to 80% and preferably up to 50% by weight based on the total weight of the powder. The amount of any fine excipient material, if present, may be up to 50% and advantageously up to 30%, especially up to 20%, by weight, based on the total weight of the powder. The powder may optionally contain a performance modifier such as L-leucine or another amino acid, and/or metals salts of stearic acid such as magnesium or calcium stearate.

Compounds of formula I may also be administered in the form of suppositories for rectal administration of the drug. These compositions can be prepared by mixing the drug with a suitable non-irritating excipient which is solid at ambient temperatures but liquid at the rectal temperature and will therefore melt in the rectum to release the drug. Such materials are cocoa butter and polyethylene glycols.

For topical use, creams, ointments, gels, solutions or suspensions, etc., containing the compound of formula I are employed. (For purposes of this application, topical application shall include mouth washes and gargles.) Topical formulations may generally be comprised of a pharmaceutical carrier, cosolvent, emulsifier, penetration enhancer, preservative system, and emollient.

Combinations with Other Drugs

For the treatment and prevention of JAK mediated diseases, compound of formula I may be co-administered with other therapeutic agents. Thus in another aspect the present invention provides pharmaceutical compositions for treating JAK mediated diseases comprising a therapeutically effective amount of a compound of formula I and one or more other therapeutic agents. In particular, for the treatment of the inflammatory diseases rheumatoid arthritis, psoriasis, inflammatory bowel disease, COPD, asthma and allergic rhinitis a compound of formula I may be combined with agents such as: (1) TNF-α inhibitors such as Remicade® and Enbrel®; (2) non-selective COX-I/COX-2 inhibitors (such as piroxicam, diclofenac, propionic acids such as naproxen, flubiprofen, fenoprofen, ketoprofen and ibuprofen, fenamates such as mefenamic acid, indomethacin, sulindac, apazone, pyrazolones such as phenylbutazone, salicylates such as aspirin); (3) COX-2 inhibitors (such as meloxicam, celecoxib, rofecoxib, valdecoxib and etoricoxib); (4) other agents for treatment of rheumatoid arthritis including low dose methotrexate, lefunomide, ciclesonide, hydroxychloroquine, d-penicillamine, auranofin or parenteral or oral gold; (5) leukotriene biosynthesis inhibitor, 5-lipoxygenase (5-LO) inhibitor or 5-lipoxygenase activating protein (FLAP) antagonist such as zileuton; (6) LTD4 receptor antagonist such as zafirlukast, montelukast and pranlukast; (7) PDE4 inhibitor such as roflumilast; (8) antihistaminic H1 receptor antagonists such as cetirizine, loratadine, desloratadine, fexofenadine, astemizole, azelastine, and chlorpheniramine; (9) α1- and α2-adrenoceptor agonist vasoconstrictor sympathomimetic agent, such as propylhexedrine, phenylephrine, phenylpropanolamine, pseudoephedrine, naphazoline hydrochloride, oxymetazoline hydrochloride, tetrahydrozoline hydrochloride, xylometazoline hydrochloride, and ethylnorepinephrine hydrochloride; (10) anticholinergic agents such as ipratropium bromide, tiotropium bromide, oxitropium bromide, aclindinium bromide, glycopyrrolate, pirenzepine, and telenzepine; (11) β-adrenoceptor agonists such as metaproterenol, isoproterenol, isoprenaline, albuterol, salbutamol, formoterol, salmeterol, terbutaline, orciprenaline, bitolterol mesylate, and pirbuterol, or methylxanthanines including theophylline and aminophylline, sodium cromoglycate; (12) insulin-like growth factor type I (IGF-1) mimetic; (13) inhaled glucocorticoid with reduced systemic side effects, such as prednisone, prednisolone, flunisolide, triamcinolone acetonide, beclomethasone dipropionate, budesonide, fluticasone propionate, ciclesonide and mometasone furoate.

SCHEMES AND EXAMPLES

The abbreviations used herein have the following tabulated meanings. Abbreviations not tabulated below have their meanings as commonly used unless specifically stated otherwise

| | |
|---|---|
| ACN | acetonitrile |
| MeCN | acetonitrile |
| BAST | bis(2-methoxyethyl)aminosulfur trifluoride |
| Chiral SFC | chiral super critical fluid chromatography |
| $CO_2$ | carbon dioxide |
| $Cs_2CO_3$ | cesium carbonate |
| DBU | 1,8-diazabicyclo[5.4.0]undec-7-ene |
| DCE | 1,2-dichloroethane |
| DCM | dichloromethane |
| DIPEA | N,N-diisopropylethylamine |
| DMF | N,N-dimethylformamide |
| DMSO | dimethyl sulfoxide |
| DSC | N,N-disuccinimidyl carbonate |
| EDC | 3-(ethyliminomethyleneamino)-N,N-dimethyl-propan-1-amine |
| EtOAc | ethyl acetate |
| HATU | O-(7-aza-1H-benzotriazol-1-yl)-N,N,N',N'-tetramethyluronium hexafluorophosphate |
| hr or h | hour |
| HCl | hydrogen chloride |
| HOBt | 1-hydroxybenzotriazole |
| HPLC | high pressure liquid chromatography |
| IPA | 2-propanol |
| LDA | lithium diisopropylamide |
| m-CPBA | meta-chloroperoxybenzoic acid |
| LRMS | low resolution mass spectrometry |
| MeI | iodomethane |
| Me—THF | 2-methyltetrahydrofuran |
| MgSO4 | magnesium sulfate |
| $MP-(OAc)_3BH$ | solid supported (macro porous) triacetoxyborohydride |
| MPLC | medium pressure liquid chromatography |
| NaH | sodium hydride |
| $Na_2SO_4$ | sodium sulfate |
| NaBH4 | sodium borohydride |
| NaHCO3 | sodium bicarbonate |
| NaOMe | sodium methoxide |
| $Pd_2(dba)_3$ | tris(dibenzylideneacetone)dipalladium(0) |
| $POCl_3$ | phosphorus (V) oxychloride |
| Prep | preparative |
| PyBOP | (7-azabenzotriazol-1-yloxy)tripyrrolidinophosphonium hexafluorophosphate |
| SFC | Supercritical Fluid Chromatography |
| Sat. | saturated |
| SEM-Cl | 2-(trimethylsilyl)ethoxymethyl chloride |
| SiliaCat ® DPP-Pd | silica bound diphenylphosphine palladium (II) |
| TBAF | tetra-n-butylammonium fluoride |
| TBS-Cl | tert-butyldimethylsilyl chloride |
| t-BuOH (tert-BuOH) | tert-butanol |
| TEA | triethylamine |
| TFA | trifluoroacetic acid |
| THF | tetrahydrofuran |
| X-Phos | 2-dicyclohexylphosphino-2',4',6'-triisopropylbiphenyl |
| $Me_4$—$^tBu$—X-Phos | di-tert-butyl[3,4,5,6-tetramethyl-2',4',6'-tri(propan-2-yl)biphenyl-2-yl]phosphane |
| NMO | 4-methylmorpholine N-oxide |
| rt or RT | Room temperature |
| Sat. aq. | Saturated, aqueous |
| TPAP | tetra-n-propylammonium perruthenate (VII) |
| HCOOH | formic acid |
| $K^tOBu$ | potassium tert-butoxide |
| $Na_2S_2O_5$ | sodium metabisulfite |
| NMR | nuclear magnetic resonance |
| TLC | thin layer chromatography |
| $(EtO)_2P(O)CH_2CN$ | diethyl (cyanomethyl)phosphonate |
| MsCl | methanesulfonyl chloride |
| TsOH | p-toluenesulfonic acid |
| KCN | potassium cyanide |
| Si-DMT | silica supported Dimercaptotriazine |
| TMS | trimethylsilane |
| $CF_3TMS$ | (trifluoromethyl)trimethylsilane |
| $PhI(OAc)_2$ | Iodosobenzene diacetate |
| $Ti(OEt)_4$ | Titanium (IV) ethoxide |
| $Ti(Oi-Pr)_4$ | Titanium (IV) isopropoxide |
| $TMSCF_3$ | trimethyl(trifluoromethyl)silane |
| $BH_3$ | borane |
| $SOCl_2$ | Thionyl chloride |
| LiHMDS | Lithium bis(trimethylsilyl)amide |
| $BOC_2O$ | Boc-anhydride, or di-tert-butyl dicarbonate |
| NaBH4 | Sodium borohydride |
| i-PrMgCl | Isopropylmagnesium chloride |
| KOAc | Potassium acetate |
| $K_3PO_4$ | Potassium phosphate tribasic |
| PG | Protecting group |
| IBX | 2-Iodoxybenzoic acid |
| HNRR | A disubstituted amine |

| | |
|---|---|
| Ph₃PMeBr | Methyltriphenylphosphonium bromide |
| AlCl₃ | Aluminum trichloride |

Alkyl Group Abbreviations

| | |
|---|---|
| Me | methyl |
| Et | ethyl |
| n-Pr | normal propyl |
| i-Pr | isopropyl |
| n-Bu | normal butyl |
| i-Bu | isobutyl |
| s-Bu | secondary butyl |
| t-Bu | tertiary butyl |
| c-Pr | cyclopropyl |
| c-Bu | cyclobutyl |
| c-Pen | cyclopentyl |
| c-Hex | cyclohexyl |

Methods of Synthesis

The compounds of the present invention can be prepared according to the following general schemes using appropriate materials, and are further exemplified by the subsequent specific examples. The compounds illustrated in the examples are not to be construed as forming the only genus that is considered as the invention. The illustrative Examples below, therefore, are not limited by the compounds listed or by any particular substituents employed for illustrative purposes. Substituent numbering as shown in the schemes does not necessarily correlate to that used in the claims and often, for clarity, a single substituent is shown attached to the compound where multiple substituents are allowed under the definitions of the instant invention herein above.

Those skilled in the art will readily understand that known variations of the conditions and processes of the following preparative procedures can be used to prepare these compounds. The invention will now be illustrated in the following non-limiting Examples in which, unless otherwise stated:

All reactions were stirred (mechanically, stir bar/stir plate, or shaken) and conducted under an inert atmosphere of nitrogen or argon unless specifically stated otherwise.

All starting materials used to prepare the intermediates and final compounds described herein were obtained from commercial vendors, and were used as is upon receipt.

All temperatures are degrees Celsius (° C.) unless otherwise noted.

Ambient temperature is 15-25° C.

Most compounds were purified by reverse-phase preparative HPLC, MPLC on silica gel, recrystallization and/or swish (suspension in a solvent followed by filtration of the solid).

The course of the reactions was followed by thin layer chromatography (TLC) and/or LCMS and/or NMR and reaction times are given for illustration only.

All end products were analyzed by NMR and LCMS. Intermediates were analyzed by NMR and/or TLC and/or LCMS.

Method 1

General procedures to prepare intermediates of the instant invention are described in Scheme 1. Using standard enolization conditions, such as KOt-Bu or TEA/LiBr, in a suitable solvent, such as THF, PhMe, at a temperature between 0° C. and room temperature aldehyde 1A can undergo olefination to yield α,β-unsaturated nitrile 1B. Using an appropriate base, such as DBU, in a suitable solvent, such as MeCN, EtOH, n-BuOH or tert-BuOH, at a temperature between 25-110° C. either protected pyrazolopyridone 1C (PG=a suitable protecting group) can undergo conjugate addition to optionally substituted nitriles 1B to yield adduct 1D, in racemic form. The stereoisomers of intermediate 1D can be separated into its respective individual optical isomers using the appropriate chromatographic method (achiral and/or chiral). Intermediate 1D is cross coupled to substituted aryl and heteroaryl halides 1E using an appropriate catalytic palladium/ligand system, such as Pd₂(dba)₃ or Pd₂(dba)₃.CHCl₃, and 2-di-tert-butylphosphino-2',4',6'-triisopropylbiphenyl (t-Bu XPhos) or di-tert-butyl[3,4,5,6-tetramethyl-2',4',6'-tri(propan-2-yl)biphenyl-2-yl]phosphane (Me₄ ᵗBu-XPhos), or 2-dicyclohexylphosphino-2',4',6'-triisopropylbiphenyl (XPhos). Typical conditions employ 1-2 equivalents of the aryl/heteroaryl halide relative to the pyrazolopyrimidine with 10-25% Pd precatalyst loading, using an approximate Pd:ligand ratio of 1:2 to 1:2.5. Typically, the cross coupling is carried out using either 2-propanol or t-amyl alcohol solvents, and between 1-3.1 equivalents of KOAc or K₃PO₄ base. Reactions were typically carried out between 65-89° C., to yield intermediates 1F of the instant invention. Intermediates 1F can be deprotected using either hydrogenolysis conditions (H₂ gas, Pd/C, in a suitable solvent such as EtOAc, EtOH, MeOH, or using combinations of solvents thereof), or promoted by a suitable acid to afford Examples 1G of the instant invention.

SCHEME 1

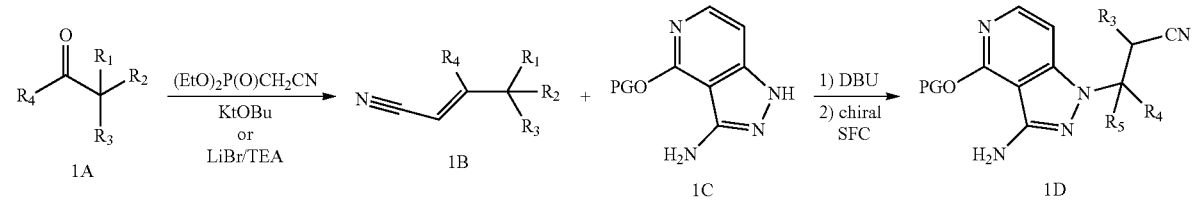

+

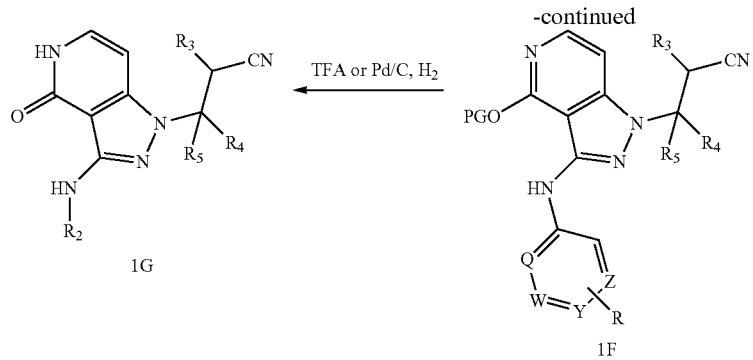 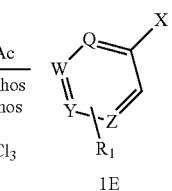

INTERMEDIATES

The following experimental procedures detail the preparation of chemical materials used in the synthesis of Examples of the instant invention. The exemplified procedures are for illustrative purposes only, and are not intended to limit the scope of the instant invention in any way.

Intermediate 1

4-(Benzyloxy)-1H-pyrazolo[4,3-c]pyridin-3-amine

I-1

Step 1: 2-(Benzyloxy)-4-methoxynicotinonitrile

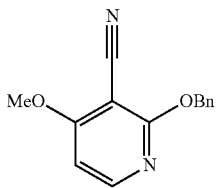

I-1a

To a solution of 2-hydroxy-4-methoxynicotinonitrile (60 g, 0.4 mol) in toluene (0.6 L) was added $Ag_2CO_3$ (140 g, 0.51 mol) and BnBr (87 g, 0.51 mol) at room temperature. The mixture was stirred at 50° C. for 3 h. TLC showed the reaction was complete. The mixture was filtered off solids, washed with DCM and concentrated in vacuum. Petroleum ether (100 mL) was added to the residue, the solid was collected by filter to give compound I-la as a white solid. $^1$H NMR (400 MHz, DMSO-d6): δ 8.32 (d, 1H), 7.31-7.45 (m, 5H), 6.97 (d, 1H), 5.47 (s, 2H), 3.98 (s, 3H).

Step 2: 4-(Benzyloxy)-1H-pyrazolo[4,3-c]pyridin-3-amine

A suspension of 2-(benzyloxy)-4-methoxynicotinonitrile (100 g, 410 mmol) in hydrazine hydrate (200 g, 4.1 mol) and n-BuOH (600 mL) was heated to reflux overnight. The mixture was concentrated in vacuum and purified by chromatography (petroleum ether: ethyl acetate=3:1) to give I-1 as a white solid. $^1$H NMR (400 MHz, DMSO-d6): δ11.89 (s, 1H), 7.69 (d, 1H), 7.50 (d, 2H), 7.38-7.39 (d, 2H), 7.31 (d, 1H), 6.82 (d, 1H), 5.51 (s, 2H), 5.17 (s, 2H).

Intermediate 2A and 2B 2-(4-bromophenyl)-1,1,1-trifluoropropan-2-ol

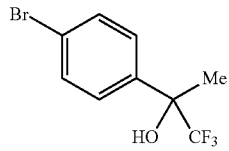

I-2

To 4'-bromo-2,2,2-trifluoroacetophenone (890 mg, 3.52 mmol) in tetrahydrofuran (11.73 ml) under an atmosphere of $N_2$ at 0° C. was added methyl magnesium bromide (17.6 mL, 17.6 mmol). The reaction was stirred at that temperature for 1 hour, and then warmed to room temperature overnight. The reaction was quenched with sat. $NH_4Cl$, and diluted with EtOAc (20 mL). The layers were separated, and the aqueous layer was extracted with EtOAc (3×20 mL). The combined organic layers were washed with brine, dried over $Na_2SO_4$, and concentrated in vacuo. The resulting oil was purified using an ISCO chromatography system, eluting with 5-50% EA/hexanes. The desired fractions were concentrated in vacuo to afford 2-(4-bromophenyl) 1,1,1-trifluoropropan-2-ol I-2 as a colorless oil. LRMS (ESI) calc'd for $C_9H_9BrF_3O$ $[M+H]^+$:269. found 269. $^1$H NMR (500 MHz, $CDCl_3$): δ7.52 (d, J=7.0 Hz, 2H), 7.45 (d, J=7.5 Hz, 2H), 1.78 (s, 3H).

Resolution of enantiomers was achieved by SFC purification using a Chiral Technology AZ-H 2.1×25 cm, 5 uM column, at 70 mL/min with 5%/95% (methanol/$CO_2$) solvent system. Retention times were 2.55 minutes (Intermediate I-2A) & 3.19 minutes (Intermediate I-2B).

I-2A (S or R)-2-(4-bromophenyl)-1,1,1-trifluoropropan-2-ol. LRMS (ESI) calc'd for $C_9H_9BrF_3O$ $[M+H]^+$: 270, found 270.

I-2B (S or R)-2-(4-bromophenyl)-1,1,1-trifluoropropan-2-ol. LRMS (ESI) calc'd for $C_9H_9BrF_3O$ $[M+H]^+$: 270, found 270.

Intermediate I-3A and I-3B 5-bromo-1-(trifluoromethyl)-2,3-dihydro-1H-inden-1-ol

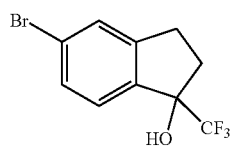

I-3

To 5-bromo-2,3-dihydro-1H-inden-1-one (500 mg, 2.37 mmol) in tetrahydrofuran (2.39 mL) under an atmosphere of $N_2$ at 0° C. was added (trifluoromethyl)trimethylsilane (9.48 mL, 4.74 mmol), and tetrabutylammonium fluoride (2.37 mL, 2.37 mmol). The reaction was stirred at 0° C. for 1 hour, and then warmed to room temperature overnight. The reaction was quenched with sat. $NaHCO_3$, and diluted with EtOAc (20 mL). The layers were separated, and the aqueous layer was extracted with EtOAc (3×20 mL). The combined organic layers were washed with brine, dried over $Na_2SO_4$, and concentrated in vacuo. The resulting oil was purified using an ISCO chromatography system, eluting with 5-50% EA/hexanes. The desired fractions were concentrated in vacuo to afford 5-bromo-1-(trifluoromethyl)-2,3-dihydro-1H-inden-1-ol, I-3 as brown solid. LRMS (ESI) calc'd for $C_{10}H_9BrF_3O$ [M+H]$^+$: 282, found 282. $^1$H NMR (500 MHz, CDCl$_3$): δ7.46-7.43 (m, 2H), 7.37-7.35 (d, J=7.5 Hz, 1H), 3.16-3.12 (m, 1H), 3.10-3.03 (m, 1H), 2.70-2.60 (m, 1H), 2.29-2.21 (m, 1H).

Resolution of enantiomers was achieved by SFC purification using a Chiral Technology AZ-H 2.1×25 cm, 5 uM column, at 70 mL/min with 15%/85% (methanol/CO$_2$) solvent system. Retention times were 1.73 minutes (Intermediate I-3A) & 2.13 minutes (Intermediate I-3B).

I-3A (S or R)-5-bromo-1-(trifluoromethyl)-2,3-dihydro-1H-inden-1-ol. LRMS (ESI) calc'd for $C_{10}H_9BrF_3O$ [M+H]$^+$:282, found 282.

I-3B (S or R)-5-bromo-1-(trifluoromethyl)-2,3-dihydro-1H-inden-1-ol. LRMS (ESI) calc'd for $C_{10}H_9BrF_3O$ [M+H]$^+$:282, found 282.

Following analogous methodology to that outlined for Intermediate I-3 above, the following intermediates in Table 1 were synthesized.

TABLE 1

| Intermediate | Structure | Name | NMR |
| --- | --- | --- | --- |
| I-4 | 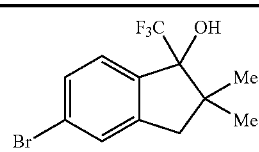 | 5-Bromo-2,2-dimethyl-1-(trifluoromethyl)-2,3-dihydro-1H-inden-1-ol | $^1$H NMR (CDCl$_3$, 500 MHz): δ 7.43-7.41 (m, 2H), 7.33 (d, J = 8.11 Hz, 1H), 2.89 (d, J = 15.69 Hz, 1H), 2.82 (d, J = 15.64 Hz, 1H), 1.27 (s, 3H), 1.16 (s, 3H). |
| I-5 | 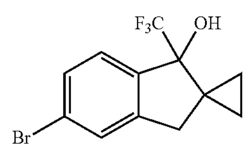 [SMILES: OC1(C(F)(F)F)c2ccc(Br)cc2CC12CC2] | 5'-bromo-1'-(trifluoromethyl)-1',3'-dihydrospiro[cyclopropane-1,2'-inden]-1'-ol | $^1$H NMR (CDCl$_3$, 500 MHz): δ 7.46-7.38 (m, 2H), 7.35 (d, J = 15.78 Hz, 1H), 3.33 (d, J = 16.20 Hz, 1H), 2.66 (d, J = 16.20 Hz, 1H), 2.26 (br s, 1H), 1.08-1.01 (m, 2H), 0.98-0.88 (m, 2H). |
| I-6 | 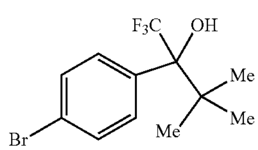 [SMILES: CC(C)(C)C(O)(c1ccc(Br)cc1)C(F)(F)F] | 2-(4-bromophenyl)-1,1,1-trifluoro-3,3-dimethylbutan-2-ol | $^1$H NMR (CDCl$_3$, 500 MHz): δ 7.55-7.47 (m, 4H), 1.04 (s, 9H). |
| I-7A | 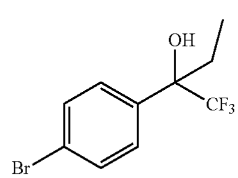 | (R or S)-2-(4-bromophenyl)-1,1,1-trifluorobutan-2-ol (Peak 1, Chiralpak, AD-H, 10% MeOH in CO$_2$, rT = 2.55 minutes) | $^1$H NMR (400 MHz, CDCl$_3$): δ 7.51-7.50 (d, J = 8.80 Hz, 2H), 7.40-7.38 (d, J = 8.80 Hz, 2H), 2.25 (s, 1H), 2.21-2.14 (m, 1H), 2.04-1.98 (m, 1H), 0.77 (t, J = 7.04 Hz, 3H). |
| I-7B | 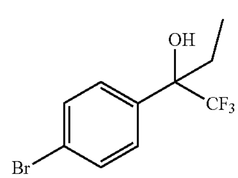 | (R or S)-2-(4-bromophenyl)-1,1,1-trifluorobutan-2-ol SFC retention time (Peak 1, Chiralpak, AD-H, 10% MeOH in CO$_2$, rT = 2.86 minutes) | $^1$H NMR (400 MHz, CDCl$_3$): δ 7.51-7.50 (d, J = 8.80 Hz, 2H), 7.40-7.38 (d, J = 8.80 Hz, 2H), 2.25 (s, 1H), 2.21-2.14 (m, 1H), 2.04-1.98 (m, 1H), 0.77 (t, J = 7.04 Hz, 3H). |
| I-8 | 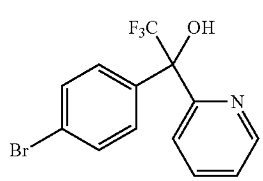 [SMILES: OC(c1ccc(Br)cc1)(c1ccccn1)C(F)(F)F] | 1-(4-bromophenyl)-2,2,2-trifluoro-1-(pyridin-2-yl)ethanol | $^1$H NMR (CDCl$_3$, 500 MHz): δ 8.59 (d, J = 4.89 Hz, 1H), 7.75 (td, J = 7.77, 1.73 Hz, 1H), 7.52-7.44 (m, 5H), 7.37-7.35 (m, 1H), 7.00 (br s, 1H). |

TABLE 1-continued

| Intermediate | Structure | Name | NMR |
|---|---|---|---|
| I-9 | F₃C, OH on carbon bonded to 4-bromophenyl and pyridin-4-yl | 1-(4-bromophenyl)-2,2,2-trifluoro-1-(pyridin-4-yl)ethanol | ¹H NMR (CDCl₃, 500 MHz): δ 8.45 (br s, 1H), 7.53-7.38 (m, 6H), 7.36-7.31 (m, 2H). |

Intermediate I-10

1-(4-Bromo-2-methylphenyl)-2,2,2-trifluoroethanol

I-10a 1-(4-Bromo-2-methylphenyl)-2,2,2-trifluoroethanone (2.00 g, 7.49 mmol) was dissolved in THF (7.0 mL) and treated with sodium borohydride (0.312 g, 8.24 mmol) at 0° C. The ice bath was removed and the reaction was warmed to room temperature and stirred overnight. The reaction was then diluted with dichloromethane and washed with water and brine. The organic layer was dried over sodium sulfate, filtered, concentrated in vacuo and the residue oil was purified by silica chromatography, eluting with 5-30% to give 1-(4-bromo-2-methylphenyl)-2,2,2-trifluoroethanol I-10a. ¹H NMR (600 MHz, CDCl₃) δ7.48 (d, 1H, J=7.8 Hz), 7.42 (dd, 1H, J=1.2, 8.4 Hz), 7.37 (br s, 1H), 5.27 (m, 1H), 2.61 (d, 1H, J=4.2 Hz), 2.36 (s, 3H).

Intermediate I-11

5-bromo-2,3-dihydrobenzo[b]thiophene 1,1-dioxide

I-11

To a solution of 5-bromo-benzo[b]thiophene 1,1-dioxide (1.0 g, 4.08 mmol) in ethanol (13.6 mL) at 0° C., sodium borohydride (965 mg, 20.2 mmol) was added. The reaction mixture was warmed to room temperature, and stirred overnight. The solution was cooled to 0° C., quenched with 1N HCl (15 mL), and diluted with ethyl acetate (25 mL), the layers were separated, and the aqueous layer was extracted with ethyl acetate (3×25 mL). The combined organic layers were washed with brine, dried over Na₂SO₄, and concentrated in vacuo. The crude oil was purified using an ISCO chrolmatography system eluting with Hexanes/EtOAc (5:1) to give 5-bromo-2,3-dihydrobenzo[b]thiophene 1,1-dioxide, I-11. ¹H NMR (500 MHz, CDCl₃): δ7.62-7.53 (m, 2H), 7.51 (s, 1H), 3.55-3.45 (m, 2H), 3.39-3.29 (m, 2H).

Intermediate I-12

5-bromo-2-(tert-butyl)-2,3-dihydrobenzo[d]isothiazole 1,1-dioxide

I-12

Step 1: 4-bromo-2-methylbenzene-1-sulfonyl chloride

I-12a

Chlorosulfonic acid (63 g, 0.54 mol) was added slowly to a cold solution (0° C.) of 1-bromo-3-methylbenzene (10.0 g, 58 mmol) in CHCl₃ (100 mL). The reaction was allowed to proceed with stirring for 2 hours at 0° C., then reaction mixture was poured into ice water and extracted with EtOAc, and the organic layer was washed with brine, dried over Na₂SO₄, filtered and concentrated in vacuo to afford compound I-12a. ¹H NMR (400 MHz, CDCl₃) δ7.90 (d, J=8.4 Hz, 1H), 7.59-7.53 (m, 2H), 2.75 (s, 3H).

Step 2: 4-bromo-N-(tert-butyl)-2-methylbenzenesulfonamide

I-12b

To a solution of 4-bromo-2-methylbenzene-1-sulfonyl chloride, I-12a, (2.0 g, 7.4 mmol) in CH₂Cl₂ (15 mL) was added a solution of 2-methylpropan-2-amine (0.65 g, 8.9 mmol) and triethylamine (0.90 g, 8.9 mmol) in CH$_2$Cl$_2$ (30 mL) at 0° C. The reaction mixture was stirred at 0° C. for 2 hours, and then at room temperature for 16 hours. The mixture was washed with 0.1 M HCl, saturated aqueous NaHCO$_3$, dried over Na$_2$SO$_4$, filtered and the filtrate was concentrated in vacuo. After removal of the solvent under reduced pressure, I-12b was obtained. $^1$H NMR (400 MHz, CDCl$_3$) δ7.78 (d, J=8.4 Hz, 1H), 7.63 (d, J=1.6 Hz, 1H), 7.59-7.56 (m, 2H), 2.57 (s, 3H), 1.09 (s, 9H).

Step 3: 5-bromo-2-(tert-butyl)benzo[d]isothiazol-3 (2H)-one 1,1-dioxide

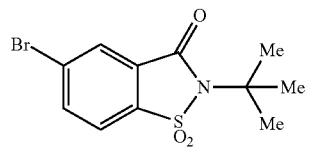

I-12c

A mixture of H$_5$IO$_6$ (5.9 g, 26 mmol) in acetonitrile (50 mL) was stirred at room temperature for 1 hour, then CrO$_3$ (33 mg, 0.33 mmol) was added followed by acetic anhydride (2.67 g, 26 mmol). The resulting orange solution was cooled to 0° C., and to it was added 4-bromo-N-(tert-butyl)-2-methyl benzenesulfonamide, I-10b, (1.0 g, 3.3 mmol). After stirring at 0° C. for 15 minutes, the reaction was allowed to warm to room temperature and was stirred for 16 hours. The solvent was removed in vacuo, and the residue was extracted with EtOAc (3x), the combined organic layers were washed with saturated aqueous NaHCO$_3$, brine, dried over Na$_2$SO$_4$, filtered and the filtrate was concentrated in vacuo. The residue was purified by silica chromatography, eluting with 5% EtOAc in hexanes and the desired fractions were concentrated in vacuo to afford I-12c as a white solid. $^1$H NMR (400 MHz, CDCl$_3$): δ8.82-8.14 (m, 3H), 1.66 (s, 9H).

Step 4: 5-bromo-2-(tert-butyl)-2,3-dihydrobenzo[d] isothiazole 1,1-dioxide

To a solution of I-12c (0.20 g, 0.63 mmol) in THF (4 mL) was added BH$_3$.Me$_2$S (240 mg, 3.16 mmol). The reaction mixture was refluxed for 16 hours. After being cooled to room temperature, the reaction was quenched with 2 M HCl, and extracted with EtOAc (2x), the combined extracts were wash with brine, dried over Na$_2$SO$_4$, filtered, and the filtrate was concentrated in vacuo. The residue was purified by preparative TLC to afford I-12. $^1$H NMR (400 MHz, CDCl$_3$) δ7.83-7.56 (m, 3H), 4.55 (s, 2H), 1.46 (s, 9H).

Following analogous methodology to that outlined for Intermediate I-12 above, the following intermediate in Table 2 was synthesized.

Intermediate I-14

1-bromo-4-(tert-butylsulfonyl)benzene

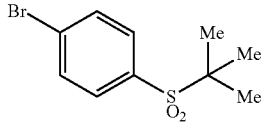

I-14

To a solution of (4-bromophenyl)(tert-butyl)sulfane (1.00 g, 4.08 mmol) in DCM (10.0 mL) was added m-CPBA (2.01 g, 8.97 mmol, 77 wt. %) at room temperature. The resulting solution was stirred at room temperature for one hour, and then quenched with saturated aqueous Na$_2$S$_2$O$_3$ and saturated aqueous Na$_2$CO$_3$. The reaction was extracted with DCM (3x), dried over Na$_2$SO$_4$, filtered and concentrated in vacuo to afford I-14. $^1$H NMR (600 MHz, CDCl$_3$): δ7.89 (d, J=8.7 Hz, 2H), 7.75 (d, J=8.7 Hz, 2H), 1.24 (s, 9H).

Intermediate 15A and 15B 1-(4-bromophenyl)-2,2,2-trifluoroethanamine

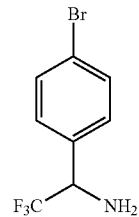

I-15

To a solution of 1-(4-bromophenyl)-2,2,2-trifluoroethanone (1.00 g, 3.95 mmol) in toluene (14 mL) at room temperature, was added (dropwise) a solution of lithium bis(trimethylsilyl)amide (4.35 mL, 4.35 mmol, 1M in THF). The reaction was stirred at room temperature for 15 minutes and then BH$_3$.THF (7.90 mL, 7.90 mmol, 1M in THF) was added. The reaction was stirred at room temperature for 20 minutes, then quenched at 0° C. by slow addition of 2M aqueous NaOH (5.93 mL, 11.9 mmol). The mixture was stirred at room temperature for 90 minutes, then the organic layer was separated and washed with 1N aqueous NaOH solution, dried over Na$_2$SO$_4$, filtered and concentrated in vacuo. SFC separation of the enantiomers on the crude reaction mixture was achieved using a ChiralPak AZ-H, with 7% methanol modifier in CO$_2$: retention times=2.37 (I-15A) & 2.89 (I-15B) minutes. LRMS (ESI) calc'd for C$_8$H$_8$NBrF$_3$ [M+H]$^+$: 255, found 255. $^1$H NMR (600 MHz, CDCl$_3$): δ7.53 (d, J=8.5 Hz, 2H), 7.32 (d, J=8.5 Hz, 2H), 4.38 (q, J=7.5 Hz, 1H), 1.78 (br s, 2H).

TABLE 1

| Intermediate | Structure | Name | NMR |
|---|---|---|---|
| I-13 | ![structure] | 5-bromo-2-methyl-2,3-dihydrobenzo[d]isothiazole 1,1-dioxide | $^1$H NMR (400 MHz, CDCl$_3$): δ 7.63-7.60 (m, 2H), 7.5 (s, 1H), 4.25 (s, 2H), 2.89 (s, 3H). |

Intermediate 16

4-bromo-N-isopropylbenzenesulfonamide

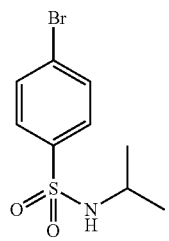

I-16

To a solution of propan-2-amine (160 mg, 2.6 mmol) and DIPEA (780 mg, 6.0 mmol) in $CH_2Cl_2$ (7 mL) was added a solution of 4-bromobenzene-1-sulfonyl chloride (510 mg, 2.0 mmol) in $CH_2Cl_2$ (14 mL). The resulting reaction mixture was stirred at rt overnight, then was poured into water (20 mL), and extracted with $CH_2Cl_2$ (3×15 ml). The combined organic layers were concentrated in vacuo to afford a residue that was purified by column chromatography on silica (pet ether/EtOAc: 20/1) to give 4-bromo-N-isopropylbenzenesulfonamide. $^1H$ NMR (400 MHz, $CDCl_3$): δ7.75-7.72 (m, 2H), 7.65-7.62 (m, 2H), 4.43 (d, J=7.52 Hz, 1H), 3.49-3.44 (m, 1H), 1.08 (d, J=6.4 Hz, 6H).

Table 3 discloses intermediates that were prepared in an analogous manner to that of Intermediate 16.

TABLE 3

| Intermediate | Structure | Compound Name | NMR/MS |
|---|---|---|---|
| I-17A | 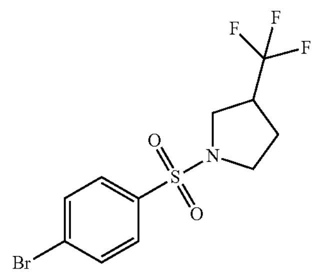 [SMILES: O=S(=O)(c1ccc(Br)cc1)N1CCC(C(F)(F)F)C1] | (R or S)-1-((4-bromophenyl)sulfonyl)-3-(trifluoromethyl)pyrrolidine SFC retention time (Chiralpak, IF, 20% MeOH in $CO_2$) = 1.91 minutes. | LRMS (ESI) calc'd for $C_{11}H_{12}BrF_3NO_2S$ [M + H]+: 359, found 359 |
| I-17B | 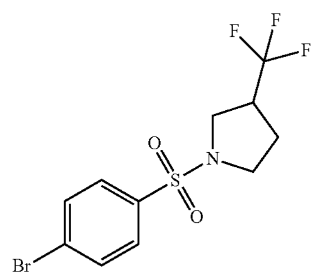 [SMILES: O=S(=O)(c1ccc(Br)cc1)N1CCC(C(F)(F)F)C1] | (R or S)-1-((4-bromophenyl)sulfonyl)-3-(trifluoromethyl)pyrrolidine SFC retention time (Chiralpak, IF, 20% MeOH in $CO_2$) = 2.23 minutes. | LRMS (ESI) calc'd for $C_{11}H_{12}BrF_3NO_2S$ [M + H]+: 359, found 359 |
| I-18A | 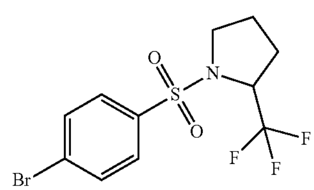 [SMILES: O=S(=O)(c1ccc(Br)cc1)N1CCCC1C(F)(F)F] | (R or S)-1-((4-bromophenyl)sulfonyl)-2-(trifluoromethyl)pyrrolidine SFC retention time (Chiralpak, IF, 15% isopropanol in $CO_2$) = 1.88 minutes. | LRMS (ESI) calc'd for $C_{11}H_{12}BrF_3NO_2S$ [M + H]+: 359, found 359 |
| I-18B | 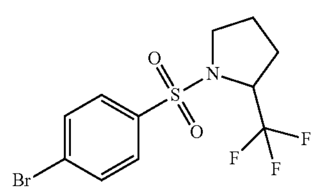 [SMILES: O=S(=O)(c1ccc(Br)cc1)N1CCCC1C(F)(F)F] | (R or S)-1-((4-bromophenyl)sulfonyl)-2-(trifluoromethyl)pyrrolidine SFC retention time (Chiralpak, IF, 15% isopropanol in $CO_2$) = 2.21 minutes. | LRMS (ESI) calc'd for $C_{11}H_{12}BrF_3NO_2S$ [M + H]+: 359, found 359 |
| I-19A | 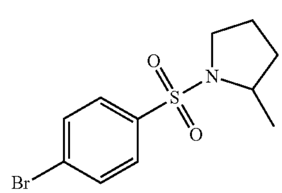 [SMILES: CC1CCCN1S(=O)(=O)c1ccc(Br)cc1] | (R or S)-1-((4-bromophenyl)sulfonyl)-2-methylpyrrolidine SFC retention time (Chiralpak, AD-H, 15% MeOH in $CO_2$) = 3.03 minutes. | LRMS (ESI) calc'd for $C_{11}H_{15}BrNO_2S$ [M + H]+: 305, found 305 |

TABLE 3-continued

| Intermediate | Structure | Compound Name | NMR/MS |
|---|---|---|---|
| I-19B | 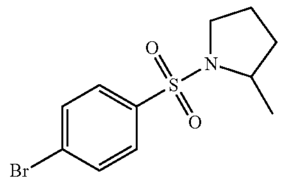 [SMILES: CC1CCCN1S(=O)(=O)c1ccc(Br)cc1] | (R or S)-1-((4-bromophenyl)sulfonyl)-2-methylpyrrolidine SFC retention time (Chiralpak, AD-H, 15% MeOH in $CO_2$) = 4.40 minutes. | LRMS (ESI) calc'd for $C_{11}H_{15}BrNO_2S$ [M + H]+: 305, found 305 |
| I-20A | 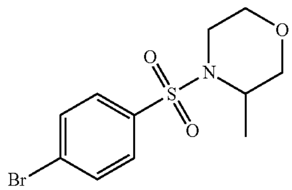 [SMILES: CC1COCCN1S(=O)(=O)c1ccc(Br)cc1] | (R or S)-4-((4-bromophenyl)sulfonyl)-3-methylmorpholine SFC retention time (Chiralpak, AZ-H, 15% MeOH in $CO_2$) = 3.29 minutes. | LRMS (ESI) calc'd for $C_{11}H_{15}BrNO_3S$ [M + H]+: 321, found 321 |
| I-20B | 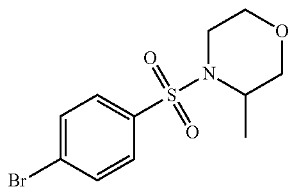 [SMILES: CC1COCCN1S(=O)(=O)c1ccc(Br)cc1] | (R or S)-4-((4-bromophenyl)sulfonyl)-3-methylmorpholine SFC retention time (Chiralpak, AZ-H, 15% MeOH in $CO_2$) = 5.52 minutes. | LRMS (ESI) calc'd for $C_{11}H_{15}BrNO_3S$ [M + H]+: 321, found 321 |
| I-21A | 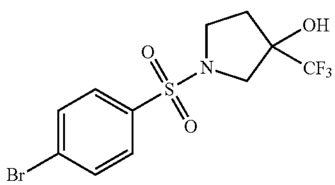 [SMILES: O=S(=O)(c1ccc(Br)cc1)N1CCC(O)(C(F)(F)F)C1] | (R or S)-1-((4-bromophenyl)sulfonyl)-3-(trifluoromethyl)pyrrolidin-3-ol SFC retention time (Chiralpak, AZ-H, 15% MeOH in $CO_2$) = 2.01 minutes. | LRMS (ESI) calc'd for $C_{11}H_{12}BrF_3NO_3S$ [M + H]+: 375, found 375 |
| I-21B | 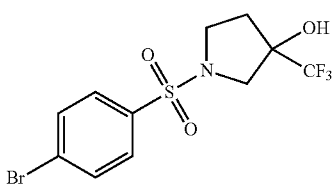 [SMILES: O=S(=O)(c1ccc(Br)cc1)N1CCC(O)(C(F)(F)F)C1] | (R or S)-1-((4-bromophenyl)sulfonyl)-3-(trifluoromethyl)pyrrolidin-3-ol SFC retention time (Chiralpak, AZ-H, 15% MeOH in $CO_2$) = 4.02 minutes. | LRMS (ESI) calc'd for $C_{11}H_{12}BrF_3NO_3S$ [M + H]+: 375, found 375 |
| I-22A | 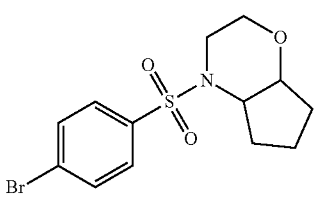 [SMILES: O=S(=O)(c1ccc(Br)cc1)N1CCOC2CCCC21] | (4a R or S,7a R or S)-4-((4-bromophenyl)sulfonyl)octahydrocyclopenta[b][1,4]oxazine SFC retention time (Chiralpak, AD-H, 25% MeOH in $CO_2$) = 3.85 minutes. | LRMS (ESI) calc'd for $C_{13}H_{17}BrNO_3S$ [M + H]+: 347, found 347 |
| I-22B | 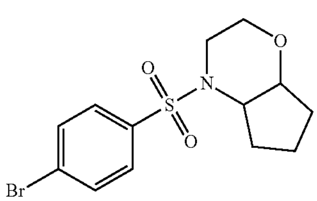 [SMILES: O=S(=O)(c1ccc(Br)cc1)N1CCOC2CCCC21] | (4a R or S,7a R or S)-4-((4-bromophenyl)sulfonyl)octahydrocyclopenta[b][1,4]oxazine SFC retention time (Chiralpak, AD-H, 25% MeOH in $CO_2$) = 4.98 minutes. | LRMS (ESI) calc'd for $C_{13}H_{17}BrNO_3S$ [M + H]+: 347, found 347 |
| I-23A | 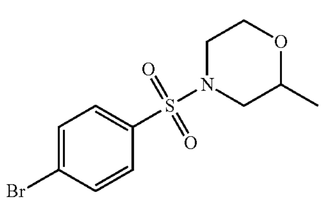 [SMILES: CC1CN(S(=O)(=O)c2ccc(Br)cc2)CCO1] | (R or S)-4-((4-bromophenyl)sulfonyl)-2-methylmorpholine SFC retention time (Chiralpak, AD-H, 20% MeOH in $CO_2$) = 3.15 minutes. | LRMS (ESI) calc'd for $C_{11}H_{15}BrNO_3S$ [M + H]+: 321, found 321 |

TABLE 3-continued

| Intermediate | Structure | Compound Name | NMR/MS |
|---|---|---|---|
| I-23B | 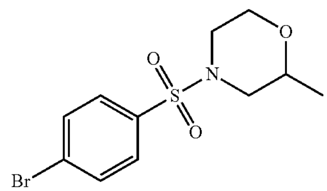 [SMILES: CC1CN(S(=O)(=O)c2ccc(Br)cc2)CCO1] | (R or S)-4-((4-bromophenyl)sulfonyl)-2-methylmorpholine SFC retention time (Chiralpak, AD-H, 20% MeOH in $CO_2$) = 3.85minutes. | LRMS (ESI) calc'd for $C_{11}H_{15}BrNO_3S$ [M + H]+: 321, found 321 |
| I-24A | 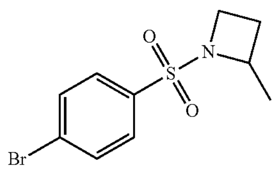 | (R or S)-1-((4-bromophenyl)sulfonyl)-2-methylazetidine SFC retention time (Chiralpak, AD-H, 10% MeOH in $CO_2$) = 3.92 minutes. | LRMS (ESI) calc'd for $C_{10}H_{13}BrNO_2S$ [M + H]+: 291, found 291 |
| I-24B | 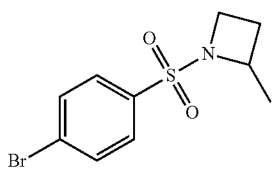 | (R or S)-1-((4-bromophenyl)sulfonyl)-2-methylazetidine SFC retention time (Chiralpak, AD-H, 10% MeOH in $CO_2$) = 4.54 minutes. | LRMS (ESI) calc'd for $C_{10}H_{13}BrNO_2S$ [M + H]+: 291, found 291 |
| I-25 | 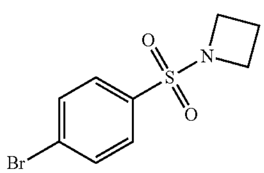 [SMILES: O=S(=O)(c1ccc(Br)cc1)N1CCC1] | 1-((4-bromophenyl)sulfonyl)azetidine | LRMS (ESI) calc'd for $C_9H_{11}BrNO_2S$ [M + H]+: 277, found 277 |
| I-26 | 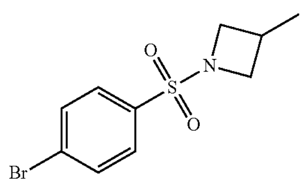 | 1-((4-bromophenyl)sulfonyl)-3-methylazetidine | LRMS (ESI) calc'd for $C_{10}H_{13}BrNO_2S$ [M + H]+: 291, found 291 |
| I-27 | 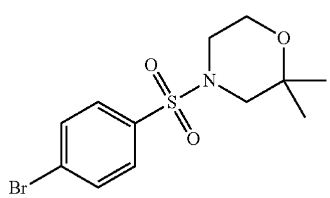 [SMILES: CC1(C)CN(S(=O)(=O)c2ccc(Br)cc2)CCO1] | 4-((4-bromophenyl)sulfonyl)-2,2-dimethylmorpholine | LRMS (ESI) calc'd for $C_{12}H_{17}BrNO_3S$ [M + H]+: 335, found 335 |
| I-28 | 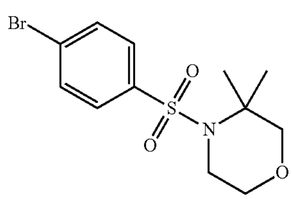 [SMILES: CC1(C)COCCN1S(=O)(=O)c1ccc(Br)cc1] | 4-((4-bromophenyl)sulfonyl)-3,3-dimethylmorpholine | LRMS (ESI) calc'd for $C_{12}H_{17}BrNO_3S$ [M + H]+: 335, found 335 |
| I-29 | 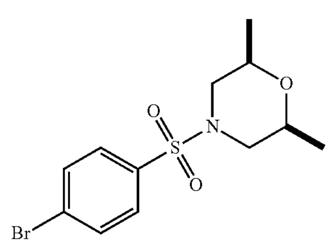 [SMILES: C[C@@H]1CN(S(=O)(=O)c2ccc(Br)cc2)C[C@H](C)O1] | (cis)-4-((4-bromophenyl)sulfonyl)-2,6-dimethylmorpholine | LRMS (ESI) calc'd for $C_{12}H_{17}BrNO_3S$ [M + H]+: 335, found 335 |

TABLE 3-continued

| Intermediate | Structure | Compound Name | NMR/MS |
|---|---|---|---|
| I-30 | 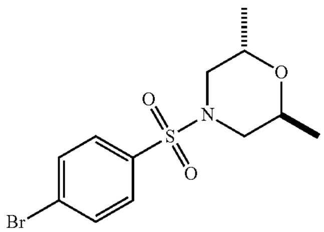 [SMILES: C[C@H]1CN(S(=O)(=O)c2ccc(Br)cc2)C[C@H](C)O1] | (trans)-4-((4-bromophenyl)sulfonyl)-2,6-dimethylmorpholine | LRMS (ESI) calc'd for $C_{12}H_{17}BrNO_3S$ [M + H]+: 335, found 335 |
| I-31 | 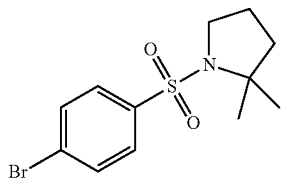 [SMILES: CC1(C)CCCN1S(=O)(=O)c1ccc(Br)cc1] | 1-((4-bromophenyl)sulfonyl)-2,2-dimethylpyrrolidine | LRMS (ESI) calc'd for $C_{12}H_{17}BrNO_2S$ [M + H]+: 319, found 319 |
| I-32 | 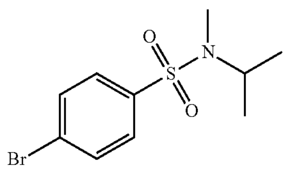 | 4-bromo-N-isopropyl-N-methylbenzenesulfonamide | LRMS (ESI) calc'd for $C_{10}H_{15}BrNO_2S$ [M + H]+: 293, found 293 |
| I-33 | 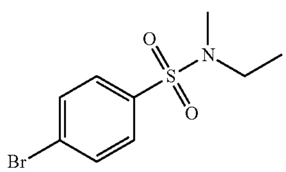 | 4-bromo-N-ethyl-N-methylbenzenesulfonamide | LRMS (ESI) calc'd for $C_9H_{13}BrNO_2S$ [M + H]+: 279, found 279 |
| I-34 | 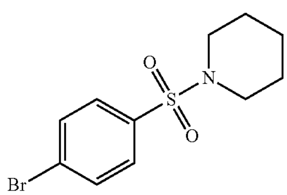 [SMILES: O=S(=O)(c1ccc(Br)cc1)N1CCCCC1] | 1-((4-bromophenyl)sulfonyl)piperidine | LRMS (ESI) calc'd for $C_{11}H_{15}BrNO_2S$ [M + H]+: 305, found 305 |
| I-35 | 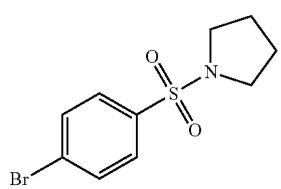 [SMILES: O=S(=O)(c1ccc(Br)cc1)N1CCCC1] | 1-((4-bromophenyl)sulfonyl)pyrrolidine | LRMS (ESI) calc'd for $C_{10}H_{13}BrNO_2S$ [M + H]+: 291, found 291 |
| I-36 | 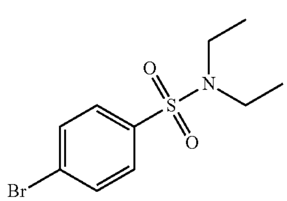 | 4-bromo-N,N-diethylbenzenesulfonamide | LRMS (ESI) calc'd for $C_{10}H_{15}BrNO_2S$ [M + H]+: 293, found 293 |
| I-37 | 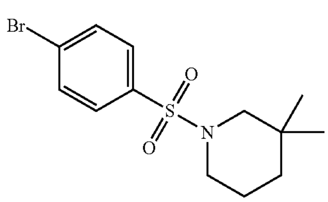 [SMILES: CC1(C)CCCN(S(=O)(=O)c2ccc(Br)cc2)C1] | 1-((4-bromophenyl)sulfonyl)-3,3-dimethylpiperidine | LRMS (ESI) calc'd for $C_{13}H_{19}BrNO_2S$ [M + H]+: 333, found 333 |

TABLE 3-continued

| Intermediate | Structure | Compound Name | NMR/MS |
|---|---|---|---|
| I-38 | 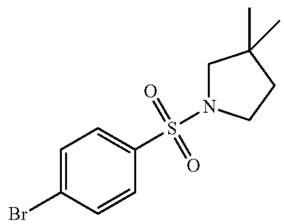 [SMILES: CC1(C)CCN(S(=O)(=O)c2ccc(Br)cc2)C1] | 1-((4-bromophenyl)sulfonyl)-3,3-dimethylpyrrolidine | LRMS (ESI) calc'd for $C_{12}H_{17}BrNO_2S$ [M + H]+: 319, found 319 |
| I-39 | 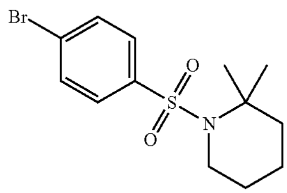 [SMILES: CC1(C)CCCCN1S(=O)(=O)c1ccc(Br)cc1] | 1-((4-bromophenyl)sulfonyl)-2,2-dimethylpiperidine | LRMS (ESI) calc'd for $C_{13}H_{19}BrNO_2S$ [M + H]+: 333, found 333 |
| I-40 | 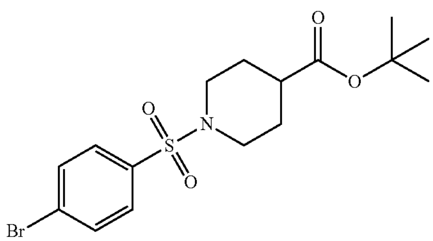 [SMILES: CC(C)(C)OC(=O)C1CCN(S(=O)(=O)c2ccc(Br)cc2)CC1] | tert-butyl 1-((4-bromophenyl)sulfonyl)piperidine-4-carboxylate | LRMS (ESI) calc'd for $C_{16}H_{23}BrNO_4S$ [M + H]+: 405, found 405 |
| I-41 | 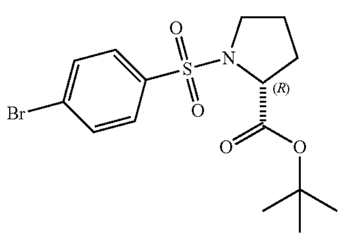 | (R)-tert-butyl 1-((4-bromophenyl)sulfonyl)pyrrolidine-2-carboxylate | LRMS (ESI) calc'd for $C_{15}H_{21}BrNO_4S$ [M + H]+: 391, found 413 |
| I-42 | 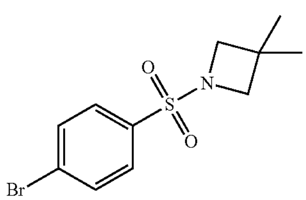 [SMILES: CC1(C)CN(S(=O)(=O)c2ccc(Br)cc2)C1] | 1-((4-bromophenyl)sulfonyl)-3,3-dimethylazetidine | LRMS (ESI) calc'd for $C_{11}H_{15}BrNO_2S$ [M + H]+: 305, found 306 |
| I-43 | 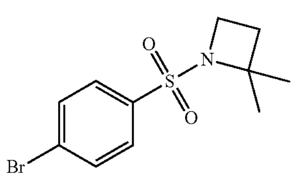 [SMILES: CC1(C)CCN1S(=O)(=O)c1ccc(Br)cc1] | 1-((4-bromophenyl)sulfonyl)-2,2-dimethylazetidine | LRMS (ESI) calc'd for $C_{11}H_{15}BrNO_2S$ [M + H]+: 305, found 306 |
| I-44 | 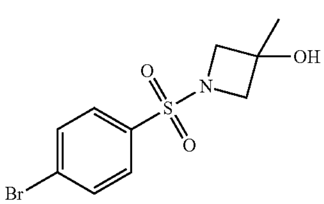 [SMILES: CC1(O)CN(S(=O)(=O)c2ccc(Br)cc2)C1] | 1-((4-bromophenyl)sulfonyl)-3-methylazetidin-3-ol | LRMS (ESI) calc'd for $C_{10}H_{13}BrNO_3S$ [M + H]+: 307, found 308 |

TABLE 3-continued

| Intermediate | Structure | Compound Name | NMR/MS |
|---|---|---|---|
| I-45 | 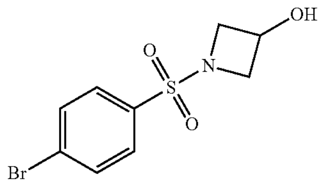 [SMILES: O=S(=O)(c1ccc(Br)cc1)N1CC(O)C1] | 1-((4-bromophenyl)sulfonyl)azetidin-3-ol | LRMS (ESI) calc'd for $C_9H_{11}BrNO_3S$ [M + H]+: 294, found 294 |
| I-46 | 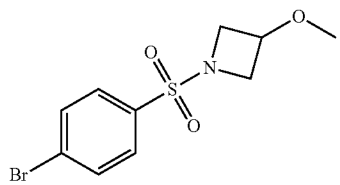 [SMILES: COC1CN(S(=O)(=O)c2ccc(Br)cc2)C1] | 1-((4-bromophenyl)sulfonyl)-3-methoxyazetidine | LRMS (ESI) calc'd for $C_{10}H_{13}BrNO_3S$ [M + H]+: 307, found 308 |
| I-47 | 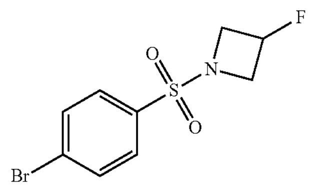 [SMILES: O=S(=O)(c1ccc(Br)cc1)N1CC(F)C1] | 1-((4-bromophenyl)sulfonyl)azetidin-3-ol | LRMS (ESI) calc'd for $C_9H_{10}BrFNO_2S$ [M + H]+: 295, found 295 |

Intermediate I-48

(S)-(4-Bromo-2-methylphenyl)(2-methylpiperidin-1-yl)methanone

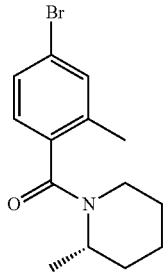

I-48

Step 1: 4-bromo-2-methylbenzoyl chloride

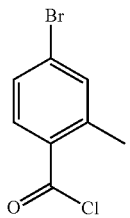

I-48a

4-Bromo-2-methylbenzoic acid (1.40 g, 6.50 mmol) was dissolved in thionyl chloride (20 mL). The mixture was heated at 80° C. for 2 hours and then concentrated in vacuo to afford 1.35 g of crude title acid chloride as a yellow solid.

Step 2: (S)-(4-bromo-2-methylphenyl)(2-methylpiperidin-1-yl)methadone

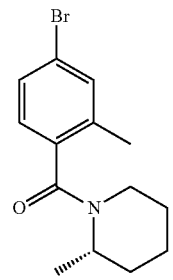

I-48

A 50 mL round-bottom flask was charged with triethylamine (1.43 g, 14.22 mmol) and (S)-2-methylpiperidine (0.52 g, 5.21 mmol) in DCM (20 mL). The resulting solution was cooled in an ice bath. A solution of 4-bromo-2-methylbenzoyl chloride (1.10 g, 4.74 mmol) in DCM (20 mL) was added dropwise at 0-4° C. The cooling bath was removed and the reaction stirred at ambient temperature for 2 hours at which time water (10 mL) was added. The quenched reaction was extracted with EtOAc (2×30 mL), and combined organic layers washed with brine (2×20 mL), dried over anhydrous $Na_2SO_4$ and filtered. The filtrate was concentrated in vacuo and the resulted residue purified by silica gel column chromatography eluting with EtOAc/petroleum ether (1/8) to afford the title amide. LCMS (ESI) calc'd for $C_{14}H_{18}BrNO$ [M+H]+:296, 298 (1:1), found 296, 298 (1:1); $^1H$ NMR (300 MHz, DMSO-$d_6$) δ 7.51-7.41 (m, 2H), 7.12-7.02 (m, 1H), 4.85-4.35 (m, 1H), 3.71-3.45 (m, 0.5H), 3.07-3.04 (m, 1H), 2.90-2.71 (m, 0.5H), 2.23-2.14 (m, 3H), 1.66-1.45 (m, 4H), 1.17-0.95 (m, 5H).

Table 4 discloses intermediates that were prepared in an analogous manner to that for (S)-(4-bromo-2-methylphenyl)(2-methylpiperidin-1-yl)methadone I-48 using appropriate bromobenzoic acids and amines.

TABLE 4

| Intermediate | Structure | Name | ¹H NMR/MS |
|---|---|---|---|
| I-49 | ![structure] | (R)-(4-bromo-2-methylphenyl)(2-methylpiperidin-1-yl)methanone | ¹H NMR (600 MHz, CDCl$_3$) δ 7.77 (d, 1H, J = 8.4 Hz), 7.48 (s, 1H), 7.44 (dd, 1H, J = 8.4, 1.8 Hz), 3.29 (m, 4H), 2.61 (s, 3H), 1.90 (m, 4H). |
| I-50 | ![structure] | (4-bromo-2-methylphenyl)(2-azaspiro[3.3]heptan-2-yl)methanone | LRMS (ESI) calc'd for C$_{14}$H$_{17}$BrNO [M + H]$^+$: 296, 298 (1:1), found 296, 298 (1:1). ¹H NMR (400 MHz, CDCl$_3$) δ 7.42 (d, J = 1.2 Hz, 1H), 7.42-7.34 (m, 1H), 7.12 (d, J = 8.4 Hz, 1H), 4.87-4.77 (m, 4H), 4.34 (s, 2H), 4.09 (s, 2H), 2.39 (d, J = 7.6 Hz, 3H). |

Intermediate I-51 tert-butyl 2-(4-bromo-N-methylphenylsulfonamido)-2-methylpropanoate

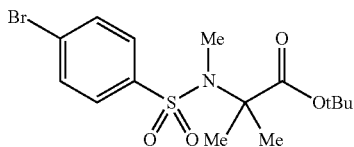

I-51

Step 1: tert-butyl 2-(4-bromophenylsulfonamido)-2-methylpropanoate

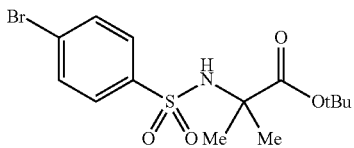

I-51a

An oven dried round bottom flask with magnetic sir bar under an atmosphere of N$_2$ was charged with 4-bromobenzene-1-sulfonyl chloride (1 g, 4 mmol), DCM (9 mL), and triethylamine (1.3 mL, 9.4 mmol). The solution was cooled to 0° C., and tert-butyl 2-amino-2-methylpropanoate (0.5 g, 3.1 mmol) was added. The reaction mixture stirred and warmed to rt overnight. The reaction was quenched with sat. NH$_4$Cl and diluted with DCM (50 mL). The organic layer was washed with brine (20 mL), dried over Na$_2$SO$_4$, filtered through celite, and concentrated in vacuo. The crude tert-butyl 2-(4-bromophenylsulfonamido)-2-methylpropanoate I-51a was of sufficient purity to carry on to the next step. ¹H NMR (CDCl$_3$, 500 MHz): δ7.75-7.73 (m, 2H), 7.62-7.60 (m, 2H), 5.40 (bs, 1H), 1.44 (s, 9H), 1.40 (s, 6H).

Step 2: tert-butyl 2-(4-bromo-N-methylphenylsulfonamido)-2-methylpropanoate

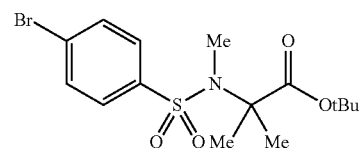

I-51

An oven dried round bottom flask with magnetic sir bar under an atmosphere of N2 was charged with tert-butyl 2-(4-bromophenylsulfonamido)-2-methylpropanoate I-51a (815 mg, 2.2 mmol), and DMF (6.5 mL). The solution was cooled to 0° C., and sodium hydride (129 mg, 3.2 mmol) was added. The reaction mixture was stirred for 30 min followed by the addition of methyl iodide (0.4 mL, 6.5 mmol). The reaction was warmed to rt over 1-2 h. The quenched with sat. NH$_4$Cl (20 mL) and diluted with Et$_2$O (50 mL). The organic layer was washed with brine (20 mL), dried over Na$_2$SO$_4$, filtered through celite, and concentrated in vacuo. The crude tert-butyl 2-(4-bromo-N-methylphenylsulfonamido)-2-methylpropanoate I-51 was purified by column chromatography on silica gel (hexanes/EtOAc gradient). 1H NMR (CDCl$_3$, 500 MHz): δ7.87-7.85 (m, 2H), 7.64-7.62 (m, 2H), 2.72 (s, 3H), 1.48 (s, 15H).

Intermediate I-52 ethyl 2-(4-bromo-N-methylphenylsulfonamido)-2-methylpropanoate

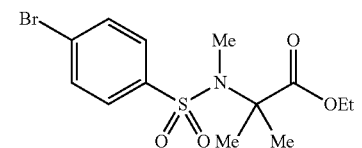

I-52

An oven dried round bottom flask with magnetic sir bar under an atmosphere of N$_2$ was charged with 4-bromobenzene-1-sulfonyl chloride (1.1 g, 4.3 mmol), DCM (9 mL), and triethylamine (1.4 mL, 10.3 mmol). The solution was cooled to 0° C., and ethyl 2-methyl-2-(methylamino)propanoate (0.5 g, 3.4 mmol) was added. The reaction mixture stirred and warmed to rt overnight. The reaction was quenched with sat. NH₄Cl and diluted with DCM (50 mL). The organic layer was washed with brine (20 mL), dried over Na₂SO₄, filtered through celite, and concentrated in vacuo. The residue was purified by column chromatography on silica gel (hexanes/EtOAc gradient) to yield ethyl 2-(4-bromo-N-methylphenylsulfonamido)-2-methylpropanoate I-52. ¹H NMR (CDCl₃, 500 MHz): δ7.86 (d, J=8.20 Hz, 2H), 7.64 (d, J=8.15 Hz, 2H), 4.25 (q, J=7.07 Hz, 2H), 2.72 (s, 3H), 1.58 (s, 6H), 1.30-1.26 (m, 3H).

Intermediate I-53 tert-butyl 2-(5-bromo-1-oxoisoindolin-2-yl)-2-methylpropanoate

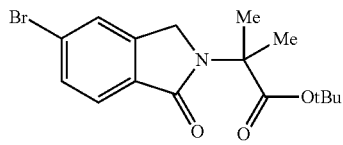

An oven dried round bottom flask with magnetic sir bar under an atmosphere of N2 was charged with methyl 4-bromo-2-(bromomethyl)benzoate (1 g, 3.3 mmol), tBuOH (15.5 mL), triethylamine (0.7 mL, 4.9 mmol), and tert-butyl 2-amino-2-methylpropanoate (775 mg, 4.9 mmol). The solution was heated to reflux for 24 h. The reaction mixture was concentrated in vacuo, and the residue was purified by column chromatography on silica gel (hexanes/EtOAc gradient) to yield tert-butyl 2-(5-bromo-1-oxoisoindolin-2-yl)-2-methylpropanoate I-53. ¹H NMR (CDCl₃, 500 MHz): δ7.68 (d, J=7.95 Hz, 1H), 7.59-7.57 (m, 2H), 4.46 (s, 2H), 1.63 (s, 6H), 1.45 (s, 9H).

Intermediate I-54 tert-butyl 4-(5-bromo-1-oxoisoindolin-2-yl)cyclohexanecarboxylate

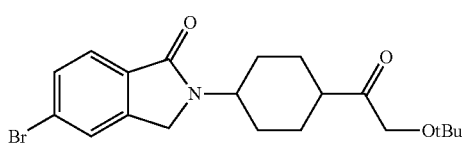

An oven dried round bottom flask with magnetic sir bar under an atmosphere of N₂ was charged with methyl 4-bromo-2-(bromomethyl)benzoate (500 mg, 1.6 mmol), THF (4.8 mL), triethylamine (0.6 mL, 4.1 mmol), and tert-butyl 4-aminocyclohexanecarboxylate (647 mg, 3.3 mmol). The reaction mixture was heated to reflux for 12-16 h, and was concentrated in vacuo. The crude oil was purified by column chromatography on silica gel eluting with Hexanes/EtOAc gradient to yield tert-butyl 4-(5-bromo-1-oxoisoindolin-2-yl)cyclohexanecarboxylate I-54. ¹H NMR (500 MHz, CDCl₃): δ7.70 (d, J=7.92 Hz, 1H), 7.62-7.58 (m, 2H), 4.33-4.29 (m, 2H), 4.24 (m, 1H), 2.60 (m, 1H), 1.74-1.66 (m, 3H), 1.60-1.52 (m, 5H).

1-Bromo-4-((1-methylcyclopropyl)sulfonyl)benzene

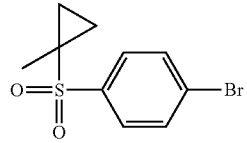

To 1-bromo-4-(cyclopropanesulfonyl)benzene (100 mg, 0.383 mmol) in THF (1.5 mL) at −78° C., was added TMEDA (69.4 μL, 0.460 mmol) followed by BuLi (239 μL, 0.383 mmol) and the reaction was stirred at this temperature for 45 minutes, then iodomethane (239 μl, 3.83 mmol) was added and the reaction was stirred to room temperature overnight. The reaction was concentrated and purified by loading onto silica directly and eluting with 5-40% EtOAc/hexanes afforded 1-Bromo-4-((1-methylcyclopropyl)sulfonyl)benzene. ¹H NMR (600 MHz, CDCl₃) δ7.74 (d, 2H, J=8.4 Hz), 7.71 (d, 2H, J=8.4 Hz), 1.60 (m, 2H), 1.35 (s, 3H), 0.84 (m, 2H).

Intermediate I-56

4-Bromo-N,N,2-trimethylbenzenesulfonamide

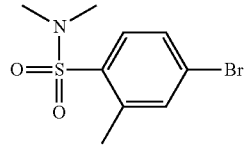

To a stirred solution of 4-bromo-2-methylbenzene-1-sulfonyl chloride (0.300 g, 1.11 mmol) in DCM (2.0 mL) was added TEA (0.310 mL, 2.23 mmol) followed by dimethylamine (1.11 ml, 2.23 mmol, 2M in THF). The resulting solution was stirred at room temperature for 3 hours, then the reaction was concentrated in vacuo and the reaction was loaded directly onto silica, and purified by column chromatography on silica gel eluting with 5-40% EtOAc/Hexanes. 1H NMR (600 MHz, CDCl₃) δ7.74 (d, 1H, J=7.8 Hz), 7.49 (s, 1H), 7.46 (dm, 1H, J=8.4 Hz), 2.79 (s, 6H), 2.60 (s, 3H).

Intermediate I-57

1-(4-Bromophenyl)-5,5-dimethyl-2-oxabicyclo[2.2.2]octan-3-one

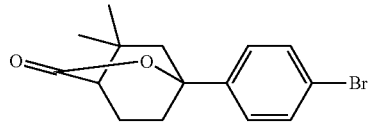

To 1-bromo-4-iodobenzene (600 mg, 2.12 mmol) in THF (7.1 mL) at −78° C. was added (dropwise) n-BuLi (1.46 mL, 2.33 mmol, 1.60 M in hexanes) and the reaction was stirred at −78° C. for 2 hours before a solution of methyl 2,2-dimethyl-4-oxocyclohexanecarboxylate (430 mg, 2.33 mmol) in THF (1.5 mL) was added dropwise and the reaction was stirred to room temperature overnight. The reaction was then quenched by pouring into a separatory funnel containing water and was extracted with ethyl acetate (3×50 mL). The organic layers were combined and dried over $Na_2SO_4$, filtered, and concentrated in vacuo. The crude product was then purified by silica chromatography, eluting with 0-50% EtOAc/hexane. The product was collected and concentrated to afford the desired product. LRMS (ESI) calc'd for $C_{15}H_{18}BrO_2$ [M+H]$^+$: 309, found 309.

Intermediate I-58

N-(1-(4-Bromophenyl)-2,2,2-trifluoroethyl)-2-methylpropan-2-amine

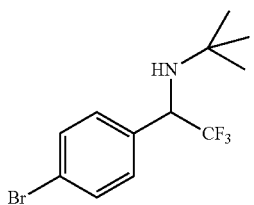

I-58

Step 1: 1-(4-Bromophenyl)-2,2,2-trifluoroethanol

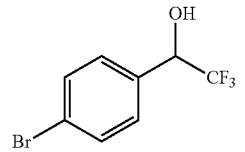

I-58a 1-(4-Bromophenyl)-2,2,2-trifluoroethanone (1.73 g, 6.84 mmol) was dissolved in THF (3.4 mL) and treated with sodium borohydride (0.285 g, 7.52 mmol) at 0° C. The reaction was then warmed to room temperature and stirred overnight. The reaction mixture was then diluted with DCM and washed with water and brine. The combined organic layers were dried over $Na_2SO_4$, and the filtrate was concentrated in vacuo. The residue was purified by silica chromatography, eluting with 5-30% EtOAc in hexanes and the desired fractions were concentrated in vacuo to afford 1-(4-Bromophenyl)-2,2,2-trifluoroethanol. 1H NMR (500 MHz, $CDCl_3$) δ7.56 (d, J=8.5 Hz, 2H), 7.36 (d, J=8.5 Hz, 2H), 5.06-4.96 (m, 1H), 2.63 (d, J=4.5 Hz, 1H).

Step 2: 1-(4-Bromophenyl)-2,2,2-trifluoroethyl trifluoromethanesulfonate

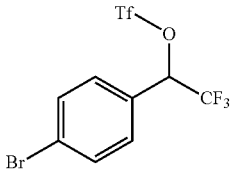

I-58b

A solution of 1-(4-bromophenyl)-2,2,2-trifluoroethanol (1.5 g, 5.9 mmol) and 2,6-lutidine (1.10 mL, 9.41 mmol) in DCE (12 mL) was cooled to −15° C. and triflic anhydride (8.82 mL, 8.82 mmol, 1.0 M DCM) was added dropwise. The reaction stirred between −15° C. and rt for 1 hr. The reaction mixture was diluted with DCM and washed with water, HCl (1 N), and brine. The combined organic layers were dried over $Na_2SO_4$, filtered, and the filtrate was concentrated in vacuo to give 1-(4-Bromophenyl)-2,2,2-trifluoroethyl trifluoromethanesulfonate. $^1$H NMR (500 MHz, $CDCl_3$) δ7.64 (d, J=8.3 Hz, 2H), 7.37 (d, J=8.3 Hz, 2H), 5.85-5.74 (m, 1H).

Step 3: N-(1-(4-Bromophenyl)-2,2,2-trifluoroethyl)-2-methylpropan-2-amine 1-(4-Bromophenyl)-2,2,2-trifluoroethyl trifluoromethanesulfonate (7.59 g, 19.6 mmol) was dissolved in cyclohexane (70 mL) and 2-methylpropan-2-amine (6.23 mL, 58.8 mmol), DMAP (0.240 g, 1.96 mmol), and ground, dried potassium carbonate (5.42 g, 39.2 mmol) (dried over vacuum at 60° C. for one hour) was added. The reaction mixture was heated to 75° C. and stirred for 48 hours. The reaction mixture was diluted with DCM and washed with water. The combined organic layers were dried over $Na_2SO_4$, filtered, and the filtrate was concentrated in vacuo. The residue was purified by silica chromatography, eluting with 2-20% EtOAc in hexanes and the desired fractions were concentrated in vacuo to afford N-(1-(4-Bromophenyl)-2,2,2-trifluoroethyl)-2-methylpropan-2-amine. LRMS (ESI) calc'd for $C_{12}H_{16}BrF_3N$ [M+H]$^+$: 310, found 310.

Following analogous methodology to that outlined for Intermediate I-58 above, the following intermediates in Table 5 were synthesized. In select cases, the general procedure was modified by not using DMAP and/or the crude product was used as is, and/or to alternatively utilize 2.0-3.0 equivalents of amine and/or 1.5-3.0 equivalents of ground, dried potassium carbonate.

TABLE 5

| Intermediate | Structure | Name | LCMS |
| --- | --- | --- | --- |
| I-59 | 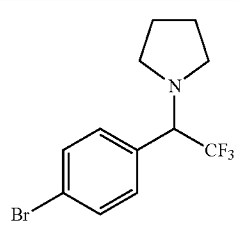 [SMILES: FC(F)(F)C(c1ccc(Br)cc1)N1CCCC1] | 1-(1-(4-bromophenyl)-2,2,2-trifluoroethyl)pyrrolidine | LRMS (ESI) calc'd for $C_{12}H_{14}BrF_3N$ [M + H]$^+$: 308, found 308 |

TABLE 5-continued

| Intermediate | Structure | Name | LCMS |
|---|---|---|---|
| I-60 | 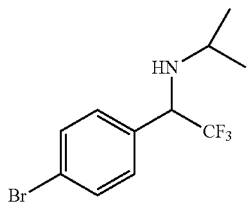 [SMILES: CC(C)NC(c1ccc(Br)cc1)C(F)(F)F] | N-(1-(4-bromophenyl)2,2,2-trifluoroethyl)propan-2-amine | LRMS (ESI) calc'd for $C_{11}H_{14}BrF_3N$ [M + H]$^+$: 296, found 296 |
| I-61 | 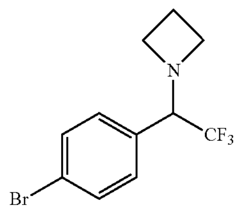 [SMILES: FC(F)(F)C(c1ccc(Br)cc1)N1CCC1] | 1-(1-(4-bromophenyl)-2,2,2-trifluoroethyl)azetidine | LRMS (ESI) calc'd for $C_{11}H_{12}BrF_3N$ [M + H]$^+$: 294, found 294 |
| I-62 | 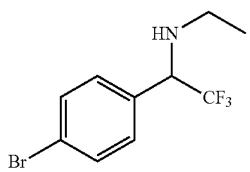 | 1-(4-bromophenyl)-N-ethyl-2,2,2-trifluoroethanamine | LRMS (ESI) calc'd for $C_{10}H_{12}BrF_3N$ [M + H]$^+$: 282, found 282 |
| I-63 | 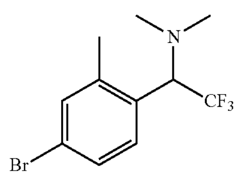 [SMILES: Cc1cc(Br)ccc1C(N(C)C)C(F)(F)F] | 1-(4-bromo-2-methylphenyl)-2,2,2-trifluoro-N,N-dimethylethanamine | LRMS (ESI) calc'd for $C_{11}H_{14}BrF_3N$ [M + H]$^+$: 296, found 296. |
| I-64 | 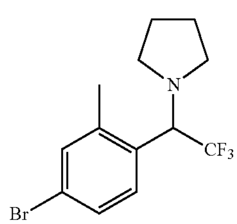 [SMILES: Cc1cc(Br)ccc1C(N1CCCC1)C(F)(F)F] | 1-(1-(4-bromo-2-methylphenyl)-2,2,2-trifluoroethyl)pyrrolidine | $^1$H NMR (600 MHz, CDCl$_3$) δ 7.77 (d, 1H, J = 8.4 Hz), 7.48 (s, 1H), 7.44 (dd, 1H, J = 8.4, 1.8 Hz), 3.29 (m, 4H), 2.61 (s, 3H), 1.90 (m, 4H). |

Intermediate I-65

Ethyl 3-(4-bromophenyl)-4,4,4-trifluoro-3-hydroxy-2,2-dimethylbutanoate

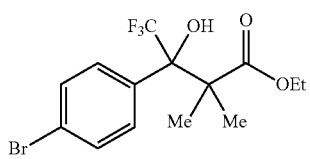

I-65

An oven dried round bottom flask with magnetic stir bar under an atmosphere of N$_2$ was charged with ethyl isobutyrate (689 mg, 5.9 mmol) and THF (2.5 ml). The solution was cooled to −78° C., and lithium diisopropylamide (3.0 mL, 5.9 mmol, 2.0 M in THF) was added. The reaction mixture stirred for 30 min followed by the addition of 1-(4-bromophenyl)-2,2,2-trifluoroethanone (0.5 g, 2.0 mmol). The reaction mixture was warmed to rt over 1-2 h, and was quenched by the addition of saturated aqueous NH$_4$Cl (10 mL). The resulting mixture was extracted with EtOAc (3×10 mL), and the combined organic layers were concentrated in vacuo to afford a residue that was purified by column chromatography on silica gel (hexanes/EtOAc gradient) to yield ethyl 3-(4-bromophenyl)-4,4,4-trifluoro-3-hydroxy-2,2-dimethylbutanoate I-65. LRMS (ESI) calc'd for $C_{14}H_{17}BrF_3O_3$[M+H]$^+$: 370, found 370. $^1$H NMR (CDCl$_3$, 500 MHz): δ7.60 (d, J=8.2 Hz, 2H), 7.53 (d, J=8.5 Hz, 2H), 4.31-4.27 (m, 2H), 1.38 (d, J=3.5 Hz, 3H), 1.30 (s, 6H).

Intermediate I-66

Isopropyl 3-(4-bromophenyl)-4,4,4-trifluoro-3-hydroxy-2,2-dimethylbutanoate

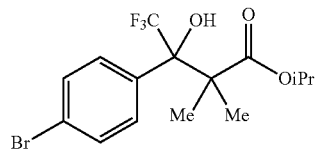

I-66

An oven dried round bottom flask with magnetic sir bar under an atmosphere of $N_2$ was charged with isopropyl isobutyrate (772 mg, 5.9 mmol) and THF (2.5 ml). The solution was cooled to −78° C., and lithium diisopropylamide (3.0 mL, 5.9 mmol, 2.0 M in THF) was added. The reaction mixture stirred for 30 min followed by the addition of 1-(4-bromophenyl) -2,2,2-trifluoroethanone (0.5 g, 2.0 mmol). The reaction mixture was warmed to rt over 1-2 h, and was quenched by the addition of saturated aqueous $NH_4Cl$ (10 mL). The resulting mixture was extracted with EtOAc (3×10 mL), and the combined organic layers were concentrated in vacuo to afford a residue that was purified by column chromatography on silica gel (hexanes/EtOAc gradient) to yield isopropyl 3-(4-bromophenyl)-4,4,4-trifluoro-3-hydroxy-2,2-dimethylbutanoate I-66. $^1$H NMR ($CDCl_3$, 500 MHz): δ7.60 (d, J=8.2 Hz, 2H), 7.53 (d, J=8.5 Hz, 2H), 4.31 (m, 1H), 1.30 (s, 6H), 1.27 (d, J=1.2 Hz, 3H), 1.16 (d, J=1.3 Hz, 3H).

Intermediate I-67

4-(4-Bromo-2-chlorophenyl)-1-methyl-1H-pyrazole

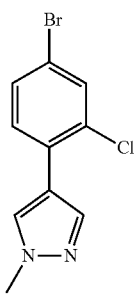

I-67

4-Bromo-2-chloro-1-iodobenzene (500 mg, 1.58 mmol), 1-methyl-4-(4,4,5,5-tetramethyl-1,3,2-dioxaborolan-2-yl)-1H-pyrazole (295 mg, 1.41 mmol), $PdCl_2(dppf)$ (115 mg, 0.158 mmol), and potassium phosphate tribasic (1.03 g, 4.73 mmol) were combined in a 20 mL microwave vial and dissolved in dioxane (10 mL) and water (1.0 mL). The vial was sealed and flushed with argon. The reaction was stirred at 90° C. for 2 hours. The vial was then cooled to room temperature and diluted with ethyl acetate. The organic layer was washed with water and brine and then dried using magnesium sulfate. The solution was then filtered and concentrated in vacuo. The crude material was purified by silica chromatography, eluting with 10-50% EtOAc in hexanes and the desired fractions were concentrated in vacuo to give 4-(4-bromo-2-chlorophenyl)-1-methyl-1H-pyrazole. LRMS (ESI) calc'd for $C_{10}H_9BrClN_2$ [M+H]$^+$: 273, found 273.

Intermediate I-68

4-(4-Bromophenyl)-1-(2-methoxyethyl)-1H-pyrazole

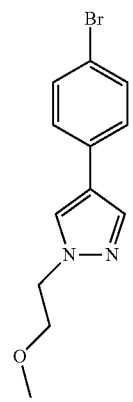

I-68

4-(4-Bromophenyl)pyrazole (150 mg, 0.672 mmol) and cesium carbonate (876 mg, 2.69 mmol) were combined in a 20 mL vial and dissolved in DMF (1.3 mL). 2-bromoethyl methyl ether (0.253 mL, 2.69 mmol) was then added. The reaction was stirred overnight at 60° C. The reaction was then diluted with ethyl acetate and washed with water (×2). The organic solution was dried with $MgSO_4$ and concentrated in vacuo to afford 4-(4-bromophenyl)-1-(2-methoxyethyl)-1H-pyrazole which was carried onto the next step without further purification. LRMS (ESI) calc'd for $C_{12}H_{14}BrN_2O$ [M+H]$^+$: 283, found 283.

Intermediate I-69

Isopropyl 6-bromoquinoline-2-carboxylate

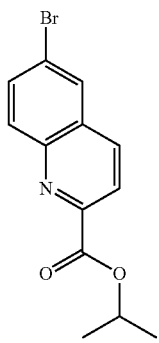

I-69

6-Bromoquinoline-2-carboxylic acid (40 mg, 0.16 mmol) and HATU (121 mg, 0.317 mmol) were dissolved in DMF (0.5 mL) in a 4 mL vial and allowed to stir at room temperature for 5 minutes. 2-Propanol (24 μL, 0.31 mmol) and N,N-diisopropylethylamine (83 μL, 0.48 mmol) in DMF (0.5 mL) was then added to the reaction. The reaction mixture was stirred at room temperature for 1 hour. The reaction was then diluted with ethyl acetate and washed with copious amounts of water. The organic layer was then dried using MgSO$_4$, filtered, and concentrated in vacuo to give isopropyl 6-bromoquinoline-2-carboxylate which was carried onto the next step without further purification. LRMS (ESI) calc'd for C$_{13}$H$_{13}$BrNO$_2$ [M+H]$^+$: 294, found 294.

Intermediate I-70

3-(4-(4-Bromo-2-methylphenyl)-1H-pyrazol-1-yl)propanenitrile

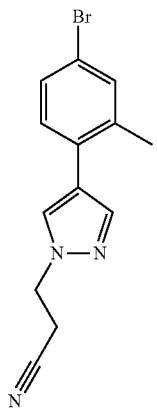

I-70

5-Bromo-2-iodotoluene (0.077 mL, 0.539 mmol), 3-(4-(4,4,5,5-tetramethyl-1,3,2-dioxaborolan-2-yl)-1H-pyrazol-1-yl)propanenitrile (120 mg, 0.485 mmol), PdCl$_2$(dppf) (39.4 mg, 0.054 mmol), and potassium phosphate tribasic (343 mg, 1.62 mmol) were combined in a 20 mL microwave vial and dissolved in dioxane (2.5 mL) and water (0.25 mL). The vial was sealed and flushed with argon. The reaction was stirred at 90° C. for 2 hours. The vial was then cooled to room temperature and diluted with ethyl acetate. The organic layer was washed with water and brine and then dried using magnesium sulfate. The solution was then filtered and concentrated in vacuo. The crude material was purified by silica chromatography, eluting with 10-50% EtOAc in hexanes. The desired fractions were concentrated in vacuo to give 3-(4-(4-bromo-2-methylphenyl)-1H-pyrazol-1-yl)propanenitrile. LRMS (ESI) calc'd for C$_{13}$H$_{13}$BrN$_3$ [M+H]$^+$: 290, found 290.

Intermediate I-71

(4-bromo-2-methylphenyl)(1,1-dioxidothiomorpholino)methanone

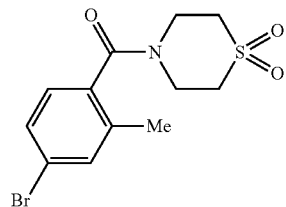

I-71

An oven dried round bottom flask with magnetic sir bar under an atmosphere of N2 was charged with 4-bromo-2-methylbenzoic acid (300 mg, 1.4 mmol), DMF (3.9 mL), (1-[Bis(dimethylamino)methylene]-1H-1,2,3-triazolo[4,5-b]pyridinium 3-oxid hexafluorophosphate; HATU) (663 mg, 1.7 mmol), Huenig's base (0.73 mL, 4.2 mmol), and thiomorpholine-1,1-dioxide (236 mg, 1.7 mmol). The resulting reaction mixture was stirred for 12-16 h, and was concentrated in vacuo. The crude oil was purified by column chromatography on silica gel eluting with Hexanes/EtOAc gradient to yield (4-bromo-2-methylphenyl)(1,1-dioxidothiomorpholino)methanone I-71. $^1$H NMR (500 MHz, CDCl3): δ7.44-7.39 (m, 2H), 7.06 (d, J=8.09 Hz, 1H), 4.46-4.42 (m, 2H), 3.77-3.73 (m, 2H), 3.19-3.15 (m, 2H), 2.93-2.89 (m, 2H), 2.30 (s, 3H).

The following compounds outlined in Table 6 were prepared by analogy using the general procedure outlined above for Intermediate I-71 above.

TABLE 6

| Intermediate | Structure | Name | $^1$H NMR/MS |
|---|---|---|---|
| I-72 | ![structure] | (4-bromo-2-methylphenyl)(2-ethylpiperidin-1-yl)methanone | LRMS (ESI) calc'd for C$_{14}$H$_{19}$BrNO$_2$ [M + H]$^+$: 313, found 313 |
| I-73 | ![structure] | (4-bromo-2-methylphenyl)(2-isopropylpiperidin-1-yl)methanone | LRMS (ESI) calc'd for C$_{15}$H$_{21}$BrNO$_2$ [M + H]$^+$: 327, found 327 |

Intermediate I-74

(2R,5S)-4-(6-bromoquinolin-2-yl)-2,5-dimethylmorpholine

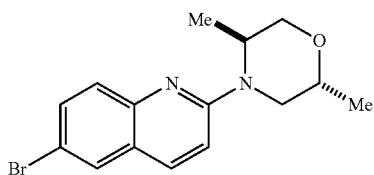

I-74

An oven dried microwave vial with magnetic sir bar under an atmosphere of $N_2$ was charged with 6-bromo-2-chloroquinoline (200 mg, 0.8 mmol), ACN (0.4 mL), triethylamine (0.8 mL, 5.8 mmol), and (2R,5S)-dimethylmorpholine (475 mg, 4.1 mmol). The reaction mixture was heated to 90° C. for 12-16 h, and was concentrated in vacuo. The crude oil was purified by column chromatography on silica gel eluting with Hexanes/EtOAc gradient to yield (2R,5S)-4-(6-bromo-quinolin-2-yl)-2,5-dimethylmorpholine I-74. $^1$H NMR (500 MHz, CDCl$_3$): δ7.81 (d, J=9.19 Hz, 1H), 7.74 (s, 1H), 7.60-7.55 (m, 2H), 6.94 (d, J=9.22 Hz, 1H), 4.39 (m, 1H), 4.28 (m, 1H), 3.89-3.85 (m, 2H), 3.66 (m, 1H), 2.90 (m, 1H), 1.34-1.29 (m, 6H).

Intermediate I-75

(2S,5S)-4-(6-bromoquinolin-2-yl)-2,5-dimethylmorpholine

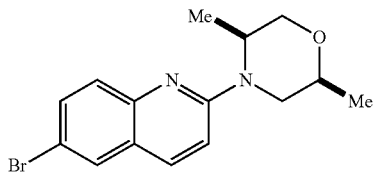

I-75

An oven dried microwave vial with magnetic sir bar under an atmosphere of $N_2$ was charged with 6-bromo-2-chloroquinoline (200 mg, 0.8 mmol), ACN (0.4 mL), triethylamine (0.8 mL, 5.8 mmol), and (2S,5S)-2,5-dimethylmorpholine (475 mg, 4.1 mmol). The reaction mixture was heated to 90° C. for 12-16 h, and was concentrated in vacuo. The crude oil was purified by column chromatography on silica gel eluting with Hexanes/EtOAc gradient to yield (2S,5S)-4-(6-bromo-quinolin-2-yl)-2,5-dimethylmorpholine I-75. $^1$H NMR (500 MHz, CDCl$_3$): δ7.81 (d, J=9.19 Hz, 1H), 7.74 (s, 1H), 7.60-7.55 (m, 2H), 6.94 (d, J=9.22 Hz, 1H), 4.39 (m, 1H), 4.28 (m, 1H), 3.89-3.85 (m, 2H), 3.66 (m, 1H), 2.90 (m, 1H), 1.34-1.29 (m, 6H).

Intermediate I-76

(2R,5R)-4-(6-bromoquinolin-2-yl)-2,5-dimethylmorpholine

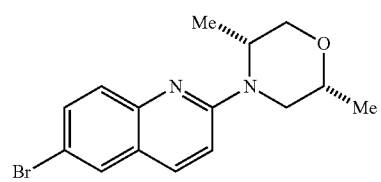

I-76

An oven dried microwave vial with magnetic sir bar under an atmosphere of $N_2$ was charged with 6-bromo-2-chloroquinoline (200 mg, 0.8 mmol), ACN (0.4 mL), triethylamine (0.8 mL, 5.8 mmol), and (2R,5R)-2,5-dimethylmorpholine (475 mg, 4.1 mmol). The reaction mixture was heated to 90° C. for 12-16 h, and was concentrated in vacuo. The crude oil was purified by column chromatography on silica gel eluting with Hexanes/EtOAc gradient to yield (2R,5R)-4-(6-bromo-quinolin-2-yl)-2,5-dimethylmorpholine I-76. $^1$H NMR (500 MHz, CDCl$_3$): δ7.81 (d, J=9.19 Hz, 1H), 7.74 (s, 1H), 7.60-7.55 (m, 2H), 6.94 (d, J=9.22 Hz, 1H), 4.39 (m, 1H), 4.28 (m, 1H), 3.89-3.85 (m, 2H), 3.66 (m, 1H), 2.90 (m, 1H), 1.34-1.29 (m, 6H).

Intermediate I-77 and I-78

2-(1-(4-Bromophenyl)ethyl)-2H-1,2,3-triazole I-77 and 1-(1-(4-bromophenyl)ethyl)-4,5-dihydro-1H-1,2,3-triazole I-78

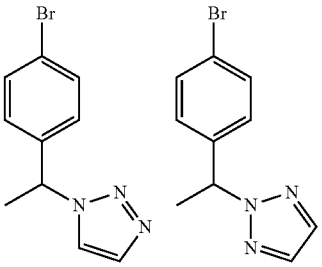

I-77 and I-78

Step 1: 1-bromo-4-(1-bromoethyl)benzene

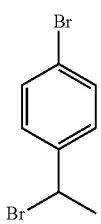

I-77a

To a 100 mL 3-necked round-bottom flask were placed 1-bromo-4-ethylbenzene (5.10 g, 27.6 mmol, 1.0 equiv), N-bromosuccinimide (5.77 g, 32.4 mmol, 1.2 equiv) and azo-bis-isobutyronitrile (0.89 g, 5.4 mmol, 0.2 equiv) in chloroform (100 mL). The mixture was heated at reflux for 3 hours and cooled to ambient temperature. Then water (100 mL) was added and the organic layer washed with brine, dried over anhydrous sodium sulfate and filtered. The filtrate was concentrated under reduced pressure and the residue purified by silica gel column chromatography eluting with $C_{10}H_{11}BrN_3$ [M-69]+: 183, 185 (1:1), found 183, 185 (1:1); $^1$H NMR (300 MHz, $CDCl_3$) δ7.72 (s, 1H), 7.49 (d, J=8.4 Hz, 2H), 7.44 (s, 1H), 7.14 (d, J=8.4 Hz, 2H), 5.81 (q, J=7.2 Hz, 1H), 1.98 (d, J=7.2 Hz, 3H).

Table 7 discloses the compound prepared in an analogous procedure to that for 1-(1-(4-bromophenyl)ethyl)-4,5-dihydro-1H-1,2,3-triazole using 1-bromo-4-(1-bromo-2-methylpropyl)benzene.

TABLE 7

| Intermediate | Structure | Compound Name | MS/$^1$H NMR |
|---|---|---|---|
| I-79 | | 2-(1-(4-bromophenyl)-2-methylpropyl)-2H-1,2,3-triazole | LCMS (ESI) calc'd for $C_{12}H_{14}BrN_3$ [M + 1]$^+$: 280, 282 (1:1), found 280, 282 (1:1); $^1$H NMR (300 MHz, $CDCl_3$) δ 7.76 (s, 1H), 7.71 (s, 1H), 7.54 (d, J = 8.4 Hz, 2H), 7.33 (d, J = 8.4 Hz, 2H), 5.07 (d, J = 10.8 Hz, 1H), 2.81 (m, 1H), 0.92-0.86 (m, 6H). | ethyl acetate/petroleum ether (1:20) to afford the title compound. $^1$H NMR (300 MHz, $CDCl_3$) δ7.44 (d, J=8.4 Hz, 2H), 7.31 (d, J=8.4 Hz, 2H), 5.15 (q, J=6.9 Hz, 1H), 2.01 (d, J=6.9 Hz, 3H)

Step 2: 2-(1-(4-bromophenyl)ethyl)-2H-1,2,3-triazole and 1-(1-(4-Bromophenyl)ethyl)-4,5-dihydro-1H-1,2,3-triazole

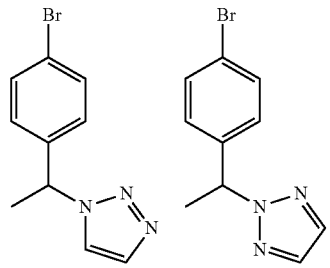

In a 100 mL 3-necked round-bottom flask, 1-bromo-4-(1-bromoethyl)benzene (4.60 g, 17.5 mmol) was combined with N,N-dimethylformamide (60 mL). 1H-1,2,3-Triazole (1.45 g, 21 mmol) and potassium carbonate (6.04 g, 43.75 mmol) were added. The solution was heated at 80° C. for 5 hours at which time it was poured in water (100 mL). The resulting mixture was extracted with ethyl acetate (3×60 mL) and the organic layers combined, dried over anhydrous sodium sulfate and filtered. The filtrate was concentrated under reduced pressure; the resulting solid was triturated with ethyl acetate/petroleum ether (1/3, 10 mL) and filtered to give the two title products. 2-(1-(4-Bromophenyl)ethyl)-2H-1,2,3-triazole, LCMS (ESI) calc'd for $C_{10}H_{11}BrN_3$ [M+H]$^+$: 252, 254 (1:1), found 252, 254 (1:1) and $C_{10}H_{11}BrN_3$ [M -69]+: 183, 185 (1:1), found 183, 185 (1:1); $^1$H NMR (300 MHz, $CDCl_3$) δ7.62 (s, 2H), 7.44 (d, J=8.4 Hz, 2H), 7.16 (d, J=8.4 Hz, 2H), 5.82 (q, J=7.2 Hz, 1H), 1.96 (d, J=7.2 Hz, 3H). 1-(1-(4-Bromophenyl)ethyl)-4,5-dihydro-1H-1,2,3-triazole, LCMS (ESI) calc'd for $C_{10}H_{11}BrN_3$ [M+H]$^+$: 252, 254 (1:1), found 252, 254 (1:1) and Intermediate I-80 and I-81

1-(2-(4-Bromo-2-methylphenyl)propan-2-yl)-1H-1,2,3-triazole and 2-(2-(4-bromo-2-methylphenyl)propan-2-yl)-2H-1,2,3-triazole

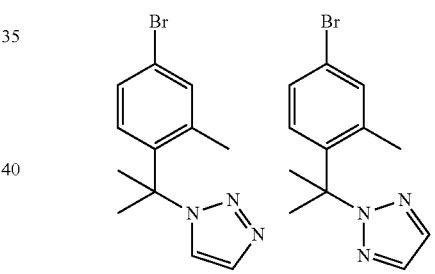

I-80 and I-81

Step 1: 2-(4-bromo-2-methylphenyl)propan-2-ol

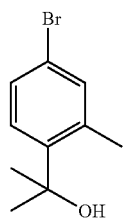

I-80a

In a 3-necked round bottom flask, methyl 4-bromo-2-methylbenzoate (10.00 g, 43.70 mmol) was combined with tetrahydrofuran (60 mL) under nitrogen atmosphere. Methylmagesium bromide ether solution (3 M, 58.2 mL, 175.00 mmol) was added dropwise at −40° C. The solution was stirred at the same temperature for 30 min and warmed to ambient temperature. After being stirred at ambient temperature for additional 3 hours, the reaction was quenched by adding a saturated aqueous ammonium chloride solution followed by extraction with ethyl acetate (2×200 mL). The combined organic layers was washed with brine (2×100 mL), dried over anhydrous sodium sulfate and filtered. The filtrate was concentrated under vacuum to afford the title compound. $^1$H NMR (300 MHz, CDCl$_3$) δ7.33-7.24 (m, 3H), 2.56 (s, 3H), 1.63 (s, 6H).

Step 2: 1-(2-(4-bromo-2-methylphenyl)propan-2-1)-1H-1,2,3-triazole and 2-(2-(4-bromo-2-methylphenyl)propan-2-yl)-2H-1,2,3-triazole

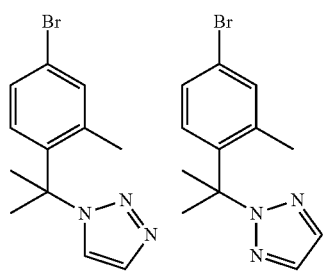

In a round-bottom flask, 2-(4-bromo-2-methylphenyl)propan-2-ol (2.00 g, 8.77 mmol), acetonitrile (12 mL), iron(III) chloride (0.28 g, 8.29 mmol) and 1H-1,2,3-triazole (1.21 g, 17.54 mmol) were combined. The reaction was heated at 80° C. for 16 hour and then quenched by a saturated aqueous ammonium chloride solution. The mixture was extracted with ethyl acetate (2×60 mL) and the combined organic layers washed with brine (2×10 mL), dried over anhydrous sodium sulfate and filtered. The filtrate was concentrated under vacuum and the residue purified by reversed phase C18 flash chromatography eluting with acetonitrile/water (0.05% 2,2,2-trifluoroacetic acid, 45% to 70% in 15 min) to afford the title compounds. 1-(2-(4-Bromo-2-methylphenyl)propan-2-yl)-1H-1,2,3-triazole, LCMS (ESI) calc'd for C$_{12}$H$_{15}$BrN$_3$ [M+H]$^+$ 280, 282 (1:1) found 280, 282 (1:1); 1H NMR (300 MHz, CDCl$_3$) δ7.74 (s, 1H), 7.42-7.26 (m, 4H), 2.06 (s, 6H), 1.67 (s, 3H). 2-(2-(4-Bromo-2-methylphenyl)propan-2-yl)-2H-1,2,3-triazole, LCMS (ESI) calc'd for C$_{12}$H$_{15}$BrN$_3$ [M+H]$^+$ 280, 282 (1:1) found 280, 282 (1:1); $^1$H NMR (300 MHz, CDCl$_3$) δ 7.63 (s, 2H), 7.36-7.33 (m, 2H), 7.26-7.25 (m, 1H), 2.02 (s, 6H), 1.55 (s, 3H).

Intermediate I-82 and I-83

1-(2-(4-Bromophenyl)propan-2-yl)-1H-1,2,3-triazole and 2-(2-(4-bromophenyl)propan-2-yl)-2H-1,2,3-triazole I-82 and I-83

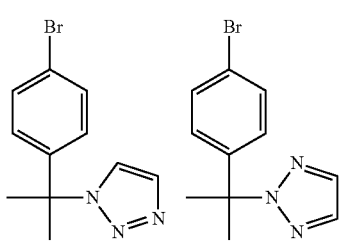

To a 50 mL round-bottom flask were placed 2-(4-bromophenyl) propan-2-ol (5.10 g, 23.71 mmol), 2H-1,2,3-triazole (3.28 g, 47.4 mmol), acetonitrile (10 mL) and iron (III) trichloride (1.50 g, 9.48 mmol). The reaction mixture was heated at 60° C. for 16 hours and then quenched by a saturated aqueous ammonium chloride solution (50 mL). The mixture was extracted with ethyl acetate (3×80 mL) and the combined organic layers dried over sodium sulfate and filtered. The filtrate was concentrated under vacuum to afford 3.50 g of the crude product mixture as a yellow oil that was then purified by prep-HPLC (column: X Bridge C18, 19×150 mm, 5 um; mobile phase A: water/0.05% trifluoroacetic acid, mobile phase B: acetonitrile; flow rate: 20 mL/min; gradient: 30% B to 70% B in 10 min; 220 nm) to give the title compounds: 1-(2-(4-Bromophenyl)propan-2-yl)-1H-1,2,3-triazole, LCMS (ESI) calc'd for C$_{11}$H$_{13}$BrN$_3$ [M+H]$^+$:266, 268 (1:1), found 266, 268 (1:1); $^1$H NMR (400 MHz, CDCl$_3$) δ7.68 (s, 2H), 7.43 (d, J=8.8 Hz, 2H), 6.93 (d, J=8.8 Hz, 2H), 2.10 (s, 6H); 2-(2-(4-Bromophenyl)propan-2-yl)-2H-1,2,3-triazole, LCMS (ESI) calc'd for C$_{11}$H$_{13}$BrN$_3$ [M+H]$^+$: 266, 268 (1:1), found 266, 268 (1:1); $^1$H NMR (400 MHz, DMSO-d$_6$) δ8.28 (s, 1H), 7.82 (s, 1H), 7.54 (d, J=8.4 Hz, 2H), 6.93 (d, J=8.4 Hz, 2H), 2.02 (s, 6H).

Intermediate I-84

5-Bromo-2-(tetrahydro-2H-pyran-4-yl)-2,3-dihydrobenzo[d]isothiazole 1,1-dioxide

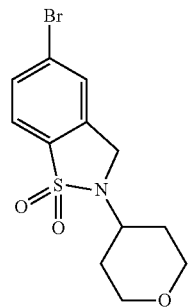

I-84

Step 1: 4-bromo-2-methyl-N-(tetrahydro-2H-pyran-4-yl)benzenesulfonamide

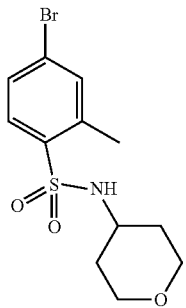

I-84a

To a 250 mL 3-necked round-bottom flask was placed a solution of tetrahydro-2H-pyran-4-amine (2.00 g, 19.7 mmol) in DCM (100 mL) followed by triethyl amine (7.97 g, 78.8 mmol) at ambient temperature. 4-Bromo-2-methylbenzene-1-sulfonyl chloride (5.00 g, 19.7 mmol) was then added at the same temperature. The reaction was stirred at ambient temperature for 2 hours and then poured into water (100 mL). The organic layer was separated and washed with brine, dried over anhydrous sodium sulfate and filtered. The filtrate was concentrated under reduced pressure to afford a residue which was purified by silica gel column chromatography eluting with petroleum ether/EtOAc (1/1) to afford the title compound. LCMS (ESI) calc'd for $C_{12}H_{17}BrNO_3S$ [M+H]$^+$: 334, 336 (1:1), found 334, 336 (1:1); $^1$H NMR (400 MHz, CDCl$_3$) δ7.90 (d, J=4.8 Hz, 1H), 7.52-7.48 (m, 2H), 4.70 (d, J=8.0 Hz, 1H), 3.92-3.87 (m, 2H), 3.41-3.32 (m, 3H), 2.67 (s, 3H), 1.79-1.75 (m, 2H), 1.56-1.50 (m, 2H).

Step 2: 4-bromo-2-(bromomethyl)-N-(tetrahydro-2H-pyran-4-)benzenesulfonamide

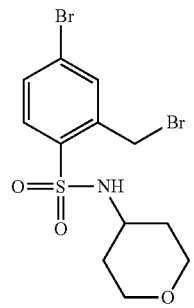

I-84b

To a chloroform solution (200 mL), of 4-bromo-2-methyl-N-tetrahydro-2H-pyran-4-yl) benzenesulfonamide (3.80 g, 11.37 mmol) was added at ambient temperature N-bromosuccinimide (2.43 g, 13.64 mmol) followed by azo-bis-isobutyronitrile (0.37 g, 2.27 mmol). The resulting solution was heated at reflux for 14 hours and quenched by addition of water (200 mL). The resulting mixture was washed with brine, dried over anhydrous Na$_2$SO$_4$ and filtered. The filtrate was concentrated in vacuo, and the residue purified by silica gel column chromatography eluting with ethyl acetate/petroleum ether (1/1) to afford 2.00 g of a mixture of starting material, 4-bromo-2-methyl-N-(tetrahydro-2H-pyran-4-yl) benzenesulfonamide, and the title benzylbromide. This mixture was used in the next step without further purification. LCMS (ESI) calc'd for $C_{12}H_{16}Br_2NO_2S$ [M+H]$^+$: 414, 416 (1:1), found 414, 416 (1:1).

Step 3: 5-bromo-2-(tetrahydro-2H-pyran-4-yl)-2,3-dihydrobenzo[d]isothiazole 1,1-dioxide

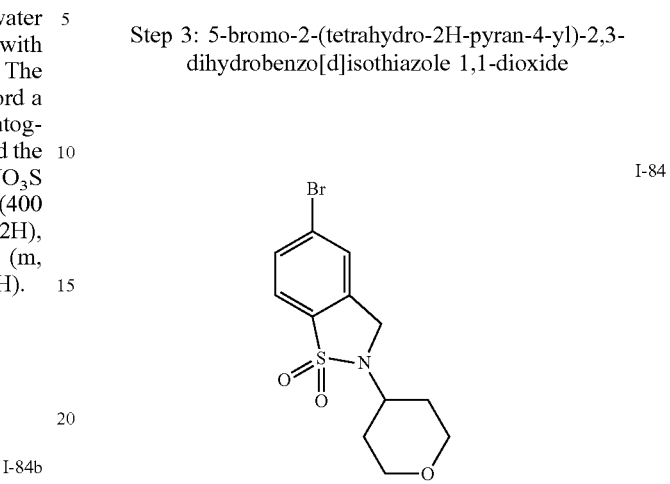

I-84

To a 250 mL 3-necked round-bottom flask was placed 2.00 g of the mixture of 4-bromo-2-methyl-N-(tetrahydro-2H-pyran-4-yl)benzenesulfonamide and 4-bromo-2-(bromomethyl)-N-(tetrahydro-2H-pyran-4-yl)benzenesulfonamide in acetonitrile/water (100 mL, 1/1). Then saturated aqueous sodium bicarbonate (1.63 g, 19 mmol, 4.00 equiv) was added in one portion. The reaction mixture was heated at reflux for 14 hours at which time it was, allowed to cool to ambient temperature and extracted with EtOAc (3×100 mL). The combined organic layers was washed with brine, dried over anhydrous Na$_2$SO$_4$ and filtered. The filtrate was concentrated in vacuo and resulting crude product purified by silica gel column chromatography with petroleum ether/ehtyl acetate (1/1) to afford the title compound. LCMS (ESI) calc'd for $C_{12}H_{15}BrNO_3S$ [M+H]$^+$:332, 334 (1:1), found 332, 334 (1:1); $^1$H NMR (400 MHz, CDCl$_3$) δ7.72-7.69 (m, 2H), 7.62 (s, 1H), 4.41 (s, 2H). 4.11-4.08 (m, 2H), 3.97-3.89 (m, 1H), 3.56-3.53 (m, 2H), 2.08-1.92 (m, 4H).

Table 8 discloses intermediates that were prepared in an analogous manner to that for 5-bromo -2-(tetrahydro-2H-pyran-4-yl)-2,3-dihydrobenzo[d]isothiazole 1,1-dioxide I-84, using cyclohexanamine to replace tetrahydro-2H-pyran-4-amine.

TABLE 8

| Intermediate | Structure | Compound Name | MS/$^1$H NMR |
|---|---|---|---|
| I-85 | ![structure] | 5-bromo-2-cyclohexyl-2,3-dihydrobenzo[d]isothiazole 1,1-dioxide | LCMS (ESI) calc'd for $C_{13}H_{17}BrNO_2S$ [M + H]$^+$: 330, 332 (1:1), found 330, 332 (1:1); $^1$H NMR (300 MHz, CDCl$_3$) δ 7.68-7.63 (m, 2H), 7.56 (s, 1H), 4.37 (s, 2H), 3.63-3.73 (m, 1H), 2.26-2.25 (m, 2H), 1.84-1.89 (m, 2H), 1.10-1.72 (m, 6H). |

TABLE 8-continued

| Intermediate | Structure | Compound Name | MS/¹H NMR |
|---|---|---|---|
| I-86 | 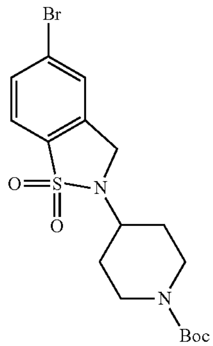 [SMILES: CC(C)(C)OC(=O)N1CCC(N2Cc3cc(Br)ccc3S2(=O)=O)CC1] | 5-bromo-2-(N-tert-butyl carbomatepiperidine-4-yl)cyclohexyl-2,3-dihydrobenzo[d]isothiazole 1,1-dioxide | LCMS (ESI) calc'd for $C_{17}H_{24}BrN_2O_4S$ [M + H]⁺: 431, 433 (1:1), found 431, 433 (1:1); ¹H NMR (400 MHz, CDCl₃) δ 7.66 (s, 2H), 7.57 (s, 1H), 4.35 (s, 2H), 4.20 (d, J = 13.6 Hz, 2H), 3.81 (t, J = 11.2 Hz, 1H), 2.89 (t, J = 12.4 Hz, 2H), 2.03 (d, J = 12.8 Hz, 2H), 1.81-1.71 (m, 2H), 1.47 (s, 9H). |
| I-87 | 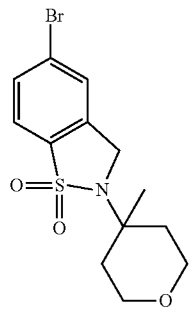 [SMILES: CC1(N2Cc3cc(Br)ccc3S2(=O)=O)CCOCC1] | 5-bromo-2-(4-methyltetrahydro-2H-pyran-4-yl)-2,3-dihydrobenzo[d]isothiazole 1,1-dioxide | LCMS (ESI) calc'd for $C_{13}H_{17}BrNO_3S$ [M + H]⁺: 346, 348 (1:1), found 346, 348 (1:1); ¹H NMR (400 MHz, CDCl₃) δ 7.69-7.63 (m, 2H), 7.58 (s, 1H), 4.42 (s, 2H), 3.94-3.88 (m, 2H), 3.81-3.75 (m, 2H), 2.36-2.32 (m, 2H), 1.89-1.79 (m, 2H), 1.69 (s, 3H). |

Intermediate I-88

5-Bromo-2,2-dimethylbenzo[b]thiophen-3(2H)-one 1,1-dioxide

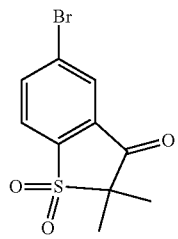

I-88

Step 1: methyl 2-((4-bromophenyl)thio)acetate

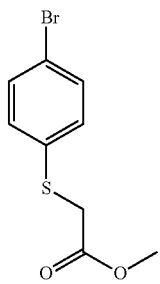

I-88a

To a 250 mL round-bottom flask were placed 4-bromobenzenethiol (5.00 g, 26.4 mmol), methyl-2-bromoacetate (6.07 g, 39.7 mmol), triethylamine (7.37 mL, 52.9 mmol) and tetrahydrofuran (130 mL). The mixture was heated at 70° C. for 4 hours and then concentrated in cacuo. The residue was dissolved in water (100 mL) and then extracted with ethyl acetate (3×150 mL). The organic layers were combined, washed with brine (100 mL), dried over anhydrous sodium sulfate and filtered. The filtrate was concentrated under vacuum to afford the title compound. GCMS (ES) calc'd for $C_9H_{10}BrO_2S$ [M]: 260, 262 (1:1), found 260, 262 (1:1).

Step 2: 2-((4-bromophenyl)thio)acetic acid

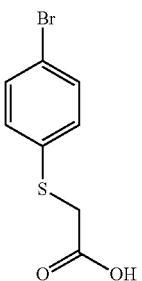

I-88b

To a 500 mL round-bottom flask were placed methyl 2-((4-bromophenyl)thio) acetate (7.40 g, 28.3 mmol), sodium hydroxide (2.26 g, 56.6 mmol) in methanol (200 mL) and water (20 mL). The mixture was stirred at ambient temperature for 16 hours and then concentrated under vacuum. Water (100 mL) was added to the residue followed by hydrochloric acid (6 M) until pH~5. The mixture was extracted with ethyl acetate (3×100 mL) and the combined organic layers washed with brine (100 mL), dried over anhydrous sodium sulfate and filtered. The filtrate was concentrate under vacuum to afford the title acid. GCMS (ES) calc'd for $C_8H_8BrO_2S$ [M]: 246, 248 (1:1), found 246, 248 (1:1).

Step 3: 2-((4-bromophenyl)thio)acetyl chloride

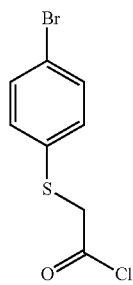

I-88c

A solution of 2-((4-bromophenyl)thio)acetic acid (6.20 g, 25.09 mmol) in thionyl chloride (150 mL) was heated at reflux for 1 hour and then concentrated under vacuum to afford (crude) of 2-((4-bromophenyl)thio)acetyl chloride that was used directly in the next step.

Step 4: 5-bromobenzo[b]thiophen-3(2H)-one

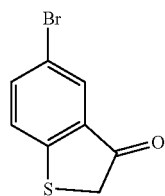

I-88d 2-((4-Bromophenyl)thio)acetyl chloride (21.00 g, 79 mmol) was added dropwised to a suspension of aluminum chloride (13.71 g, 103 mmol) in 1,2-dichloroethane (150 mL) at 0-4° C. The mixture was warmed and maintained at ambient temperature for 16 hours. The reaction mixture was added to hydrochloric acid (1.5 M, 150 mL) and then extracted with 1,2-dichloroethane (3×300 mL). The combined organic layers was washed with brine (2×200 mL), dried over anhydrous sodium sulfate and filtered. The filtrate was concentrated under reduced pressure and the residue purified by silica gel column chromatography eluting with ethyl acetate/petroleum ether (1/30) to afford the title compound. $^1$H NMR (300 MHz, CDCl$_3$) δ7.88 (d, J=2.1 Hz, 1H), 7.66-7.62 (m, 1H), 7.31 (d, J=8.4 Hz, 1H), 3.83 (s, 2H).

Step 5: 5-bromobenzo[b]thiophen-32H)-one 1,1-dioxide

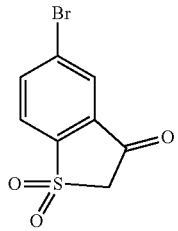

I-88e

To a 500 mL round-bottom flask was placed at 0-4° C. 5-bromobenzo[b]thiophen-3(2H)-one (10.00 g, 43.7 mmol) in 1,2-dichloroethane (200 mL) followed by 3-chlorobenzoperoxoic acid (22.60 g, 131 mmol). The reaction was stirred at ambient temperature for 5 hours and saturated sodium bicarbonate (150 mL) and water (200 mL) were added and the mixture extracted with 1,2-dichloroethane (3×500 mL). The combined organic fractions was washed with brine (saturated, 2×200 mL), dried with sodium sulfate and filtered. The filtrate was concentrated under reduced pressure. The residue was purified by silica gel column chromatography eluting with ethyl acetate/petroleum ether (1/10) to give the title compound. $^1$H NMR (300 MHz, CDCl$_3$) δ8.15 (d, J=1.8 Hz, 1H), 8.08-8.04 (m, 1H), 7.86 (d, J=8.4 Hz, 1H), 4.13 (s, 2H).

Step 6: 5-bromo-2,2-dimethylbenzo[b]thiophen-3 (2H)-one

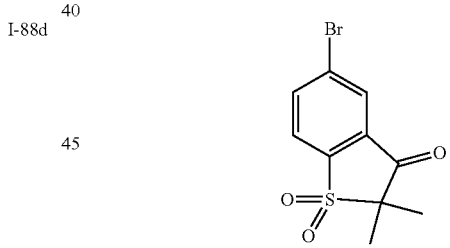

I-88f

To a 50 mL round-bottom flask were added 5-bromobenzo[b]thiophen-3(2H)-one 1,1-dioxide (0.51 g, 1.95 mmol), iodomethane (0.69 g, 4.88 mmol) and 1,5-diazabicyclo[4.3.0]non-5-ene (0.73 mL, 4.88 mmol) in tetrahydrofuran (20 mL). The mixture was heated at 70° C. for 3 hours at which time it was cooled. Water (50 mL) was added and the resulting mixture extracted with ethyl acetate (3×50 mL). The organic layers was combined, washed with brine (2×100 mL), dried over anhydrous sodium sulfate and filtered. The filtrate was concentrated under vacuum and the residue purified by silica gel column chromatography eluting with ethyl acetate/petroleum ether (1/30) to afford the title compound. GCMS (ES) calc'd for $C_{10}H_{10}BrO_3S$ [M]+: 288, 290 (1:1), found 288, 290 (1:1); $^1$H NMR (400 MHz, CDCl$_3$) δ8.17 (d, J=1.8 Hz, 1H), 8.09-8.07 (m, 1H), 7.91 (d, J=6.4 Hz, 1H), 1.65 (s, 6H).

Intermediate I-89

Bromo-3-hydroxy-2,2-dimethyl-2,3-dihydrobenzo[b]thiophene-1,1-dioxide

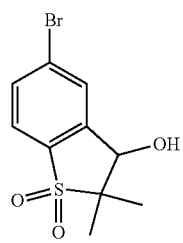

I-89

To a 50 mL round-bottom flask was placed 5-bromo-2,2-dimethylbenzo[b]thiophen-3 (2H)-one 1,1-dioxide (0.60 g, 2.08 mmol) in methanol (20 mL). Sodium borohydride (0.45 g, 10.40 mmol) was added. The reaction was stirred for 1 h and then quenched by water (2 mL). The mixture was extracted with ethyl acetate (3×20 mL). The organic layers were combined, dried over anhydrous sodium sulfate and filtered. The filtrate was concentrated under vacuum to afford the title compound. $^1$H NMR (400 MHz, DMSO-d$_6$) δ7.85-7.80 (m, 3H), 6.62 (d, J=6.0 Hz, 1H), 5.99 (d, J=6.0 Hz, 1H), 1.46 (s, 3H), 1.18 (s, 3H).

Intermediate I-90

5-Bromo-3-hydroxy-3H-spiro[benzo[b]thiophene-2,1'-cyclopentane]-1,1-dioxide

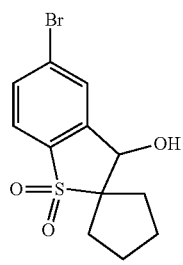

I-90

Step 1: 5-bromo-3H-spiro[benzo[b]thiophene-2,1'-cyclopentane]-3-one-1,1-dioxide

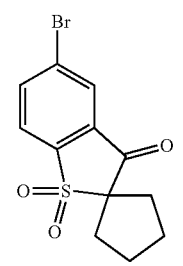

I-90

To a 250 mL round-bottom flask were placed 5-bromobenzo[b]thiophen-3(2H)-one-1,1-dioxide (2.00 g, 7.60 mmol), 1,4-diiodobutane (6.80 g, 22.80 mmol), 1,8-diazabicyclo[4.4.0]undec-7-ene (3.50 g, 22.80 mmol) and tetrahydrofuran (150 mL). The reaction mixture was heated at 70° C. for 2 hours and then quenched by addition of water (20 mL). The mixture was extracted with ethyl acetate (3×100 mL) and the combined organic layers washed with brine (2×100 mL), dried over anhydrous sodium sulfate and filtered. The filtrate was concentrated in vacuo and the residue purified by silica gel column chromatography eluting with ethyl acetate/petroleum ether (1/8) to afford the title compound. $^1$H NMR (300 MHz, DMSO-d$_6$) δ8.06 (d, J=1.2 Hz, 1H), 7.98-7.95 (m, 1H), 7.82 (d, J=8.4 Hz, 1H), 2.18-2.07 (m, 4H), 1.92-1.87 (m, 4H).

Step 2: 5-bromo-3-hydroxy-3H-spiro[benzo[b]thiophene-2,1'-cyclopentane]-1,1-dioxide

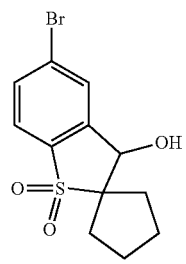

I-90

To a 50 mL round-bottom flask were placed 5-bromo-3H-spiro[benzo[b]thiophene-2,1'-cyclopentane]-3-one-1,1-dioxide (0.36 g, 1.13 mmol), sodium borohydride (0.25 g, 6.65 mmol) and methanol (20 mL). The reaction was stirred at ambient temperature for 1 hour and then quenched by water (50 mL). The resulting solution was extracted with ethyl acetate (3×100 mL) and the combined organic layers washed with brine (2×100 mL), dried over anhydrous sodium sulfate and filtered. The filtrate was concentrated under vacuum to afford title compound. $^1$H NMR (300 MHz, DMSO-d$_6$) δ7.79-7.73 (m, 3H), 6.62 (d, J=6.3 Hz, 1H), 5.54 (d, J=6.3 Hz, 1H), 2.24-1.73 (m, 8H).

The compound in Table 9 was prepared in an analogous manner to that for 5-bromo-3-hydroxy-3H-spiro[benzo[b]thiophene-2,1'-cyclopentane]1,1-dioxide using 1,5-diiodopentane as an electrophile.

TABLE 9

| Intermediate | Structure | Compound Name | MS/¹H NMR |
|---|---|---|---|
| I-91 | 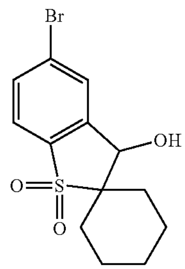 [SMILES: O=S1(=O)c2ccc(Br)cc2C(O)C12CCCCC2] | 5-Bromo-3-hydroxy-3H-spiro[benzo[b]thiophene-2,1'-cyclohexane]1,1-dioxide | ¹H NMR (300 MHz, DMSO-d$_6$) δ 7.78-7.74 (m, 3H), 6.43 (d, J = 6 Hz, 1H), 5.96 (d, J = 5.4 Hz, 1H), 1.98-1.96 (m, 2H), 1.69-1.41 (m, 8H). |

Intermediate I-92

Bromo-2-(1-(trifluoromethyl)cyclohexyl)isoindolin-1-one

I-92

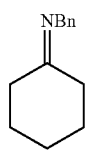

Step 1: N-cyclohexylidene-1-phenylmethanamine

I-92a

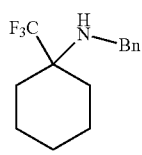

A suspension of magnesium sulfate (24.53 g, 204 mmol), phenylmethanamine (21.84 g, 0.21 mol) and cyclohexanone (20.00 g, 0.21 mol) in DCM (200 mL) was stirred at ambient temperature for 5 days. The mixture was filtered and the filtrate concentrated in vacuo to afford the crude product. LCMS (ESI) calc'd for $C_{13}H_{18}N$ [M+H]$^+$: 188, found 188.

Step 2: N-benzyl-1-(trifluoromethyl)cyclohexanamine

I-92b

To a solution of crude N-cyclohexylidene-1-phenylmethanamine (10.00 g, 53.40 mmol) in acetonitrile (50 mL) were added at ambient temperature trifluoroacetic acid (4.11 mL, 53.40 mmol), potassium hydrogen fluoride (4.17 g, 53.40 mmol) and N,N-dimethylformamide (5 mL). The mixture was stirred at ambient temperature for 30 min at which time it was cooled to 0° C. followed by addition of trimethyl(trifluoromethyl)silane (15.19 g, 0.11 mol). Then the mixture was warmed to ambient temperature and stirred at the same temperature for additional 5 hours. Saturated aqueous Na$_2$CO$_3$ (40 mL) was added and the resulting mixture stirred for 5 min before it was diluted with water (50 mL). It was extracted with EtOAc (3×50 mL) and combined organic layers washed with water (50 mL)/brine (50 mL), dried over anhydrous Na$_2$SO$_4$, filtered and concentrated in vacuo. The residue was purified by silica gel column chromatography eluting with petroleum ether to afford the title product. LCMS (ESI) calc'd for $C_{14}H_{19}F_3N$ [M+H]$^+$: 258, found 258; 1H NMR (300 MHz, DMSO-d$_6$) δ7.41-7.20 (m, 5H), 3.75 (d, J=7.5 Hz, 2H), 2.35-2.30 (m, 1H), 1.84-1.09 (m, 10H).

Step 3: 1-(trifluoromethyl)cyclohexanamine hydrochloride salt

I-92c

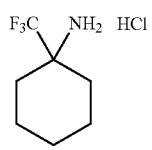

A suspension of N-benzyl-1-(trifluoromethyl)cyclohexanamine (1.40 g, 5.44 mmol), concentrated HCl (12 N, 0.5 mL) and palladium on carbon (0.87 g, 0.82 mmol, 10% wet) in methanol (20 mL) was vigorously stirred under hydrogen (1.5 atm) atmosphere at ambient temperature for 18 hours. The catalyst was removed by filtration and the filtrate concentrated in vacuo to afford the title amine. LCMS (ESI) calc'd for $C_7H_{14}F_3NCl$ [M-HCl+H]$^+$: 168, found 168; 1H NMR (300 MHz, CDCl$_3$) δ9.21 (br, 3H), 1.96-1.51 (m, 10H).

85

Step 4: methyl 4-bromo-2-(((1-(trifluoromethyl) cyclohexyl) amino)methyl)benzoate

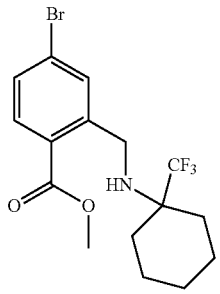

I-92d

A mixture of potassium carbonate (2.04 g, 14.73 mmol), methyl 4-bromo-2-(bromomethyl)benzoate (1.82 g, 5.89 mmol) and 1-(trifluoromethyl)cyclohexanamine hydrochloride (0.60 g, 2.95 mmol) in acetonitrile (50 mL) was heated at 90° C. for 96 hours. The solid was removed by filtration after the reaction was cooled to ambient temperature. The filtrate was concentrated in vacuo and the residue purified by silica gel column chromatography eluting with EtOAc/petroleum ether (1/50) to afford the title compound. LCMS (ESI) calc'd for $C_{16}H_{20}BrF_3NO_2$ [M+H]$^+$: 394, 396 (1:1) found 394, 396 (1:1).

Step 5: 4-bromo-2-(((1-(trifluoromethyl)cyclohexyl) amino)methyl)benzoic acid

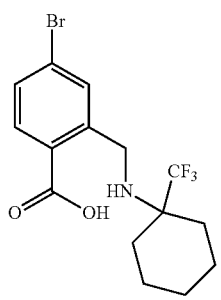

I-92e

Potassium hydroxide (78 mg, 1.40 mmol) was added in one portion to a solution of methyl 4-bromo-2-(((1-(trifluoromethyl)cyclohexyl)amino)methyl)benzoate (55 mg, 0.14 mmol) in THF (2 mL) and water (2 mL) at ambient temperature. The reaction mixture was heated at 40° C. for one day and then cooled. It was acidified with hydrochloric acid (2 N) to pH 6 and then extracted with EtOAc (3×20 mL), dried over anhydrous Na$_2$SO$_4$ and filtered. The filtrate was concentrated in vacuo to afford the title product. LCMS (ESI) calc'd for $C_{15}H_{18}BrF_3NO_2$ [M+H]$^+$: 380, 382 (1:1), found 380, 382 (1:1).

86

Step 6: 5-bromo-2-(1-(trifluoromethyl)cyclohexyl) isoindolin-1-one

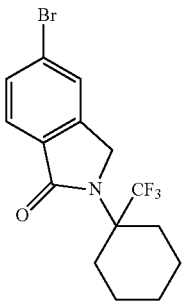

I-92

A solution of 2-(7-aza-1H-benzotriazole-1-yl)-1,1,3,3-tetramethyluronium hexafluorophosphate (84 mg, 0.22 mmol) and 4-bromo-2-(((1-(trifluoromethyl)cyclohexyl)amino) methyl)benzoic acid (42 mg, 0.11 mmol) in N,N-dimethylformamide (1 mL) was heated at 55° C. for 20 hours. The reaction was poured into water (10 mL), extracted with EtOAc (3×10 mL). The combined organic layers was washed with brine (15 mL), dried over anhydrous Na$_2$SO$_4$ and filtered. The filtrate was concentrated in vacuo. The residue was purified by prep-TLC with EtOAc/petroleum ether (1/10) to afford the title product. LCMS (ESI) calc'd for $C_{15}H_{16}BrF_3NO$ [M+H]$^+$: 362, 364 (1:1), found 362, 364 (1:1); $^1$H NMR (400 MHz, CDCl$_3$) δ7.77-7.70 (m, 1H), 7.62 (d, J=8.0 Hz, 2H), 4.58 (s, 2H), 3.12-2.98 (m, 2H), 1.85-1.37 (m, 8H).

Intermediate I-93

3-(5-Bromo-1-oxoisoindolin-2-yl)-3-methylbutanoate

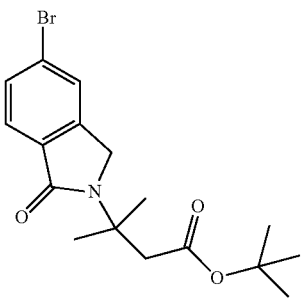

I-93

Step 1: ethyl 3-(5-bromo-1-oxoisoindolin-2-yl)-3-methylbutanoate

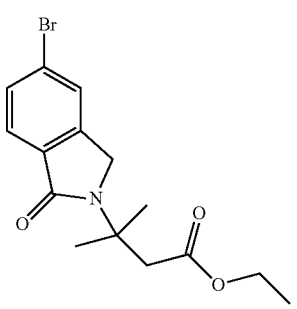

I-93a

To a 500 mL round-bottom flask were placed at ambient temperature methyl 4-bromo-2-(bromomethyl)benzoate (10.00 g, 32.50 mmol), ethyl 3-amino-3-methylbutanoate (7.06 g, 39.00 mmol), triethylamine (9.85 g, 97.50 mmol) and toluene (300 mL). The resulting solution was heated at 110° C. for 16 hours. The reaction was then quenched by addition of water (50 mL) and resulting mixture extracted with EtOAc (3×100 mL). The organic layers was combined, washed with brine (2×10 mL), dried over anhydrous Na$_2$SO$_4$, filtered and concentrated in vacuo. The residue was purified by silica gel column chromatography eluting with EtOAc/petroleum ether (1/6) to afford the title compound. LCMS (ESI) calc'd for C$_{15}$H$_{19}$BrNO$_3$ [M+H]$^+$: 340, 342 (1:1), found 340, 342 (1:1).

Step 2: 3-(5-bromo-1-oxoisoindolin-2-yl)-3-methyl butanoic acid

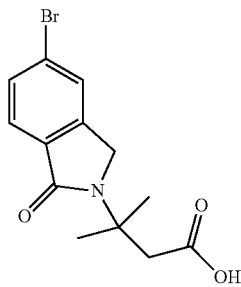

I-93b

To a MeOH solution (30 mL) of ethyl 3-(5-bromo-1-oxoisoindolin-2-yl)-3-methylbutanoate (3.20 g, 9.40 mmol) cooled in an ice bath was added in one portion an aqueous solution (5 mL) of sodium hydroxide (0.75 g, 18.80 mmol). Then the ice bath was removed and reaction maintained at 0° C. to ambient temperature for 1 hour. The mixture was concentrated in vavuo to remove MeOH and resulted aqueous mixture acidified with hydrochloric acid (4 M) until pH 5-6 followed by extraction with EtOAc (3×100 mL). The organic layers was combined, washed with brine (2×100 mL), dried over anhydrous Na$_2$SO$_4$ and filtered. The filtrate was concentrated in vacuo to afford the title compound. LCMS (ESI) calc'd for C$_{13}$H$_{15}$BrNO$_3$ [M+H]$^+$: 312, 314 (1:1), found 312, 314 (1:1).

Step 3: tert-butyl 3-(5-bromo-1-oxoisoindolin-2-yl)-3-methylbutanoate

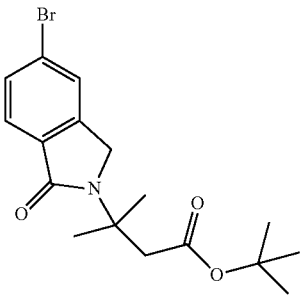

I-93

3-(5-Bromo-1-oxoisoindolin-2-yl)-3-methyl butanoic acid (1.00 g, 3.20 mmol) and tert-butyl-2,2,2-trichloroacetimidate (2.10 g, 9.60 mmol) were combined in DCM (5 mL), and resulting solution maintained at ambient temperature for 36 hours at which time the reaction was quenched by addition of water (10 mL). The mixture was extracted with EtOAc (3×50 mL), and organic layers washed with brine (2×50 mL), dried over anhydrous Na$_2$SO$_4$ and filtered. The filtrate was concentrated in vacuo, and the residue purified by silica gel column chromatography eluting with EtOAc/petroleum ether (1/3) to afford the title product. LCMS (ESI) calc'd for C$_{17}$H$_{23}$BrNO$_3$ [M+H]$^+$:368, 370 (1:1), found 368, 370 (1:1); $^1$H NMR (300 MHz, DMSO-d$_6$) δ7.68-7.66 (m, 1H), 7.60-7.58 (m, 2H), 4.55 (s, 2H), 3.07 (s, 2H), 1.64 (s, 6H), 1.31 (s, 9H).

Intermediate I-94A and I-94B (R) and (S)-2-(4-bromophenyl)-2-(trifluoromethyl) pyrrolidine

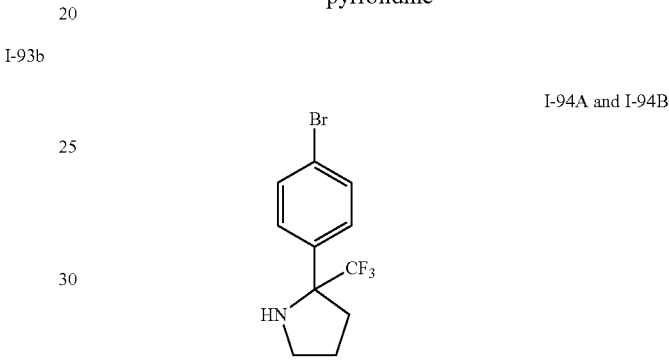

I-94A and I-94B

Step 1: 3-(4-bromobenzoyl)-1-vinylpyrrolidin-2-one as a colorless solid

I-94a

Potassium tert-butoxide (6.26 g, 55.80 mmol) was added to a solution of 1-vinylpyrrolidin-2-one (6.20 g, 55.80 mmol) and methyl 4-bromobenzoate (10.00 g, 46.50 mmol) in tetrahydrofuran (150 mL). The mixture was stirred at ambient temperature for an hour at which time water (200 mL) was added and pH adjusted to 7 (pH paper) with hydrochloric acid (1 M). The resulting mixture was extracted with EtOAc (3×200 mL). The combined organic layers was dried over anhydrous Na$_2$SO$_4$, filtered and concentrated in vacuo. The resulting residue was purified by silica gel column chromatography eluting with EtOAc/petroleum ether (0/1-1/4) to afford the title ketone. LCMS (ESI) calc'd for C$_{13}$H$_{13}$BrNO$_2$ [M+H]$^+$: 294, 296 (1:1), found 294, 296 (1:1); $^1$H NMR (300 MHz, CDCl$_3$) δ7.90 (d, J=6.6 Hz, 2H), 7.65 (d, J=6.6 Hz, 2H), 7.06-6.97 (m, 1H), 4.55-4.50 (m, 3H), 3.77-3.68 (m, 1H), 3.62-3.55 (m, 1H), 2.80-2.71 (m, 1H), 2.37-2.28 (m, 1H).

Step 2: 5-(4-bromophenyl)-3,4-dihydro-2H-pyrrole

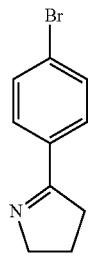

I-94b

A suspension of 3-(4-bromobenzoyl)-1-vinylpyrrolidin-2-one (5.00 g, 17.00 mmol) in HCl (8 M, 20 mL, 160 mmol) was heated at reflux for 16 hours. The mixture was cooled to ambient temperature and extracted with EtOAc (3×20 mL). The aqueous layer was basified to pH 13 with NaOH (15% aqueous solution) and then extracted with DCM (5×20 mL). The combined organic layers was dried over anhydrous $Na_2SO_4$, filtered and concentrated in vacuo. The resulting residue was purified by silica gel column chromatography eluting with EtOAc/petroleum ether (0/1 to 1/4) to afford the title dihydropyrrole. LCMS (ESI) calc'd for $C_{10}H_{11}BrN$ $[M+H]^+$:224, 226 (1:1), found 224, 226 (1:1); $^1H$ NMR (300 MHz, $CDCl_3$) δ7.74-7.69 (m, 2H), 7.56-7.52 (m, 2H), 4.09-4.02 (m, 2H), 2.96-2.88 (m, 2H), 2.10-2.00 (m, 2H).

Step 3: (S) and (R)-2-(4-bromophenyl)-2-(trifluoromethyl)pyrrolidine

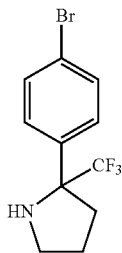

I-94A and I-94B

To an ice-cooled solution of 5-(4-bromophenyl)-3,4-dihydro-2H-pyrrole (0.80 g, 3.57 mmol) in dry acetonitrile (3 mL) were added trifluoromethanesulfonic acid (0.67 g, 4.46 mmol), potassium hydrogen fluoride (0.84 g, 10.71 mmol) and trimethyl(trifluoromethyl)silane (5.08 g, 35.70 mmol) successively. The resulted mixture was warmed to ambient temperature and maintained at the same temperature for 48 hour at which time saturated aqueous $NaHCO_3$ was added with caution until pH>7. The solution was extracted with EtOAc (3×10 mL). The combined organic layers was dried over anhydrous $Na_2SO_4$, filtered and concentrated in vacuo. The residue was purified by silica gel column chromatography eluting with DCM/petroleum ether (0/1 to 1/5) to afford the title compound. LCMS (ESI) calc'd for $C_{11}H_{12}BrF_3N$ $[M+H]^+$: 294, 296 (1:1), found 294, 296 (1:1); $^1H$ NMR (300 MHz, $CDCl_3$) δ7.49 (d, J=5.4 Hz, 2H), 7.42 (d, J=5.4 Hz, 2H), 3.29-3.21 (m, 1H), 3.16-3.08 (m, 1H), 2.60-2.51 (m, 1H), 2.25-2.16 (m, 1H), 2.08-1.94 (m, 1H), 1.89-1.75 (m, 1H). This racemic mixture was resolved by preparative chiral HPLC (column: CHIRALPAK AD-H SFC 5×25 cm, 5 um; mobile phase: methanol (0.2% DEA), detector 254/220 nm to afford (R or S)-2-(4-bromophenyl)-2-(trifluoromethyl)pyrrolidine I-94A (retention time=4.41 min), and (R or S)-2-(4-bromophenyl)-2-(trifluoromethyl)pyrrolidine I-94B (retention time=5.23 min).

Intermediate I-95

2-(4-Bromo-2-methylphenyl)-2-(trifluoromethyl)pyrrolidine

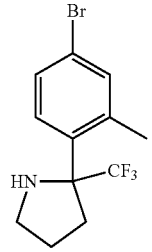

The titled compound was prepared in an analogous manner to that described for 2-(4-bromophenyl)-2-(trifluoromethyl)pyrrolidine I-94 starting with methyl 4-bromo-2-methylbenzoate to replace methyl 4-bromobenzoate. LRMS (ESI) calc'd for: $C_{12}H_{14}BrF_3N$ $[M+H]^+$: 308, 310 (1:1), found 308, 310 (1:1); $^1H$ NMR (300 MHz, $CDCl_3$) δ7.47 (d, J=8.1 Hz, 1H), 7.35 (s, 1H), 7.33 (d, J=8.1 Hz, 1H), 3.31-3.15 (m, 2H), 2.81-2.72 (m, 1H), 2.53 (s, 3H), 2.34-2.13 (m, 1H), 2.06-1.86 (m, 2H).

Intermediate I-96

(R or S)-2-(4-Bromophenyl)-1-methyl-2-(trifluoromethyl)pyrrolidine

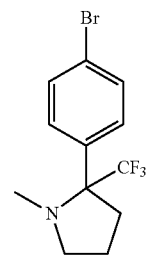

I-96

A solution of (R or S)-2-(4-bromophenyl)-2-(trifluoromethyl)pyrrolidine I-94A (80 mg, 0.27 mmol), iodomethane (0.39 g, 2.72 mmol) and NaH (60% in mineral oil, 0.11 g, 2.72 mmol) in N,N-dimethylformamide (2.7 mL) was stirred at ambient temperature for 16 hours. The mixture was concentrated in vacuo and the resulting residue poured into saturated $NaHCO_3$ (20 mL). The mixture was extracted with EtOAc (3×20 mL) and combined organic layers dried over anhydrous $Na_2SO_4$ and filtered. The filtrate was concentrated in vacuo and resulting crude product purified by silica gel column chromatography eluting with DCM/petroleum ether (0/1-1/1) to afford the title product. LCMS (ESI) calc'd for $C_{12}H_{14}BrF_3N$ $[M+H]^+$:308, 310 (1:1), found 308, 310 (1:1); $^1H$ NMR (300 MHz, $CDCl_3$) δ7.61-7.47 (m, 4H), 3.55-3.45 (m, 1H), 3.31-3.23 (m, 1H), 2.73-2.66 (m, 1H), 2.64 (s, 3H), 2.41-2.16 (m, 1H), 2.07-2.03 (m, 2H).

The compound in Table 10 was prepared in an analogous manner to that described for (R or S)-2-(4-bromophenyl)-1-methyl-2-(trifluoromethyl)pyrrolidine I-96 starting from (S or R)-2-(4-bromophenyl)-2-(trifluoromethyl)pyrrolidine I-94B.

TABLE 10

| Intermediate | Structure | Compound Name | ¹H NMR/MS |
|---|---|---|---|
| I-97 | 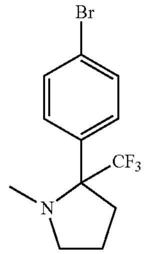 [SMILES: CN1CCCC1(c1ccc(Br)cc1)C(F)(F)F] | (S or R)-2-(4-bromophenyl)-1-methyl-2-(trifluoromethyl)pyrrolidine | LRMS (ESI) calc'd for: $C_{12}H_{14}BrF_3N$ [M + H]⁺: 308, 310 (1:1), found 308, 310 (1:1). ¹H NMR (300 MHz, CDCl₃) δ 7.61-7.47 (m, 4H), 3.55-3.45 (m, 1H), 3.31-3.23 (m, 1H), 2.73-2.66 (m, 1H), 2.64 (s, 3H), 2.41-2.16 (m, 1H), 2.07-2.03 (m, 2H). |

Intermediate I-98

1-(4-Bromo-2-methylphenyl)-2,2,2-trifluoroethan-amine hydrochloride

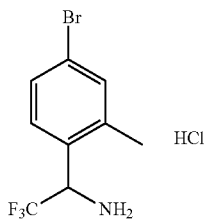

I-98

To an anhydrous toluene solution (20 mL) of 1-(4-bromo-2-methylphenyl)-2,2,2-trifluoroethanone (2.53 g, 9.42 mmol) was added dropwise over 10 min at ambient temperature a THF solution of lithium bis(trimethylsilyl)amide (1 M, 10.6 mL, 10.55 mmol) followed by borane-methyl sulfide complex (10 M in THF, 1.88 mL, 18.80 mmol). The mixture was stirred at ambient temperature for 30 min at which time it was quenched by addition of water (10 mL). The resulting mixture was extracted with ethyl acetate (3×30 mL) and the combined organic layers washed with brine (3×50 mL), dried over anhydrous sodium sulfate and filtered. The filtrate was concentrated under vacuum and the residue dissolved in ethyl acetate (5 mL) followed by treatment with an EtOAc solution of acetate (5 mL). The resulting solid was collected by filtration and dried under vacuum to give the title compound. ¹H NMR (300 MHz, DMSO-d₆) δ9.68 (br, 3H), 7.68-7.45 (m, 3H), 5.56-5.49 (m, 1H), 2.40 (s, 3H).

Intermediate I-99

Racemic 2-(4-Bromophenyl)-2-(trifluoromethyl)-tetrahydrofuran

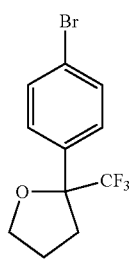

I-99

Step 1: 1-(4-bromophenyl)-4-hydroxybutan-1-one

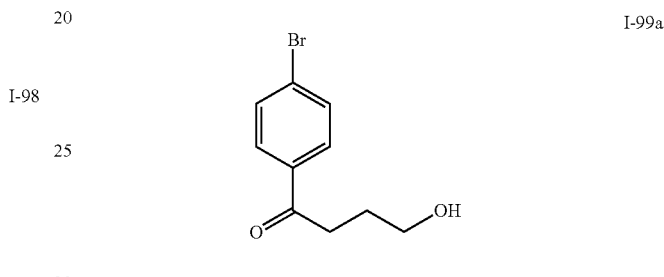

I-99a

To a 250 mL round-bottom flask was placed a THF solution (200 mL) of 4-(4-bromophenyl)-4-oxobutanoic acid (4.00 g, 16.01 mmol), and the resulting solution cold in an ice bath. Borane THF solution (1 M, 40 mL, 40.00 mmol)) was added at 0° C. The mixture was stirred at ambient temperature for 2 hours and then quenched by addition of ice water (20 mL). The mixture was extracted with EtOAc (2×40 mL), amd combined organic layers washed with brine (2×30 mL), dried over anhydrous Na₂SO₄ and filtered. The filtrate was concentrated in vacuo to afford the title compound. LCMS (ESI) calc'd for $C_{10}H_{12}BrO_2$ [M+H]⁺: 243, 245 (1:1), found 243, 245 (1:1).

Step 2: 4-(4-bromophenyl)-5,5,5-trifluoropentane-1,4-diol

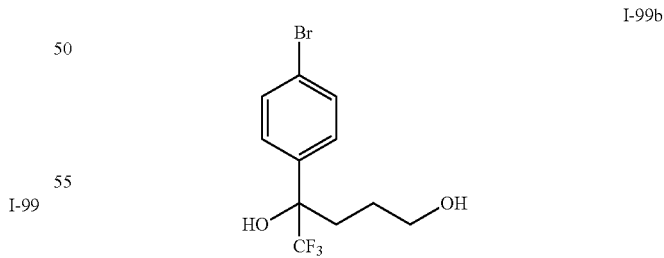

I-99b

To a 8 mL vial was placed a solution of 1-(4-bromophenyl)-4-hydroxybutan-1-one (0.30 g, 1.23 mmol) and tetramethylammonium fluoride (23 mg, 0.25 mmol) in CH₂Cl₂ (4 mL). The mixture was degassed with nitrogen for 3 times, and then trimethyl(trifluoromethyl)silane (0.35 g, 2.47 mmol) added at −50° C. The reaction was warmed to ambient temperature and maintained at the temperature for 16 hours. It was quenched by addition of ice water (10 mL).

The mixture was extracted with EtOAc (2×20 mL), and combined organic layers washed with brine (2×20 mL), dried over anhydrous sodium sulfate and filtered. The filtrate was concentrated in vacuo. The residue was dissolved in tetrahydrofuran (10 mL) and tetrabutylammonium fluoride (1.60 g, 6.15 mmol) was added. The mixture was stirred at ambient temperature for 2 hours at which time water (10 mL) was added. The quenched reaction was extracted with EtOAc (3×30 mL) and combined organic phases, washed with brine (2×20 mL), dried over anhydrous sodium sulfate and filtered. The filtrate was concentrated under vacuum. The residue was purified by silica gel column chromatography eluting with EtOAc/petroleum ether (1/3) to afford the title diol. LCMS (ESI) calc'd for $C_1H_{13}BrF_3O_2[M+H]^+$: 313, 315 (1:1), found 313, 315 (1:1).

Step 3: 2-(4-bromophenyl)-2-(trifluoromethyl)tetrahydrofuran

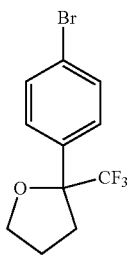

I-99

To a 8 mL vial was placed a solution of 4-(4-bromophenyl)-5,5,5-trifluoropentane-1,4-diol (80 mg, 0.26 mmol) and tributylphosphine (0.13 g, 0.51 mmol) in anhydrous THF (5 mL). $N_1,N_1,N_2,N_2$-teramethyldiazene-1,2-dicarboxamide (88 mg, 0.51 mmol) was then added. The resulted solution was stirred at ambient temperature for 16 hours at which time the reaction was diluted with water (20 mL) followed by extraction with DCM (2×20 mL). The combined organic layers was washed with water (2×20 mL), brine (2×20 mL), dried over anhydrous $Na_2SO_4$, filtered and concentrated in vacuo. The residue was purified by silica gel column chromatography eluting with EtOAc/petroleum ether (3/97) to afford the title compound. GCMS (EI) calc'd for $C_{11}H_{11}BrF_3O$ [M]+: 294, 296 (1:1), found 294, 296 (1:1); $^1$HNMR (300 MHz, CDCl$_3$) δ7.44-7.42 (m, 2H), 7.35-7.32 (m, 2H), 4.06-3.91 (m, 2H), 2.62-2.54 (m, 2H), 2.21-2.03 (m, 2H).

Intermediate I-100

Racemic N-(1-(4-bromophenyl)-2,2,2-trifluoroethyl)-2-methylpropan-2-amine

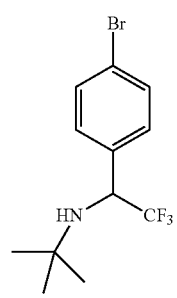

I-100

Step 1: 1-(4-bromophenyl)-2,2,2-trifluoroethanol

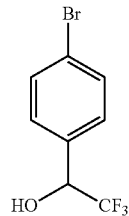

I-100a

To a MeOH solution (100 mL) of 1-(4-bromophenyl)-2,2,2-trifluoroethanone was added portionwise at 0-4° C. sodium borohydride (4.50 g, 120.00 mmol). The reaction mixture was stirred at ambient temperature for an hour and then quenched by addition of water (150 mL). The mixture was extracted by EtOAc (3×50 mL); combined organic layers was washed with water (100 mL) then brine (100 mL), dried over anhydrous $Na_2SO_4$ and filtered. The filtrate was concentrated in vacuo to give the title alcohol. $^1$H NMR (300 MHz, CDCl$_3$) δ7.62 (d, J=8.4 Hz, 2H), 7.45 (d, J=8.4 Hz, 2H), 6.94-6.85 (m 1H), 5.25-5.16 (m, 1H).

Step 2: 1-(4-bromophenyl)-2,2,2-trifluoroethyl trifluoromethanesulfonate

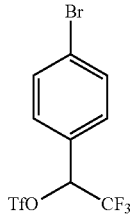

I-100b

In a 100 mL round-bottom flask, 1-(4-bromophenyl)-2,2,2-trifluoroethanol (3.00 g, 11.76 mmol), 2,6-lutidine (1.52 g, 14.18 mmol) were combined with DCM (40 mL). The resulting solution was cooled in an ice bath, and trifluoromethanesulfonic anhydride (5.00 mL, 23.6 mmol) added portionwise. The reaction was stirred at 0-4° C. for 1.5 hours and then quenched by addition of water (100 mL). The mixture was extracted with DCM (3×30 mL); the combined organic layers was washed with water (3×100 mL) followed by brine (3×100 mL), dried over anhydrous $Na_2SO_4$ and filtered. The filtrate was concentrated in vacuo to give the title triflate as that was used without further purification.

Step 3: N-(1-(4-bromophenyl)-2,2,2-trifluoroethyl)-2-methylpropan-2-amine

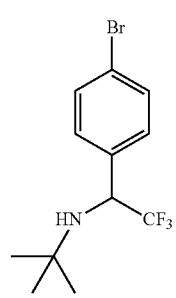

I-100

In a 100 mL round-bottom flask, 1-(4-bromophenyl)-2,2,2-trifluoroethyl trifluoromethanesulfonate (4.20 g, 10.88 mmol), tert-butylamine (1.90 mL, 17.72 mmol), and potassium carbonate (2.93 g, 21.24 mmol) were combined with DCM (40 mL). The resulting solution was heated at 75° C. for 16 hours at which time it was cooled, diluted with DCM (100 mL) and washed with HCl (1 N, 150 mL) followed by brine (150 mL). The organic layer was separated, dried over anhydrous $Na_2SO_4$ and filtered. The filtrate was concentrated in vacuo, and the resulting residue purified by silica gel column chromatography eluting with petroleum ether to afford the title amine. LCMS (ESI) calc'd for $C_{12}H_{16}BrF_3N$ [M+H]$^+$: 310, 312 (1:1), found 310, 312 (1:1); $^1$H NMR (300 MHz, DMSO-$d_6$) δ7.57 (s, 4H), 4.57-4.53 (m, 1H), 2.55-2.50 (m, 1H), 0.96 (s, 9H).

Table 11 discloses intermediates that were prepared in an analogous manner to that of N-(1-(4-bromophenyl)-2,2,2-trifluoroethyl)-2-methylpropan-2-amine I-100 using different amines.

TABLE 11

| Intermediate | Structure | Compound Name | MS/$^1$H NMR |
|---|---|---|---|
| I-101 | 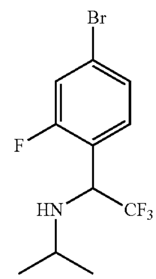 | N-(1-(4-bromo-2-fluorophenyl)-2,2,2-trifluoroethyl)propan-2-amine | LRMS (ESI) calc'd for $C_{11}H_{13}BrF_4N$ [M + H]$^+$: 314, 316 (1:1), found 314, 316 (1:1). $^1$H NMR (300 MHz, CDCl$_3$) δ 7.40-7.28 (m, 2H), 7.28 (d, J = 0.9 Hz, 1H), 4.62 (q, J = 15 Hz, 1H), 2.78-2.70 (m, 1H), 1.06 (d, J = 6.0 Hz, 6H). |
| I-102 | 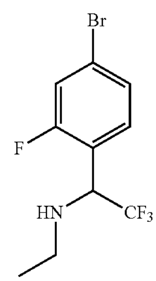 [SMILES: CCNC(c1ccc(Br)cc1F)C(F)(F)F] | 1-(4-bromo-2-fluorophenyl)-N-ethyl-2,2,2-trifluoroethanamine | LRMS (ESI) calc'd for $C_{10}H_{11}BrF_4N$ [M + H]$^+$: 300, 302 (1:1), found 300, 302 (1:1). $^1$H NMR (300 MHz, CDCl$_3$) δ 7.43-7.34 (m, 2H), 7.31-7.26 (m, 1H), 4.56 (q, J = 14.4 Hz, 1H), 2.70-2.57 (m, 2H), 1.11 (t, J = 7.2 Hz, 3H). |
| I-103 | 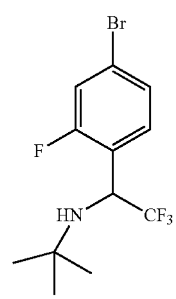 [SMILES: CC(C)(C)NC(c1ccc(Br)cc1F)C(F)(F)F] | N-(1-(4-bromo-2-fluorophenyl)-2,2,2-trifluoroethyl)-2-methylpropan-2-amine | LRMS (ESI) calc'd for $C_{12}H_{15}BrF_4N$ [M + H]$^+$: 328, 330 (1:1), found 328, 330 (1:1). $^1$H NMR (300 MHz, CDCl$_3$) δ 7.46-7.25 (m, 3H), 4.61 (q, J = 7.8 Hz, 1H), 1.06 (s, 9H). |
| I-104 | 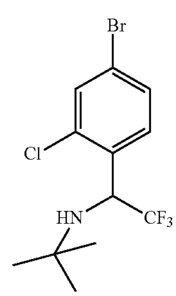 [SMILES: CC(C)(C)NC(c1ccc(Br)cc1Cl)C(F)(F)F] | N-(1-(4-Bromo-2-chlorophenyl)-2,2,2-trifluoroethyl)-2-methylpropan-2-amine | LRMS (ESI) calc'd for $C_{12}H_{15}BrClF_3N$ [M + H]+: 344, 346 (1:1), found 344, 346 (1:1). 1H NMR (300 MHz, CDCl$_3$) δ 7.81-7.70 (m, 1H), 7.62-7.58 (m, 1H), 7.53-7.49 (m, 1H), 5.03-4.97 (m, 1H), 1.60 (s, 9H). |

TABLE 11-continued

| Intermediate | Structure | Compound Name | MS/¹H NMR |
|---|---|---|---|
| I-105 | 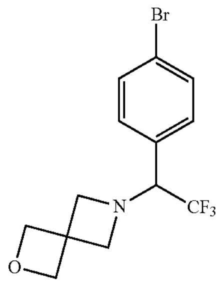 [SMILES: FC(F)(F)C(c1ccc(Br)cc1)N1CC2(COC2)C1] | 6-(1-(4-Bromophenyl)-2,2,2-trifluoroethyl)-2-oxa-6-azaspiro[3.3]heptane | LRMS (ESI) calc'd for $C_{13}H_{14}BrF_3NO$ [M + H]+: 336, 338 (1:1), found 336, 338 (1:1). ¹H NMR (300 MHz, CDCl$_3$) δ 7.51 (dd, J = 6.6, 1.8 Hz, 2H), 7.24 (dd, J = 6.6, 1.8 Hz, 2H), 4.73 (s, 4H), 3.69 (q, J = 6.6 Hz, 1H), 3.50-3.40 (m, 4H). |
| I-106a | 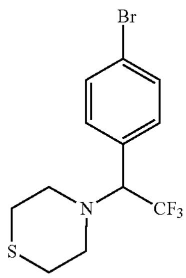 [SMILES: FC(F)(F)C(c1ccc(Br)cc1)N1CCSCC1] | (R or S)-4-(1-(4-bromophenyl)-2,2,2-trifluoroethyl)thio-morpholine, SFC retention time (Chiralcel OJ-3, 0.46*15 cm, 3 um, Hexane/EtOH, 95:05) = 3.79 minutes. | LRMS (ESI) calc'd for $C_{12}H_{14}BrF_3NS$ [M + H]+: 341. |
| I-106b | 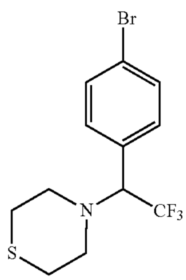 [SMILES: FC(F)(F)C(c1ccc(Br)cc1)N1CCSCC1] | (R or S)-4-(1-(4-bromophenyl)-2,2,2-trifluoroethyl)thio-morpholine, SFC retention time (Chiralcel OJ-3, 0.46*15 cm, 3 um, Hexane/EtOH, 95:05) = 6.26 minutes. | LRMS (ESI) calc'd for $C_{12}H_{14}BrF_3NS$ [M + H]+: 341. |

Intermediate I-107A and 107B (S) and (R)-5-bromo-2-(trifluoromethyl)-2,3-dihydro-1H-inden-2-ol

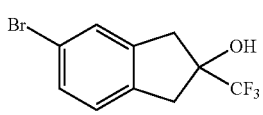

I-107A and 107B (Trifluoromethyl)trimethylsilane (6.06 g, 42.60 mmol) was added dropwise over 5 min to a solution of cesium fluoride (0.22 g, 1.42 mmol) and 5-bromo-1H-inden-2(3H)-one (3.00 g, 14.21 mmol) in THF (70 mL) at 0-4° C. The resulting solution was stirred at ambient temperature for 3 hours at which time tetrabutylammonium fluoride (5.90 g, 22.65 mmol) was added. The mixture was stirred at ambient temperature for 3 additional hours, and water (100 mL) added to quench the reaction. The resulting mixture was extracted with EtOAc (3×200 mL) and combined organic layers washed with brine (2×200 mL), dried over anhydrous sodium sulfate and filtered. The filtrate was concentrated in vacuo, and resulting residue purified by silica gel column chromatgraphy eluting with petroleum ether/ethyl acetate (5/1) to afford 0.55 g (17%) of racemic sample of the title alcohol as a brown oil. ¹H NMR (300 MHz, CDCl$_3$) δ7.49-7.33 (m, 2H), 7.13 (d, J=8.1 Hz, 1H), 3.55-3.35 (m, 2H), 3.13-2.93 (m, 2H). This racemate (0.30 g, 1.07 mmol) was resolved by chiral prep-HPLC using the conditions: chiralpak IA-3 column (0.46×15 cm, 3 m); mobile phase, hexane/ethanol (95/5); flow at 1.0 mL/min; detector: UV-220 nm. This chiral purification provided (S or R)-5-bromo-2-(trifluoromethyl)-2,3-dihydro-1H-inden-2-ol I-107A (retention time=7.50 min): ¹H NMR (300 MHz, CDCl$_3$) δ7.48 (d, J=2.1 Hz, 1H), 7.44-7.33 (m, 1H), 7.22 (d, J=8.1 Hz, 1H), 6.30 (s, 1H), 3.37-3.17 (m, 2H), 3.12-2.90 (m, 2H); and (S or R)-5-bromo-2-(trifluoromethyl)-2,3-dihydro-1H-inden-2-ol I-107B (retention time=9.93 min): ¹H NMR (300 MHz, CDCl$_3$) δ7.48 (d, J=2.1 Hz, 1H), 7.45-7.33 (m, 1H), 7.23 (d, J=8.1 Hz, 1H), 6.30 (s, 1H), 3.39-3.17 (m, 2H), 3.12-2.92 (m, 2H).

Intermediate I-108A and I-108B (S) and (R)-5-bromo-2-methyl-2,3-dihydro-1H-inden-2-ol

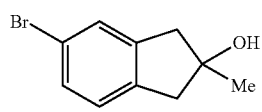

I-108A and 108B

Methylmagnesium bromide $Et_2O$ solution (3 M, 1.58 mL, 4.74 mmol) was diluted with 12 mL of anhydrous $Et_2O$ at 0-4° C. Then an $Et_2O$ (1 mL) solution of 5-bromo-1H-inden-2(3H)-one (0.50 g, 2.37 mmol) was added dropwise over 2 min. The reaction was allowed to warm to ambient temperature and maintained at the same temperature for additional 2 hours. It was then quenched by addition of saturated aqueous ammonium chloride (10 mL; the quenched reaction was extracted with EtOAc (3×10 mL), and combined organic layers washed with brine (2×50 mL), dried over anhydrous $Na_2SO_4$ and filtered; the filtrate was concentrated in vacuo; the resulting residue was purified by silica gel column chromatography, eluting with petroleum ether/EtOAc (5/1) to afford 0.35 g (65%) of the racemic title alcohols as a light oil. $^1$H NMR (300 MHz, DMSO-$d_6$) δ7.43-7.32 (m, 1H), 7.32-7.23 (m, 1H), 7.11 (d, J=8.0 Hz, 1H), 4.74 (s, 1H), 2.86 (s, 2H), 2.81 (s, 2H), 1.33 (s, 3H). This racemate (0.32 g, 1.41 mmol) was purified further by chiral prep-HPLC (column: chiralpak IA 2×25 cm, 5 μm; detector UV 254/220; mobile phase A: hexane (95%)/B: EtOH (5%); flow rate 20 mL/min) to give 0.12 g (38%) of (S or R)-5-bromo-2-methyl-2,3-dihydro-1H-inden-2-ol I-108A (retention time=9.31 min): $^1$H NMR (300 MHz, DMSO-$d_6$) δ7.38-7.33 (m, 1H), 7.31-7.23 (m, 1H), 7.11 (d, J=8.0 Hz, 1H), 4.74 (s, 1H), 2.86 (s, 2H), 2.81 (s, 2H), 1.33 (s, 3H), and 0.12 g (38%) of (S or R)-5-bromo-2-methyl-2,3-dihydro-1H-inden-2-ol I-108B (retention time=11.79 min): $^1$H NMR (300 MHz, DMSO-$d_6$) δ7.39-7.32 (m, 1H), 7.31-7.23 (m, 1H), 7.11 (d, J=8.0 Hz, 1H), 4.73 (s, 1H), 2.87 (s, 2H), 2.81 (s, 2H), 1.33 (s, 3H).

Intermediate I-109A and 109B (R) and (S)-2-(4-bromophenyl)-2-(trifluoromethyl)piperidine

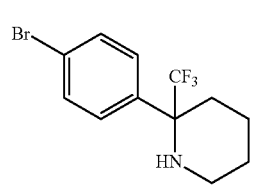

I-109A and 109B

Step 1: 4-bromobenzoyl chloride

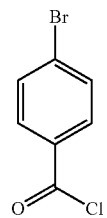

I-109a

A solution of 4-bromobenzoic acid (10.00 g, 49.70 mmol) in sulfurous dichloride (59.20 g, 0.50 mol) was heated at 80° C. for 16 hours. The mixture was then concentrated in vacuo to afford crude product that was used without further purification.

Step 2: tert-butyl 3-(4-bromobenzoyl)-2-oxopiperidine-1-carboxylate

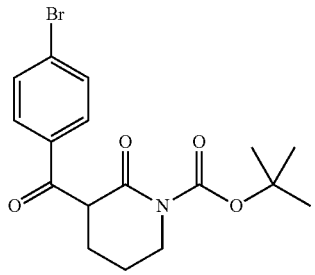

I-109b

Lithium bis(trimethylsilyl)amide (1 M THF solution, 2.11 mL, 2.11 mmol) was added to a solution of tert-butyl 2-oxopiperidine-1-carboxylate (0.20 g, 1.00 mmol) in THF (2 mL) at −78° C. The resulting mixture was stirred at the same temperature for 10 min at which time 4-bromobenzoyl chloride (0.22 g, 1.00 mmol) was added. The reaction was warmed to ambient temperature and stirred for an additional hour before the addition of saturated aqueous ammonium chloride solution (20 mL). The quenched reaction was extracted with EtOAc (3×10 mL), and the combined organic phases dried over anhydrous $Na_2SO_4$, filtered and concentrated in vacuo. The residue was purified by silica gel column chromatography eluting with EtOAc/petroleum (0/1 to 1/1) to afford crude tert-butyl 3-(4-bromobenzoyl)-2-oxopiperidine-1-carboxylate. LCMS (ESI) calc'd for: $C_{17}H_{21}BrNO_4$ $[M+H]^+$: 382, 384 (1:1), found 382, 384 (1:1).

Step 3: 6-(4-bromophenyl)-2,3,4,5-tetrahydropyridine

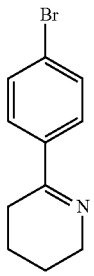

I-109c tert-Butyl 3-(4-bromobenzoyl)-2-oxopiperidine-1-carboxylate (2.00 g, 5.23 mmol) was combined with HCl (8 M, 43.6 mL, 0.52 mol) at ambient temperature. The resulting solution was heated at 80° C. for 16 hours. The reaction was then poured into saturated aqueous $Na_2CO_3$ (50 mL) and extracted with EtOAc (3×50 mL). The combined organic layers was dried over $Na_2SO_4$ filtered and concentrated in vacuo. The residue was purified by silica gel column chromatography eluting with EtOAc/petroleum (0/1-1/1) to afford the title imine. LCMS (ESI) calc'd for: $C_{11}H_{13}BrN$ $[M+H]^+$:238, 240 (1:1), found 238, 240 (1:1); 1H NMR (300 MHz, CDCl$_3$) δ7.66-7.63 (m, 2H), 7.52-7.47 (m, 2H), 3.92-3.80 (m, 2H), 2.62-2.56 (m, 2H), 1.88-1.79 (m, 2H), 1.78-1.66 (m, 2H).

Step 4: (R) and (S)-2-(4-bromophenyl)-2-(trifluoromethyl)piperidine

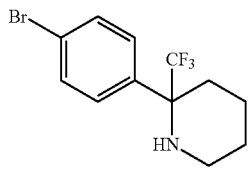

I-109A and 109B

To a solution of 6-(4-bromophenyl)-2,3,4,5-tetrahydropyridine in dry acetonitrile (3 mL) were added trifluoromethanesulfonic acid (3.30 g, 21.96 mmol), potassium hydrogen fluoride (3.94 g, 50.40 mmol) and trimethyl(trifluoromethyl)silane (5.97 g, 42.00 mmol) successively at 0-4° C. The resulted mixture was stirred at ambient temperature for 48 hours. Then the reaction was quenched by addition of saturated aqueous NaHCO$_3$ (50 mL) followed by extraction with EtOAc (3×30 mL). The combined organic layers was dried over anhydrous Na$_2$SO$_4$, filtered and concentrated in vacuo. The residue was purified by silica gel column chromatography eluting with DCM/petroleum (0/1-1/1) to afford 0.70 g (54%) of racemic sample of the title products. This racemate (0.60 g, 1.95 mmol) was then subjected to preparative chiral HPLC chromatography (column: Chiralpak IA, 2×25 cm; mobile phase: 10% EtOH in hexane, V/V) to afford (R or S)-2-(4-bromophenyl)-2-(trifluoromethyl)piperidine I-109A (retention time=4.74 min); LRMS (ESI) calc'd for C$_{12}$H$_{14}$BrF$_3$N [M+H]$^+$:308, 310 (1:1), found 308, 310 (1:1); $^1$H NMR (300 MHz, CDCl$_3$) δ7.67-7.65 (m, 2H), 7.60-7.57 (m, 2H), 3.16-3.03 (m, 1H), 2.73-2.63 (m, 1H), 2.50-2.42 (m, 1H), 2.25-1.93 (m, 1H), 1.79-1.71 (m, 1H), 1.67-1.53 (m, 3H), 1.36-1.30 (m, 1H), and (R or S)-2-(4-bromophenyl)-2-(trifluoromethyl)piperidine I-109B (retention time=5.48 min). LRMS (ESI) calc'd for C$_{12}$H$_{14}$BrF$_3$N [M+H]$^+$:308, 310 (1:1), found 308, 310 (1:1); $^1$H NMR (300 MHz, CDCl$_3$) δ7.67-7.65 (m, 2H), 7.59-7.49 (m, 2H), 3.10-2.95 (m, 1H), 2.73-2.63 (m, 1H), 2.50-2.42 (m, 1H), 2.25-1.93 (m, 1H), 1.79-1.71 (m, 1H), 1.67-1.53 (m, 3H), 1.38-1.32 (m, 1H).

Intermediates I-110A and 110B 3-(3-amino-4-(benzyloxy)-1H-pyrazolo[4,3-c]pyridin-1-yl)butanenitrile

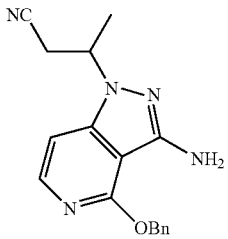

I-110A and 110B

To 4-(benzyloxy)-1H-pyrazolo[4,3-c]pyridin-3-amine (5.00 g, 20.8 mmol) in acetonitrile (69.4 ml) was added (E)-but-2-enenitrile (1.54 g, 22.9 mmol) and DBU (3.45 ml, 22.89 mmol). The flask was sealed and heated to 25° C. for 23 hours, before being concentrated and purified directly on silica, eluting with 5-50% EA/hexanes. The desired fractions were concentrated in vacuo to afford the desired product. LRMS (ESI) calc'd for C$_{17}$H$_{18}$N$_5$O [M+H]$^+$: 308, found 308 $^1$H NMR (600 MHz, CDCl$_3$): δ7.84 (d, J=6.0 Hz, 1H), 7.45 (d, J=7.2 Hz, 2H), 7.37 (m, 2H), 7.32 (m, 1H), 6.73 (d, J=6.6 Hz, 1H), 5.51 (s, 2H), 4.67 (br s, 1H), 4.46 (br s, 2H), 2.92 (dd, J=16.8, 7.8 Hz, 1H), 2.82 (dd, J=16.8, 7.8 Hz, 1H), 1.59 (d, J=6.6 Hz, 3H).

Resolution of enantiomers was achieved by SFC purification using a Chiralpak AD-H, 21×250 mm column, at 70 mL/min with 20% methanol modifier. Retention times were 3.74 minutes (Intermediate I-110A) & 4.41 minutes (Intermediate I-110B).

I-110A (S or R)-3-(3-amino-4-(benzyloxy)-1H-pyrazolo [4,3-c]pyridin-1-yl)-3-cyclopropylpropanenitrile. LRMS (ESI) calc'd for C$_{19}$H$_{20}$N$_5$O [M+H]$^+$: 334, found 334.

I-110B (S or R)-3-(3-amino-4-(benzyloxy)-1H-pyrazolo [4,3-c]pyridin-1-yl)-3-cyclopropylpropanenitrile. LRMS (ESI) calc'd for C$_{19}$H$_{20}$N$_5$O [M+H]$^+$: 334, found 334. The following examples outlined in Table 12 were prepared by analogy using the general procedure outlined above for Intermediates I-110A & I-110B above.

TABLE 12

| Intermediate | Structure | Compound Name | MS |
|---|---|---|---|
| I-111A | (structure shown) | (S)-3-(3-amino-4-(benzyloxy)-1H-pyrazolo[4,3-c]pyridin-1-yl)-3-cyclopropylpropanenitrile (Derived from Peak 1 via SFC: Phenomenex Lux-2, 21 × 250 (mm), 25% MeOH in CO$_2$, rT = 4.36) | LRMS (ESI) calc'd for C$_{19}$H$_{20}$N$_5$O [M + H]$^+$: 334, found 334 |

TABLE 12-continued

| Intermediate | Structure | Compound Name | MS |
|---|---|---|---|
| I-111B | 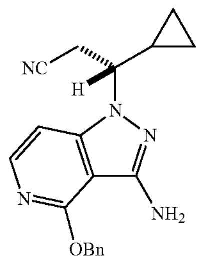 [SMILES: N#CC[C@H](C1CC1)n1nc(N)c2c(OCc3ccccc3)nccc21] | (R)-3-(3-amino-4-(benzyloxy)-1H-pyrazolo[4,3-c]pyridin-1-yl)-3-cyclopropylpropanenitrile (Derived from Peak 2 via SFC: Phenomenex Lux-2, 21x 250 (mm), 25% MeOH in $CO_2$, rT = 5.21) | LRMS (ESI) calc'd for $C_{19}H_{20}N_5O$ [M + H]$^+$: 334, found 334 |
| I-112A-1 | 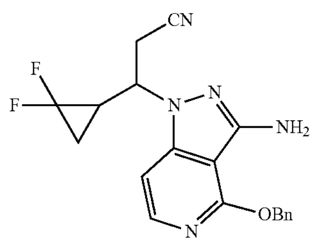 [SMILES: N#CCC(C1CC1(F)F)n1nc(N)c2c(OCc3ccccc3)nccc21] | (S or R)-3-(3-amino-4-(benzyloxy)-1H-pyrazolo[4,3-c]pyridin-1-yl)-3-((S or R)-2,2-difluorocyclopropyl)propanenitrile (Derived from diastereomer 1, Peak 1 via SFC: Phenomenex Lux-2, 21 x 250 (mm), 20% methanol containing 0.25% DMEA in $CO_2$, rT = 3.16) | LRMS (ESI) calc'd for $C_{19}H_{18}F_2N_5O$ [M + H]$^+$: 370, found 370. |
| I-112A-2 | 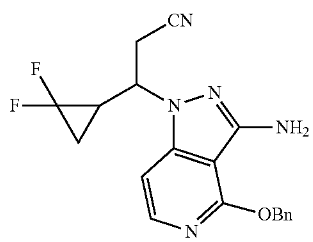 [SMILES: N#CCC(C1CC1(F)F)n1nc(N)c2c(OCc3ccccc3)nccc21] | (S or R)-3-(3-amino-4-(benzyloxy)-1H-pyrazolo[4,3-c]pyridin-1-yl)-3-((S or R)-2,2-difluorocyclopropyl)propanenitrile (Derived from diastereomer 1, Peak 2 via SFC: Phenomenex Lux-2, 21 x 250 (mm), 20% methanol containing 0.25% DMEA in $CO_2$, rT = 4.02) | LRMS (ESI) calc'd for $C_{19}H_{18}F_2N_5O$ [M + H]$^+$: 370, found 370. |
| I-112B-1 | 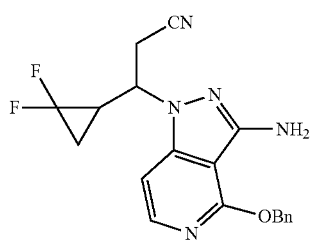 [SMILES: N#CCC(C1CC1(F)F)n1nc(N)c2c(OCc3ccccc3)nccc21] | (S or R)-3-(3-amino-4-(benzyloxy)-1H-pyrazolo[4,3-c]pyridin-1-yl)-3-((S or R)-2,2-difluorocyclopropyl)propanenitrile (Derived from diastereomer 2, Peak 1 via SFC: Phenomenex Lux-2, 21 x 250 (mm), 20% methanol containing 0.25% DMEA in $CO_2$, rT = 3.16) | LRMS (ESI) calc'd for $C_{19}H_{18}F_2N_5O$ [M + H]$^+$: 370, found 370. |
| I-112B-2 | 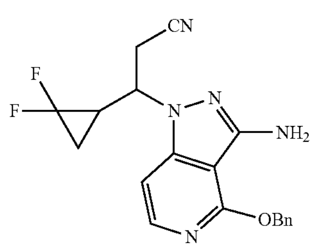 [SMILES: N#CCC(C1CC1(F)F)n1nc(N)c2c(OCc3ccccc3)nccc21] | (S or R)-3-(3-amino-4-(benzyloxy)-1H-pyrazolo[4,3-c]pyridin-1-yl)-3-((S or R)-2,2-difluorocyclopropyl)propanenitrile (Derived from diastereomer 2, Peak 2 via SFC: Phenomenex Lux-2, 21 x 250 (mm), 20% methanol containing 0.25% DMEA in $CO_2$, rT = 4.02) | LRMS (ESI) calc'd for $C_{19}H_{18}F_2N_5O$ [M + H]$^+$: 370, found 370. |
| I-113A-1 | 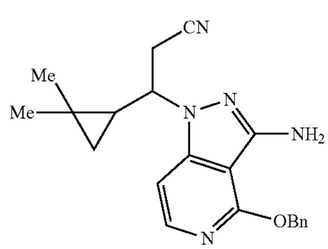 [SMILES: CC1(C)CC1C(CC#N)n1nc(N)c2c(OCc3ccccc3)nccc21] | (R or S)-3-(3-amino-4-(benzyloxy)-1H-pyrazolo[4,3-c]pyridin-1-yl)-3-((S or R)-2,2-dimethylcyclopropyl)propanenitrile (Derived from diastereomer 1, Peak 1 via SFC: Phenomenex Lux-2, 21 x 250 (mm), 20% methanol in $CO_2$, rT = 5.04) | LRMS (ESI) calc'd for $C_{21}H_{24}N_5O$ [M + H]$^+$: 362, found 362. |

TABLE 12-continued

| Intermediate | Structure | Compound Name | MS |
|---|---|---|---|
| I-113A-2 | 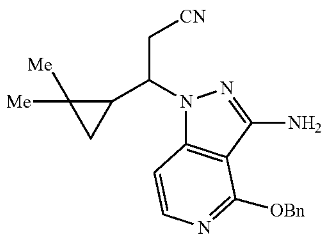 [SMILES: CC1(C)CC1C(CC#N)n1nc(N)c2c(OCc3ccccc3)nccc21] | (R or S)-3-(3-amino-4-(benzyloxy)-1H-pyrazolo[4,3-c]pyridin-1-yl)-3-((S or R)-2,2-dimethylcyclopropyl)propanenitrile (Derived from diastereomer 1, Peak 2 via SFC: Phenomenex Lux-2, 21 x 250 (mm), 20% methanol in $CO_2$, rT = 6.47) | LRMS (ESI) calc'd for $C_{21}H_{24}N_5O$ $[M + H]^+$: 362, found 362. |
| I-113B-1 | 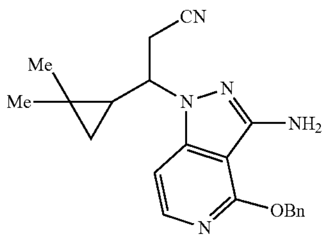 [SMILES: CC1(C)CC1C(CC#N)n1nc(N)c2c(OCc3ccccc3)nccc21] | (R or S)-3-(3-amino-4-(benzyloxy)-1H-pyrazolo[4,3-c]pyridin-1-yl)-3-((S or R)-2,2-dimethylcyclopropyl)propanenitrile (Derived from diastereomer 2, Peak 1 via SFC: Phenomenex Lux-2, 21 x 250 (mm), 20% methanol in $CO_2$, rT = 5.21) | LRMS (ESI) calc'd for $C_{21}H_{24}N_5O$ $[M + H]^+$: 362, found 362. |
| I-113B-2 | 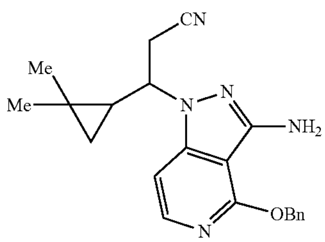 [SMILES: CC1(C)CC1C(CC#N)n1nc(N)c2c(OCc3ccccc3)nccc21] | (R or S)-3-(3-amino-4-(benzyloxy)-1H-pyrazolo[4,3-c]pyridin-1-yl)-3-((S or R)-2,2-dimethylcyclopropyl)propanenitrile (Derived from diastereomer 2, Peak 2 via SFC: Phenomenex Lux-2, 21 x 250 (mm), 20% methanol in $CO_2$, rT = 6.31) | LRMS (ESI) calc'd for $C_{21}H_{24}N_5O$ $[M + H]^+$: 362, found 362. |
| I-114A | 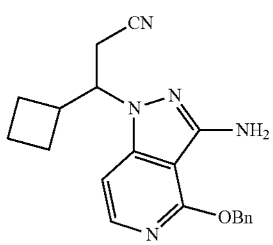 [SMILES: N#CCC(C1CCC1)n1nc(N)c2c(OCc3ccccc3)nccc21] | (R or S)-3-(3-amino-4-(benzyloxy)-1H-pyrazolo[4,3-c]pyridin-1-yl)-3-cyclobutylpropanenitrile (Derived from Peak 1 via SFC: Chiralpak, AS-H, 21 x 250 (mm), 15% methanol in $CO_2$, rT = 3.30) | LRMS (ESI) calc'd for $C_{20}H_{22}N_5O$ $[M + H]^+$: 348, found 348. |
| I-114B | 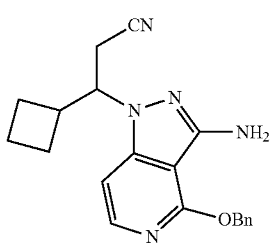 [SMILES: N#CCC(C1CCC1)n1nc(N)c2c(OCc3ccccc3)nccc21] | (R or S)-3-(3-amino-4-(benzyloxy)-1H-pyrazolo[4,3-c]pyridin-1-yl)-3-cyclobutylpropanenitrile (Derived from Peak 2 via SFC: Chiralpak, AS-H, 21 x 250 (mm), 15% methanol in $CO_2$, rT = 3.61) | LRMS (ESI) calc'd for $C_{20}H_{22}N_5O$ $[M + H]^+$: 348, found 348. |

Example II-1

(R or S)-4-((1-(1-cyanopropan-2-yl)-4-oxo-4,5-dihydro-1H-pyrazolo[4,3-c]pyridin-3-yl)amino)-N,N-dimethylbenzenesulfonamide

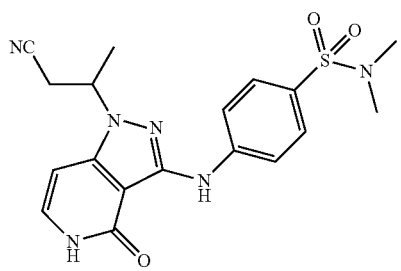

II-1

Step 1: (R or S)-4-((4-(benzyloxy)-1-(1-cyanopropan-2-yl)-1H-pyrazolo[4,3-c]pyridin-3-yl)amino)-N,N-dimethylbenzenesulfonamide

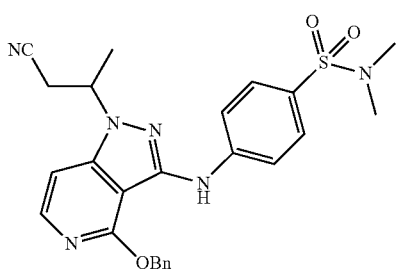

II-1a

To (R or S)-3-(3-amino-4-(benzyloxy)-1H-pyrazolo[4,3-c]pyridin-1-yl)butanenitrile (I-108A) (40 mg, 0.13 mmol), N,N-dimethyl-4-bromophenyl sulfonamide (68.8 mg, 0.260 mmol), $Pd_2dba_3$ (30 mg, 0.033 mmol), 2-di-tert-butylphosphino-3,4,5,6-tetramethyl-2',4',6'-triisopropyl-1,1'-biphenyl (47 mg, 0.098 mmol), and potassium phosphate tribasic (55.3 mg, 0.260 mmol) in a degassed sealed microwave vial, was added t-amyl alcohol (1.74 mL) and the reaction was degassed again by successive evacuation/argon backfill (×3) prior to heating at 75° C. overnight. The reaction was concentrated and purified directly by silica chromatography, eluting with 5-40% EtOAc/hexane. The product was collected and concentrated to afford the desired product, 1-la, as a light colorless solid. LRMS (ESI) calc'd for $C_{25}H_{27}N_6O_3S$ $[M+H]^{+:491}$. found 491.

Step 2: (R or S)-4-((1-(1-cyanopropan-2-yl)-4-oxo-4,5-dihydro-1H-pyrazolo[4,3-c]pyridin-3-yl)amino)-N,N-dimethylbenzenesulfonamide To (R or S)-4-((4-(benzyloxy)-1-(1-cyanopropan-2-yl)-1H-pyrazolo[4,3-c]pyridin-3-yl)amino)-N,N-dimethylbenzenesulfonamide, 1-la, (84.2 mg, 0.172 mmol) was added Pd/C (18 mg, 0.17 mmol, 10 wt. % Pd loading) and ethyl acetate (0.60 mL) and the reaction was evacuated/backfilled with hydrogen and stirred at 25° C. under 1 atm overnight. The reaction was then diluted with DCM and filtered through Celite and washed with DCM and the filtrate was concentrated in vacuo and purified by silica chromatography, eluting with 0-5% MeOH/DCM to afford a white solid, II-1. LRMS (ESI) calc'd for $C_{18}H_{21}N_6O_3S$ $[M+H]^+$: 401. found 401 $^1$H NMR (600 MHz, $CDCl_3$): δ 11.17 (d, J=6.0 Hz, 1H), 8.67 (s, 1H), 7.93 (d, J=9.0 Hz, 2H), 7.62 (d, J=9.0 Hz, 2H), 7.25 (app. t, J=6.6 Hz, 1H), 6.65 (d, J=7.2 Hz, 1H), 5.04 (app. sextet, J=6.6 Hz, 1H), 3.20-3.10 (m, 2H), 2.58 (s, 6H), 1.51 (d, J=6.0 Hz, 3H).

The following Intermediates outlined in Table 13 were prepared by analogy using the general procedure outlined above for Intermediate II-1 above.

TABLE 13

| Example | Structure | Name | MS |
|---|---|---|---|
| II-2 | 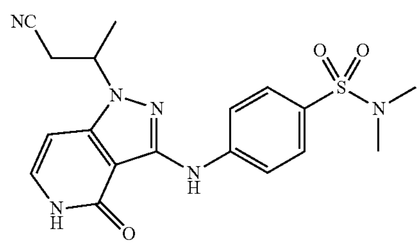 [SMILES: CC(CC#N)n1nc(Nc2ccc(S(=O)(=O)N(C)C)cc2)c2c(=O)[nH]ccc21] | (R or S)-4-((1-(1-cyanopropan-2-yl)-4-oxo-4,5-dihydro-1H-pyrazolo[4,3-c]pyridin-3-yl)amino)-N,N-dimethylbenzenesulfonamide (derived from I-108B) | LRMS (ESI) calc'd for $C_{18}H_{21}N_6O_3S$ $[M + H]^+$: 401, found 401 |
| II-3 | 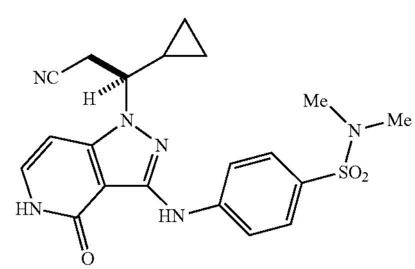 [SMILES: CN(C)S(=O)(=O)c1ccc(Nc2nn([C@@H](CC#N)C3CC3)c3cc[nH]c(=O)c23)cc1] | (S)-4-((1-(2-cyano-1-cyclopropylethyl)-4-oxo-4,5-dihydro-1H-pyrazolo[4,3-c]pyridin-3-yl)amino)-N,N-dimethylbenzenesulfonamide (derived from I-109A) | LRMS (ESI) calc'd for $C_{20}H_{23}N_6O_3S$ $[M + H]^+$: 427, found 427 |

TABLE 13-continued

| Example | Structure | Name | MS |
|---|---|---|---|
| II-4 | 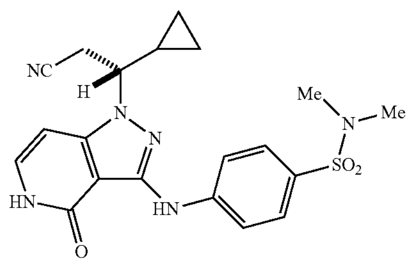 [SMILES: CN(C)S(=O)(=O)c1ccc(Nc2nn([C@H](CC#N)C3CC3)c3cc[nH]c(=O)c23)cc1] | (R)-4-((1-(2-cyano-1-cyclopropyl-ethyl)-4-oxo-4,5-dihydro-1H-pyrazolo[4,3-c]pyridin-3-yl)amino)-N,N-dimethylbenzenesulfonamide (derived from I-109B) | LRMS (ESI) calc'd for $C_{20}H_{23}N_6O_3S$ [M + H]$^+$: 427, found 427 |
| II-5 | 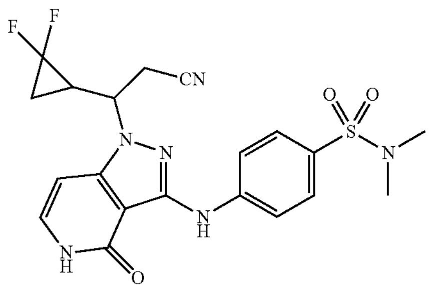 [SMILES: CN(C)S(=O)(=O)c1ccc(Nc2nn(C(CC#N)C3CC3(F)F)c3cc[nH]c(=O)c23)cc1] | 4-((1-((S or R)-2-cyano-1-((S or R)-2,2-difluorocyclopropyl)ethyl)-4-oxo-4,5-dihydro-1H-pyrazolo[4,3-c]pyridin-3-yl)amino)-N,N-dimethylbenzenesulfonamide (derived from I-110A-1) | LRMS (ESI) calc'd for $C_{20}H_{21}F_2N_6O_3S$ [M + H]$^+$: 463, found 463 |
| II-6 | 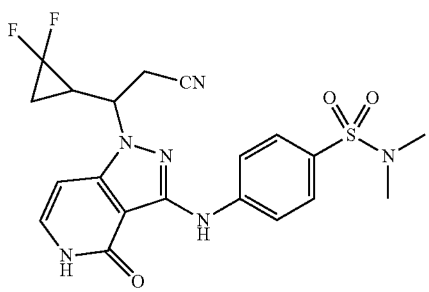 [SMILES: CN(C)S(=O)(=O)c1ccc(Nc2nn(C(CC#N)C3CC3(F)F)c3cc[nH]c(=O)c23)cc1] | 4-((1-((S or R)-2-cyano-1-((S or R)-2,2-difluorocyclopropyl)ethyl)-4-oxo-4,5-dihydro-1H-pyrazolo[4,3-c]pyridin-3-yl)amino)-N,N-dimethylbenzenesulfonamide (derived from I-110A-2) | LRMS (ESI) calc'd for $C_{20}H_{21}F_2N_6O_3S$ [M + H]$^+$: 463, found 463 |
| II-7 | 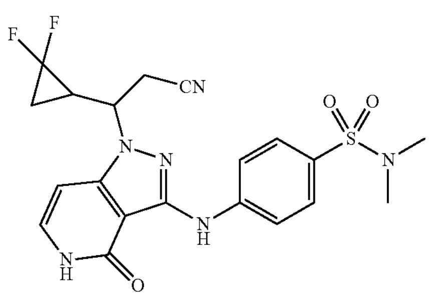 [SMILES: CN(C)S(=O)(=O)c1ccc(Nc2nn(C(CC#N)C3CC3(F)F)c3cc[nH]c(=O)c23)cc1] | 4-((1-((S or R)-2-cyano-1-((S or R)-2,2-difluorocyclopropyl)ethyl)-4-oxo-4,5-dihydro-1H-pyrazolo[4,3-c]pyridin-3-yl)amino)-N,N-dimethylbenzenesulfonamide (derived from I-110B-1) | LRMS (ESI) calc'd for $C_{20}H_{21}F_2N_6O_3S$ [M + H]$^+$: 463, found 463 |
| II-8 | 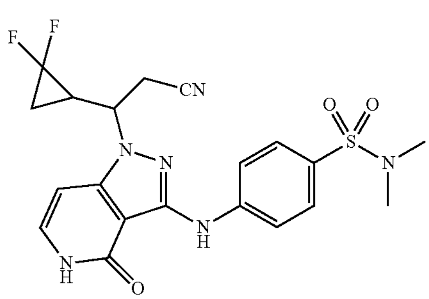 [SMILES: CN(C)S(=O)(=O)c1ccc(Nc2nn(C(CC#N)C3CC3(F)F)c3cc[nH]c(=O)c23)cc1] | 4-((1-((S or R)-2-cyano-1-((S or R)-2,2-difluorocyclopropyl)ethyl)-4-oxo-4,5-dihydro-1H-pyrazolo[4,3-c]pyridin-3-yl)amino)-N,N-dimethylbenzenesulfonamide (derived from I-110B-2) | LRMS (ESI) calc'd for $C_{20}H_{21}F_2N_6O_3S$ [M + H]$^+$: 463, found 463 |

TABLE 13-continued

| Example | Structure | Name | MS |
|---|---|---|---|
| II-9 | 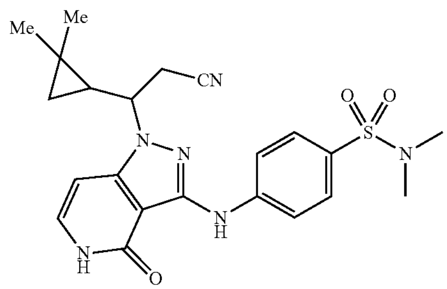 [SMILES: CN(C)S(=O)(=O)c1ccc(Nc2nn(C(CC#N)C3CC3(C)C)c3cc[nH]c(=O)c23)cc1] | 4-((1-((S or R)-2-cyano-1-((S or R)-2,2-dimethylcyclopropyl)ethyl)-4-oxo-4,5-dihydro-1H-pyrazolo[4,3-c]pyridin-3-yl)amino)-N,N-dimethylbenzenesulfonamide (derived from I-111A-1) | LRMS (ESI) calc'd for $C_{22}H_{27}N_6O_3S$ [M + H]$^+$: 455, found 455 |
| II-10 | 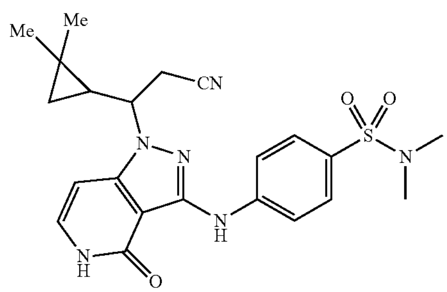 [SMILES: CN(C)S(=O)(=O)c1ccc(Nc2nn(C(CC#N)C3CC3(C)C)c3cc[nH]c(=O)c23)cc1] | 4-((1-((S or R)-2-cyano-1-((S or R)-2,2-dimethylcyclopropyl)ethyl)-4-oxo-4,5-dihydro-1H-pyrazolo[4,3-c]pyridin-3-yl)amino)-N,N-dimethylbenzenesulfonamide (derived from I-111A-2) | LRMS (ESI) calc'd for $C_{22}H_{27}N_6O_3S$ [M + H]$^+$: 455, found 455 |
| II-11 | 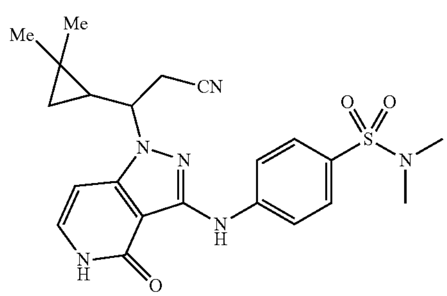 [SMILES: CN(C)S(=O)(=O)c1ccc(Nc2nn(C(CC#N)C3CC3(C)C)c3cc[nH]c(=O)c23)cc1] | 4-((1-((S or R)-2-cyano-1-((S or R)-2,2-dimethylcyclopropyl)ethyl)-4-oxo-4,5-dihydro-1H-pyrazolo[4,3-c]pyridin-3-yl)amino)-N,N-dimethylbenzenesulfonamide (derived from I-111B-1) | LRMS (ESI) calc'd for $C_{22}H_{27}N_6O_3S$ [M + H]$^+$: 455, found 455 |
| II-12 | 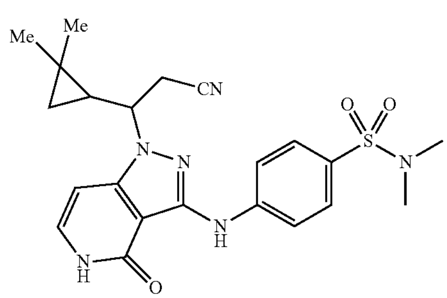 [SMILES: CN(C)S(=O)(=O)c1ccc(Nc2nn(C(CC#N)C3CC3(C)C)c3cc[nH]c(=O)c23)cc1] | 4-((1-((S or R)-2-cyano-1-((S or R)-2,2-dimethylcyclopropyl)ethyl)-4-oxo-4,5-dihydro-1H-pyrazolo[4,3-c]pyridin-3-yl)amino)-N,N-dimethylbenzenesulfonamide (derived from I-111B-2) | LRMS (ESI) calc'd for $C_{22}H_{27}N_6O_3S$ [M + H]$^+$: 455, found 455 |
| II-13 | 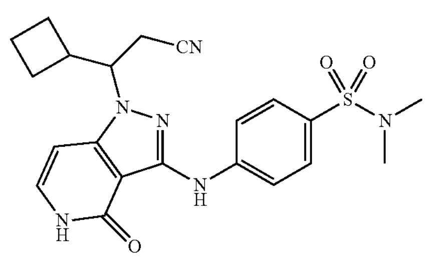 [SMILES: CN(C)S(=O)(=O)c1ccc(Nc2nn(C(CC#N)C3CCC3)c3cc[nH]c(=O)c23)cc1] | (S or R)-4-((1-(2-cyano-1-cyclobutylethyl)-4-oxo-4,5-dihydro-1H-pyrazolo[4,3-c]pyridin-3-yl)amino)-N,N-dimethylbenzenesulfonamide (derived from I-112A) | LRMS (ESI) calc'd for $C_{21}H_{25}N_6O_3S$ [M + H]$^+$: 441, found 441 |

TABLE 13-continued

| Example | Structure | Name | MS |
|---|---|---|---|
| II-14 | 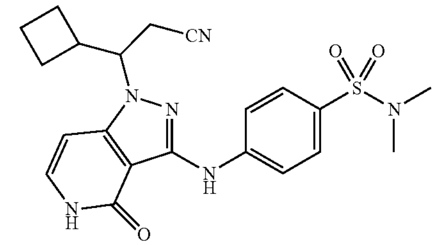 [SMILES: CN(C)S(=O)(=O)c1ccc(Nc2nn(C(CC#N)C3CCC3)c3cc[nH]c(=O)c23)cc1] | (S or R)-4-((1-(2-cyano-1-cyclobutylethyl)-4-oxo-4,5-dihydro-1H-pyrazolo[4,3-c]pyridin-3-yl)amino)-N,N-dimethylbenzene sulfonamide (derived from I-112B) | LRMS (ESI) calc'd for $C_{21}H_{25}N_6O_3S$ $[M + H]^+$: 441, found 441 |
| II-15 | 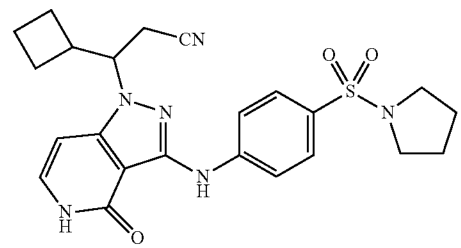 [SMILES: N#CCC(C1CCC1)n1nc(Nc2ccc(S(=O)(=O)N3CCCC3)cc2)c2c(=O)[nH]ccc21] | (S or R)-3-cyclobutyl-3-(4-oxo-3-((4-(pyrrolidin-1-ylsulfonyl)phenyl)amino)-4,5-dihydro-1H-pyrazolo[4,3-c]pyridin-1-yl)propanenitrile (derived from I-112A) | LRMS (ESI) calc'd for $C_{23}H_{28}N_6O_3S$ $[M + H]^+$: 467, found 467 |
| II-16 | 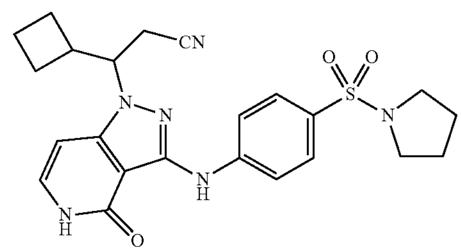 [SMILES: N#CCC(C1CCC1)n1nc(Nc2ccc(S(=O)(=O)N3CCCC3)cc2)c2c(=O)[nH]ccc21] | (S or R)-3-cyclobutyl-3-(4-oxo-3-((4-(pyrrolidin-1-ylsulfonyl)phenyl)amino)-4,5-dihydro-1H-pyrazolo[4,3-c]pyridin-1-yl)propanenitrile (derived from I-112B) | LRMS (ESI) calc'd for $C_{23}H_{28}N_6O_3S$ $[M + H]^+$: 467, found 467 |

Example II-17

(3S)-3-cyclopropyl-3-{3-[(4-fluorophenyl)amino]-4-oxo-4,5-dihydro-1H-pyrazolo[4,3-c]pyridin-1-yl}propanenitrile

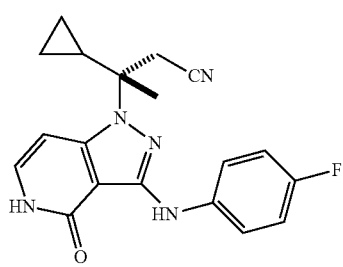

II-17

To (S)-3-(3-amino-4-(benzyloxy)-1H-pyrazolo[4,3-c]pyridin-1-yl)-3-cyclopropylpropanenitrile (I-109A) (30 mg, 0.09 mmol), 1-bromo-4-fluoro-benzene (24.5 mg, 0.135 mmol), Pd₂(dba)₃ (20.6 mg, 0.022 mmol), 2-di-tert-butylphosphino-3,4,5,6-tetramethyl -2',4',6'-triisopropyl-1,1'-biphenyl (26 mg, 0.054 mmol), and potassium acetate (17.7 mg, 0.180 mmol) in a degassed sealed reaction vial, was added isopropanol (0.360 mL). The reaction mixture was heated to 80° C. overnight. The reaction was cooled to rt, and 0.2 mL of trifluoroacetic acid was added. The reaction was stirred at room temperature for an additional 3 h. The reaction mixture was diluted with 3.5 mL of DMSO, filtered using a 0.2 micron WHATMAN syringe, and purified with reverse phase chromatography, to afford compound II-17. LRMS (ESI) calc'd for $C_{18}H_{16}F N_5O$ $[M+H]^+$: 338.1. found 338.14.

The following examples outlined in Table 14 were prepared by analogy using the general procedure outlined above for Example II-17 above.

TABLE 14

| Example | Compound Name | MS |
|---|---|---|
| II-18 | (3S)-3-cyclopropyl-3-[4-oxo-3-({4-[(1R or S)-2,2,2-trifluoro-1-hydroxy-1-methylethyl]phenyl}amino)-4,5-dihydro-1H-pyrazolo[4,3-c]pyridin-1-yl]propanenitrile (from I-2A) | LRMS (ESI) calc'd for $C_{21}H_{21}F_3N_5O_2$ [M + H]$^+$: 432, found 432 |
| II-19 | (3S)-3-cyclopropyl-3-[4-oxo-3-({4-[(1S or R)-2,2,2-trifluoro-1-hydroxy-1-methylethyl]phenyl}amino)-4,5-dihydro-1H-pyrazolo[4,3-c]pyridin-1-yl]propanenitrile (from I-2B) | LRMS (ESI) calc'd for $C_{21}H_{21}F_3N_5O_2$ [M + H]$^+$: 432, found 432 |
| II-20 | (3S)-3-cyclopropyl-3-(3-{[(1R or S)-1-hydroxy-1-(trifluoromethyl)-2,3-dihydro-1H-inden-5-yl]amino}-4-oxo-4,5-dihydro-1H-pyrazolo[4,3-c]pyridin-1-yl)propanenitrile (from I-3A) | LRMS (ESI) calc'd for $C_{22}H_{21}F_3N_5O_2$ [M + H]$^+$: 444, found 444. |
| II-21 | (3S)-3-cyclopropyl-3-(3-{[(1S or R)-1-hydroxy-1-(trifluoromethyl)-2,3-dihydro-1H-inden-5-yl]amino}-4-oxo-4,5-dihydro-1H-pyrazolo[4,3-c]pyridin-1-yl)propanenitrile (from I-3B) | LRMS (ESI) calc'd for $C_{22}H_{21}F_3N_5O_2$ [M + H]$^+$: 444, found 444. |
| II-22 | (3S)-3-cyclopropyl-3-{3-[(1,1-dioxido-2,3-dihydro-1-benzothiophen-5-yl)amino]-4-oxo-4,5-dihydro-1H-pyrazolo[4,3-c]pyridin-1-yl}propanenitrile | LRMS (ESI) calc'd for $C_{20}H_{20}N_5O_3S$ [M + H]$^+$: 410, found 410. |
| II-23 | (3S)-3-{3-[(2-tert-butyl-1,1-dioxido-2,3-dihydro-1,2-benzisothiazol-5-yl)amino]-4-oxo-4,5-dihydro-1H-pyrazolo[4,3-c]pyridin-1-yl}-3-cyclopropylpropanenitrile | LRMS (ESI) calc'd for $C_{23}H_{27}N_6O_3S$ [M + H]$^+$: 467, found 467. |

TABLE 14-continued

| Example | Structure | Compound Name | MS |
|---|---|---|---|
| II-24 | 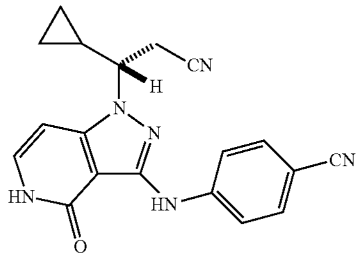 [SMILES: N#CC[C@@H](C1CC1)n1nc(Nc2ccc(C#N)cc2)c2c(=O)[nH]ccc21] | 4-({1-[(1S)-2-cyano-1-cyclopropylethyl]-4-oxo-4,5-dihydro-1H-pyrazolo[4,3-c]pyridin-3-yl}amino)benzonitrile | LRMS (ESI) calc'd for $C_{19}H_{17}N_6O$ $[M + H]^+$: 345, found 345. |
| II-25 | 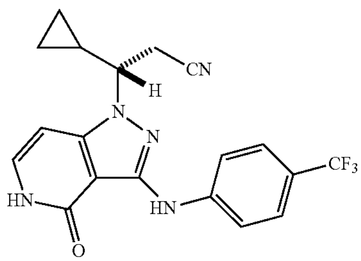 [SMILES: N#CC[C@@H](C1CC1)n1nc(Nc2ccc(C(F)(F)F)cc2)c2c(=O)[nH]ccc21] | (3S)-3-cyclopropyl-3-(4-oxo-3-{[4-(trifluoromethyl)phenyl]amino}-4,5-dihydro-1H-pyrazolo[4,3-c]pyridin-1-yl)propanenitrile | LRMS (ESI) calc'd for $C_{19}H_{17}F_3N_5O$ $[M + H]^+$: 388, found 388. |
| II-26 | 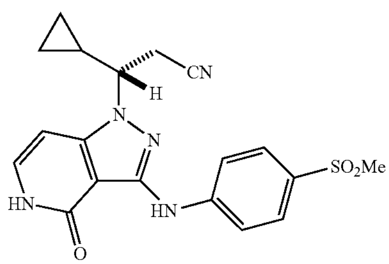 [SMILES: CS(=O)(=O)c1ccc(Nc2nn([C@@H](CC#N)C3CC3)c3cc[nH]c(=O)c23)cc1] | (3S)-3-cyclopropyl-3-(3-{[4-(methylsulfonyl)phenyl]amino}-4-oxo-4,5-dihydro-1H-pyrazolo[4,3-c]pyridin-1-yl)propanenitrile | LRMS (ESI) calc'd for $C_{19}H_{20}N_5O_3S$ $[M + H]^+$: 398, found 398. |
| II-27 | 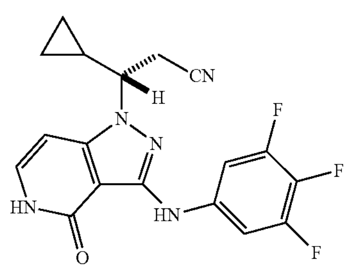 [SMILES: N#CC[C@@H](C1CC1)n1nc(Nc2cc(F)c(F)c(F)c2)c2c(=O)[nH]ccc21] | (3S)-3-cyclopropyl-3-{4-oxo-3-[(3,4,5-trifluorophenyl)amino]-4,5-dihydro-1H-pyrazolo[4,3-c]pyridin-1-yl}propanenitrile | LRMS (ESI) calc'd for $C_{18}H_{15}F_3N_5O$ $[M + H]^+$: 374, found 374. |
| II-28 | 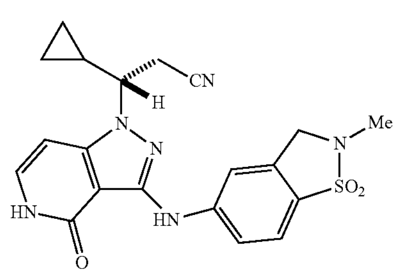 | (3S)-3-cyclopropyl-3-{3-[(2-methyl-1,1-dioxido-2,3-dihydro-1,2-benzisothiazol-5-yl)amino]-4-oxo-4,5-dihydro-1H-pyrazolo[4,3-c]pyridin-1-yl}propanenitrile | LRMS (ESI) calc'd for $C_{20}H_{21}N_6O_3S$ $[M + H]^+$: 425, found 425. |
| II-29 | 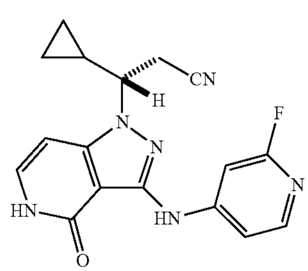 [SMILES: N#CC[C@@H](C1CC1)n1nc(Nc2ccnc(F)c2)c2c(=O)[nH]ccc21] | (3S)-3-cyclopropyl-3-{3-[(2-fluoropyridin-4-yl)amino]-4-oxo-4,5-dihydro-1H-pyrazolo[4,3-c]pyridin-1-yl}propanenitrile | LRMS (ESI) calc'd for $C_{17}H_{16}FN_6$ $[M + H]^+$: 339, found 339. |

TABLE 14-continued

| Example | Structure | Compound Name | MS |
|---|---|---|---|
| II-30 | 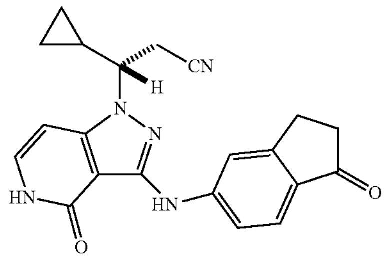 [SMILES: N#CC[C@@H](C1CC1)n1nc(Nc2ccc3c(c2)CCC3=O)c2c(=O)[nH]ccc21] | (3S)-3-cyclopropyl-3-{4-oxo-3-[(1-oxo-2,3-dihydro-1H-inden-5-yl)amino]-4,5-dihydro-1H-pyrazolo[4,3-c]pyridin-1-yl}propanenitrile | LRMS (ESI) calc'd for $C_{21}H_{20}N_5O_2$ [M + H]$^+$: 374, found 374. |
| II-31 | 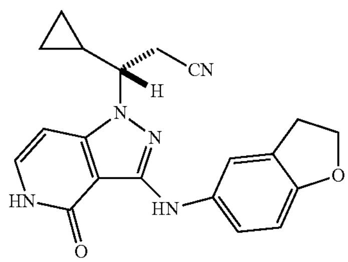 [SMILES: N#CC[C@@H](C1CC1)n1nc(Nc2ccc3c(c2)CCO3)c2c(=O)[nH]ccc21] | (3S)-3-cyclopropyl-3-[3-(2,3-dihydro-1-benzofuran-5-ylamino)-4-oxo-4,5-dihydro-1H-pyrazolo[4,3-c]pyridin-1-yl]propanenitrile | LRMS (ESI) calc'd for $C_{20}H_{20}N_5O_2$ [M + H]$^+$: 362, found 362. |
| II-32 | 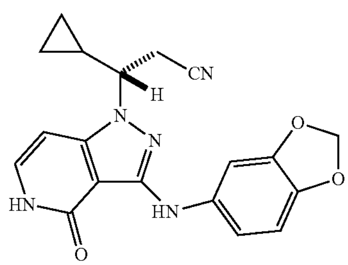 [SMILES: N#CC[C@@H](C1CC1)n1nc(Nc2ccc3c(c2)OCO3)c2c(=O)[nH]ccc21] | (3S)-3-[3-(1,3-benzodioxol-5-ylamino)-4-oxo-4,5-dihydro-1H-pyrazolo[4,3-c]pyridin-1-yl]-3-cyclopropylpropanenitrile | LRMS (ESI) calc'd for $C_{19}H_{18}N_5O_3$ [M + H]$^+$: 364, found 364. |
| II-33 | 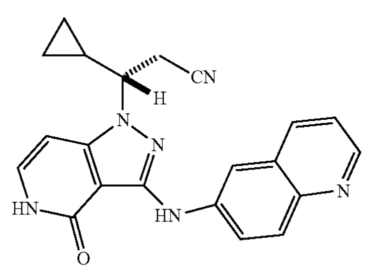 [SMILES: N#CC[C@@H](C1CC1)n1nc(Nc2ccc3ncccc3c2)c2c(=O)[nH]ccc21] | (3S)-3-cyclopropyl-3-[4-oxo-3-(quinolin-6-ylamino)-4,5-dihydro-1H-pyrazolo[4,3-c]pyridin-1-yl]propanenitrile | LRMS (ESI) calc'd for $C_{21}H_{19}N_6O$ [M + H]$^+$: 371, found 371. |
| II-34 | 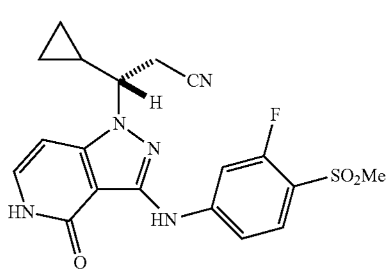 [SMILES: CS(=O)(=O)c1ccc(Nc2nn([C@@H](CC#N)C3CC3)c3cc[nH]c(=O)c23)cc1F] | (3S)-3-cyclopropyl-3-(3-{[3-fluoro-4-(methylsulfonyl)phenyl]amino}-4-oxo-4,5-dihydro-1H-pyrazolo[4,3-c]pyridin-1-yl)propanenitrile | LRMS (ESI) calc'd for $C_{19}H_{19}FN_5O_3S$ [M + H]$^+$: 416, found 416. |
| II-35 | 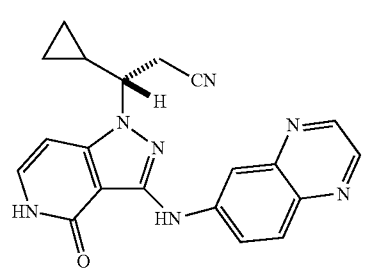 [SMILES: N#CC[C@@H](C1CC1)n1nc(Nc2ccc3nccnc3c2)c2c(=O)[nH]ccc21] | (3S)-3-cyclopropyl-3-[4-oxo-3-(quinoxalin-6-ylamino)-4,5-dihydro-1H-pyrazolo[4,3-c]pyridin-1-yl]propanenitrile | LRMS (ESI) calc'd for $C_{20}H_{18}N_7$ [M + H]$^+$: 372, found 372. |

TABLE 14-continued

| Example | Compound Name | MS |
|---|---|---|
| II-36 | (3S)-3-{3-[(4-chlorophenyl)amino]-4-oxo-4,5-dihydro-1H-pyrazolo[4,3-c]pyridin-1-yl}-3-cyclopropylpropanenitrile | LRMS (ESI) calc'd for $C_{18}H_{17}ClN_5O$ [M + H]$^+$: 354, found 354. |
| II-37 | (3S)-cyclopropyl-3-[3-({4-[(1-methylethyl)sulfonyl]phenyl}amino)-4-oxo-4,5-dihydro-1H-pyrazolo[4,3-c]pyridin-1-yl]propanenitrile | LRMS (ESI) calc'd for $C_{21}H_{24}N_5O_3S$ [M + H]$^+$: 426, found 426. |
| II-38 | (3S)-(3-{[4-(tert-butylsulfonyl)phenyl]amino}-4-oxo-4,5-dihydro-1H-pyrazolo[4,3-c]pyridin-1-yl)-3-cyclopropylpropanenitrile | LRMS (ESI) calc'd for $C_{22}H_{26}N_5O_3S$ [M + H]$^+$: 440, found 440. |
| II-39 | N-tert-butyl-4-{[1S-(2-cyano-1-cyclopropylethyl)-4-oxo-4,5-dihydro-1H-pyrazolo[4,3-c]pyridin-3-yl]amino}benzenesulfonamide | LRMS (ESI) calc'd for $C_{22}H_{27}N_6O_3S$ [M + H]$^+$: 455, found 455. |
| II-40 | (3S)-3-[3-({4-[(1R or 1S)-1-amino-2,2,2-trifluoroethyl]phenyl}amino)-4-oxo-4,5-dihydro-1H-pyrazolo[4,3-c]pyridin-1-yl]-3-cyclopropylpropanenitrile | LRMS (ESI) calc'd for $C_{24}H_{28}F_3N_6O$ [M + H]$^+$: 473, found 473 |
| II-40 | (3S)-3-[3-({4-[(1S or 1R)-1-amino-2,2,2-trifluoroethyl]phenyl}amino)-4-oxo-4,5-dihydro-1H-pyrazolo[4,3-c]pyridin-1-yl]-3-cyclopropylpropanenitrile | LRMS (ESI) calc'd for $C_{24}H_{28}F_3N_6O$ [M + H]$^+$: 473, found 473 |

TABLE 14-continued

| Example | Compound Name | MS |
|---------|---------------|-----|
| II-41 | 4-({1-[(1S)-2-cyano-1-cyclopropylethyl]-4-oxo-4,5-dihydro-1H-pyrazolo[4,3-c]pyridin-3-yl}amino)-N-ethyl-N-methylbenzenesulfonamide | LRMS (ESI) calc'd for $C_{21}H_{25}N_6O_3S$ [M + H]$^+$: 441, found 441 |
| II-42 | (3S)-3-cyclopropyl-3-(4-oxo-3-{[4-(piperidin-1-ylsulfonyl)phenyl]amino}-4,5-dihydro-1H-pyrazolo[4,3-c]pyridin-1-yl)propanenitrile | LRMS (ESI) calc'd for $C_{23}H_{27}N_6O_3S$ [M + H]$^+$: 467, found 467 |
| II-43 | 4-({1-[(1S)-2-cyano-1-cyclopropylethyl]-4-oxo-4,5-dihydro-1H-pyrazolo[4,3-c]pyridin-3-yl}amino)-N-methyl-N-(1-methylethyl)benzenesulfonamide | LRMS (ESI) calc'd for $C_{22}H_{27}N_6O_3S$ [M + H]$^+$: 455, found 455 |
| II-44 | 4-({1-[(1S)-2-cyano-1-cyclopropylethyl]-4-oxo-4,5-dihydro-1H-pyrazolo[4,3-c]pyridin-3-yl}amino)-N-methylbenzenesulfonamide | LRMS (ESI) calc'd for $C_{19}H_{21}N_6O_3S$ [M + H]$^+$: 413, found 413 |
| II-45 | (3S)-3-cyclopropyl-3-(4-oxo-3-{[4-(pyrrolidin-1-ylsulfonyl)phenyl]amino}-4,5-dihydro-1H-pyrazolo[4,3-c]pyridin-1-yl)propanenitrile | LRMS (ESI) calc'd for $C_{22}H_{25}N_6O_3S$ [M + H]$^+$: 453, found 453 |
| II-46 | 4-({1-[(1S)-2-cyano-1-cyclopropylethyl]-4-oxo-4,5-dihydro-1H-pyrazolo[4,3-c]pyridin-3-yl}amino)-N,N-diethylbenzenesulfonamide | LRMS (ESI) calc'd for $C_{22}H_{27}N_6O_3S$ [M + H]$^+$: 455, found 455 |

TABLE 14-continued

| Example | Compound Name | MS |
|---|---|---|
| II-47 | (3S)-3-cyclopropyl-3-[3-({4-[(3,3-dimethylpiperidin-1-yl)sulfonyl]phenyl}amino)-4-oxo-4,5-dihydro-1H-pyrazolo[4,3-c]pyridin-1-yl]propanenitrile | LRMS (ESI) calc'd for $C_{25}H_{31}N_6O_3S$ $[M + H]^+$: 495, found 495 |
| II-48 | (3S)-3-cyclopropyl-3-[3-({4-[(3,3-dimethylpyrrolidin-1-yl)sulfonyl]phenyl}amino)-4-oxo-4,5-dihydro-1H-pyrazolo[4,3-c]pyridin-1-yl]propanenitrile | LRMS (ESI) calc'd for $C_{24}H_{27}N_6O_3S$ $[M + H]^+$: 481, found 481 |
| II-49 | (3S)-3-{3-[(2-tert-butyl-1-oxo-2,3-dihydro-1H-isoindol-5-yl)amino]-4-oxo-4,5-dihydro-1H-pyrazolo[4,3-c]pyridin-1-yl}-3-cyclopropylpropanenitrile | LRMS (ESI) calc'd for $C_{24}H_{27}N_6O_2$ $[M + H]^+$: 431, found 431 |
| II-50 | (3S)-3-{3-[(2-cyclopentyl-1-oxo-2,3-dihydro-1H-isoindol-5-yl)amino]-4-oxo-4,5-dihydro-1H-pyrazolo[4,3-c]pyridin-1-yl}-3-cyclopropylpropanenitrile | LRMS (ESI) calc'd for $C_{25}H_{27}N_6O_2$ $[M + H]^+$: 443, found 443 |
| II-51 | (3S)-3-{3-[(2-cyclohexyl-1-oxo-2,3-dihydro-1H-isoindol-5-yl)amino]-4-oxo-4,5-dihydro-1H-pyrazolo[4,3-c]pyridin-1-yl}-3-cyclopropylpropanenitrile | LRMS (ESI) calc'd for $C_{26}H_{29}N_6O_2$ $[M + H]^+$: 457, found 457 |
| II-52 | (3S)-3-cyclopropyl-3-[3-({4-[(2,2-dimethylpiperidin-1-yl)sulfonyl]phenyl}amino)-4-oxo-4,5-dihydro-1H-pyrazolo[4,3-c]pyridin-1-yl]propanenitrile | LRMS (ESI) calc'd for $C_{25}H_{31}N_6O_3S$ $[M + H]^+$: 495, found 495 |

TABLE 14-continued

| Example | Compound Name | MS |
|---|---|---|
| II-53 | tert-butyl 1-{[4-({1-[(1S)-2-cyano-1-cyclopropylethyl]-4-oxo-4,5-dihydro-1H-pyrazolo[4,3-c]pyridin-3-yl}amino)phenyl]sulfonyl}piperidine-4-carboxylate | LRMS (ESI) calc'd for $C_{28}H_{35}N_6O_5S$ [M + H]$^+$: 567, found 567 |
| II-54 | (3S)-3-cyclopropyl-3-{3-[(4-{[(3S)-3-hydroxypyrrolidin-1-yl]sulfonyl}phenyl)amino]-4-oxo-4,5-dihydro-1H-pyrazolo[4,3-c]pyridin-1-yl}propanenitrile | LRMS (ESI) calc'd for $C_{22}H_{25}N_6O_4S$ [M + H]$^+$: 469, found 469 |
| II-55 | (3S)-3-cyclopropyl-3-{3-[(4-{[(3R)-3-hydroxypyrrolidin-1-yl]sulfonyl}phenyl)amino]-4-oxo-4,5-dihydro-1H-pyrazolo[4,3-c]pyridin-1-yl}propanenitrile | LRMS (ESI) calc'd for $C_{22}H_{25}N_6O_4S$ [M + H]$^+$: 469, found 469 |
| II-56 | tert-butyl 1-{[4-({1-[(1S)-2-cyano-1-cyclopropylethyl]-4-oxo-4,5-dihydro-1H-pyrazolo[4,3-c]pyridin-3-yl}amino)phenyl]sulfonyl}-D-prolinate | LRMS (ESI) calc'd for $C_{27}H_{33}N_6O_5S$ [M + H]$^+$: 553, found 553 |
| II-57 | (3S)-3-cyclopropyl-3-{4-oxo-3-[(4-{[(3R or 3S)-3-(trifluoromethyl)pyrrolidin-1-yl]sulfonyl}phenyl)amino]-4,5-dihydro-1H-pyrazolo[4,3-c]pyridin-1-yl}propanenitrile | LRMS (ESI) calc'd for $C_{23}H_{24}F_3N_6O_3S$ [M + H]$^+$: 521, found 521 |

TABLE 14-continued

| Example | Structure | Compound Name | MS |
|---|---|---|---|
| II-58 | 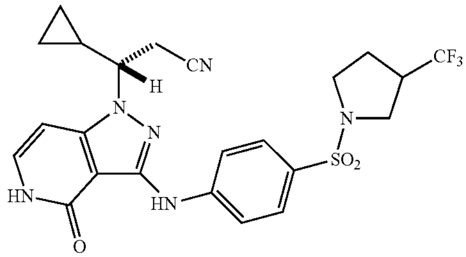 [SMILES: N#CC[C@@H](C1CC1)n1nc(Nc2ccc(S(=O)(=O)N3CCC(C(F)(F)F)C3)cc2)c2c(=O)[nH]ccc21] | (3S)-3-cyclopropyl-3-{4-oxo-3-[(4-{[(3R or 3S)-3-(trifluoromethyl)pyrrolidin-1-yl]sulfonyl}phenyl)amino]-4,5-dihydro-1H-pyrazolo[4,3-c]pyridin-1-yl}propanenitrile | LRMS (ESI) calc'd for $C_{23}H_{24}F_3N_6O_3S$ $[M + H]^+$: 521, found 521 |
| II-59 | 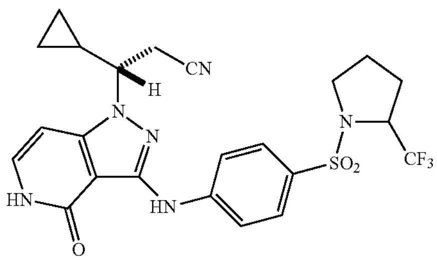 [SMILES: N#CC[C@@H](C1CC1)n1nc(Nc2ccc(S(=O)(=O)N3CCCC3C(F)(F)F)cc2)c2c(=O)[nH]ccc21] | (3S)-3-cyclopropyl-3-{4-oxo-3-[(4-{[(2R or 2S)-2-(trifluoromethyl)pyrrolidin-1-yl]sulfonyl}phenyl)amino]-4,5-dihydro-1H-pyrazolo[4,3-c]pyridin-1-yl}propanenitrile | LRMS (ESI) calc'd for $C_{23}H_{24}F_3N_6O_3S$ $[M + H]^+$: 521, found 521 |
| II-60 | 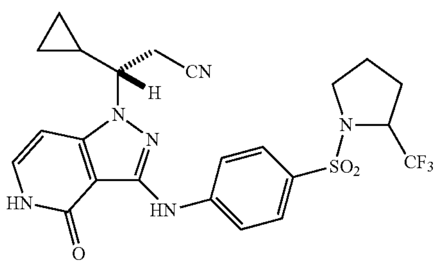 [SMILES: N#CC[C@@H](C1CC1)n1nc(Nc2ccc(S(=O)(=O)N3CCCC3C(F)(F)F)cc2)c2c(=O)[nH]ccc21] | (3S)-3-cyclopropyl-3-{4-oxo-3-[(4-{[(2R or 2S)-2-(trifluoromethyl)pyrrolidin-1-yl]sulfonyl}phenyl)amino]-4,5-dihydro-1H-pyrazolo[4,3-c]pyridin-1-yl}propanenitrile | LRMS (ESI) calc'd for $C_{23}H_{23}F_3N_6O_3S$ $[M + H]^+$: 521, found 521 |
| II-61 | 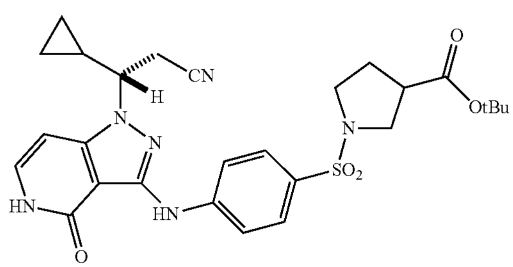 [SMILES: CC(C)(C)OC(=O)C1CCN(S(=O)(=O)c2ccc(Nc3nn([C@@H](CC#N)C4CC4)c4cc[nH]c(=O)c34)cc2)C1] | tert-butyl (3S)-1-{[4-({1-[(1R or 1S)-2-cyano-1-cyclopropylethyl]-4-oxo-4,5-dihydro-1H-pyrazolo[4,3-c]pyridin-3-yl}amino)phenyl]sulfonyl}pyrrolidine-3-carboxylate (derived fron Bn protected intermediate peak 1, SFC retention time (Chiralpak, IB, 30% isopropanol in $CO_2$) = 9.44 minutes) | LRMS (ESI) calc'd for $C_{27}H_{33}F_3N_6O_5S$ $[M + H]^+$: 553, found 553 |
| II-62 | 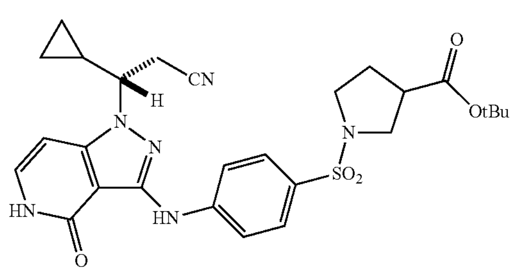 [SMILES: CC(C)(C)OC(=O)C1CCN(S(=O)(=O)c2ccc(Nc3nn([C@@H](CC#N)C4CC4)c4cc[nH]c(=O)c34)cc2)C1] | tert-butyl (3S)-1-{[4-({1-[(1R or 1S)-2-cyano-1-cyclopropylethyl]-4-oxo-4,5-dihydro-1H-pyrazolo[4,3-c]pyridin-3 yl}amino)phenyl]sulfonyl}pyrrolidine-3-carboxylate (derived fron Bn protected intermediate peak 2, SFC retention time (Chiralpak, IB, 30% isopropanol in $CO_2$) = 10.53 minutes) | LRMS (ESI) calc'd for $C_{27}H_{33}F_3N_6O_5S$ $[M + H]^+$: 553, found 553 |
| II-63 | 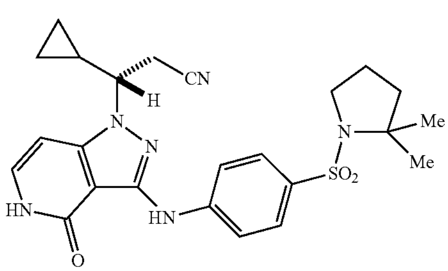 [SMILES: CC1(C)CCCN1S(=O)(=O)c1ccc(Nc2nn([C@@H](CC#N)C3CC3)c3cc[nH]c(=O)c23)cc1] | (3S)-3-cyclopropyl-3-[3-({4-[(2,2-dimethylpyrrolidin-1-yl)sulfonyl]phenyl}amino)-4-oxo-4,5-dihydro-1H-pyrazolo[4,3-c]pyridin-1-yl]propanenitrile | LRMS (ESI) calc'd for $C_{24}H_{29}N_6O_3S$ $[M + H]^+$: 481, found 481 |

TABLE 14-continued

| Example | Compound Name | MS |
|---|---|---|
| II-64 | (3S)-3-cyclopropyl-3-{3-[(4-{[(2R or 2S)-2-methylpyrrolidin-1-yl]sulfonyl}phenyl)amino]-4-oxo-4,5-dihydro-1H-pyrazolo[4,3-c]pyridin-1-yl}propanenitrile | LRMS (ESI) calc'd for $C_{23}H_{27}N_6O_3S$ $[M + H]^+$: 467, found 467 |
| II-65 | (3S)-3-cyclopropyl-3-{3-[(4-{[(2R or 2S)-2-methylpyrrolidin-1-yl]sulfonyl}phenyl)amino]-4-oxo-4,5-dihydro-1H-pyrazolo[4,3-c]pyridin-1-yl}propanenitrile | LRMS (ESI) calc'd for $C_{23}H_{27}N_6O_3S$ $[M + H]^+$: 467, found 467 |
| II-66 | (3S)-3-(3-{[4-(azetidin-1-ylsulfonyl)phenyl]amino}-4-oxo-4,5-dihydro-1H-pyrazolo[4,3-c]pyridin-1-yl)-3-cyclopropylpropanenitrile | LRMS (ESI) calc'd for $C_{21}H_{23}N_6O_3S$ $[M + H]^+$: 439, found 439 |
| II-67 | (3S)-3-cyclopropyl-3-(3-{[4-(morpholin-4-ylsulfonyl)phenyl]amino}-4-oxo-4,5-dihydro-1H-pyrazolo[4,3-c]pyridin-1-yl)propanenitrile | LRMS (ESI) calc'd for $C_{22}H_{25}N_6O_4S$ $[M + H]^+$: 469, found 469 |
| II-68 | (3S)-3-cyclopropyl-3-[3-({4-[(3,3-dimethylazetidin-1-yl)sulfonyl]phenyl}amino)-4-oxo-4,5-dihydro-1H-pyrazolo[4,3-c]pyridin-1-yl]propanenitrile | LRMS (ESI) calc'd for $C_{23}H_{27}N_6O_3S$ $[M + H]^+$: 467, found 467 |
| II-69 | (3S)-3-cyclopropyl-3-[3-({4-[(3-methylazetidin-1-yl)sulfonyl]phenyl}amino)-4-oxo-4,5-dihydro-1H-pyrazolo[4,3-c]pyridin-1-yl]propanenitrile | LRMS (ESI) calc'd for $C_{22}H_{25}N_6O_3S$ $[M + H]^+$: 453, found 453 |

TABLE 14-continued

| Example | Structure | Compound Name | MS |
|---|---|---|---|
| II-70 | 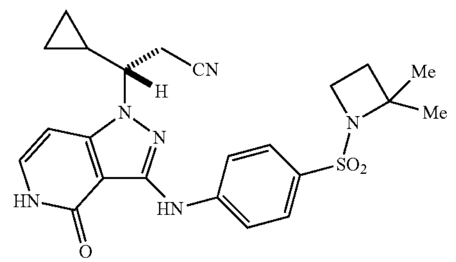 [SMILES: CC1(C)CCN1S(=O)(=O)c1ccc(Nc2nn([C@@H](CC#N)C3CC3)c3cc[nH]c(=O)c23)cc1] | (3S)-3-cyclopropyl-3-[3-({4-[(2,2-dimethylazetidin-1-yl)sulfonyl]phenyl}amino)-4-oxo-4,5-dihydro-1H-pyrazolo[4,3-c]pyridin-1-yl]propanenitrile | LRMS (ESI) calc'd for $C_{23}H_{27}N_6O_3S$ $[M + H]^+$: 467, found 467 |
| II-71 | 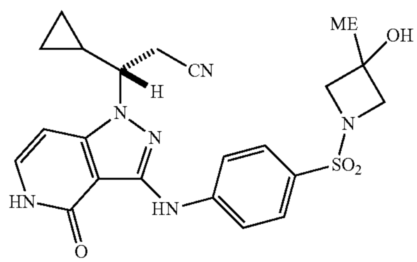 | (3S)-3-cyclopropyl-3-[3-({4-[(3-hydroxy-3-methylazetidin-1-yl)sulfonyl]phenyl}amino)-4-oxo-4,5-dihydro-1H-pyrazolo[4,3-c]pyridin-1-yl]propanenitrile | LRMS (ESI) calc'd for $C_{22}H_{25}N_6O_4S$ $[M + H]^+$: 469, found 469 |
| II-72 | 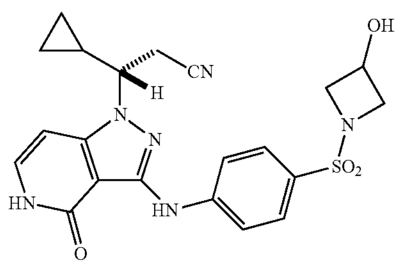 [SMILES: N#CC[C@@H](C1CC1)n1nc(Nc2ccc(S(=O)(=O)N3CC(O)C3)cc2)c2c(=O)[nH]ccc21] | (3S)-3-cyclopropyl-3-[3-({4-[(3-hydroxyazetidin-1-yl)sulfonyl]phenyl}amino)-4-oxo-4,5-dihydro-1H-pyrazolo[4,3-c]pyridin-1-yl]propanenitrile | LRMS (ESI) calc'd for $C_{21}H_{23}N_6O_4S$ $[M + H]^+$: 455, found 455 |
| II-73 | 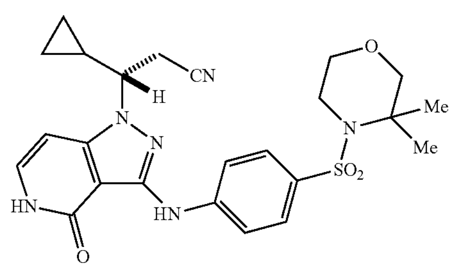 [SMILES: CC1(C)COCCN1S(=O)(=O)c1ccc(Nc2nn([C@@H](CC#N)C3CC3)c3cc[nH]c(=O)c23)cc1] | (3S)-3-cyclopropyl-3-[3-({4-[(3,3-dimethylmorpholin-4-yl)sulfonyl]phenyl}amino)-4-oxo-4,5-dihydro-1H-pyrazolo[4,3-c]pyridin-1-yl]propanenitrile | LRMS (ESI) calc'd for $C_{24}H_{29}N_6O_4S$ $[M + H]^+$: 497, found 497 |
| II-74 | 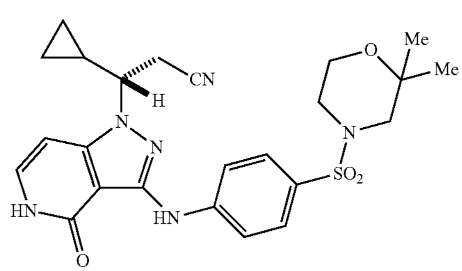 [SMILES: CC1(C)CN(S(=O)(=O)c2ccc(Nc3nn([C@@H](CC#N)C4CC4)c4cc[nH]c(=O)c34)cc2)CCO1] | (3S)-3-cyclopropyl-3-[3-({4-[(2,2-dimethylmorpholin-4-yl)sulfonyl]phenyl}amino)-4-oxo-4,5-dihydro-1H-pyrazolo[4,3-c]pyridin-1-yl]propanenitrile | LRMS (ESI) calc'd for $C_{24}H_{29}N_6O_4S$ $[M + H]^+$: 497, found 497 |
| II-75 | 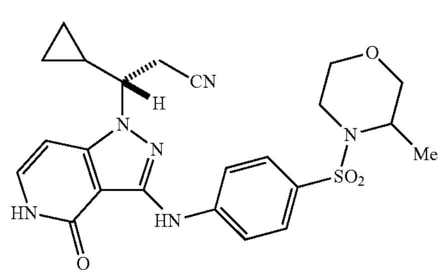 [SMILES: CC1COCCN1S(=O)(=O)c1ccc(Nc2nn([C@@H](CC#N)C3CC3)c3cc[nH]c(=O)c23)cc1] | (3S)-3-cyclopropyl-3-{3-[(4-{[(3R or 3S)-3-methylmorpholin-4-yl]sulfonyl}phenyl)amino]-4-oxo-4,5-dihydro-1H-pyrazolo[4,3-c]pyridin-1-yl}propanenitrile | LRMS (ESI) calc'd for $C_{23}H_{27}N_6O_4S$ $[M + H]^+$: 483, found 483 |

TABLE 14-continued

| Example | Structure | Compound Name | MS |
|---|---|---|---|
| II-76 | 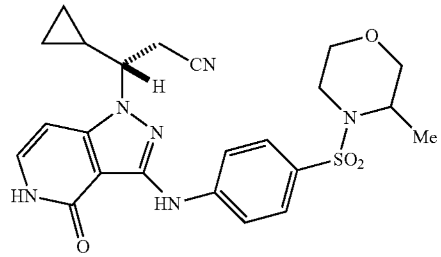 [SMILES: CC1COCCN1S(=O)(=O)c1ccc(Nc2nn([C@@H](CC#N)C3CC3)c3cc[nH]c(=O)c23)cc1] | (3S)-3-cyclopropyl-3-{3-[(4-{[(3R or 3S)-3-methylmorpholin-4-yl]sulfonyl}phenyl)amino]-4-oxo-4,5-dihydro-1H-pyrazolo[4,3-c]pyridin-1-yl}propanenitrile | LRMS (ESI) calc'd for $C_{23}H_{27}N_6O_4S$ [M + H]$^+$: 483, found 483 |
| II-77 | 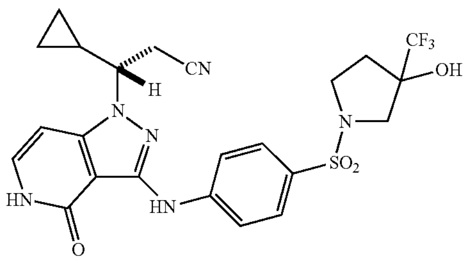 [SMILES: N#CC[C@@H](C1CC1)n1nc(Nc2ccc(S(=O)(=O)N3CCC(O)(C(F)(F)F)C3)cc2)c2c(=O)[nH]ccc21] | (3S)-3-cyclopropyl-3-{3-[(4-{[(3R or 3S)-3-hydroxy-3-(trifluoromethyl)pyrrolidin-1-yl]sulfonyl}phenyl)amino]-4-oxo-4,5-dihydro-1H-pyrazolo[4,3-c]pyridin-1-yl}propanenitrile | LRMS (ESI) calc'd for $C_{23}H_{24}F_3N_6O_4S$ [M + H]$^+$: 537, found 537 |
| II-78 | 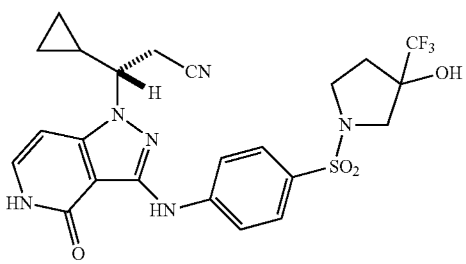 [SMILES: N#CC[C@@H](C1CC1)n1nc(Nc2ccc(S(=O)(=O)N3CCC(O)(C(F)(F)F)C3)cc2)c2c(=O)[nH]ccc21] | (3S)-3-cyclopropyl-3-{3-[(4-{[(3R or 3S)-3-hydroxy-3-(trifluoromethyl)pyrrolidin-1-yl]sulfonyl}phenyl)amino]-4-oxo-4,5-dihydro-1H-pyrazolo[4,3-c]pyridin-1-yl}propanenitrile | LRMS (ESI) calc'd for $C_{23}H_{24}F_3N_6O_4S$ [M + H]$^+$: 537, found 537 |
| II-79 | 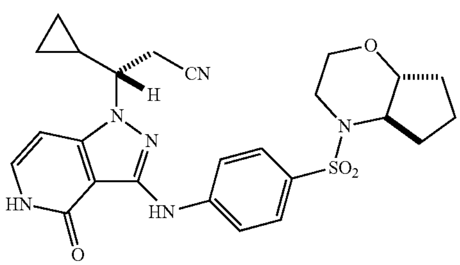 | (3S)-3-cyclopropyl-3-[3-({4-[(4aR,7aR or 4aS,7aS)-hexahydro-cyclopenta[b][1,4]oxazin-4(4aH)-ylsulfonyl]phenyl}amino)-4-oxo-4,5-dihydro-1H-pyrazolo[4,3-c]pyridin-1-yl]propanenitrile | LRMS (ESI) calc'd for $C_{25}H_{29}N_6O_4S$ [M + H]$^+$: 509, found 509 |
| II-80 | 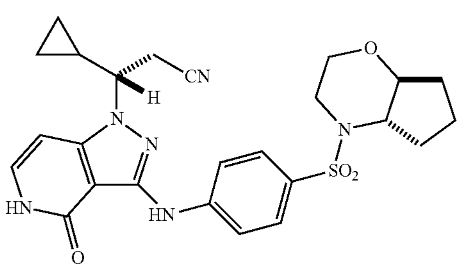 | (3S)-3-cyclopropyl-3-[3-({4-[(4aR,7aR or 4aS,7aS)-hexahydro-cyclopenta[b][1,4]oxazin-4(4aH)-ylsulfonyl]phenyl}amino)-4-oxo-4,5-dihydro-1H-pyrazolo[4,3-c]pyridin-1-yl]propanenitrile | LRMS (ESI) calc'd for $C_{25}H_{29}N_6O_4S$ [M + H]$^+$: 509, found 509 |
| II-81 | 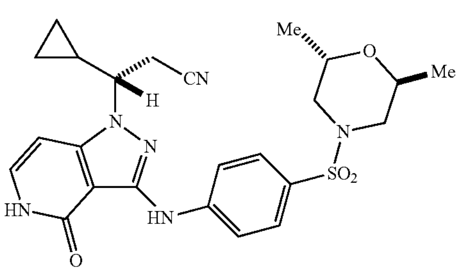 [SMILES: C[C@H]1CN(S(=O)(=O)c2ccc(Nc3nn([C@@H](CC#N)C4CC4)c4cc[nH]c(=O)c34)cc2)C[C@H](C)O1] | (3S)-3-cyclopropyl-3-{3-[(4-{[(2S,6S)-2,6-dimethylmorpholin-4-yl]sulfonyl}phenyl)amino]-4-oxo-4,5-dihydro-1H-pyrazolo[4,3-c]pyridin-1-yl}propanenitrile | LRMS (ESI) calc'd for $C_{24}H_{29}N_6O_4S$ [M + H]$^+$: 497, found 497 |

TABLE 14-continued

| Example | Structure | Compound Name | MS |
|---|---|---|---|
| II-82 | 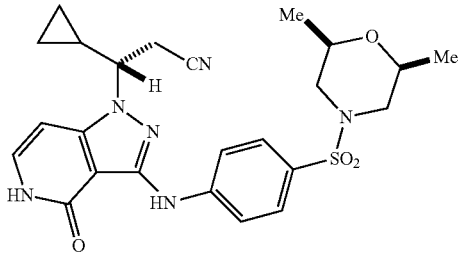 [SMILES: C[C@@H]1CN(S(=O)(=O)c2ccc(Nc3nn([C@@H](CC#N)C4CC4)c4cc[nH]c(=O)c34)cc2)C[C@H](C)O1] | (3S)-3-cyclopropyl-3-{3-[(4-{[(2R,6S)-2,6-dimethyl-morpholin-4-yl]sulfonyl}phenyl)amino]-4-oxo-4,5-dihydro-1H-pyrazolo[4,3-c]pyridin-1-yl}propanenitrile | LRMS (ESI) calc'd for $C_{24}H_{29}N_6O_4S$ [M + H]$^+$: 497, found 497 |
| II-83 | 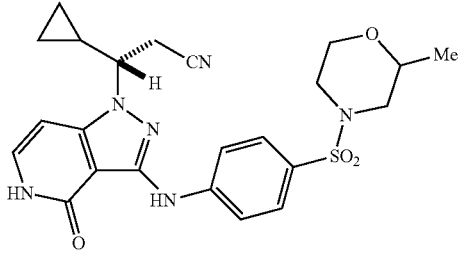 [SMILES: CC1CN(S(=O)(=O)c2ccc(Nc3nn([C@@H](CC#N)C4CC4)c4cc[nH]c(=O)c34)cc2)CCO1] | (3S)-3-cyclopropyl-3-(3-[(4-{[(2R or 2S)-2-methylmorpholin-4-yl]sulfonyl}phenyl)amino]-4-oxo-4,5-dihydro-1H-pyrazolo[4,3-c]pyridin-1-yl}propanenitrile | LRMS (ESI) calc'd for $C_{23}H_{27}N_6O_4S$ [M + H]$^+$: 483, found 483 |
| II-84 | 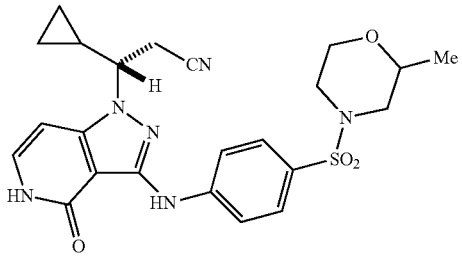 [SMILES: CC1CN(S(=O)(=O)c2ccc(Nc3nn([C@@H](CC#N)C4CC4)c4cc[nH]c(=O)c34)cc2)CCO1] | (3S)-3-cyclopropyl-3-{3-[(4-{[(2R or 2S)-2-methyl-morpholin-4-yl]sulfonyl}phenyl)amino]-4-oxo-4,5-dihydro-1H-pyrazolo[4,3-c]pyridin-1-yl}propanenitrile | LRMS (ESI) calc'd for $C_{23}H_{27}N_6O_4S$ [M + H]$^+$: 483, found 483 |
| II-85 | 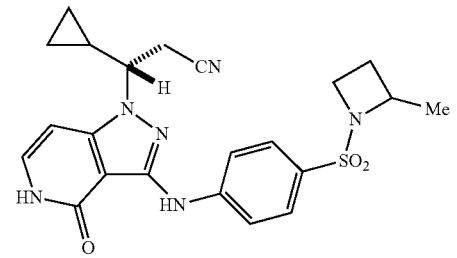 [SMILES: CC1CCN1S(=O)(=O)c1ccc(Nc2nn([C@@H](CC#N)C3CC3)c3cc[nH]c(=O)c23)cc1] | (3S)-3-cyclopropyl-3-{3-[(4-{[(2R or 2S)-2-methylazetidin-1-yl]sulfonyl}phenyl)amino]-4-oxo-4,5-dihydro-1H-pyrazolo[4,3-c]pyridin-1-yl}propanenitrile | LRMS (ESI) calc'd for $C_{22}H_{25}N_6O_3S$ [M + H]$^+$: 453, found 453 |
| II-86 | 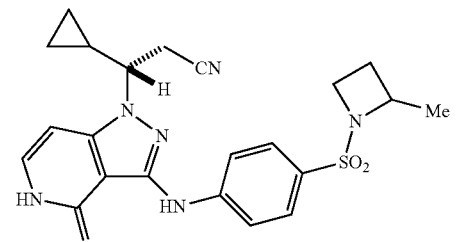 | (3S)-3-cyclopropyl-3-{3-[(4-{[(2R or 2S)-2-methylazetidin-1-yl]sulfonyl}phenyl)amino]-4-oxo-4,5-dihydro-1H-pyrazolo[4,3-c]pyridin-1-yl}propanenitrile | LRMS (ESI) calc'd for $C_{22}H_{25}N_6O_3S$ [M + H]$^+$: 453, found 453 |
| II-87 | 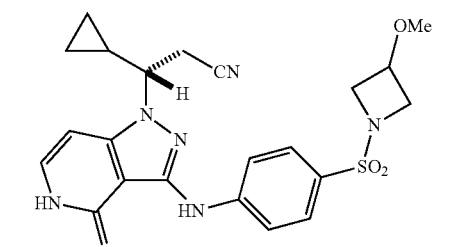 | (3S)-3-cyclopropyl-3-[3-({4-[(3-methoxyazetidin-1-yl)sulfonyl]phenyl}amino)-4-oxo-4,5-dihydro-1H-pyrazolo[4,3-c]pyridin-1-yl]propanenitrile | LRMS (ESI) calc'd for $C_{22}H_{25}N_6O_4S$ [M + H]$^+$: 469, found 469 |

TABLE 14-continued

| Example | Structure | Compound Name | MS |
|---|---|---|---|
| II-88 | 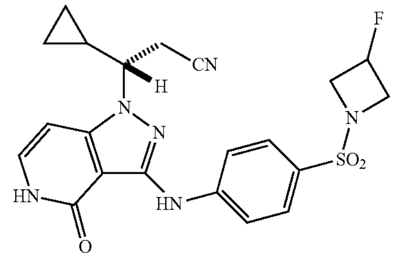 [SMILES: N#CC[C@@H](C1CC1)n1nc(Nc2ccc(S(=O)(=O)N3CC(F)C3)cc2)c2c(=O)[nH]ccc21] | (3S)-3-cyclopropyl-3-[3-({4-[(3-fluoroazetidin-1-yl)sulfonyl]phenyl}amino)-4-oxo-4,5-dihydro-1H-pyrazolo[4,3-c]pyridin-1-yl]propanenitrile | LRMS (ESI) calc'd for $C_{21}H_{22}FN_6O_3S$ $[M + H]^+$: 457, found 457 |
| II-89 | 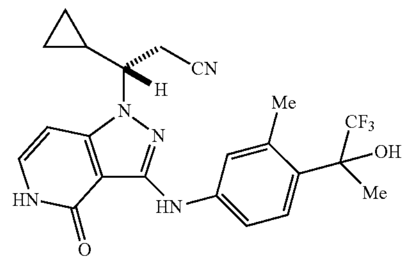 [SMILES: Cc1cc(Nc2nn([C@@H](CC#N)C3CC3)c3cc[nH]c(=O)c23)ccc1C(C)(O)C(F)(F)F] | (3S)-3-cyclopropyl-3-[3-({3-methyl-4-[(1R or 1S)-2,2,2-trifluoro-1-hydroxy-1-methylethyl]phenyl}amino)-4-oxo-4,5-dihydro-1H-pyrazolo[4,3-c]pyridin-1-yl]propanenitrile | LRMS (ESI) calc'd for $C_{22}H_{23}F_3N_5O_2$ $[M + H]^+$: 446, found 446 |
| II-90 | 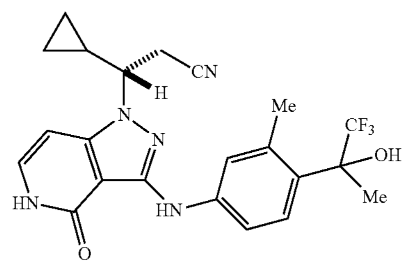 [SMILES: Cc1cc(Nc2nn([C@@H](CC#N)C3CC3)c3cc[nH]c(=O)c23)ccc1C(C)(O)C(F)(F)F] | (3S)-3-cyclopropyl-3-[3-({3-methyl-4-[(1R or 1S)-2,2,2-trifluoro-1-hydroxy-1-methylethyl]phenyl}amino)-4-oxo-4,5-dihydro-1H-pyrazolo[4,3-c]pyridin-1-yl]propanenitrile | LRMS (ESI) calc'd for $C_{22}H_{23}F_3N_5O_2$ $[M + H]^+$: 446, found 446 |
| II-91 | 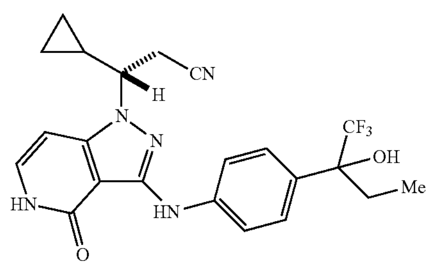 [SMILES: CCC(O)(c1ccc(Nc2nn([C@@H](CC#N)C3CC3)c3cc[nH]c(=O)c23)cc1)C(F)(F)F] | (3S)-3-cyclopropyl-3-[3-({4-[(1R or 1S)-1-hydroxy-1-(trifluoromethyl)propyl]phenyl}amino)-4-oxo-4,5-dihydro-1H-pyrazolo[4,3-c]pyridin-1-yl]propanenitrile | LRMS (ESI) calc'd for $C_{22}H_{23}F_3N_5O_2$ $[M + H]^+$: 446, found 446 |
| II-92 | 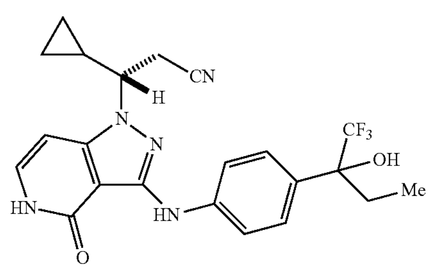 [SMILES: CCC(O)(c1ccc(Nc2nn([C@@H](CC#N)C3CC3)c3cc[nH]c(=O)c23)cc1)C(F)(F)F] | (3S)-3-cyclopropyl-3-[3-({4-[(1R or 1S)-1-hydroxy-1-(trifluoromethyl)propyl]phenyl}amino)-4-oxo-4,5-dihydro-1H-pyrazolo[4,3-c]pyridin-1-yl]propanenitrile | LRMS (ESI) calc'd for $C_{22}H_{23}F_3N_5O_2$ $[M + H]^+$: 446, found 446 |
| II-93 | 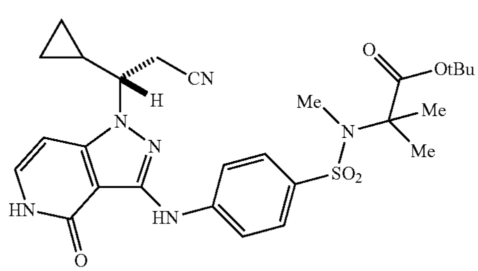 [SMILES: CN(C(C)(C)C(=O)OC(C)(C)C)S(=O)(=O)c1ccc(Nc2nn([C@@H](CC#N)C3CC3)c3cc[nH]c(=O)c23)cc1] | (S)-tert-butyl 2-(4-((1-(2-cyano-1-cyclopropylethyl)-4-oxo-4,5-dihydro-1H-pyrazolo[4,3-c]pyridin-3-yl)amino)-N-methylphenylsulfonamido)-2-methylpropanoate | LRMS (ESI) calc'd for $C_{27}H_{35}N_6O_5S$ $[M + H]^+$: 555, found 555 |

TABLE 14-continued

| Example | Structure | Compound Name | MS |
|---|---|---|---|
| II-94 | 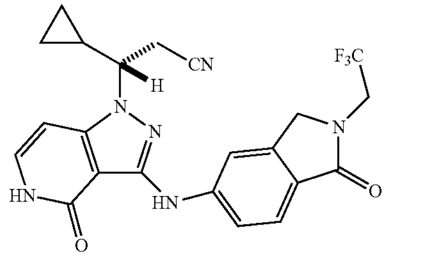 [SMILES: N#CC[C@@H](C1CC1)n1nc(Nc2ccc3c(c2)CN(CC(F)(F)F)C3=O)c2c(=O)[nH]ccc21] | (S)-3-cyclopropyl-3-(4-oxo-3-((1-oxo-2-(2,2,2-trifluoroethyl)isoindolin-5-yl)amino)-4,5-dihydro-1H-pyrazolo[4,3-c]pyridin-1-yl)propanenitrile | LRMS (ESI) calc'd for $C_{22}H_{20}F_3N_6O_2$ $[M + H]^+$: 457, found 457 |
| II-95 | 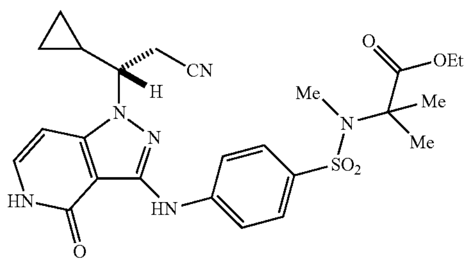 [SMILES: CCOC(=O)C(C)(C)N(C)S(=O)(=O)c1ccc(Nc2nn([C@@H](CC#N)C3CC3)c3cc[nH]c(=O)c23)cc1] | (S)-ethyl 2-(4-((1-(2-cyano-1-cyclopropylethyl)-4-oxo-4,5-dihydro-1H-pyrazolo[4,3-c]pyridin-3-yl)amino)-N-methylphenylsulfonamido)-2-methylpropanoate | LRMS (ESI) calc'd for $C_{25}H_{31}N_6O_5S$ $[M + H]^+$: 527, found 527 |
| II-96 | 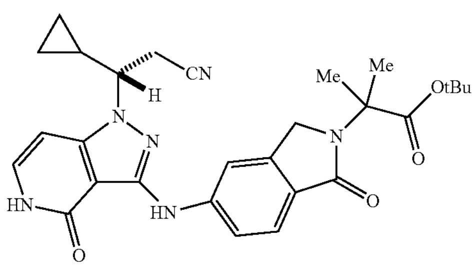 [SMILES: CC(C)(C)OC(=O)C(C)(C)N1Cc2cc(Nc3nn([C@@H](CC#N)C4CC4)c4cc[nH]c(=O)c34)ccc2C1=O] | (S)-tert-butyl 2-(5-((1-(2-cyano-1-cyclopropylethyl)-4-oxo-4,5-dihydro-1H-pyrazolo[4,3-c]pyridin-3-yl)amino)-1-oxoisoindolin-2-yl)-2-methylpropanoate | LRMS (ESI) calc'd for $C_{28}H_{33}N_6O_4$ $[M + H]^+$: 517, found 517 |
| II-97 | 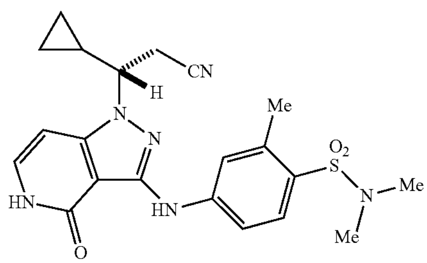 [SMILES: Cc1cc(Nc2nn([C@@H](CC#N)C3CC3)c3cc[nH]c(=O)c23)ccc1S(=O)(=O)N(C)C] | 4-({1-[(1S)-2-cyano-1-cyclopropylethyl]-4-oxo-4,5-dihydro-1H-pyrazolo[4,3-c]pyridin-3-yl}amino)-N,N,2-trimethylbenzenesulfonamide | LRMS (ESI) calc'd for $C_{21}H_{25}N_6O_3S$ $[M + H]^+$: 441, found 441. |
| II-98 | 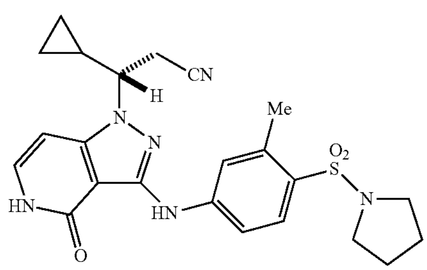 [SMILES: Cc1cc(Nc2nn([C@@H](CC#N)C3CC3)c3cc[nH]c(=O)c23)ccc1S(=O)(=O)N1CCCC1] | (3S)-3-cyclopropyl-3-(3-{[3-methyl-4-(pyrrolidin-1-ylsulfonyl)phenyl]amino}-4-oxo-4,5-dihydro-1H-pyrazolo[4,3-c]pyridin-1-yl)propanenitrile | LRMS (ESI) calc'd for $C_{23}H_{27}N_6O_3S$ $[M + H]^+$: 467, found 467. |
| II-99 | 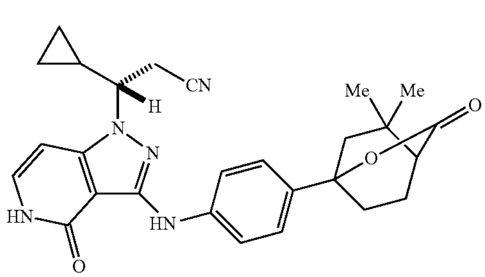 [SMILES: CC1(C)CC2(c3ccc(Nc4nn([C@@H](CC#N)C5CC5)c5cc[nH]c(=O)c45)cc3)CCC1C(=O)O2] | (3S)-3-cyclopropyl-3-(3-{[4-(5,5-dimethyl-3-oxo-2-oxabicyclo[2.2.2]oct-1-yl)phenyl]amino}-4-oxo-4,5-dihydro-1H-pyrazolo[4,3-c]pyridin-1-yl)propanenitrile (from I-8A and racemic I-X, derived from Peak 1 (OBn intermediate) obtained by SFC, Chiralpak AS-H, 20% MeOH in $CO_2$ (MeOH with 0.25% DMEA), tR = 10.9) | LRMS (ESI) calc'd for $C_{27}H_{30}N_5O_3$ $[M + H]^+$: 472, found 472. |

TABLE 14-continued

| Example | Compound Name | MS |
|---|---|---|
| II-100 | (3S)-3-cyclopropyl-3-(3-{[4-(5,5-dimethyl-3-oxo-2-oxabicyclo[2.2.2]oct-1-yl)phenyl]amino}-4-oxo-4,5-dihydro-1H-pyrazolo[4,3-c]pyridin-1-yl)propanenitrile (from I-8A and racemic I-X, derived from Peak 2 (OBn intermediate) obtained by SFC, Chiralpak AS-H, 20% MeOH in $CO_2$ (MeOH with 0.25% DMEA), tR = 14.0) | LRMS (ESI) calc'd for $C_{27}H_{30}N_5O_3$ [M + H]$^+$: 472, found 472. |
| II-101 | (3S)-3-cyclopropyl-3-[3-({4-[(1R or 1S)-1-(dimethylamino)-2,2,2-trifluoroethyl]-3-methylphenyl}amino)-4-oxo-4,5-dihydro-1H-pyrazolo[4,3-c]pyridin-1-yl]propanenitrile (SFC Peak 2, Chiralpak AD-H, 20% EtOH in $CO_2$ (EtOH with 0.25% DMEA), tR = 4.6) | LRMS (ESI) calc'd for $C_{23}H_{26}N_6OF_3$ [M + H]$^+$: 459, found 459. |
| II-102 | (3S)-3-cyclopropyl-3-[3-({4-[(1S or 1R)-1-(dimethylamino)-2,2,2-trifluoroethyl]-3-methylphenyl}amino)-4-oxo-4,5-dihydro-1H-pyrazolo[4,3-c]pyridin-1-yl]propanenitrile (SFC Peak 1, Chiralpak AD-H, 20% EtOH in $CO_2$ (EtOH with 0.25% DMEA), tR = 5.7) | LRMS (ESI) calc'd for $C_{23}H_{26}N_6OF_3$ [M + H]$^+$: 459, found 459. |
| II-103 | (3S)-3-cyclopropyl-3-[3-({4-[(1-methylcyclopropyl)sulfonyl]phenyl}amino)-4-oxo-4,5-dihydro-1H-pyrazolo[4,3-c]pyridin-1-yl]propanenitrile | LRMS (ESI) calc'd for $C_{22}H_{24}N_5O_3S$ [M + H]$^+$: 438, found 438. |
| II-104 | (3S)-3-[3-({4-[(1R or 1S)-1-(tert-butylamino)-2,2,2-trifluoroethyl]phenyl}amino)-4-oxo-4,5-dihydro-1H-pyrazolo[4,3-c]pyridin-1-yl]-3-cyclopropylpropanenitrile (SFC Peak 1, AD-H, 10% MeOH in $CO_2$, Tr = 5.83) | LRMS (ESI) calc'd for $C_{24}H_{27}F_3N_6ON$ a [M + Na]$^+$: 495, found 495 |
| II-105 | (3S)-3-[3-({4-[(1S or 1R)-1-(tert-butylamino)-2,2,2-trifluoroethyl]phenyl}amino)-4-oxo-4,5-dihydro-1H-pyrazolo[4,3-c]pyridin-1-yl]-3-cyclopropylpropanenitrile (SFC Peak 2, AD-H, 10% MeOH in $CO_2$, Tr = 6.7) | LRMS (ESI) calc'd for $C_{24}H_{27}F_3N_6ON$ a [M + Na]$^+$: 495, found 495 |

TABLE 14-continued

| Example | Structure | Compound Name | MS |
| --- | --- | --- | --- |
| II-106 | 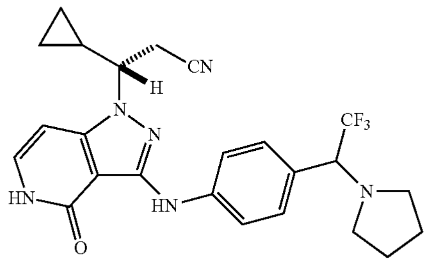 [SMILES: N#CC[C@@H](C1CC1)n1nc(Nc2ccc(C(N3CCCC3)C(F)(F)F)cc2)c2c(=O)[nH]ccc21] | (3S)-3-cyclopropyl-3-[4-oxo-3-({4-[(1R or 1S)-2,2,2-trifluoro-1-pyrrolidin-1-ylethyl]phenyl}amino-4,5-dihydro-1H-pyrazolo[4,3-c]pyridin-1-yl]propanenitrile (SFC Peak 1, OD-H, 20% MeOH in $CO_2$, Tr = 12.7) | LRMS (ESI) calc'd for $C_{24}H_{26}F_3N_6O$ [M + H]$^+$: 471, found 471 |
| II-107 | 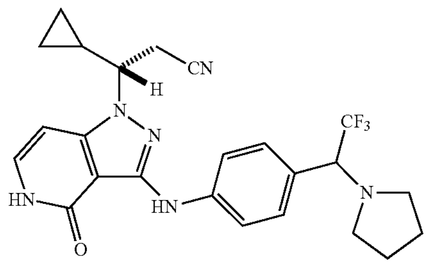 [SMILES: N#CC[C@@H](C1CC1)n1nc(Nc2ccc(C(N3CCCC3)C(F)(F)F)cc2)c2c(=O)[nH]ccc21] | (3S)-3-cyclopropyl-3-[4-oxo-3-({4-[(1S or 1R)-2,2,2-trifluoro-1-pyrrolidin-1-ylethyl]phenyl}amino-4,5-dihydro-1H-pyrazolo[4,3-c]pyridin-1-yl]propanenitrile (SFC Peak 2, OD-H, 20% MeOH in $CO_2$, Tr = 14.25) | LRMS (ESI) calc'd for $C_{24}H_{26}F_3N_6O$ [M + H]$^+$: 471, found 471 |
| II-108 | 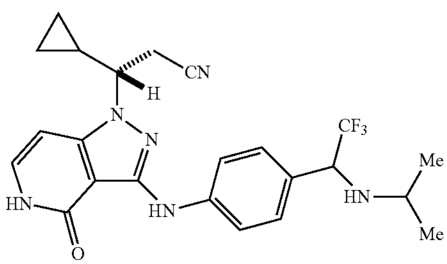 [SMILES: CC(C)NC(c1ccc(Nc2nn([C@@H](CC#N)C3CC3)c3cc[nH]c(=O)c23)cc1)C(F)(F)F] | (3S)-3-cyclopropyl-3-{4-oxo-3-[(4-{(1R or 1S)-2,2,2-trifluoro-1-[(1-methylethyl)amino]ethyl}phenyl)amino]-4,5-dihydro-1H-pyrazolo[4,3-c]pyridin-1-yl}propanenitrile (SFC Peak 1, OJ-H, 15% MeOH + 0.25% DMEA in $CO_2$, Tr = 4.06) | LRMS (ESI) calc'd for $C_{23}H_{26}F_3N_6O$ [M + H]$^+$: 459, found 459 |
| II-109 | 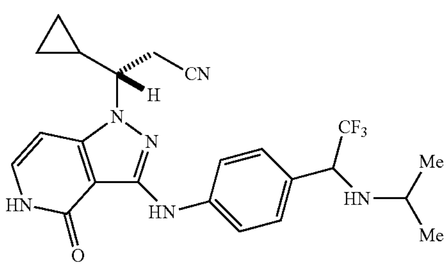 [SMILES: CC(C)NC(c1ccc(Nc2nn([C@@H](CC#N)C3CC3)c3cc[nH]c(=O)c23)cc1)C(F)(F)F] | (3S)-3-cyclopropyl-3-{4-oxo-3-[(4-{(1S or 1R)-2,2,2-trifluoro-1-[(1-methylethyl)amino]ethyl}phenyl)amino]-4,5-dihydro-1H-pyrazolo[4,3-c]pyridin-1-yl}propanenitrile (SFC Peak 2, OJ-H, 15% MeOH + 0.25% DMEA in $CO_2$, Tr = 4.97) | LRMS (ESI) calc'd for $C_{23}H_{26}F_3N_6O$ [M + H]$^+$: 459, found 459 |
| II-110 | 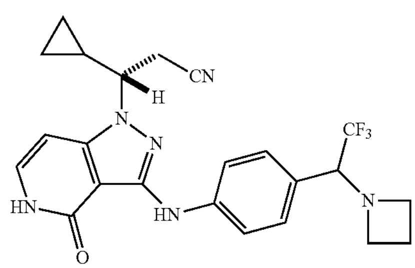 [SMILES: N#CC[C@@H](C1CC1)n1nc(Nc2ccc(C(N3CCC3)C(F)(F)F)cc2)c2c(=O)[nH]ccc21] | (3S)-3-[3-({4-[(1R or 1S)-1-azetidin-1-yl-2,2,2-trifluoroethyl]phenyl}amino)-4-oxo-4,5-dihydro-1H-pyrazolo[4,3-c]pyridin-1-yl]-3-cyclopropylpropanenitrile (SFC Peak 1, AD-H, 20% MeOH in $CO_2$, Tr = 4.61) | LRMS (ESI) calc'd for $C_{23}H_{24}F_3N_6O$ [M + H]$^+$: 457, found 457 |
| II-111 | 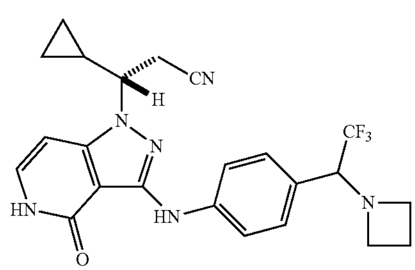 [SMILES: N#CC[C@@H](C1CC1)n1nc(Nc2ccc(C(N3CCC3)C(F)(F)F)cc2)c2c(=O)[nH]ccc21] | (3S)-3-[3-({4-[(1S or 1R)-1-azetidin-1-yl-2,2,2-trifluoroethyl]phenyl}amino)-4-oxo-4,5-dihydro-1H-pyrazolo[4,3-c]pyridin-1-yl]-3-cyclopropylpropanenitrile (SFC Peak 2, AD-H, 20% MeOH in $CO_2$, Tr = 6.05) | LRMS (ESI) calc'd for $C_{23}H_{24}F_3N_6O$ [M + H]$^+$: 457, found 457 |

TABLE 14-continued

| Example | Structure | Compound Name | MS |
|---|---|---|---|
| II-112 | 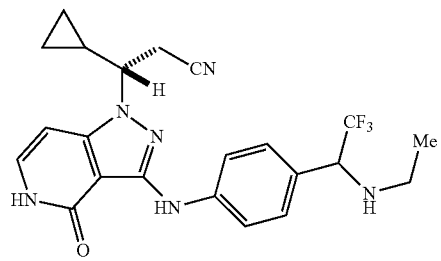 [SMILES: CCNC(c1ccc(Nc2nn([C@@H](CC#N)C3CC3)c3cc[nH]c(=O)c23)cc1)C(F)(F)F] | (3S)-3-cyclopropyl-3-[3-({4-[(1R or 1S)-1-(ethylamino)-2,2,2-trifluoroethyl]phenyl}amino)-4-oxo-4,5-dihydro-1H-pyrazolo[4,3-c]pyridin-1-yl]propanenitrile (SFC Peak 1, AD-H, 25% MeOH in CO$_2$, Tr = 3.06) | LRMS (ESI) calc'd for C$_{22}$H$_{24}$F$_3$N$_6$O [M + H]$^+$: 445, found 445 |
| II-113 | 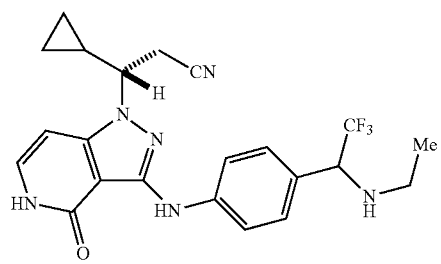 [SMILES: CCNC(c1ccc(Nc2nn([C@@H](CC#N)C3CC3)c3cc[nH]c(=O)c23)cc1)C(F)(F)F] | (3S)-3-cyclopropyl-3-[3-({4-[(1S or 1R)-1-(ethylamino)-2,2,2-trifluoroethyl]phenyl}amino)-4-oxo-4,5-dihydro-1H-pyrazolo[4,3-c]pyridin-1-yl]propanenitrile (SFC Peak 2, AD-H, 25% MeOH in CO$_2$, Tr = 6.44) | LRMS (ESI) calc'd for C$_{22}$H$_{24}$F$_3$N$_6$O [M + H]$^+$: 445, found 445 |
| II-114 | 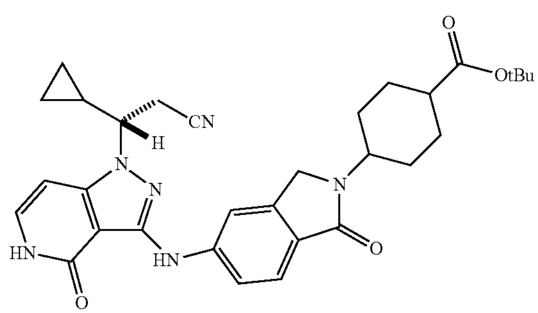 [SMILES: CC(C)(C)OC(=O)C1CCC(N2Cc3cc(Nc4nn([C@@H](CC#N)C5CC5)c5cc[nH]c(=O)c45)ccc3C2=O)CC1] | (3S)-tert-butyl 4-(5-((1-(2-cyano-1-cyclopropylethyl)-4-oxo-4,5-dihydro-1H-pyrazolo[4,3-c]pyridin-3-yl)amino)-1-oxoisoindolin-2-yl)cyclohexanecarboxylate (SFC Peak 1, ES Industries Basic, 21 × 250 (mm), 25% MeOH in CO$_2$, Tr = 4.66) | LRMS (ESI) calc'd for C$_{31}$H$_{37}$N$_6$O$_4$ [M + H]$^+$: 557, found 557 |
| II-115 | 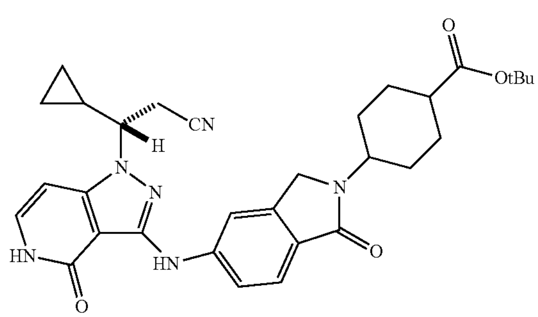 [SMILES: CC(C)(C)OC(=O)C1CCC(N2Cc3cc(Nc4nn([C@@H](CC#N)C5CC5)c5cc[nH]c(=O)c45)ccc3C2=O)CC1] | (3S)-tert-butyl 4-(5-((1-(2-cyano-1-cyclopropylethyl)-4-oxo-4,5-dihydro-1H-pyrazolo[4,3-c]pyridin-3-yl)amino)-1-oxoisoindolin-2-yl)cyclohexanecarboxylate (SFC Peak 2, ES Industries Basic, 21 × 250 (mm), 25% MeOH in CO$_2$, Tr = 5.34) | LRMS (ESI) calc'd for C$_{31}$H$_{37}$N$_6$O$_4$ [M + H]$^+$: 557, found 557 |
| II-116 | 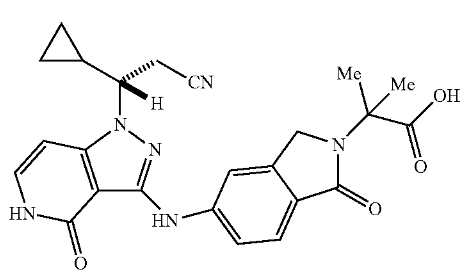 [SMILES: CC(C)(C(=O)O)N1Cc2cc(Nc3nn([C@@H](CC#N)C4CC4)c4cc[nH]c(=O)c34)ccc2C1=O] | (S)-2-(5-((1-(2-cyano-1-cyclopropylethyl)-4-oxo-4,5-dihydro-1H-pyrazolo[4,3-c]pyridin-3-yl)amino)-1-oxoisoindolin-2-yl)-2-methylpropanoic acid | LRMS (ESI) calc'd for C$_{24}$H$_{25}$N$_6$O$_4$ [M + H]$^+$: 461, found 461 |

TABLE 14-continued

| Example | Structure | Compound Name | MS |
| --- | --- | --- | --- |
| II-117 | 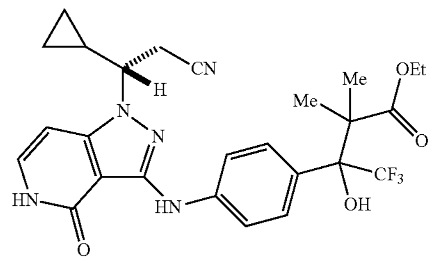 | ethyl 3-(4-((1-(S)-2-cyano-1-cyclopropylethyl)-4-oxo-4,5-dihydro-1H-pyrazolo[4,3-c]pyridin-3-yl)amino)phenyl)-4,4,4-trifluoro-3-hydroxy-2,2-dimethylbutanoate (SFC Peak 1, Chiralpak, IC, 21 × 250 (mm), 21 × 250 (mm), 25% MeOH in $CO_2$, Tr = 4.38) | LRMS (ESI) calc'd for $C_{26}H_{29}F_3N_5O_4$ [M + H]$^+$: 532, found 532 |
| II-118 | 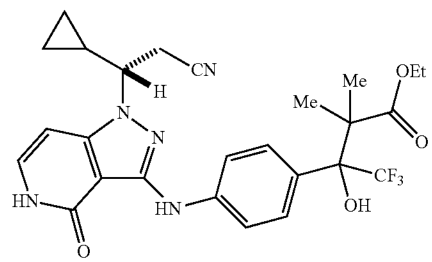 | ethyl 3-(4-((1-((S)-2-cyano-1-cyclopropylethyl)-4-oxo-4,5-dihydro-1H-pyrazolo[4,3-c]pyridin-3-yl)amino)phenyl)-4,4,4-trifluoro-3-hydroxy-2,2-dimethylbutanoate (SFC Peak 2, Chiralpak, IC, 21 × 250 (mm), 21 × 250 (mm), 25% MeOH in $CO_2$, Tr = 5.53) | LRMS (ESI) calc'd for $C_{26}H_{29}F_3N_5O_4$ [M + H]$^+$: 532, found 532 |
| II-119 | 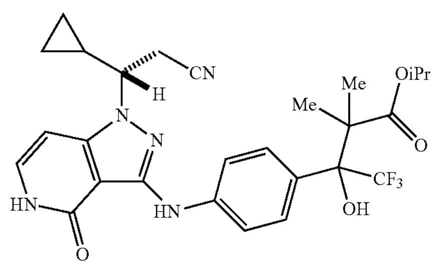 [SMILES: CC(C)OC(=O)C(C)(C)C(O)(c1ccc(Nc2nn([C@@H](CC#N)C3CC3)c3cc[nH]c(=O)c23)cc1)C(F)(F)F] | isopropyl 3-(4-((1-((S)-2-cyano-1-cyclopropylethyl)-4-oxo-4,5-dihydro-1H-pyrazolo[4,3-c]pyridin-3-yl)amino)phenyl)-4,4,4-trifluoro-3-hydroxy-2,2-dimethylbutanoate (SFC Peak 1, IC, 21 × 250 mm, 25% MeOH in $CO_2$, Tr = 3.99) | LRMS (ESI) calc'd for $C_{27}H_{31}F_3N_5O_4$ [M + H]$^+$: 546, found 546 |
| II-120 | 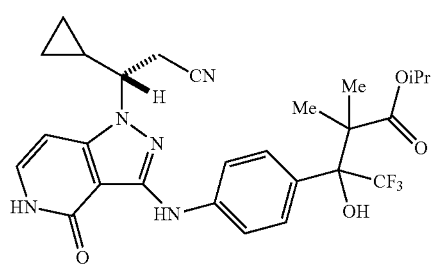 [SMILES: CC(C)OC(=O)C(C)(C)C(O)(c1ccc(Nc2nn([C@@H](CC#N)C3CC3)c3cc[nH]c(=O)c23)cc1)C(F)(F)F] | isopropyl 3-(4-((1-((S)-2-cyano-1-cyclopropylethyl)-4-oxo-4,5-dihydro-1H-pyrazolo[4,3-c]pyridin-3-yl)amino)phenyl)-4,4,4-trifluoro-3-hydroxy-2,2-dimethylbutanoate (SFC Peak 2, IC, 21 × 250 mm, 25% MeOH in $CO_2$, Tr = 4.98) | LRMS (ESI) calc'd for $C_{27}H_{31}F_3N_5O_4$ [M + H]$^+$: 546, found 546 |
| II-121 | 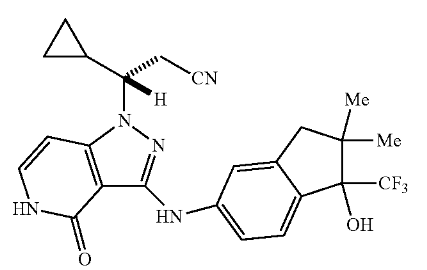 [SMILES: CC1(C)Cc2cc(Nc3nn([C@@H](CC#N)C4CC4)c4cc[nH]c(=O)c34)ccc2C1(O)C(F)(F)F] | (S)-3-cyclopropyl-3-(3-(((S or R)-1-hydroxy-2,2-dimethyl-1-(trifluoromethyl)-2,3-dihydro-1H-inden-5-yl)amino)-4-oxo-4,5-dihydro-1H-pyrazolo[4,3-c]pyridin-1-yl)propanenitrile (SFC Peak 1, Lux-4, 21 × 250 mm, 30% MeOH in $CO_2$, Tr = 3.23) | LRMS (ESI) calc'd for $C_{24}H_{25}F_3N_5O_2$ [M + H]$^+$: 472, found 472 |
| II-122 | 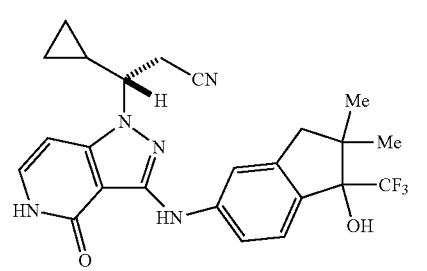 [SMILES: CC1(C)Cc2cc(Nc3nn([C@@H](CC#N)C4CC4)c4cc[nH]c(=O)c34)ccc2C1(O)C(F)(F)F] | (S)-3-cyclopropyl-3-(3-(((S or R)-1-hydroxy-2,2-dimethyl-1-(trifluoromethyl)-2,3-dihydro-1H-inden-5-yl)amino)-4-oxo-4,5-dihydro-1H-pyrazolo[4,3-c]pyridin-1-yl)propanenitrile (SFC Peak 2, Lux-4, 21 × 250 mm, 30% MeOH in $CO_2$, Tr = 4.92) | LRMS (ESI) calc'd for $C_{24}H_{25}F_3N_5O_2$ [M + H]$^+$: 472, found 472 |

TABLE 14-continued

| Example | Structure | Compound Name | MS |
|---|---|---|---|
| II-123 | 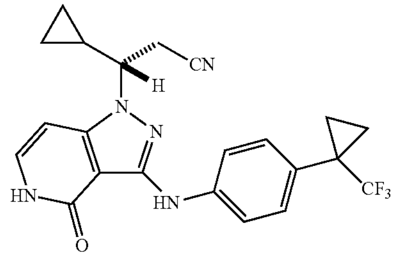 [SMILES: N#CC[C@@H](C1CC1)n1nc(Nc2ccc(C3(C(F)(F)F)CC3)cc2)c2c(=O)[nH]ccc21] | (S)-3-cyclopropyl-3-(4-oxo-3-((4-(1-(trifluoromethyl)cyclopropyl)phenyl)amino)-4,5-dihydro-1H-pyrazolo[4,3-c]pyridin-1-yl)propanenitrile | LRMS (ESI) calc'd for $C_{22}H_{21}F_3N_5O$ $[M + H]^+$: 428, found 428 |
| II-124 | 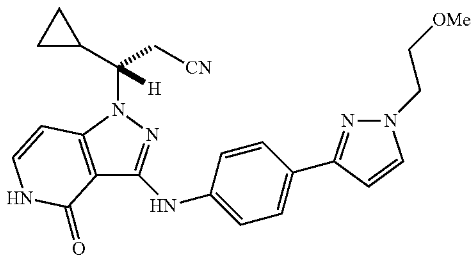 [SMILES: COCCn1ccc(-c2ccc(Nc3nn([C@@H](CC#N)C4CC4)c4cc[nH]c(=O)c34)cc2)n1] | (S)-3-cyclopropyl-3-(3-((4-(1-(2-methoxyethyl)-1H-pyrazol-3-yl)phenyl)amino)-4-oxo-4,5-dihydro-1H-pyrazolo[4,3-c]pyridin-1-yl)propanenitrile | LRMS (ESI) calc'd for $C_{24}H_{26}N_7O_2$ $[M + H]^+$: 444, found 444 |
| II-125 | 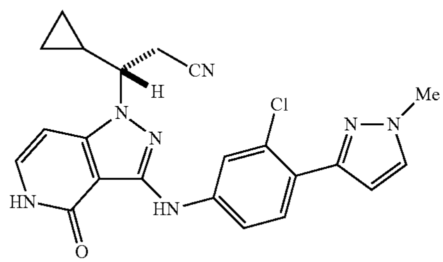 [SMILES: Cn1ccc(-c2ccc(Nc3nn([C@@H](CC#N)C4CC4)c4cc[nH]c(=O)c34)cc2Cl)n1] | (S)-3-(3-((3-chloro-4-(1-methyl-1H-pyrazol-3-yl)phenyl)amino)-4-oxo-4,5-dihydro-1H-pyrazolo[4,3-c]pyridin-1-yl)-3-cyclopropylpropanenitrile | LRMS (ESI) calc'd for $C_{22}H_{21}ClN_7O$ $[M + H]^+$: 434, found 434 |
| II-126 | 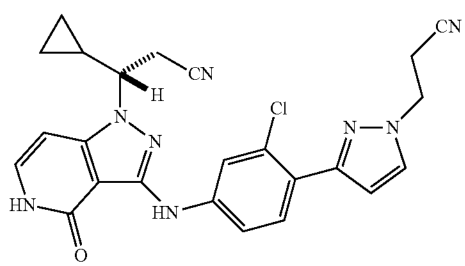 [SMILES: N#CCCn1ccc(-c2ccc(Nc3nn([C@@H](CC#N)C4CC4)c4cc[nH]c(=O)c34)cc2Cl)n1] | (S)-3-(3-((3-chloro-4-(1-(2-cyanoethyl)-1H-pyrazol-3-yl)phenyl)amino)-4-oxo-4,5-dihydro-1H-pyrazolo[4,3-c]pyridin-1-yl)-3-cyclopropylpropanenitrile | LRMS (ESI) calc'd for $C_{24}H_{23}N_8O$ $[M + H]^+$: 439, found 439 |
| II-127 | 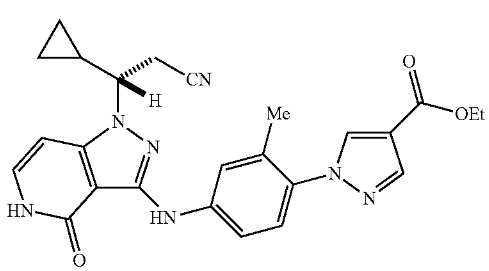 [SMILES: CCOC(=O)c1cnn(-c2ccc(Nc3nn([C@@H](CC#N)C4CC4)c4cc[nH]c(=O)c34)cc2C)c1] | (S)-ethyl 1-(4-((1-(2-cyano-1-cyclopropylethyl)-4-oxo-4,5-dihydro-1H-pyrazolo[4,3-c]pyridin-3-yl)amino)-2-methylphenyl)-1H-pyrazole-4-carboxylate | LRMS (ESI) calc'd for $C_{25}H_{26}N_7O_3$ $[M + H]^+$: 472, found 472 |
| II-128 | 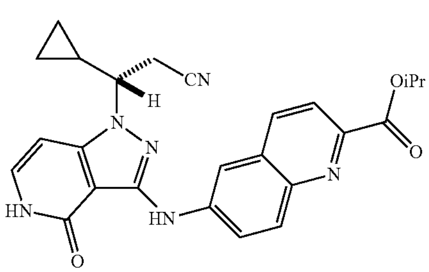 [SMILES: CC(C)OC(=O)c1ccc2cc(Nc3nn([C@@H](CC#N)C4CC4)c4cc[nH]c(=O)c34)ccc2n1] | (S)-isopropyl 6-((1-(2-cyano-1-cyclopropylethyl)-4-oxo-4,5-dihydro-1H-pyrazolo[4,3-c]pyridin-3-yl)amino)quinoline-2-carboxylate | LRMS (ESI) calc'd for $C_{25}H_{25}N_6O_3$ $[M + H]^+$: 457, found 457 |

TABLE 14-continued

| Example | Compound Name | MS |
|---------|---------------|-----|
| II-129 | (S)-3-cyclopropyl-3-(3-((2-methylbenzo[d]thiazol-6-yl)amino)-4-oxo-4,5-dihydro-1H-pyrazolo[4,3-c]pyridin-1-yl)propanenitrile | LRMS (ESI) calc'd for $C_{20}H_{19}N_6OS$ [M + H]$^+$: 391, found 391 |
| II-130 | (S)-3-cyclopropyl-3-(3-((4-(oxazol-2-yl)phenyl)amino)-4-oxo-4,5-dihydro-1H-pyrazolo[4,3-c]pyridin-1-yl)propanenitrile | LRMS (ESI) calc'd for $C_{21}H_{19}N_6O_2$ [M + H]$^+$: 387, found 387 |
| II-131 | (S)-3-cyclopropyl-3-(3-((4-(oxazol-5-yl)phenyl)amino)-4-oxo-4,5-dihydro-1H-pyrazolo[4,3-c]pyridin-1-yl)propanenitrile | LRMS (ESI) calc'd for $C_{21}H_{19}N_6O_2$ [M + H]$^+$: 387, found 387 |
| II-132 | (S)-3-cyclopropyl-3-(3-((3,3-dimethyl-2-oxoindolin-6-yl)amino)-4-oxo-4,5-dihydro-1H-pyrazolo[4,3-c]pyridin-1-yl)propanenitrile | LRMS (ESI) calc'd for $C_{22}H_{23}N_6O_2$ [M + H]$^+$: 403, found 403 |
| II-133 | (S)-3-cyclopropyl-3-(3-((4-(1,1-dioxidothiomorpholine-4-carbonyl)-3-methylphenyl)amino)-4-oxo-4,5-dihydro-1H-pyrazolo[4,3-c]pyridin-1-yl)propanenitrile | LRMS (ESI) calc'd for $C_{24}H_{27}N_6O_4S$ [M + H]$^+$: 495, found 495 |

TABLE 14-continued

| Example | Compound Name | MS |
|---|---|---|
| II-134 | (S)-4-((1-(2-cyano-1-cyclopropylethyl)-4-oxo-4,5-dihydro-1H-pyrazolo[4,3-c]pyridin-3-yl)amino)benzoic acid | LRMS (ESI) calc'd for $C_{19}H_{18}N_5O_3$ [M + H]$^+$: 364, found 364 |
| II-135 | (S)-4-((1-(2-cyano-1-cyclopropylethyl)-4-oxo-4,5-dihydro-1H-pyrazolo[4,3-c]pyridin-3-yl)amino)-N-(methylsulfonyl)benzamide | LRMS (ESI) calc'd for $C_{20}H_{21}N_6O_4S$ [M + H]$^+$: 441, found 441 |
| II-136 | (S)-3-cyclopropyl-3-(3-((2-morpholinoquinolin-6-yl)amino)-4-oxo-4,5-dihydro-1H-pyrazolo[4,3-c]pyridin-1-yl)propanenitrile | LRMS (ESI) calc'd for $C_{25}H_{26}N_7O_2$ [M + H]$^+$: 456, found 456 |
| II-137 | (S)-3-cyclopropyl-3-(3-((2-((2R,5S)-2,5-dimethylmorpholino)quinolin-6-yl)amino)-4-oxo-4,5-dihydro-1H-pyrazolo[4,3-c]pyridin-1-yl)propanenitrile | LRMS (ESI) calc'd for $C_{27}H_{30}N_7O_2$ [M + H]$^+$: 484, found 484 |
| II-138 | (S)-3-cyclopropyl-3-(3-((2-((2S,5S)-2,5-dimethylmorpholino)quinolin-6-yl)amino)-4-oxo-4,5-dihydro-1H-pyrazolo[4,3-c]pyridin-1-yl)propanenitrile | LRMS (ESI) calc'd for $C_{27}H_{30}N_7O_2$ [M + H]$^+$: 484, found 484 |
| II-139 | (S)-3-cyclopropyl-3-(3-((2-((2R,5R)-2,5-dimethylmorpholino)quinolin-6-yl)amino)-4-oxo-4,5-dihydro-1H-pyrazolo[4,3-c]pyridin-1-yl)propanenitrile | LRMS (ESI) calc'd for $C_{27}H_{30}N_7O_2$ [M + H]$^+$: 484, found 484 |

TABLE 14-continued

| Example | Structure | Compound Name | MS |
|---|---|---|---|
| II-140 | 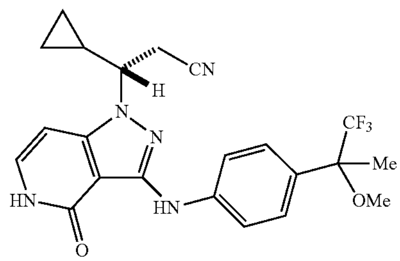 [SMILES: COC(C)(c1ccc(Nc2nn([C@@H](CC#N)C3CC3)c3cc[nH]c(=O)c23)cc1)C(F)(F)F] | (S)-3-cyclopropyl-3-(4-oxo-3-((4-((S or R)-1,1,1-trifluoro-2-methoxypropan-2-yl)phenyl)amino)-4,5-dihydro-1H-pyrazolo[4,3-c]pyridin-1-yl)propanenitrile | LRMS (ESI) calc'd for $C_{22}H_{23}F_3N_5O_2$ [M + H]$^+$: 446, found 446 |
| II-141 | 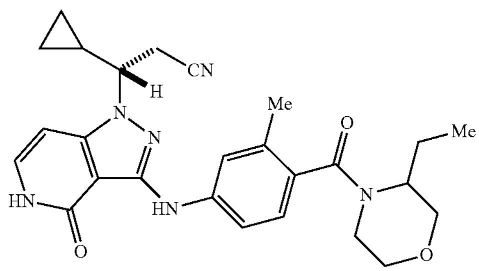 [SMILES: CCC1COCCN1C(=O)c1ccc(Nc2nn([C@@H](CC#N)C3CC3)c3cc[nH]c(=O)c23)cc1C] | (S)-3-cyclopropyl-3-(3-((4-((S or R)-3-ethylmorpholine-4-carbonyl)-3-methylphenyl)amino)-4-oxo-4,5-dihydro-1H-pyrazolo[4,3-c]pyridin-1-yl)propanenitrile (SFC Peak 1, Chiralpak AD-H, 21 x 250 (mm), 30% MeOH in CO$_2$, Tr = 3.84) | LRMS (ESI) calc'd for $C_{26}H_{31}N_6O_3$ [M + H]$^+$: 475, found 475 |
| II-142 | 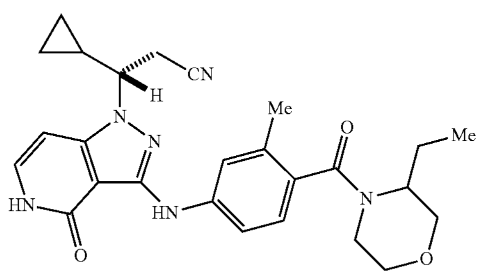 [SMILES: CCC1COCCN1C(=O)c1ccc(Nc2nn([C@@H](CC#N)C3CC3)c3cc[nH]c(=O)c23)cc1C] | (S)-3-cyclopropyl-3-(3-((4-((S or R)-3-ethylmorpholine-4-carbonyl)-3-methylphenyl)amino)-4-oxo-4,5-dihydro-1H-pyrazolo[4,3-c]pyridin-1-yl)propanenitrile (SFC Peak 2, Chiralpak AD-H, 21 x 250 (mm), 30% MeOH in CO$_2$, Tr = 6.19) | LRMS (ESI) calc'd for $C_{26}H_{31}N_6O_3$ [M + H]$^+$: 475, found 475 |
| II-143 | 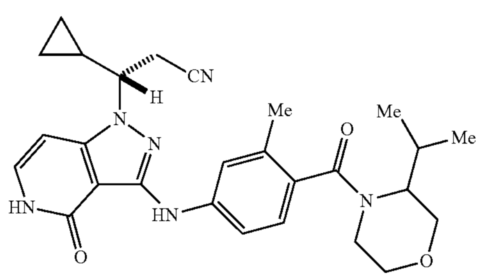 [SMILES: Cc1cc(Nc2nn([C@@H](CC#N)C3CC3)c3cc[nH]c(=O)c23)ccc1C(=O)N1CCOCC1C(C)C] | (S)-3-cyclopropyl-3-(3-((4-((S or R)-3-isopropylmorpholine-4-carbonyl)-3-methylphenyl)amino)-4-oxo-4,5-dihydro-1H-pyrazolo[4,3-c]pyridin-1-yl)propanenitrile (SFC Peak 1, Phenomenex, Lux-4, 21 x 250 (mm), 40% MeOH in CO$_2$, Tr = 5.18) | LRMS (ESI) calc'd for $C_{27}H_{33}N_6O_3$ [M + H]$^+$: 489, found 489 |
| II-144 | 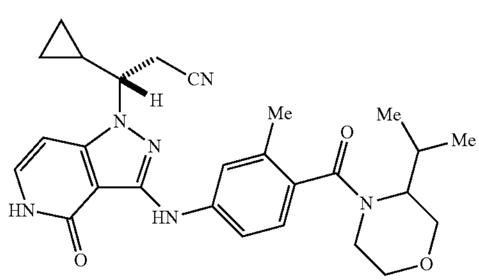 [SMILES: Cc1cc(Nc2nn([C@@H](CC#N)C3CC3)c3cc[nH]c(=O)c23)ccc1C(=O)N1CCOCC1C(C)C] | (S)-3-cyclopropyl-3-(3-((4-((S or R)-3-isopropylmorpholine-4-carbonyl)-3-methylphenyl)amino)-4-oxo-4,5-dihydro-1H-pyrazolo[4,3-c]pyridin-1-yl)propanenitrile (SFC Peak 2, Phenomenex, Lux-4, 21 x 250 (mm), 40% MeOH in CO$_2$, Tr = 6.33) | LRMS (ESI) calc'd for $C_{27}H_{33}N_6O_3$ [M + H]$^+$: 489, found 489 |

TABLE 14-continued

| Example | Compound Name | MS |
|---|---|---|
| II-145 | (S)-3-cyclopropyl-3-(3-((3-methyl-4-((S or R)-2-methyl-1-(2H-1,2,3-triazol-2-yl)propyl)phenyl)amino)-4-oxo-4,5-dihydro-1H-pyrazolo[4,3-c]pyridin-1-yl)propanenitrile (Peak 1, Chiralpak IA-3, 0.46 x 5 cm, 3 um; mobile phase: hexane (0.1% diethylamine):ethanol = 75:25; flow: 20 mL/min, pressure: 2.6 MPA, detector: 220/254 nm; Tr = 9.3 min) | LRMS (ESI) calc'd for $C_{25}H_{28}N_8O$ [M + H]+: 457, found 457 |
| II-146 | (S)-3-cyclopropyl-3-(3-((3-methyl-4-((S or R)-2-methyl-1-(2H-1,2,3-triazol-2-yl)propyl)phenyl)amino)-4-oxo-4,5-dihydro-1H-pyrazolo[4,3-c]pyridin-1-yl)propanenitrile (Peak 2, Chiralpak IA-3, 0.46 x 5 cm, 3 um; mobile phase: hexane (0.1% diethylamine):ethanol = 75:25; flow: 20 mL/min, pressure: 2.6 MPA, detector: 220/254 nm; Tr = 11.5 min) | LRMS (ESI) calc'd for $C_{25}H_{28}N_8O$ [M + H]+: 457, found 457 |
| II-147 | (S)-3-(3-((2-benzyl-1,1-dioxido-2,3-dihydrobenzo[d]isothiazol-5-yl)amino)-4-oxo-4,5-dihydro-1H-pyrazolo[4,3-c]pyridin-1-yl)-3-cyclopropylpropanenitrile | LRMS (ESI) calc'd for $C_{26}H_{25}N_6O_3S$ [M + H]+: 501, found 501 |
| II-148 | (S)-3-Cyclopropyl-3-(3-((3-methyl-4-((S or R)-2-methyl-1-(1H-1,2,3-triazol-1-yl)propyl)phenyl)amino)-4-oxo-4,5-dihydro-1H-pyrazolo[4,3-c]pyridin-1-yl)propanenitrile (Peak 1, Chiralpak IA-3, 0.46 x 5 cm, 3 um; mobile phase: hexane (0.1% diethylamine):ethanol = 60:40; flow: 1.0 mL/min pressure: 3.0 MPA; detector: 220/254 nm; Tr = 7.3) | LRMS (ESI) calc'd for $C_{25}H_{28}N_8O$ [M + H]+: 457, found 457 |
| II-149 | (S)-3-Cyclopropyl-3-(3-((3-methyl-4-((S or R)-2-methyl-1-(1H-1,2,3-triazol-1-yl)propyl)phenyl)amino)-4-oxo-4,5-dihydro-1H-pyrazolo[4,3-c]pyridin-1-yl) propanenitrile (Peak 2, Chiralpak IA-3, 0.46 x 5 cm, 3 um; mobile phase: hexane (0.1% diethylamine):ethanol = 60:40; flow: 1.0 mL/min pressure: 3.0 MPA; detector: 220/254 nm; Tr = 15.7) | LRMS (ESI) calc'd for $C_{25}H_{28}N_8O$ [M + H]+: 457, found 457 |
| II-150 | (S)-3-cyclopropyl-3-(3-((3-methyl-4-((R or S)-2,2,2-trifluoro-1-hydroxyethyl)phenyl)amino)-4-oxo-4,5-dihydro-1H-pyrazolo[4,3-c]pyridin-1-yl)propanenitrile (Peak 1, Chiralpak IA 2 x 25 cm, 5 mm; mobile phase: phase A: hexane (0.1% diethylamine); phase B: ethanol (0.1% diethylamine) 30% in 20 min, flow: 20 ml/min; detector: 220/254 nm; Tr = 7.9) | LRMS (ESI) calc'd for $C_{21}H_{20}F_3N_5O_2$ [M + H]+: 432, found 432 |

TABLE 14-continued

| Example | Structure | Compound Name | MS |
|---|---|---|---|
| II-151 | 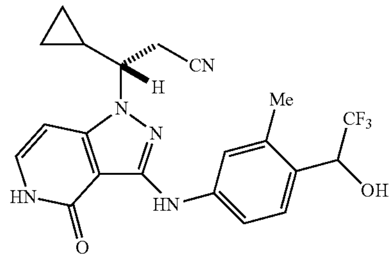 [SMILES: Cc1cc(Nc2nn([C@@H](CC#N)C3CC3)c3cc[nH]c(=O)c23)ccc1C(O)C(F)(F)F] | (S)-3-cyclopropyl-3-(3-((3-methyl-4-((R or S)-2,2,2-trifluoro-1-hydroxyethyl)phenyl)amino)-4-oxo-4,5-dihydro-1H-pyrazolo[4,3-c]pyridin-1-yl)propanenitrile (Peak 2, Chiralpak IA 2 x 25 cm, 5 mm; mobile phase: phase A: hexane (0.1% diethylamine); phase B: ethanol (0.1% diethylamine) 30% in 20 min, flow: 20 ml/min; detector: 220/254 nm; Tr = 13.6) | LRMS (ESI) calc'd for $C_{21}H_{20}F_3N_5O_2$ [M + H]+: 432, found 432 |
| II-152 | 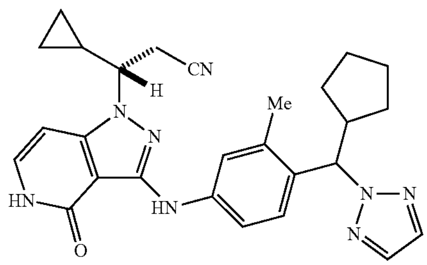 [SMILES: Cc1cc(Nc2nn([C@@H](CC#N)C3CC3)c3cc[nH]c(=O)c23)ccc1C(C1CCCC1)n1nccn1] | (S)-3-(3-((4-((S or R)-cyclopentyl(2H-1,2,3-triazol-2-yl)methyl)-3-methylphenyl)amino)-4-oxo-4,5-dihydro-1H-pyrazolo[4,3-c]pyridin-1-yl)-3-cyclopropylpropanenitrile (Peak 1, Chiralpak IA, 0.46 x 25 cm, 5 mm; mobile phase: phase A: hexane (0.1% TEA) and phase B: ethanol (hold 35% Phase B for 20 min); detector, UV 220/254 nm. Tr = 11.3) | LRMS (ESI) calc'd for $C_{27}H_{30}N_8O$ [M + H]+: 481, found 481 |
| II-153 | 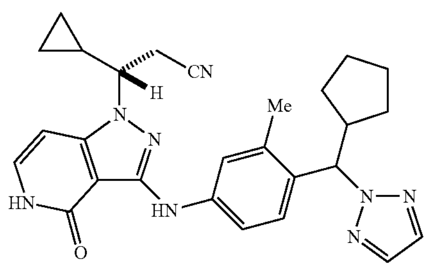 [SMILES: Cc1cc(Nc2nn([C@@H](CC#N)C3CC3)c3cc[nH]c(=O)c23)ccc1C(C1CCCC1)n1nccn1] | (S)-3-(3-((4-((S or R)-cyclopentyl(2H-1,2,3-triazol-2-yl)methyl)-3-methylphenyl)amino)-4-oxo-4,5-dihydro-1H-pyrazolo[4,3-c]pyridin-1-yl)-3-cyclopropyl-propanenitrile (Peak 2, Chiralpak IA, 0.46 x 25 cm, 5 mm; mobile phase: phase A: hexane (0.1% TEA) and phase B: ethanol (hold 35% Phase B for 20 min); detector, UV 220/254 nm. Tr = 15.8) | LRMS (ESI) calc'd for $C_{27}H_{30}N_8O$ [M + H]+: 481, found 481 |
| II-154 | 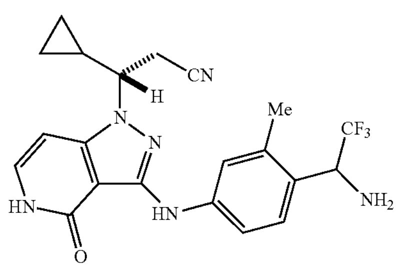 [SMILES: Cc1cc(Nc2nn([C@@H](CC#N)C3CC3)c3cc[nH]c(=O)c23)ccc1C(N)C(F)(F)F] | (S)-3-(3-((4-((R or S)-1-amino-2,2,2-trifluoroethyl)-3-methylphenyl)amino)-4-oxo-4,5-dihydro-1H-pyrazolo[4,3-c]pyridin-1-yl)-3-cyclopropyl-propanenitrile (Peak 1, Chiralpak IA 2 x 25 cm, 20 um; phase A: hexane (0.1% diethylamine); phase B: ethanol (0.1% diethylamine); flow rate: 17 mL/min; detector: 220/254 nm; Tr = 11.5) | LRMS (ESI) calc'd for $C_{21}H_{21}F_3N_6O$ [M + H]+: 431, found 431 |
| II-155 | 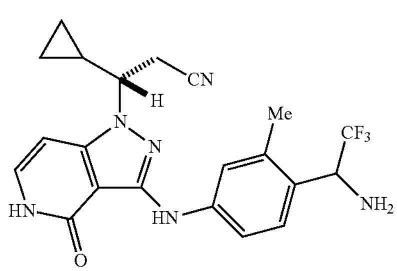 [SMILES: Cc1cc(Nc2nn([C@@H](CC#N)C3CC3)c3cc[nH]c(=O)c23)ccc1C(N)C(F)(F)F] | (S)-3-(3-((4-((R or S)-1-amino-2,2,2-trifluoroethyl)-3-methylphenyl)amino)-4-oxo-4,5-dihydro-1H-pyrazolo[4,3-c]pyridin-1-yl)-3-cyclopropyl-propanenitrile (Peak 2, Chiralpak IA 2 x 25 cm, 20 um; phase A: hexane (0.1% diethylamine); phase B: ethanol (0.1% diethylamine); flow rate: 17 mL/min; detector: 220/254 nm; Tr = 22.5) | LRMS (ESI) calc'd for $C_{21}H_{21}F_3N_6O$ [M + H]+: 431, found 431 |

TABLE 14-continued

| Example | Structure | Compound Name | MS |
|---|---|---|---|
| II-156 | 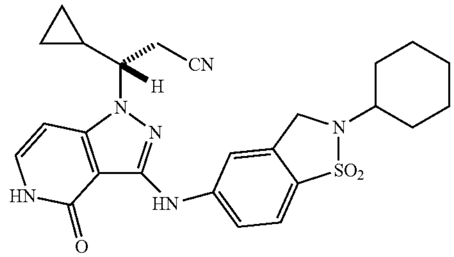 [SMILES: N#CC[C@@H](C1CC1)n1nc(Nc2ccc3c(c2)CN(C2CCCCC2)S3(=O)=O)c2c(=O)[nH]ccc21] | (S)-3-(3-((2-cyclohexyl-1,1-dioxido-2,3-dihydrobenzo[d]isothiazol-5-yl)amino)-4-oxo-4,5-dihydro-1H-pyrazolo[4,3-c]pyridin-1-yl)-3-cyclopropylpropanenitrile | LRMS (ESI) calc'd for for $C_{25}H_{28}N_6O_3S$ [M + H]+: 493, found 493 |
| II-157 | 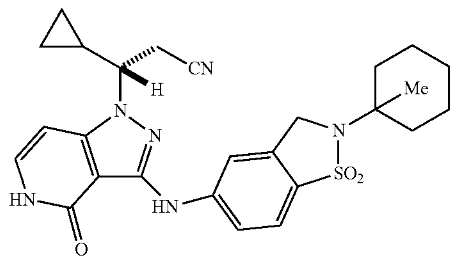 | (S)-3-cyclopropyl-3-(3-((2-(1-methylcyclohexyl)-1,1-dioxido-2,3-dihydrobenzo[d]isothiazol-5-yl)amino)-4-oxo-4,5-dihydro-1H-pyrazolo[4,3-c]pyridin-1-yl)propanenitrile | LRMS (ESI) calc'd for for $C_{26}H_{30}N_6O_3S$ [M + H]+: 507, found 507 |
| II-158 | 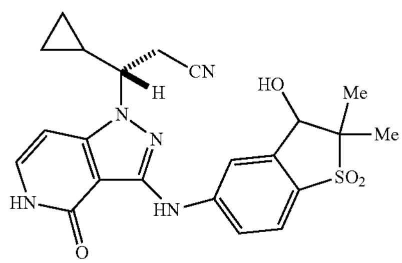 [SMILES: CC1(C)C(O)c2cc(Nc3nn([C@@H](CC#N)C4CC4)c4cc[nH]c(=O)c34)ccc2S1(=O)=O] | (S)-3-cyclopropyl-3-(3-(((S or R)-3-hydroxy-2,2-dimethyl-1,1-dioxido-2,3-dihydrobenzo[b]thiophen-5-yl)amino)-4-oxo-4,5-dihydro-1H-pyrazolo[4,3-c]pyridin-1-yl)propanenitrile (Peak 1, chiralpak IA 2 x 25 cm, 20 um; phase A: hexane (0.1% diethylamine) phase B: ethanol (0.1% dietylamine); flow rate: 16 mL/min. detector: 220/254 nm; Tr = min) | LRMS (ESI) calc'd for for $C_{22}H_{23}N_5O_4S$ [M + H]+: 454, found 454 |
| II-159 | 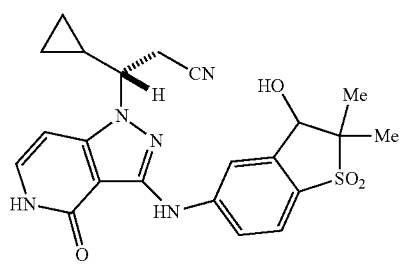 [SMILES: CC1(C)C(O)c2cc(Nc3nn([C@@H](CC#N)C4CC4)c4cc[nH]c(=O)c34)ccc2S1(=O)=O] | (S)-3-cyclopropyl-3-(3-(((S or R)-3-hydroxy-2,2-dimethyl-1,1-dioxido-2,3-dihydrobenzo[b]thiophen-5-yl)amino)-4-oxo-4,5-dihydro-1H-pyrazolo[4,3-c]pyridin-1-yl)propanenitrile (Peak 2, chiralpak IA 2 x 25 cm, 20 um; phase A: hexane (0.1% diethylamine) phase B: ethanol (0.1% dietylamine); flow rate: 16 mL/min. detector: 220/254 nm; Tr = min) | LRMS (ESI) calc'd for for $C_{22}H_{23}N_5O_4S$ [M + H]+: 454, found 454 |
| II-160 | 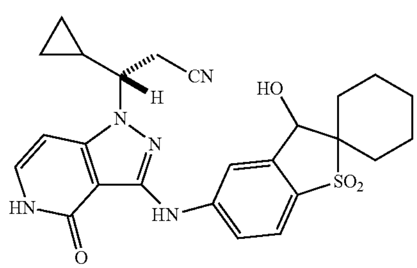 [SMILES: N#CC[C@@H](C1CC1)n1nc(Nc2ccc3c(c2)C(O)C2(CCCCC2)S3(=O)=O)c2c(=O)[nH]ccc21] | (S)-3-cyclopropyl-3-(3-(((S)-3-hydroxy-1,1-dioxido-3H-spiro[benzo[b]thiophene-2,1'-cyclohexan]-5-yl)amino)-4-oxo-4,5-dihydro-1H-pyrazolo[4,3-c]pyridin-1-yl)propanenitrile (Peak 1, Chiralpak IA 2 x 25 cm, 20 um; phase A: hexane (0.1% diethylamine); phase B: ethanol (0.1% diethylamine); flow rate: 20 mL/min; detector: 220/254 nm; Tr = 12.5) | LRMS (ESI) calc'd for for $C_{25}H_{28}N_5O_4S$ [M + H]+: 494, found 494 |
| II-161 | 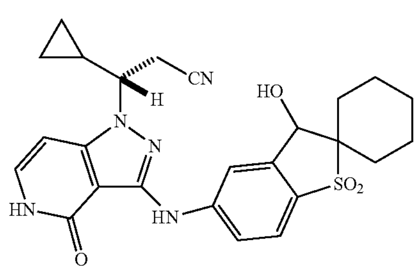 [SMILES: N#CC[C@@H](C1CC1)n1nc(Nc2ccc3c(c2)C(O)C2(CCCCC2)S3(=O)=O)c2c(=O)[nH]ccc21] | (S)-3-cyclopropyl-3-(3-(((S)-3-hydroxy-1,1-dioxido-3H-spiro[benzo[b]thiophene-2,1'-cyclohexan]-5-yl)amino)-4-oxo-4,5-dihydro-1H-pyrazolo[4,3-c]pyridin-1-yl)propanenitrile (Peak 2, Chiralpak IA 2 x 25 cm, 20 um; phase A: hexane (0.1% diethylamine); phase B: ethanol (0.1% diethylamine); flow rate: 20 mL/min; detector: 220/254 nm; Tr = 19.5) | LRMS (ESI) calc'd for for $C_{25}H_{28}N_5O_4S$ [M + H]+: 494, found 494 |

TABLE 14-continued

| Example | Structure | Compound Name | MS |
|---|---|---|---|
| II-162 | 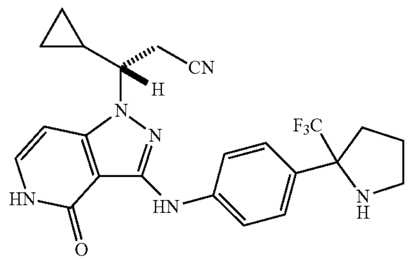 [SMILES: N#CC[C@@H](C1CC1)n1nc(Nc2ccc(C3(C(F)(F)F)CCCN3)cc2)c2c(=O)[nH]ccc21] | (S)-3-cyclopropyl-3-(4-oxo-3-((4-((R or S)-2-(trifluoromethyl)pyrrolidin-2-yl)phenyl)amino)-4,5-dihydro-1H-pyrazolo[4,3-c]pyridin-1-yl)propanenitrile (Peak 1, C18 OBD column 19 x 150 mm, 5 um; Mobile phase: hexane:ethanol = 99:1; Detector: 220/254 nm; Tr = 18) | LRMS (ESI) calc'd for for $C_{23}H_{23}F_3N_6O$ [M + H]+: 457, found 457 |
| II-163 | 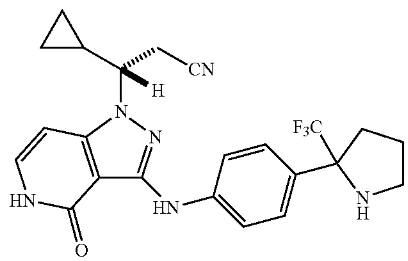 [SMILES: N#CC[C@@H](C1CC1)n1nc(Nc2ccc(C3(C(F)(F)F)CCCN3)cc2)c2c(=O)[nH]ccc21] | (S)-3-cyclopropyl-3-(4-oxo-3-((4-((R or S)-2-(trifluoromethyl)pyrrolidin-2-yl)phenyl)amino)-4,5-dihydro-1H-pyrazolo[4,3-c]pyridin-1-yl)propanenitrile (Peak 2, C18 OBD column 19 x 150 mm, 5 um; Mobile phase: hexane:ethanol = 99:1; Detector: 220/254 nm; Tr = 21) | LRMS (ESI) calc'd for for $C_{23}H_{23}F_3N_6O$ [M + H]+: 457, found 457 |
| II-164 | 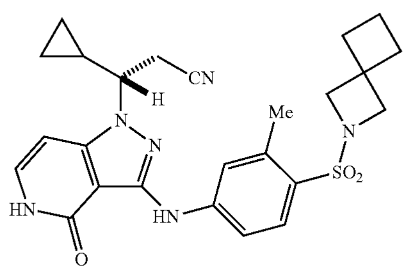 [SMILES: Cc1cc(Nc2nn([C@@H](CC#N)C3CC3)c3cc[nH]c(=O)c23)ccc1S(=O)(=O)N1CC2(CCC2)C1] | (S)-3-(3-((4-(2-azaspiro[3.3]heptan-2-ylsulfonyl)-3-methylphenyl)amino)-4-oxo-4,5-dihydro-1H-pyrazolo[4,3-c]pyridin-1-yl)-3-cyclopropylpropanenitrile | LRMS (ESI) calc'd for for $C_{25}H_{29}N_6O_3S$ [M + H]+: 493, found 493 |
| II-165 | 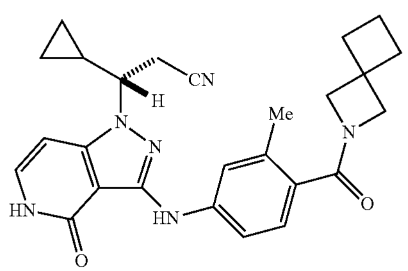 [SMILES: Cc1cc(Nc2nn([C@@H](CC#N)C3CC3)c3cc[nH]c(=O)c23)ccc1C(=O)N1CC2(CCC2)C1] | (S)-3-cyclopropyl-3-(3-((3-methyl-4-(2-azaspiro[3.3]heptane-2-carbonyl)phenyl)amino)-4-oxo-4,5-dihydro-1H-pyrazolo[4,3-c]pyridin-1-yl)propanenitrile | LRMS (ESI) calc'd for for $C_{26}H_{29}N_6O_2$ [M + H]+: 457, found 457 |
| II-166 | 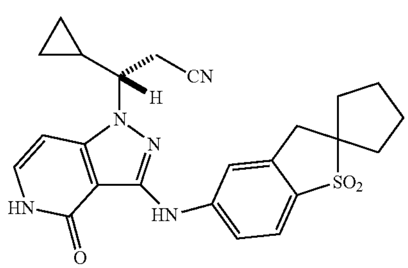 [SMILES: N#CC[C@@H](C1CC1)n1nc(Nc2ccc3c(c2)CC2(CCCC2)S3(=O)=O)c2c(=O)[nH]ccc21] | (S)-3-cyclopropyl-3-(3-((1,1-dioxido-3H-spiro[benzo[b]thiophene-2,1'-cyclopentan]-5-yl)amino)-4-oxo-4,5-dihydro-1H-pyrazolo[4,3-c]pyridin-1-yl)propanenitrile | LRMS (ESI) calc'd for for $C_{24}H_{26}N_5O_3S$ [M + H]+: 464, found 464 |
| II-167 | 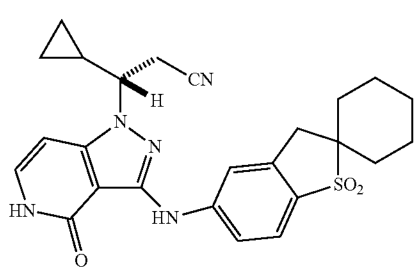 [SMILES: N#CC[C@@H](C1CC1)n1nc(Nc2ccc3c(c2)CC2(CCCCC2)S3(=O)=O)c2c(=O)[nH]ccc21] | (S)-3-cyclopropyl-3-(3-((1,1-dioxido-3H-spiro[benzo[b]thiophene-2,1'-cyclohexan]-5-yl)amino)-4-oxo-4,5-dihydro-1H-pyrazolo[4,3-c]pyridin-1-yl)propanenitrile | LRMS (ESI) calc'd for for $C_{25}H_{28}N_5O_3S$ [M + H]+: 478, found 478 |

TABLE 14-continued

| Example | Structure | Compound Name | MS |
|---|---|---|---|
| II-168 | 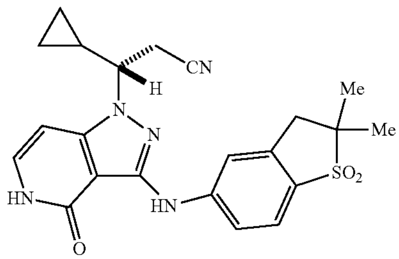 [SMILES: CC1(C)Cc2cc(Nc3nn([C@@H](CC#N)C4CC4)c4cc[nH]c(=O)c34)ccc2S1(=O)=O] | (S)-3-cyclopropyl-3-(3-((2,2-dimethyl-1,1-dioxido-2,3-dihydrobenzo[b]thiophen-5-yl)amino)-4-oxo-4,5-dihydro-1H-pyrazolo[4,3-c]pyridin-1-yl)propanenitrile | LRMS (ESI) calc'd for for $C_{22}H_{24}N_5O_3S$ [M + H]+: 438, found 438 |
| II-169 | 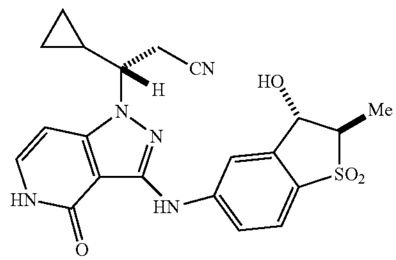 [SMILES: C[C@@H]1[C@@H](O)c2cc(Nc3nn([C@@H](CC#N)C4CC4)c4cc[nH]c(=O)c34)ccc2S1(=O)=O] | (S)-3-cyclopropyl-3-(3-(((2R,3S or 2S,3R)-3-hydroxy-2-methyl-1,1-dioxido-2,3-dihydrobenzo[b]thiophen-5-yl)amino)-4-oxo-4,5-dihydro-1H-pyrazolo[4,3-c]pyridin-1-yl)propanenitrile | LRMS (ESI) calc'd for for $C_{21}H_{22}N_5O_4S$ [M + H]+: 440, found 440 |
| II-170 | 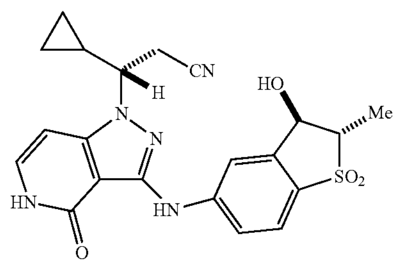 [SMILES: C[C@H]1[C@H](O)c2cc(Nc3nn([C@@H](CC#N)C4CC4)c4cc[nH]c(=O)c34)ccc2S1(=O)=O] | (S)-3-cyclopropyl-3-(3-(((2R,3S or 2S,3R)-3-hydroxy-2-methyl-1,1-dioxido-2,3-dihydrobenzo[b]thiophen-5-yl)amino)-4-oxo-4,5-dihydro-1H-pyrazolo[4,3-c]pyridin-1-yl)propanenitrile | LRMS (ESI) calc'd for for $C_{21}H_{22}N_5O_4S$ [M + H]+: 440, found 440 |
| II-171 | 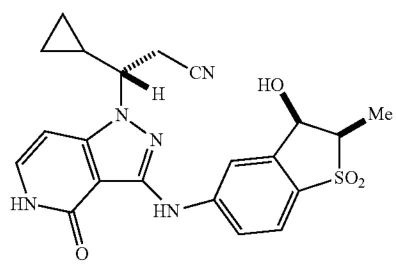 [SMILES: C[C@@H]1[C@H](O)c2cc(Nc3nn([C@@H](CC#N)C4CC4)c4cc[nH]c(=O)c34)ccc2S1(=O)=O] | (S)-3-cyclopropyl-3-(3-(((2R,3R or 2S,3S)-3-hydroxy-2-methyl-1,1-dioxido-2,3-dihydrobenzo[b]thiophen-5-yl)amino)-4-oxo-4,5-dihydro-1H-pyrazolo[4,3-c]pyridin-1-yl)propanenitrile | LRMS (ESI) calc'd for for $C_{21}H_{22}N_5O_4S$ [M + H]+: 440, found 440 |
| II-172 | 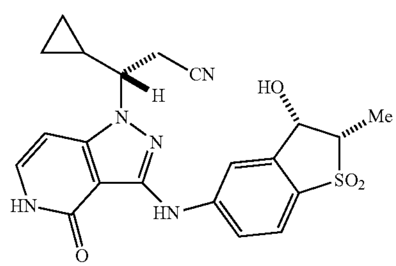 [SMILES: C[C@H]1[C@@H](O)c2cc(Nc3nn([C@@H](CC#N)C4CC4)c4cc[nH]c(=O)c34)ccc2S1(=O)=O] | (S)-3-cyclopropyl-3-(3-(((2R,3R or 2S,3S)-3-hydroxy-2-methyl-1,1-dioxido-2,3-dihydrobenzo[b]thiophen-5-yl)amino)-4-oxo-4,5-dihydro-1H-pyrazolo[4,3-c]pyridin-1-yl)propanenitrile | LRMS (ESI) calc'd for for $C_{21}H_{22}N_5O_4S$ [M + H]+: 440, found 440 |
| II-173 | 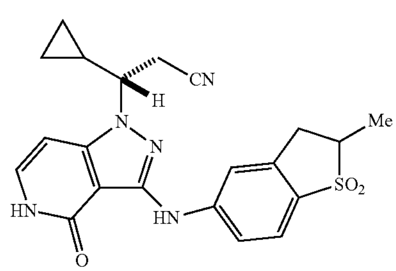 [SMILES: CC1Cc2cc(Nc3nn([C@@H](CC#N)C4CC4)c4cc[nH]c(=O)c34)ccc2S1(=O)=O] | (3S)-3-cyclopropyl-3-(3-((2-methyl-1,1-dioxido-2,3-dihydrobenzo[b]thiophen-5-yl)amino)-4-oxo-4,5-dihydro-1H-pyrazolo[4,3-c]pyridin-1-yl)propanenitrile | LRMS (ESI) calc'd for for $C_{21}H_{22}N_5O_3S$ [M + H]+: 424, found 424 |

TABLE 14-continued

| Example | Structure | Compound Name | MS |
|---|---|---|---|
| II-174 | 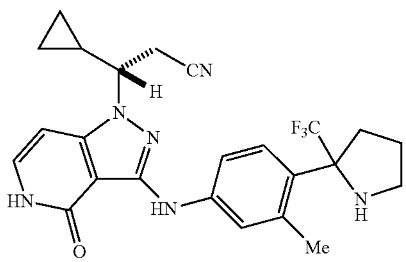 [SMILES: Cc1cc(Nc2nn([C@@H](CC#N)C3CC3)c3cc[nH]c(=O)c23)ccc1C1(C(F)(F)F)CCCN1] | (S)-3-cyclopropyl-3-(3-((3-methyl-4-((R or S)-2-(trifluoromethyl)pyrrolidin-2-yl)phenyl)amino)-4-oxo-4,5-dihydro-1H-pyrazolo[4,3-c]pyridin-1-yl)propanenitrile (Peak 2, Chiralcel OJ-3, 0.46 x 15 cm, 3 um; mobile phase: n-hexane:ethanol = 70:30. Tr = 20) | LRMS (ESI) calc'd for for $C_{24}H_{26}F_3N_6O$ [M + H]+: 471, found 471 |
| II-175 | 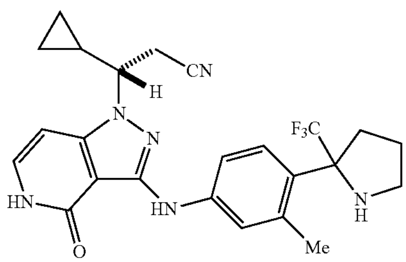 [SMILES: Cc1cc(Nc2nn([C@@H](CC#N)C3CC3)c3cc[nH]c(=O)c23)ccc1C1(C(F)(F)F)CCCN1] | (S)-3-cyclopropyl-3-(3-((3-methyl-4-((R or S)-2-(trifluoromethyl)pyrrolidin-2-yl)phenyl)amino)-4-oxo-4,5-dihydro-1H-pyrazolo[4,3-c]pyridin-1-yl)propanenitrile (Peak 1, Chiralcel OJ-3, 0.46 x 15 cm, 3 um; mobile phase: n-hexane:ethanol = 70:30. Tr = 15) | LRMS (ESI) calc'd for for $C_{24}H_{26}F_3N_6O$ [M + H]+: 471, found 471 |
| II-176 | 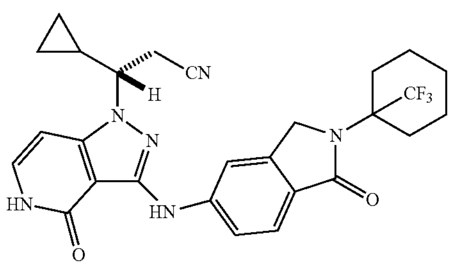 | (S)-3-cyclopropyl-3-(4-oxo-3-((1-oxo-2-(1-(trifluoromethyl)cyclohexyl)isoindolin-5-yl)amino)-4,5-dihydro-1H-pyrazolo[4,3-c]pyridin-1-yl)propanenitrile | LRMS (ESI) calc'd for for $C_{27}H_{28}F_3N_6O_2$ [M + H]+: 525, found 525 |
| II-177 | 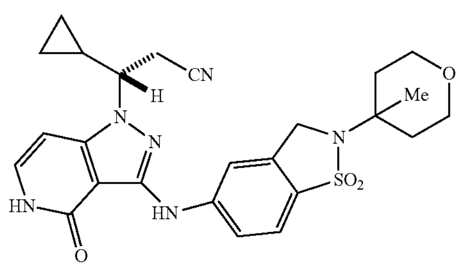 | (S)-3-cyclopropyl-3-(3-((2-(4-methyltetrahydro-2H-pyran-4-yl)-1,1-dioxido-2,3-dihydrobenzo[d]isothiazol-5-yl)amino)-4-oxo-4,5-dihydro-1H-pyrazolo[4,3-c]pyridin-1-yl)propanenitrile | LRMS (ESI) calc'd for for $C_{25}H_{29}N_6O_4S$ [M + H]+: 509, found 509 |
| II-178 | 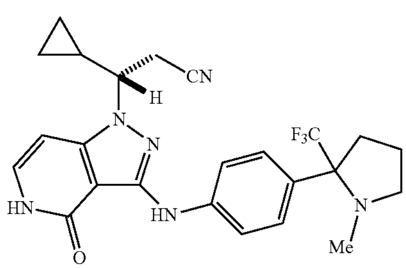 [SMILES: CN1CCCC1(c1ccc(Nc2nn([C@@H](CC#N)C3CC3)c3cc[nH]c(=O)c23)cc1)C(F)(F)F] | (S)-3-cyclopropyl-3-(3-((4-((R)-1-methyl-2-(trifluoromethyl)pyrrolidin-2-yl)phenyl)amino)-4-oxo-4,5-dihydro-1H-pyrazolo[4,3-c]pyridin-1-yl)propanenitrile | LRMS (ESI) calc'd for for $C_{24}H_{26}F_3N_6O$ [M + H]+: 471, found 471 |
| II-179 | 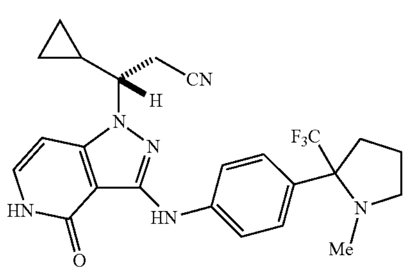 [SMILES: CN1CCCC1(c1ccc(Nc2nn([C@@H](CC#N)C3CC3)c3cc[nH]c(=O)c23)cc1)C(F)(F)F] | (S)-3-cyclopropyl-3-(3-((4-((R)-1-methyl-2-(trifluoromethyl)pyrrolidin-2-yl)phenyl)amino)-4-oxo-4,5-dihydro-1H-pyrazolo[4,3-c]pyridin-1-yl)propanenitrile | LRMS (ESI) calc'd for for $C_{24}H_{26}F_3N_6O$ [M + H]+: 471, found 471 |

TABLE 14-continued

| Example | Compound Name | MS |
|---|---|---|
| II-180 | (S)-4-((1-(2-cyano-1-cyclopropylethyl)-4-oxo-4,5-dihydro-1H-pyrazolo[4,3-c]pyridin-3-yl)amino)-N,2-dimethyl-N-(tetrahydro-2H-pyran-4-yl)benzamide | LRMS (ESI) calc'd for for $C_{26}H_{31}N_6O_3$ [M + H]+: 475, found 475 |
| II-181 | (S)-3-cyclopropyl-3-(3-((3-fluoro-4-((R or S)-2,2,2-trifluoro-1-(isopropylamino)ethyl)phenyl)amino)-4-oxo-4,5-dihydro-1H-pyrazolo[4,3-c]pyridin-1-yl)propanenitrile | LRMS (ESI) calc'd for for $C_{23}H_{25}F_4N_6O$ [M + H]+: 477, found 477 |
| II-182 | (S)-3-cyclopropyl-3-(3-((3-fluoro-4-((R or S)-2,2,2-trifluoro-1-(isopropylamino)ethyl)phenyl)amino)-4-oxo-4,5-dihydro-1H-pyrazolo[4,3-c]pyridin-1-yl)propanenitrile | LRMS (ESI) calc'd for for $C_{23}H_{25}F_4N_6O$ [M + H]+: 477, found 477 |
| II-183 | (S)-3-cyclopropyl-3-(3-((4-((R or S)-1-(ethylamino)-2,2,2-trifluoroethyl)-3-fluorophenyl)amino)-4-oxo-4,5-dihydro-1H-pyrazolo[4,3-c]pyridin-1-yl)propanenitrile | LRMS (ESI) calc'd for for $C_{22}H_{23}F_4N_6O$ [M + H]+: 463, found 463 |
| II-184 | (S)-3-cyclopropyl-3-(3-((4-((R or S)-1-(ethylamino)-2,2,2-trifluoroethyl)-3-fluorophenyl)amino)-4-oxo-4,5-dihydro-1H-pyrazolo[4,3-c]pyridin-1-yl)propanenitrile | LRMS (ESI) calc'd for for $C_{22}H_{23}F_4N_6O$ [M + H]+: 463, found 463 |
| II-185 | (S)-3-(3-((4-((R or S)-1-(tert-butylamino)-2,2,2-trifluoroethyl)-3-fluorophenyl)amino)-4-oxo-4,5-dihydro-1H-pyrazolo[4,3-c]pyridin-1-yl)-3-cyclopropyl-propanenitrile (Peak 2, Phenomenex Lux Cellulose-4 5 x 425 cm, 5 um; mobile phase: carbon dioxide:methanol with 0.1% DEA = 60:40. Tr = 4.4) | LRMS (ESI) calc'd for for $C_{24}H_{27}F_4N_6O$ [M + H]+: 491, found 491 |

TABLE 14-continued

| Example | Structure | Compound Name | MS |
|---|---|---|---|
| II-186 | 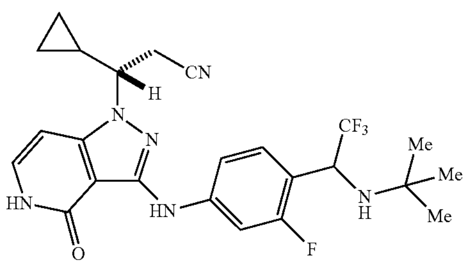 [SMILES: CC(C)(C)NC(c1ccc(Nc2nn([C@@H](CC#N)C3CC3)c3cc[nH]c(=O)c23)cc1F)C(F)(F)F] | (S)-3-(3-((4-((R or S)-1-(tert-butylamino)-2,2,2-trifluoroethyl)-3-fluorophenyl)amino)-4-oxo-4,5-dihydro-1H-pyrazolo[4,3-c]pyridin-1-yl)-3-cyclopropyl-propanenitrile (SFC Peak 1 Phenomenex Lux Cellulose-4 5 x 425 cm, 5 um; mobile phase: carbon dioxide:methanol with 0.1% DEA = 60:40. Tr = 4.1) | LRMS (ESI) calc'd for for $C_{24}H_{27}F_4N_6O$ [M + H]+: 491, found 491 |
| II-187 | 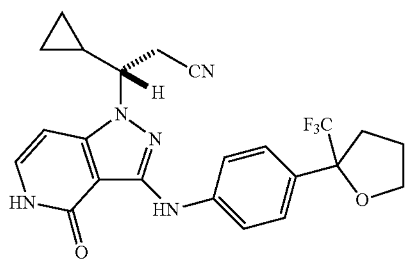 [SMILES: N#CC[C@@H](C1CC1)n1nc(Nc2ccc(C3(C(F)(F)F)CCCO3)cc2)c2c(=O)[nH]ccc21] | (S)-3-cyclopropyl-3-(4-oxo-3-((4-((S or R)-2-(trifluoromethyl)tetrahydrofuran-2-yl)phenyl)amino)-4,5-dihydro-1H-pyrazolo[4,3-c]pyridin-1-yl)propanenitrile | LRMS (ESI) calc'd for for $C_{23}H_{23}F_3N_5O_2$ [M + H]+: 458, found 458 |
| II-188 | 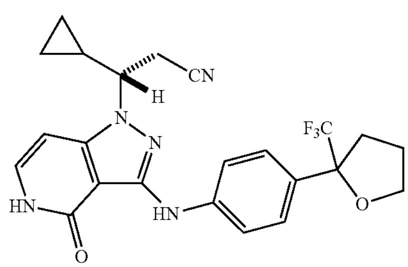 [SMILES: N#CC[C@@H](C1CC1)n1nc(Nc2ccc(C3(C(F)(F)F)CCCO3)cc2)c2c(=O)[nH]ccc21] | (S)-3-cyclopropyl-3-(4-oxo-3-((4-((S or R)-2-(trifluoromethyl)tetrahydrofuran-2-yl)phenyl)amino)-4,5-dihydro-1H-pyrazolo[4,3-c]pyridin-1-yl)propanenitrile | LRMS (ESI) calc'd for for $C_{23}H_{23}F_3N_5O_2$ [M + H]+: 458, found 458 |
| II-189 | 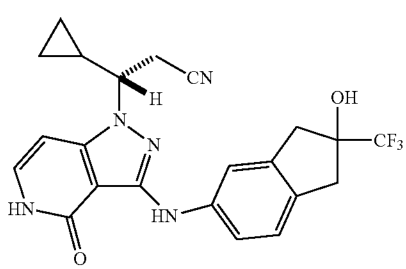 [SMILES: N#CC[C@@H](C1CC1)n1nc(Nc2ccc3c(c2)CC(O)(C(F)(F)F)C3)c2c(=O)[nH]ccc21] | (S)-3-cyclopropyl-3-(3-(((R or S)-2-hydroxy-2-(trifluoromethyl)-2,3-dihydro-1H-inden-5-yl)amino)-4-oxo-4,5-dihydro-1H-pyrazolo[4,3-c]pyridin-1-yl)propanenitrile | LRMS (ESI) calc'd for for $C_{22}H_{21}F_3N_5O_2$ [M + H]+: 444, found 444 |
| II-190 | 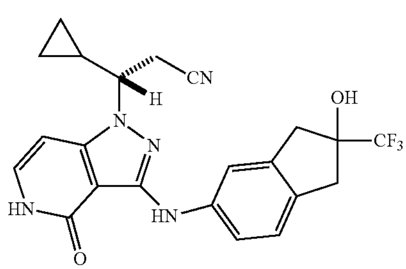 [SMILES: N#CC[C@@H](C1CC1)n1nc(Nc2ccc3c(c2)CC(O)(C(F)(F)F)C3)c2c(=O)[nH]ccc21] | (S)-3-cyclopropyl-3-(3-(((R or S)-2-hydroxy-2-(trifluoromethyl)-2,3-dihydro-1H-inden-5-yl)amino)-4-oxo-4,5-dihydro-1H-pyrazolo[4,3-c]pyridin-1-yl)propanenitrile | LRMS (ESI) calc'd for for $C_{22}H_{21}F_3N_5O_2$ [M + H]+: 444, found 444 |
| II-191 | 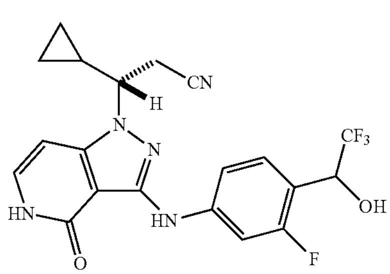 [SMILES: N#CC[C@@H](C1CC1)n1nc(Nc2ccc(C(O)C(F)(F)F)c(F)c2)c2c(=O)[nH]ccc21] | (S)-3-cyclopropyl-3-(3-((3-fluoro-4-((R or S)-2,2,2-trifluoro-1-hydroxyethyl)phenyl)amino)-4-oxo-4,5-dihydro-1H-pyrazolo[4,3-c]pyridin-1-yl)propanenitrile (Peak 2, Chiralpak IA , 2 x 25 cm, 5 um; mobile phase ethanol in n-hexane (50%); detector: 220/254 nm; Tr = 13) | LRMS (ESI) calc'd for for $C_{20}H_{18}F_4N_5O_2$ [M + H]+: 436, found 436 |

TABLE 14-continued

| Example | Structure | Compound Name | MS |
|---------|-----------|---------------|-----|
| II-192 | 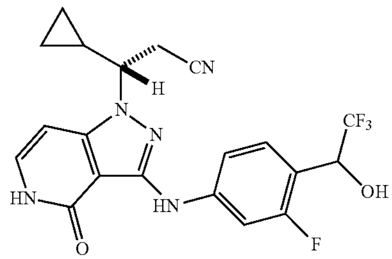 [SMILES: N#CC[C@@H](C1CC1)n1nc(Nc2ccc(C(O)C(F)(F)F)c(F)c2)c2c(=O)[nH]ccc21] | (S)-3-cyclopropyl-3-(3-((3-fluoro-4-((R or S)-2,2,2-trifluoro-1-hydroxyethyl)phenyl)amino)-4-oxo-4,5-dihydro-1H-pyrazolo[4,3-e]pyridin-1-yl)propanenitrile (Peak 1, Chiralpak IA, 2 x 25 cm, 5 um; mobile phase ethanol in n-hexane (50%); detector: 220/254 nm; Tr = 5.8) | LRMS (ESI) calc'd for for $C_{20}H_{18}F_4N_5O_2$ [M + H]+: 436, found 436 |
| II-193 | 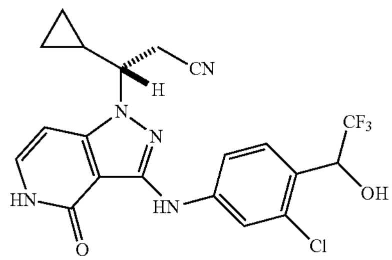 [SMILES: N#CC[C@@H](C1CC1)n1nc(Nc2ccc(C(O)C(F)(F)F)c(Cl)c2)c2c(=O)[nH]ccc21] | (S)-3-(3-((3-chloro-4-((R or S)-2,2,2-trifluoro-1-hydroxyethyl)phenyl)amino)-4-oxo-4,5-dihydro-1H-pyrazolo[4,3-c]pyridin-1-yl)-3-cyclopropylpropanenitrile (Peak 1 Chiralpak IA, 2 x 25 cm, 5 um; mobile phase ethanol in n-hexane (50%); detector: 220/254 nm; Tr = 5.7) | LRMS (ESI) calc'd for for $C_{20}H_{18}ClF_3N_5O_2$ [M + H]+: 452, found 452 |
| II-194 | 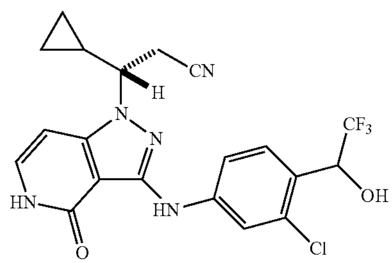 [SMILES: N#CC[C@@H](C1CC1)n1nc(Nc2ccc(C(O)C(F)(F)F)c(Cl)c2)c2c(=O)[nH]ccc21] | (S)-3-(3-((3-chloro-4-((R or S)-2,2,2-trifluoro-1-hydroxyethyl)phenyl)amino)-4-oxo-4,5-dihydro-1H-pyrazolo[4,3-c]pyridin-1-yl)-3-cyclopropylpropanenitrile (Peak 2, Chiralpak IA, 2 x 25 cm, 5 um; mobile phase ethanol in n-hexane (50%); detector: 220/254 nm; Tr = 25) | LRMS (ESI) calc'd for for $C_{20}H_{18}ClF_3N_5O_2$ [M + H]+: 452, found 452 |
| II-195 | 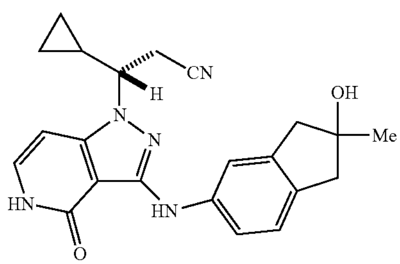 [SMILES: CC1(O)Cc2ccc(Nc3nn([C@@H](CC#N)C4CC4)c4cc[nH]c(=O)c34)cc2C1] | (S)-3-cyclopropyl-3-(3-(((R or S)-2-hydroxy-2-methyl-2,3-dihydro-1H-inden-5-yl)amino)-4-oxo-4,5-dihydro-1H-pyrazolo[4,3-c]pyridin-1-yl)propanenitrile | LRMS (ESI) calc'd for for $C_{22}H_{24}N_5O_2$ [M + H]+: 390, found 390 |
| II-196 | 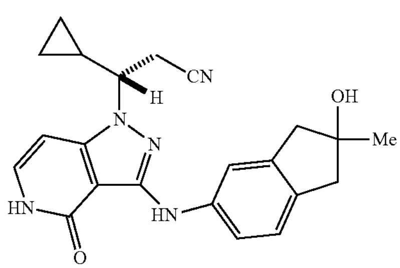 [SMILES: CC1(O)Cc2ccc(Nc3nn([C@@H](CC#N)C4CC4)c4cc[nH]c(=O)c34)cc2C1] | (S)-3-cyclopropyl-3-(3-(((R or S)-2-hydroxy-2-methyl-2,3-dihydro-1H-inden-5-yl)amino)-4-oxo-4,5-dihydro-1H-pyrazolo[4,3-c]pyridin-1-yl)propanenitrile | LRMS (ESI) calc'd for for $C_{22}H_{24}N_5O_2$ [M + H]+: 390, found 390 |
| II-197 | 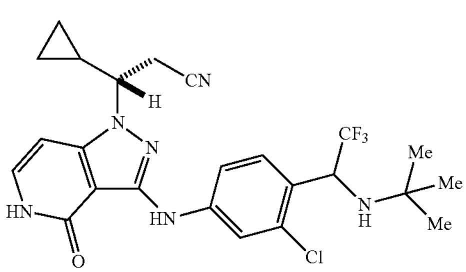 [SMILES: CC(C)(C)NC(c1ccc(Nc2nn([C@@H](CC#N)C3CC3)c3cc[nH]c(=O)c23)cc1Cl)C(F)(F)F] | (S)-3-(3-((4-((R or S)-1-(tert-butylamino)-2,2,2-trifluoroethyl)-3-chlorophenyl)amino)-4-oxo-4,5-dihydro-1H-pyrazolo[4,3-c]pyridin-1-yl)-3-cyclopropyl-propanenitrile (Peak 1, Chiralpak IA, 2 x 25 cm, 5 um; mobile phase: ethanol in n-hexane (10%). Tr = 16) | LRMS (ESI) calc'd for for $C_{24}H_{27}ClF_3N_6O$ [M + H]+: 507, found 507 |

TABLE 14-continued

| Example | Structure | Compound Name | MS |
|---|---|---|---|
| II-198 | 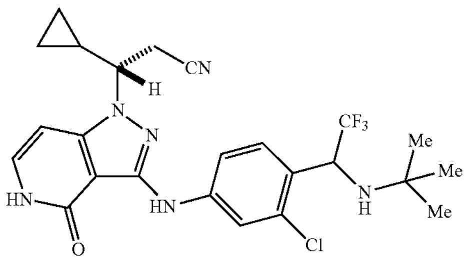 [SMILES: CC(C)(C)NC(c1ccc(Nc2nn([C@@H](CC#N)C3CC3)c3cc[nH]c(=O)c23)cc1Cl)C(F)(F)F] | (S)-3-(3-((4-((R or S)-1-(tert-butylamino)-2,2,2-trifluoroethyl)-3-chlorophenyl)amino)-4-oxo-4,5-dihydro-1H-pyrazolo[4,3-c]pyridin-1-yl)-3-cyclopropyl-propanenitrile (Chiralpak IA, 2 × 25 cm, 5 um; mobile phase: ethanol in n-hexane (10%). Tr = 26.7) | LRMS (ESI) calc'd for for $C_{24}H_{27}ClF_3N_6O$ [M + H]+: 507, found 507 |
| II-199 | 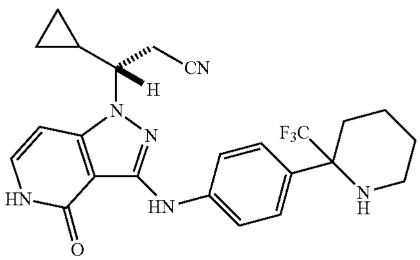 [SMILES: N#CC[C@@H](C1CC1)n1nc(Nc2ccc(C3(C(F)(F)F)CCCCN3)cc2)c2c(=O)[nH]ccc21] | (S)-3-cyclopropyl-3-(4-oxo-3-((4-((R or S)-2-(trifluoromethyl)piperidin-2-yl)phenyl)amino)-4,5-dihydro-1H-pyrazolo[4,3-c]pyridin-1-yl)propanenitrile | LRMS (ESI) calc'd for for $C_{24}H_{26}F_3N_6O$ [M + H]+: 471, found 471 |
| II-200 | 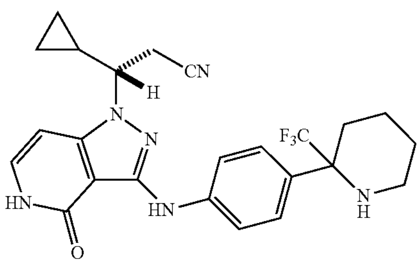 [SMILES: N#CC[C@@H](C1CC1)n1nc(Nc2ccc(C3(C(F)(F)F)CCCCN3)cc2)c2c(=O)[nH]ccc21] | (S)-3-cyclopropyl-3-(4-oxo-3-((4-((R or S)-2-(trifluoromethyl)piperidin-2-yl)phenyl)amino)-4,5-dihydro-1H-pyrazolo[4,3-c]pyridin-1-yl)propanenitrile | LRMS (ESI) calc'd for for $C_{24}H_{26}F_3N_6O$ [M + H]+: 471, found 471 |
| II-201 | 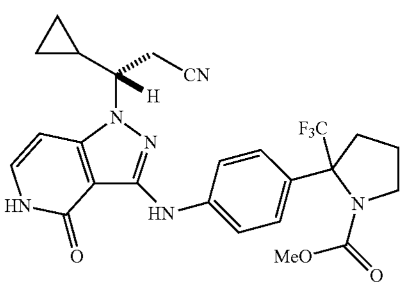 [SMILES: COC(=O)N1CCCC1(c1ccc(Nc2nn([C@@H](CC#N)C3CC3)c3cc[nH]c(=O)c23)cc1)C(F)(F)F] | (R or S)-methyl 2-(4-((1-((S)-2-cyano-1-cyclopropylethyl)-4-oxo-4,5-dihydro-1H-pyrazolo[4,3-c]pyridin-3-yl)amino)phenyl)-2-(trifluoromethyl)pyrrolidine-1-carboxylate | LRMS (ESI) calc'd for for $C_{25}H_{26}F_3N_6O_3$ [M + H]+: 515, found 515 |
| II-202 | 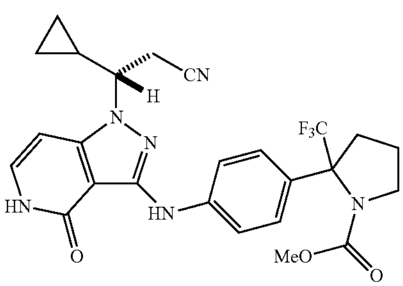 [SMILES: COC(=O)N1CCCC1(c1ccc(Nc2nn([C@@H](CC#N)C3CC3)c3cc[nH]c(=O)c23)cc1)C(F)(F)F] | (R or S)-methyl 2-(4-((1-((S)-2-cyano-1-cyclopropylethyl)-4-oxo-4,5-dihydro-1H-pyrazolo[4,3-c]pyridin-3-yl)amino)phenyl)-2-(trifluoromethyl)pyrrolidine-1-carboxylate | LRMS (ESI) calc'd for for $C_{25}H_{26}F_3N_6O_3$ [M + H]+: 515, found 515 |

TABLE 14-continued

| Example | Structure | Compound Name | MS |
|---|---|---|---|
| II-203 | 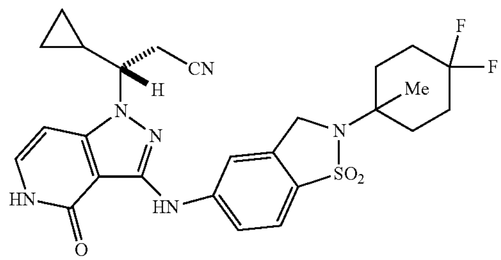 | (S)-3-cyclopropyl-3-(3-((2-(4,4-difluoro-1-methylcyclohexyl)-1,1-dioxido-2,3-dihydrobenzo[d]isothiazol-5-yl)amino)-4-oxo-4,5-dihydro-1H-pyrazolo[4,3-c]pyridin-1-yl)propanenitrile | LRMS (ESI) calc'd for for $C_{26}H_{29}F_2N_6O_3S$ [M + H]+: 543, found 543 |
| II-204 | 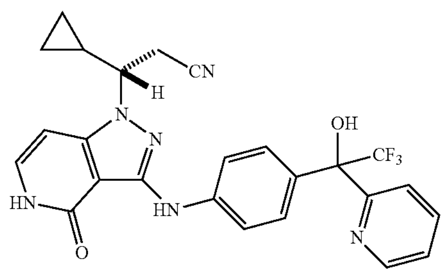 [SMILES: N#CC[C@@H](C1CC1)n1nc(Nc2ccc(C(O)(c3ccccn3)C(F)(F)F)cc2)c2c(=O)[nH]ccc21] | (S)-3-cyclopropyl-3-(4-oxo-3-((4-((S or R)-2,2,2-trifluoro-1-hydroxy-1-(pyridin-2-yl)ethyl)phenyl)amino)-4,5-dihydro-1H-pyrazolo[4,3-c]pyridin-1-yl)propanenitrile (SFC Peak 1, Chiralcel OJ-H, 21 x 250 (mm), 35% MeOH + 0.25% Dimethyl Ethyl Amine, in $CO_2$, Tr = 2.65) | LRMS (ESI) calc'd for for $C_{25}H_{22}F_3N_6O_2$ [M + H]+: 495, found 495 |
| II-205 | 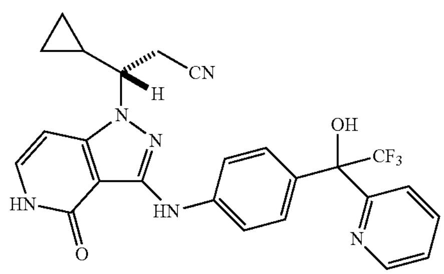 [SMILES: N#CC[C@@H](C1CC1)n1nc(Nc2ccc(C(O)(c3ccccn3)C(F)(F)F)cc2)c2c(=O)[nH]ccc21] | (S)-3-cyclopropyl-3-(4-oxo-3-((4-((S or R)-2,2,2-trifluoro-1-hydroxy-1-(pyridin-2-yl)ethyl)phenyl)amino)-4,5-dihydro-1H-pyrazolo[4,3-c]pyridin-1-yl)propanenitrile (SFC Peak 2, Chiralcel OJ-H, 21 x 250 (mm), 35% MeOH + 0.25% Dimethyl Ethyl Amine, in $CO_2$, Tr = 4.04) | LRMS (ESI) calc'd for for $C_{25}H_{22}F_3N_6O_2$ [M + H]+: 495, found 495 |
| II-206 | 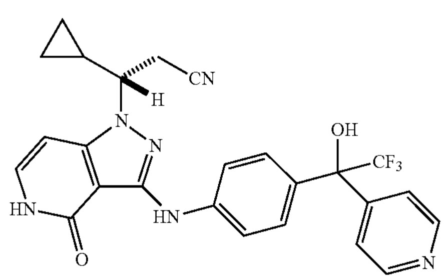 [SMILES: N#CC[C@@H](C1CC1)n1nc(Nc2ccc(C(O)(c3ccncc3)C(F)(F)F)cc2)c2c(=O)[nH]ccc21] | (S)-3-cyclopropyl-3-(4-oxo-3-((4-((S or R)-2,2,2-trifluoro-1-hydroxy-1-(pyridin-4-yl)ethyl)phenyl)amino)-4,5-dihydro-1H-pyrazolo[4,3-c]pyridin-1-yl)propanenitrile (SFC Peak 1, Chiralpak IC, 21 x 250 (mm), 35% MeOH + 0.25% Dimethyl Ethyl Amine, in $CO_2$, Tr = 3.07) | LRMS (ESI) calc'd for for $C_{25}H_{22}F_3N_6O_2$ [M + H]+: 495, found 495 |
| II-207 | 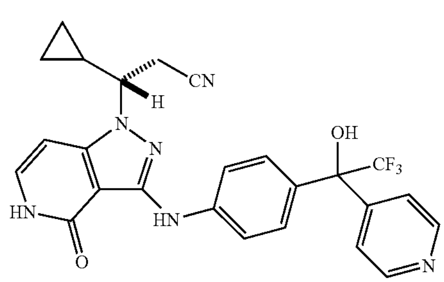 [SMILES: N#CC[C@@H](C1CC1)n1nc(Nc2ccc(C(O)(c3ccncc3)C(F)(F)F)cc2)c2c(=O)[nH]ccc21] | (S)-3-cyclopropyl-3-(4-oxo-3-((4-((S or R)-2,2,2-trifluoro-1-hydroxy-1-(pyridin-4-yl)ethyl)phenyl)amino)-4,5-dihydro-1H-pyrazolo[4,3-c]pyridin-1-yl)propanenitrile (SFC Peak 2, Chiralpak IC, 21 x 250 (mm), 35% MeOH + 0.25% Dimethyl Ethyl Amine, in $CO_2$, Tr = 3.40) | LRMS (ESI) calc'd for for $C_{25}H_{22}F_3N_6O_2$ [M + H]+: 495, found 495 |

TABLE 14-continued

| Example | Structure | Compound Name | MS |
|---|---|---|---|
| II-208 | 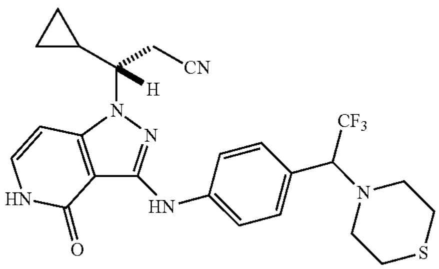 [SMILES: N#CC[C@@H](C1CC1)n1nc(Nc2ccc(C(N3CCSCC3)C(F)(F)F)cc2)c2c(=O)[nH]ccc21] | (S)-3-cyclopropyl-3-(4-oxo-3-((4-((R or S)-2,2,2-trifluoro-1-thiomorpholinoethyl)phenyl)amino)-4,5-dihydro-1H-pyrazolo[4,3-c]pyridin-1-yl)propanenitrile | LRMS (ESI) calc'd for for $C_{24}H_{26}F_3N_6OS$ [M + H]+: 503, found 503 |
| II-209 | 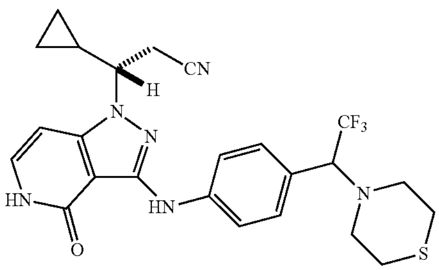 [SMILES: N#CC[C@@H](C1CC1)n1nc(Nc2ccc(C(N3CCSCC3)C(F)(F)F)cc2)c2c(=O)[nH]ccc21] | (S)-3-cyclopropyl-3-(4-oxo-3-((4-((R or S)-2,2,2-trifluoro-1-thiomorpholinoethyl)phenyl)amino)-4,5-dihydro-1H-pyrazolo[4,3-c]pyridin-1-yl)propanenitrile | LRMS (ESI) calc'd for for $C_{24}H_{26}F_3N_6OS$ [M + H]+: 503, found 503 |

Intermediate I-113

(S)-4-((1-(2-cyano-1-cyclopropylethyl)-4-oxo-4,5-dihydro-1H-pyrazolo[4,3-c]pyridin-3-yl)amino)-2-methylbenzoic acid

I-113

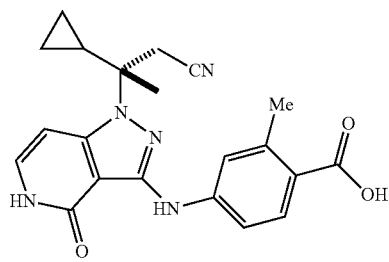

Step 1: (S)-4-((4-(benzyloxy)-1-(2-cyano-1-cyclopropylethyl)-1H-pyrazolo[4,3-c]pyridin-3-yl)amino)-2-methylbenzoic acid I-113a

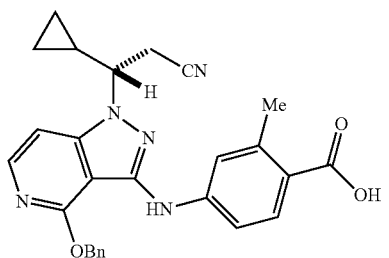

An oven dried pressure tube equipped with magnetic sir bar under an atmosphere of N2 was charged with (S)-3-(3-amino-4-(benzyloxy)-1H-pyrazolo[4,3-c]pyridin-1-yl)-3-cyclopropylpropanenitrile (2 g, 6 mmol), 4-bromo-2-methylbenzoic acid (2.2 g, 10.5 mmol), potassium acetate (1 g, 10.5 mmol), and t-Bu XPhos 3rd Generation precatalyst (524 mg, 0.7 mmol). The flask was evacuated, and purged with N2 (3 times) followed by the addition of t-amyl alcohol (15 mL). The reaction mixture stirred, and heated to 90° C. for 16 h. The reaction mixture was concentrated in vacuo, and purified by column chromatography on silica gel (hexanes/EtOAc gradient) to yield (S)-4-((4-(benzyloxy)-1-(2-cyano-1-cyclopropylethyl)-1H-pyrazolo[4,3-c]pyridin-3-yl)amino)-2-methylbenzoic acid II-204a (1.5 g, 3.21 mmol, 53%). LRMS (ESI) calc'd for $C_{27}H_{26}N_5O_3$ [M+H]+: 468. found 468.

Step 2: (S)-4-((1-(2-cyano-1-cyclopropylethyl)-4-oxo-4,5-dihydro-1H-pyrazolo[4,3-c]pyridin-3-yl)amino)-2-methylbenzoic acid

I-113

A round bottom flask with magnetic sir bar was charged with (S)-4-((4-(benzyloxy)-1-(2-cyano-1-cyclopropylethyl)-1H-pyrazolo[4,3-c]pyridin-3-yl)amino)-2-methylbenzoic acid I-113a (1.5 g, 3.2 mmol), EtOAc (32 ml), and Pd/C (683 mg, 0.2 mmol, 10% by wt). The reaction mixture was stirred under an atmosphere of $H_2$ for 4 h. The reaction mixture was filtered through a pad of celite, and the organics were concentrated in vacuo to afford a residue that was purified by column chromatography on silica gel (hexanes/EtOAc gradient) to yield (S)-4-((1-(2-cyano-1-cyclopropylethyl)-4-oxo-4,5-dihydro-1H-pyrazolo[4,3-c]pyridin-3-yl)amino)-2-methylbenzoic acid (800 mg, 2.1 mmol, 66%). LRMS (ESI) calc'd for $C_{20}H_{20}N_5O_3$ [M+H]$^+$:378. found 378. $^1$H NMR (500 MHz, DMSO): δ 11.15 (d, J=5.75 Hz; 1H), 8.35 (s, 1H), 7.83 (d, J=8.46 Hz, 1H), 7.62-7.60 (m, 1H), 7.21 (t, J=6.52 Hz, 1H), 6.61 (d, J=7.33 Hz, 1H), 4.23 (m, 1H), 3.29-3.24 (m, 2H), 2.54 (s, 3H), 1.47 (m, 1H), 1.19 (m, 1H), 0.65 (m, 1H), 0.52 (m, 1H), 0.43 (m, 1H), 0.33 (m, 1H).

Compound III-1

(S)-4-((1-(2-cyano-1-cyclopropylethyl)-4-oxo-4,5-dihydro-1H-pyrazolo[4,3-c]pyridin-3-yl)amino)-N,2-dimethyl-N-(2,2,2-trifluoroethyl)benzamide

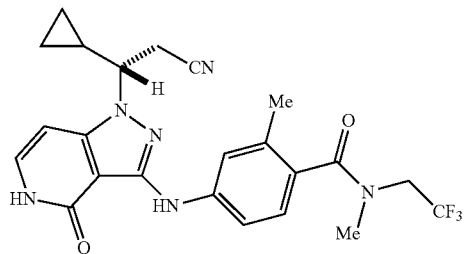

III-1

A reaction vial with magnetic sir bar was charged with (S)-4-((1-(2-cyano-1-cyclopropylethyl)-4-oxo-4,5-dihydro-1H-pyrazolo[4,3-c]pyridin-3-yl)amino)-2-methylbenzoic acid I-113 (20 mg, 0.05 mmol), hydroxybenzotriazole (HOBt) (16 mg, 0.1 mmol), 1-Ethyl-3-(3-dimethylaminopropyl)carbodiimide (EDC) (20 mg, 0.1 mmol), Hunig's base (37 uL, 0.2 mmol), and DMF (0.53 mL). To this reaction mixture, N-methyl-2,2,2-trifluoroethanamine (18 mg, 0.16 mmol) was added. The reaction mixture was stirred at rt for 16 h. The reaction mixture was purified by reverse phase chromatography to yield (S)-4-((1-(2-cyano-1-cyclopropylethyl)-4-oxo-4,5-dihydro-1H-pyrazolo[4,3-c]pyridin-3-yl)amino)-N,2-dimethyl-N-(2,2,2-trifluoroethyl)benzamide III-1 (15.3 mg, 0.03 mmol, 61%). LRMS (ESI) calc'd for $C_{23}H_{24}F_3N_6O_2$[M+H]$^+$: 473. found 473. $^1$H NMR (DMSO, 500 MHz): δ 1H NMR (499 MHz, DMSO): δ 11.12 (d, J=5.76 Hz, 1H), 8.18 (s, 1H), 7.64-7.60 (m, 2H), 7.21 (t, J=6.54 Hz, 1H), 7.07 (d, J=8.23 Hz, 1H), 6.60 (d, J=7.33 Hz, 1H), 4.36 (br s, 2H), 4.22 (m, 1H), 3.44 (s, 3H), 2.90 (s, 2H), 2.20 (s, 3H), 1.46 (m, 1H), 0.65 (m, 1H), 0.52 (m, 1H), 0.43 (m, 1H), 0.33 (m, 1H).

Table 15 discloses Examples that were prepared in analogy to Compound III-1 starting with Intermediate I-113.

TABLE 15

| Example | Structure | Compound Name | LRMS |
|---|---|---|---|
| III-2 | (structure) | (S)-4-((1-(2-cyano-1-cyclopropylethyl)-4-oxo-4,5-dihydro-1H-pyrazolo[4,3-c]pyridin-3-yl)amino)-N-ethyl-2-methyl-N-(2,2,2-trifluoroethyl)benzamide | LRMS (ESI) Calc'd for $C_{24}H_{26}F_3N_6O_2$ [M + H]$^+$: 487, found 487. |
| III-3 | (structure) | (S)-4-((1-(2-cyano-1-cyclopropylethyl)-4-oxo-4,5-dihydro-1H-pyrazolo[4,3-c]pyridin-3-yl)amino)-N-(2-(dimethylamino)ethyl)-2-methyl-N-(2,2,2-trifluoroethyl)benzamide | LRMS (ESI) Calc'd for $C_{26}H_{31}F_3N_7O_2$ [M + H]$^+$: 530, found 530. |

TABLE 15-continued

| Example | Structure | Compound Name | LRMS |
|---|---|---|---|
| III-4 | 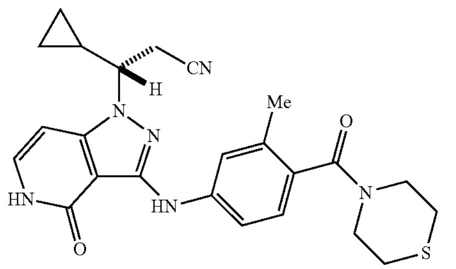 | (S)-3-cyclopropyl-3-(3-((3-methyl-4-(thiomorpholine-4-carbonyl)phenyl)amino)-4-oxo-4,5-dihydro-1H-pyrazolo[4,3-c]pyridin-1-yl)propanenitrile | LRMS (ESI) Calc'd for $C_{24}H_{27}N_6O_2S$ [M + H]$^+$: 463, found 463. |
| III-5 | 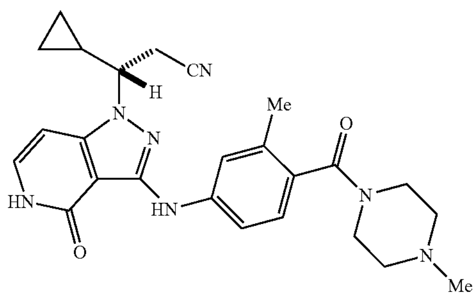 [SMILES: Cc1cc(Nc2nn([C@@H](CC#N)C3CC3)c3cc[nH]c(=O)c23)ccc1C(=O)N1CCN(C)CC1] | (S)-3-cyclopropyl-3-(3-((3-methyl-4-(4-methylpiperazine-1-carbonyl)phenyl)amino)-4-oxo-4,5-dihydro-1H-pyrazolo[4,3-c]pyridin-1-yl)propanenitrile | LRMS (ESI) Calc'd for $C_{25}H_{30}N_7O_2$ [M + H]$^+$: 460, found 460. |
| III-6 | 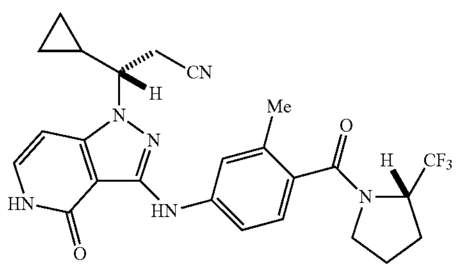 [SMILES: Cc1cc(Nc2nn([C@@H](CC#N)C3CC3)c3cc[nH]c(=O)c23)ccc1C(=O)N1CCC[C@H]1C(F)(F)F] | (S)-3-cyclopropyl-3-(3-((3-methyl-4-((S)-2-(trifluoromethyl)pyrrolidine-1-carbonyl)phenyl)amino)-4-oxo-4,5-dihydro-1H-pyrazolo[4,3-c]pyridin-1-yl)propanenitrile | LRMS (ESI) Calc'd for $C_{25}H_{26}F_3N_6O_2$ [M + H]$^+$: 499, found 499. |
| III-7 | 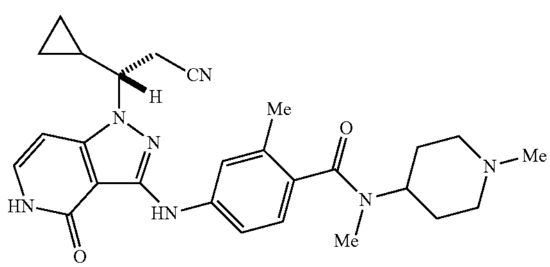 [SMILES: Cc1cc(Nc2nn([C@@H](CC#N)C3CC3)c3cc[nH]c(=O)c23)ccc1C(=O)N(C)C1CCN(C)CC1] | (S)-4-((1-(2-cyano-1-cyclopropylethyl)-4-oxo-4,5-dihydro-1H-pyrazolo[4,3-c]pyridin-3-yl)amino)-N,2-dimethyl-N-(1-methylpiperidin-4-yl)benzamide | LRMS (ESI) Calc'd for $C_{27}H_{34}N_7O_2$ [M + H]$^+$: 488, found 488. |
| III-8 | 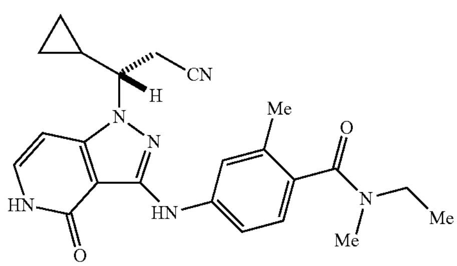 [SMILES: CCN(C)C(=O)c1ccc(Nc2nn([C@@H](CC#N)C3CC3)c3cc[nH]c(=O)c23)cc1C] | (S)-4-((1-(2-cyano-1-cyclopropylethyl)-4-oxo-4,5-dihydro-1H-pyrazolo[4,3-c]pyridin-3-yl)amino)-N-ethyl-N,2-dimethylbenzamide | LRMS (ESI) Calc'd for $C_{23}H_{27}N_6O_2$ [M + H]$^+$: 419, found 419. |

TABLE 15-continued

| Example | Structure | Compound Name | LRMS |
|---|---|---|---|
| III-9 | 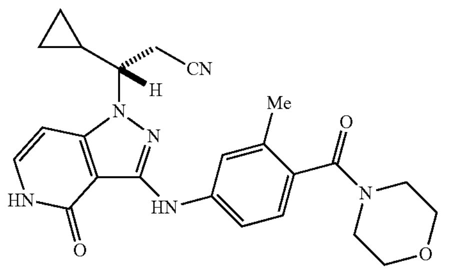 [SMILES: Cc1cc(Nc2nn([C@@H](CC#N)C3CC3)c3cc[nH]c(=O)c23)ccc1C(=O)N1CCOCC1] | (S)-3-cyclopropyl-3-(3-((3-methyl-4-(morpholine-4-carbonyl)phenyl)amino)-4-oxo-4,5-dihydro-1H-pyrazolo[4,3-c]pyridin-1-yl)propanenitrile | LRMS (ESI) Calc'd for $C_{24}H_{27}N_6O_3$ $[M + H]^+$: 447, found 447. |
| III-10 | 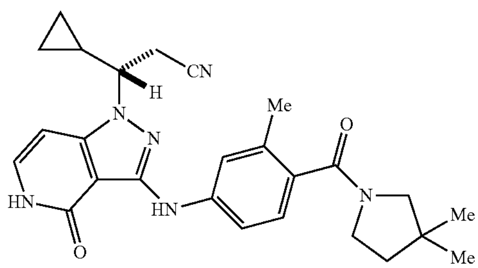 [SMILES: Cc1cc(Nc2nn([C@@H](CC#N)C3CC3)c3cc[nH]c(=O)c23)ccc1C(=O)N1CCC(C)(C)C1] | (S)-3-cyclopropyl-3-(3-((4-(3,3-dimethyl-pyrrolidine-1-carbonyl)-3-methylphenyl)amino)-4-oxo-4,5-dihydro-1H-pyrazolo[4,3-c]pyridin-1-yl)propanenitrile | LRMS (ESI) Calc'd for $C_{26}H_{31}N_6O_2$ $[M + H]^+$: 459, found 459. |
| III-11 | 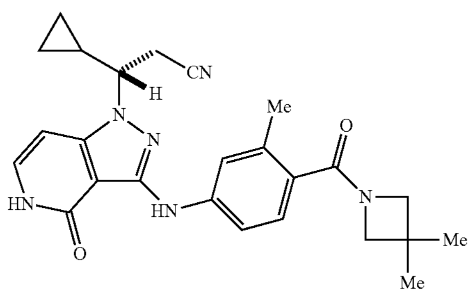 [SMILES: Cc1cc(Nc2nn([C@@H](CC#N)C3CC3)c3cc[nH]c(=O)c23)ccc1C(=O)N1CC(C)(C)C1] | (S)-3-cyclopropyl-3-(3-((4-(3,3-dimethyl-azetidine-1-carbonyl)-3-methylphenyl)amino)-4-oxo-4,5-dihydro-1H-pyrazolo[4,3-c]pyridin-1-yl)propanenitrile | LRMS (ESI) Calc'd for $C_{25}H_{29}N_6O_2$ $[M + H]^+$: 445, found 445. |
| III-12 | 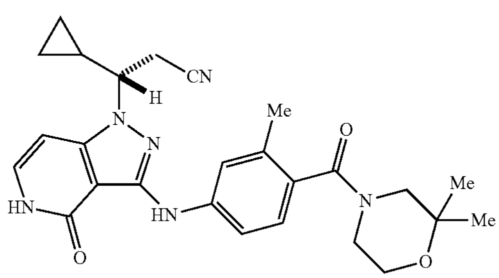 [SMILES: Cc1cc(Nc2nn([C@@H](CC#N)C3CC3)c3cc[nH]c(=O)c23)ccc1C(=O)N1CCOC(C)(C)C1] | (S)-3-cyclopropyl-3-(3-((4-(2,2-dimethyl-morpholine-4-carbonyl)-3-methylphenyl)amino)-4-oxo-4,5-dihydro-1H-pyrazolo[4,3-c]pyridin-1-yl)propanenitrile | LRMS (ESI) Calc'd for $C_{26}H_{31}N_6O_3$ $[M + H]^+$: 475, found 475. |
| III-13 | 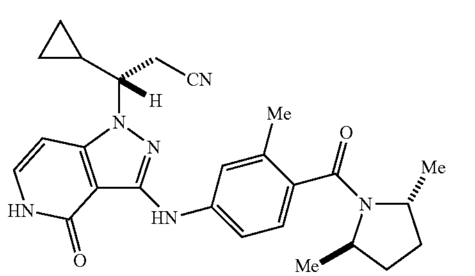 [SMILES: Cc1cc(Nc2nn([C@@H](CC#N)C3CC3)c3cc[nH]c(=O)c23)ccc1C(=O)N1[C@H](C)CC[C@H]1C] | (S)-3-cyclopropyl-3-(3-((4-((2R,5R)-2,5-dimethylpyrrolidine-1-carbonyl)-3-methylphenyl)amino)-4-oxo-4,5-dihydro-1H-pyrazolo[4,3-c]pyridin-1-yl)propanenitrile | LRMS (ESI) Calc'd for $C_{26}H_{31}N_6O_2$ $[M + H]^+$: 459, found 459. |

TABLE 15-continued

| Example | Structure | Compound Name | LRMS |
|---|---|---|---|
| III-14 | 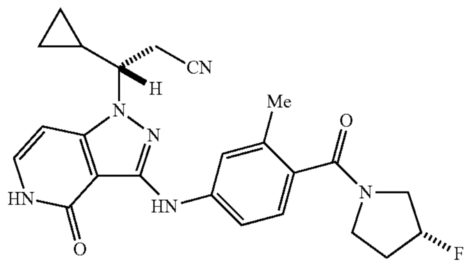 [SMILES: Cc1cc(Nc2nn([C@@H](CC#N)C3CC3)c3cc[nH]c(=O)c23)ccc1C(=O)N1CC[C@@H](F)C1] | (S)-3-cyclopropyl-3-(3-((4-((R)-3-fluoro-pyrrolidine-1-carbonyl)-3-methylphenyl)amino)-4-oxo-4,5-dihydro-1H-pyrazolo[4,3-c]pyridin-1-yl)propanenitrile | LRMS (ESI) Calc'd for $C_{24}H_{26}FN_6O_2$ [M + H]$^+$: 449, found 449. |
| III-15 | 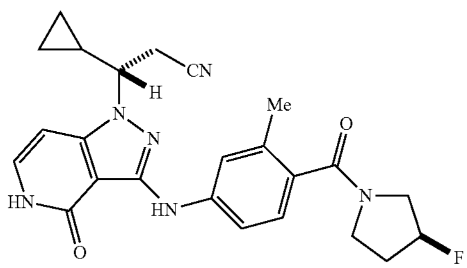 [SMILES: Cc1cc(Nc2nn([C@@H](CC#N)C3CC3)c3cc[nH]c(=O)c23)ccc1C(=O)N1CC[C@H](F)C1] | (S)-3-cyclopropyl-3-(3-((4-((S)-3-fluoro-pyrrolidine-1-carbonyl)-3-methylphenyl)amino)-4-oxo-4,5-dihydro-1H-pyrazolo[4,3-c]pyridin-1-yl)propanenitrile | LRMS (ESI) Calc'd for $C_{24}H_{26}FN_6O_2$ [M + H]$^+$: 449, found 449. |

Compound IV-1

(S)-3-cyclopropyl-3-(3-((3-methyl-4-((S)-2-methyl-piperidine-1-carbonyl)phenyl)amino)-4-oxo-4,5-dihydro-1H-pyrazolo[4,3-c]pyridin-1-yl)propanenitrile

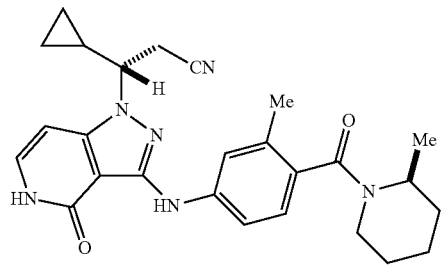

IV-1

An oven dried round bottom flask with magnetic stir bar under an atmosphere of N2 was charged with (S)-4-((1-(2-cyano-1-cyclopropylethyl)-4-oxo-4,5-dihydro-1H-pyrazolo[4,3-c]pyridin-3-yl)amino)-2-methylbenzoic acid I-113 (20 mg, 0.05 mmol), DMF (177 uL), (1-[Bis(dimethylamino)methylene]-1H-1,2,3-triazolo[4,5-b]pyridinium 3-oxid hexafluorophosphate; HATU) (81 mg, 0.2 mmol), Huenig's base (74 uL, 0.4 mmol), and (S)-2-methylpiperidine (15 mg, 0.2 mmol). The resulting reaction mixture was stirred for 12-16 h, and was concentrated in vacuo. The crude oil was purified by column chromatography on silica gel eluting with Hexanes/EtOAc gradient to yield (S)-3-cyclopropyl-3-(3-((3-methyl-4-((S)-2-methylpiperidine-1-carbonyl)phenyl)amino)-4-oxo-4,5-dihydro-1H-pyrazolo[4,3-c]pyridin-1-yl)propanenitrile IV-1 (14 mg, 0.03 mmol, 60%). LRMS (ESI) Calc'd for $C_{26}H_{31}N_6O_2$ [M+H]$^+$: 459. found 459. $^1$H NMR (500 MHz, DMSO): δ 11.09 (d, J=5.81 Hz, 1H), 8.10 (m, 1H), 7.58 (m, 1H), 7.19 (t, J=6.59 Hz, 1H), 6.58 (d, J=7.34 Hz, 1H), 4.19 (m, 1H), 3.31 (m, 1H), 3.18 (m, 1H), 2.98 (m, 1H), 2.52 (s, 3H), 2.22-2.19 (m, 3H), 1.55-1.51 (m, 5H), 1.26-1.20 (m, 4H), 0.63 (m, 1H), 0.51 (m, 1H), 0.41 (m, 1H), 0.33 (m, 1H).

The following Examples outlined in Table 16 were prepared by analogy using the general procedure outlined above for Compound IV-1 above.

TABLE 16

| Intermediate | Structure | Name | MS |
|---|---|---|---|
| IV-2 | 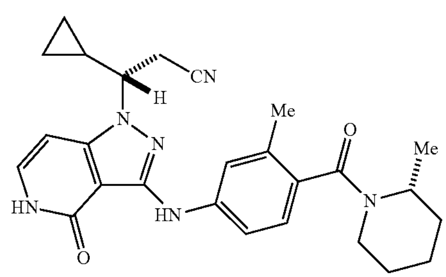 [SMILES: Cc1cc(Nc2nn([C@@H](CC#N)C3CC3)c3cc[nH]c(=O)c23)ccc1C(=O)N1CCCC[C@H]1C] | (S)-3-cyclopropyl-3-(3-((3-methyl-4-((R)-2-methylpiperidine-1-carbonyl)phenyl)amino)-4-oxo-4,5-dihydro-1H-pyrazolo[4,3-c]pyridin-1-yl)propanenitrile | LRMS (ESI) Calc'd for $C_{26}H_{31}N_6O_2$ [M + H]+: 459, found 459. |

TABLE 16-continued

| Intermediate | Structure | Name | MS |
|---|---|---|---|
| IV-3 | 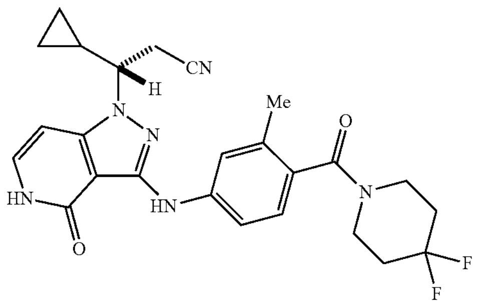 [SMILES: Cc1cc(Nc2nn([C@@H](CC#N)C3CC3)c3cc[nH]c(=O)c23)ccc1C(=O)N1CCC(F)(F)CC1] | (S)-3-cyclopropyl-3-(3-((4-(4,4-difluoro-piperidine-1-carbonyl)-3-methylphenyl)amino)-4-oxo-4,5-dihydro-1H-pyrazolo[4,3-c]pyridin-1-yl)propanenitrile | LRMS (ESI) Calc'd for $C_{26}H_{31}N_6O_2$ [M + H]+: 481, found 481. |
| IV-4 | 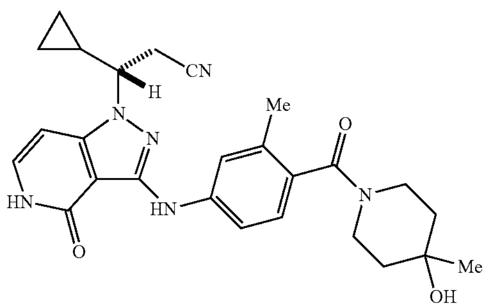 [SMILES: Cc1cc(Nc2nn([C@@H](CC#N)C3CC3)c3cc[nH]c(=O)c23)ccc1C(=O)N1CCC(C)(O)CC1] | (S)-3-cyclopropyl-3-(3-((4-(4-hydroxy-4-methyl-piperidine-1-carbonyl)-3-methylphenyl)amino)-4-oxo-4,5-dihydro-1H-pyrazolo[4,3-c]pyridin-1-yl)propanenitrile | LRMS (ESI) Calc'd for $C_{26}H_{31}N_6O_3$ [M + H]+: 475, found 475. |
| IV-5 | 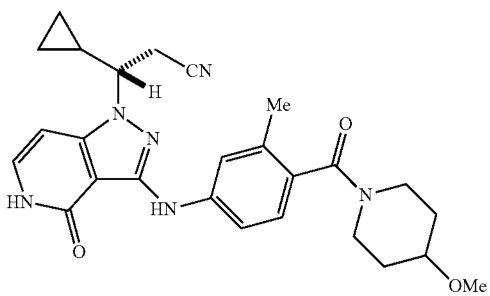 [SMILES: COC1CCN(C(=O)c2ccc(Nc3nn([C@@H](CC#N)C4CC4)c4cc[nH]c(=O)c34)cc2C)CC1] | (S)-3-cyclopropyl-3-(3-((4-(4-methoxy-piperidine-1-carbonyl)-3-methylphenyl)amino)-4-oxo-4,5-dihydro-1H-pyrazolo[4,3-c]pyridin-1-yl)propanenitrile | LRMS (ESI) Calc'd for $C_{26}H_{31}N_6O_3$ [M + H]+: 475, found 475. |
| IV-6 | 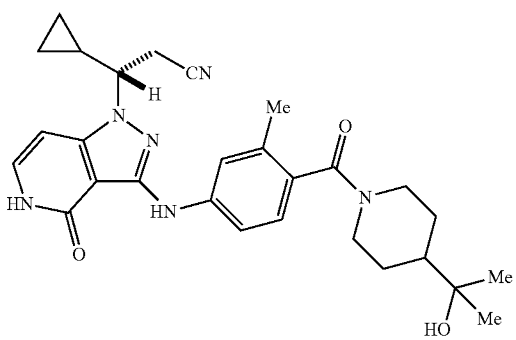 [SMILES: Cc1cc(Nc2nn([C@@H](CC#N)C3CC3)c3cc[nH]c(=O)c23)ccc1C(=O)N1CCC(C(C)(C)O)CC1] | (S) 3-cyclopropyl-3-(3-((4-(4-(2-hydroxypropan-2-yl)piperidine-1-carbonyl)-3-methyl-phenyl)amino)-4-oxo-4,5-dihydro-1H-pyrazolo[4,3-c]pyridin-1-yl) propanenitrile | LRMS (ESI) Calc'd for $C_{28}H_{35}N_6O_3$ [M + H]+: 503, found 503. |
| IV-7 | 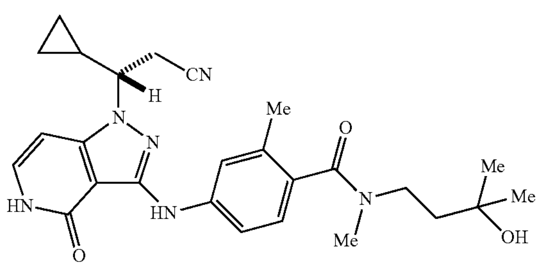 [SMILES: Cc1cc(Nc2nn([C@@H](CC#N)C3CC3)c3cc[nH]c(=O)c23)ccc1C(=O)N(C)CCC(C)(C)O] | (S)-4-((1-(2-cyano-1-cyclopropylethyl)-4-oxo-4,5-dihydro-1H-pyrazolo[4,3-c]pyridin-3-yl)amino)-N-(3-hydroxy-3-methylbutyl)-N,2-dimethylbenzamide | LRMS (ESI) Calc'd for $C_{26}H_{33}N_6O_3$ [M + H]+: 477, found 477. |

TABLE 16-continued

| Intermediate | Name | MS |
|---|---|---|
| IV-8 | (S)-3-(3-((4-(azepane-1-carbonyl)-3-methylphenyl)amino)-4-oxo-4,5-dihydro-1H-pyrazolo[4,3-c]pyridin-1-yl)-3-cyclopropylpropanenitrile | LRMS (ESI) Calc'd for $C_{26}H_{31}N_6O_2$ [M + H]+: 459, found 459. |
| IV-9 | (S)-3-cyclopropyl-3-(3-((4-(3-fluoroazetidine-1-carbonyl)-3-methylphenyl)amino)-4-oxo-4,5-dihydro-1H-pyrazolo[4,3-c]pyridin-1-yl)propanenitrile | LRMS (ESI) Calc'd for $C_{23}H_{24}FN_6O_2$ [M + H]+: 435, found 435. |
| IV-10 | (S)-3-cyclopropyl-3-(3-((4-(3-methoxyazetidine-1-carbonyl)-3-methylphenyl)amino)-4-oxo-4,5-dihydro-1H-pyrazolo[4,3-c]pyridin-1-yl)propanenitrile | LRMS (ESI) Calc'd for $C_{24}H_{27}N_6O_3$ [M + H]+: 447, found 447. |
| IV-11 | (S)-3-(3-((4-((1R,5S)-8-oxa-3-azabicyclo[3.2.1]octane-3-carbonyl)-3-methylphenyl)amino)-4-oxo-4,5-dihydro-1H-pyrazolo[4,3-c]pyridin-1-yl)-3-cyclopropylpropanenitrile | LRMS (ESI) Calc'd for $C_{26}H_{29}N_6O_3$ [M + H]+: 473, found 473. |
| IV-12 | (S)-4-((1-(2-cyano-1-cyclopropylethyl)-4-oxo-4,5-dihydro-1H-pyrazolo[4,3-c]pyridin-3-yl)amino)-N-cyclohexyl-N,2-dimethylbenzamide | LRMS (ESI) Calc'd for $C_{27}H_{33}N_6O_2$ [M + H]+: 473, found 473. |

TABLE 16-continued

| Intermediate | Structure | Name | MS |
|---|---|---|---|
| IV-13 | (structure) | (S)-tert-butyl (1-(4-((1-(2-cyano-1-cyclopropylethyl)-4-oxo-4,5-dihydro-1H-pyrazolo[4,3-c]pyridin-3-yl)amino)-2-methylbenzoyl)piperidin-4-yl)(methyl)carbamate | LRMS (ESI) Calc'd for $C_{31}H_{40}N_7O_4$ [M + H]+: 574, found 574. |

Example V-1

(S or R)-3-(3-((4-fluorophenyl)amino)-4-oxo-4,5-dihydro-1H-pyrazolo[4,3-c]pyridine-1-yl)butanenitrile

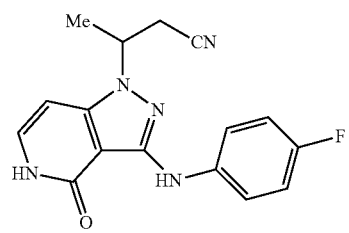

V-1

To (R or S)-3-(3-amino-4-(benzyloxy)-1H-pyrazolo[4,3-c]pyridin-1-yl)butanenitrile I-108A (30 mg, 0.098 mmol), 1-bromo-4-fluoro-benzene (25.5 mg, 0.146 mmol), Pd$_2$(dba)$_3$ (22.4 mg, 0.024 mmol), 2-di-tert-butylphosphino-3,4,5,6-tetramethyl-2',4',6'-triisopropyl-1,1'-biphenyl (28.2 mg, 0.06 mmol), and potassium acetate (19 mg, 0.195 mmol) in a degassed sealed reaction vial, was added isopropanol (0.360 mL). The reaction mixture was heated to 80° C. overnight. The reaction was cooled to rt, and 0.2 mL of trifluoroacetic acid was added. The reaction was stirred at room temperature for an additional 3 h. The reaction mixture was diluted with 3.5 mL of DMSO, filtered using a 0.2 micron WHATMAN syringe, and purified with reverse phase chromatography to afford compound, V-1. LRMS (ESI) calc'd for $C_{16}H_{15}FN_5O$ [M+H]+: 312. found 312.

The following Examples outlined in Table 17 were prepared by analogy using the general procedure outlined above for Compound V-1 above.

TABLE 17

| Example | Structure | Compound Name | MS |
|---|---|---|---|
| V-2 | (structure) | (3R or S)-3-[4-oxo-3-({4-[(1S or R)-2,2,2-trifluoro-1-hydroxy-1-methylethyl]phenyl}amino)-4,5-dihydro-1H-pyrazolo[4,3-c]pyridin-1-yl]butanenitrile (from I-2A) | LRMS (ESI) calc'd for $C_{19}H_{19}F_3N_5O_2$ [M + H]+: 406, found 406. |
| V-3 | (structure) | (3R or S)-3-[4-oxo-3-({4-[(1S or R)-2,2,2-trifluoro-1-hydroxy-1-methylethyl]phenyl}amino)-4,5-dihydro-1H-pyrazolo[4,3-c]pyridin-1-yl]butanenitrile (from I-2B) | LRMS (ESI) calc'd for $C_{19}H_{19}F_3N_5O_2$ [M + H]+: 406, found 406. |

TABLE 17-continued

| Example | Structure | Compound Name | MS |
|---|---|---|---|
| V-4 | 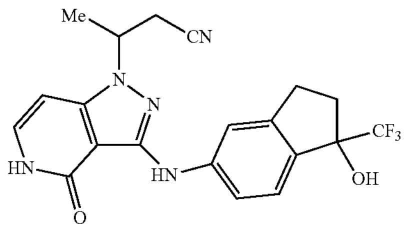 [SMILES: CC(CC#N)n1nc(Nc2ccc3c(c2)CCC3(O)C(F)(F)F)c2c(=O)[nH]ccc21] | (3R or S)-3-(3-{[(1S or R)-1-hydroxy-1-(trifluoro-methyl)-2,3-dihydro-1H-inden-5-yl]amino}-4-oxo-4,5-dihydro-1H-pyrazolo[4,3-c]pyridin-1-yl)butanenitrile (from I-3A) | LRMS (ESI) calc'd for $C_{20}H_{19}F_3N_5O_2$ [M + H]$^+$: 418, found 418. |
| V-5 | 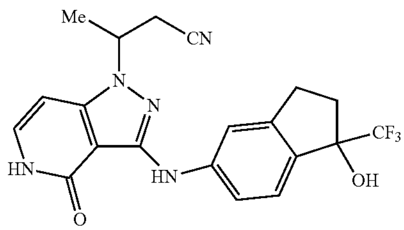 [SMILES: CC(CC#N)n1nc(Nc2ccc3c(c2)CCC3(O)C(F)(F)F)c2c(=O)[nH]ccc21] | (3R or S)-3-(3-{[(1S or R)-1-hydroxy-1-(trifluoro-methyl)-2,3-dihydro-1H-inden-5-yl]amino}-4-oxo-4,5-dihydro-1H-pyrazolo[4,3-c]pyridin-1-yl)butanenitrile (from I-3B) | LRMS (ESI) calc'd for $C_{20}H_{19}F_3N_5O_2$ [M + H]$^+$: 418, found 418. |
| V-6 | 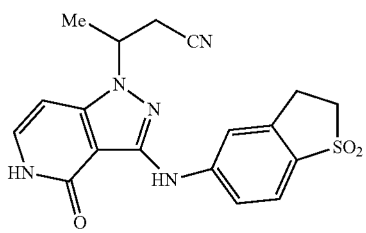 [SMILES: CC(CC#N)n1nc(Nc2ccc3c(c2)CCS3(=O)=O)c2c(=O)[nH]ccc21] | (3R or S)-3-{3-[(1,1-dioxido-2,3-dihydro-1-benzothiophen-5-yl)amino]-4-oxo-4,5-dihydro-1H-pyrazolo[4,3-c]pyridin-1-yl}butanenitrile | LRMS (ESI) calc'd for $C_{18}H_{18}N_5O_3S$ [M + H]$^+$: 384, found 384. |
| V-7 | 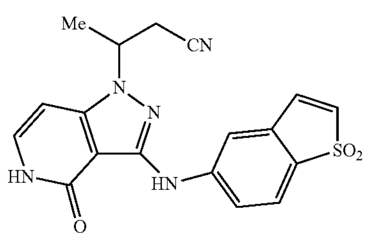 [SMILES: CC(CC#N)n1nc(Nc2ccc3c(c2)C=CS3(=O)=O)c2c(=O)[nH]ccc21] | (3R or S)-3-{3-[(1,1-dioxido-1-benzothiophen-5-yl)amino]-4-oxo-4,5-dihydro-1H-pyrazolo[4,3-c]pyridin-1-yl}butanenitrile | LRMS (ESI) calc'd for $C_{18}H_{16}N_5O_3S$ [M + H]$^+$: 382, found 382. |
| V-8 | 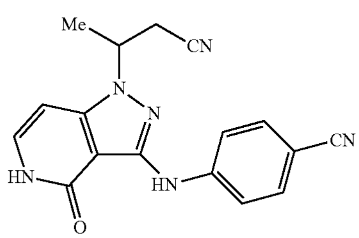 [SMILES: CC(CC#N)n1nc(Nc2ccc(C(F)(F)F)cc2)c2c(=O)[nH]ccc21] | 4-({1-[(1S or R)-2-cyano-1-methylethyl]-4-oxo-4,5-dihydro-1H-pyrazolo[4,3-c]pyridin-3-yl}amino)benzonitrile | LRMS (ESI) calc'd for $C_{17}H_{15}N_6O$ [M + H]$^+$: 319, found 319. |
| V-9 | 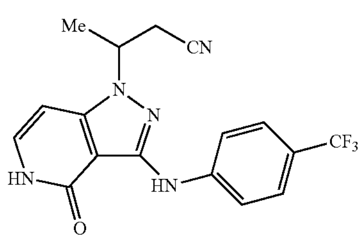 | (3R or S)-3-(4-oxo-3-{[4-(trifluoromethyl)phenyl]amino}-4,5-dihydro-1H-pyrazolo[4,3-c]pyridin-1-yl)butanenitrile | LRMS (ESI) calc'd for $C_{17}H_{14}F_3N_5O$ [M + H]$^+$: 362, found 362. |

TABLE 17-continued

| Example | Structure | Compound Name | MS |
|---|---|---|---|
| V-10 | 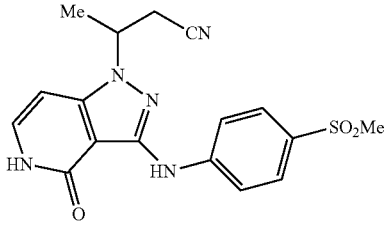 [SMILES: CC(CC#N)n1nc(Nc2ccc(S(C)(=O)=O)cc2)c2c(=O)[nH]ccc21] | (3R or S)-3-(3-{[4-(methyl-sulfonyl)phenyl]amino}-4-oxo-4,5-dihydro-1H-pyrazolo[4,3-c]pyridin-1-yl) butanenitrile | LRMS (ESI) calc'd for $C_{17}H_{18}N_5O_3S$ $[M + H]^+$: 372, found 372. |
| V-11 | 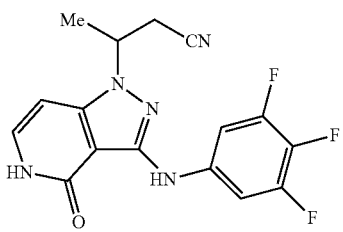 [SMILES: CC(CC#N)n1nc(Nc2cc(F)c(F)c(F)c2)c2c(=O)[nH]ccc21] | (3R or S)-3-{4-oxo-3-[(3,4,5-trifluorophenyl)amino]-4,5-dihydro-1H-pyrazolo[4,3-c]pyridin-1-yl}butanenitrile | LRMS (ESI) calc'd for $C_{16}H_{12}F_3N_5O$ $[M + H]^+$: 348, found 348. |
| V-12 | 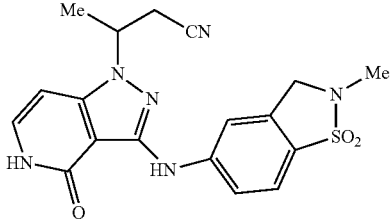 [SMILES: CC(CC#N)n1nc(Nc2ccc3c(c2)CN(C)S3(=O)=O)c2c(=O)[nH]ccc21] | (3R or S)-3-{3-[(2-methyl-1,1-dioxido-2,3-dihydro-1,2-benzisothiazol-5-yl)amino]-4-oxo-4,5-dihydro-1H-pyrazolo[4,3-c]pyridin-1-yl}butanenitrile | LRMS (ESI) calc'd for $C_{19}H_{19}N_6O_3S$ $[M + H]^+$: 399, found 399. |
| V-13 | 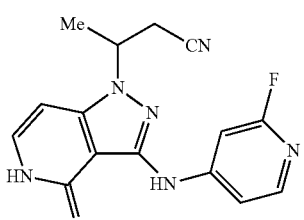 | (3R or S)-3-{3-[(2-fluoro-pyridin-4-yl)amino]-4-oxo-4,5-dihydro-1H-pyrazolo[4,3-c]pyridin-1-yl}butanenitrile | LRMS (ESI) calc'd for $C_{15}H_{14}FN_6O$ $[M + H]^+$: 313, found 313. |
| V-14 | 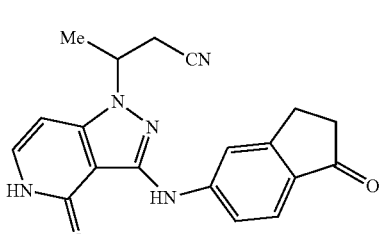 | (3R or S)-3-{4-oxo-3-[(1-oxo-2,3-dihydro-1H-inden-5-yl)amino]-4,5-dihydro-1H-pyrazolo[4,3-c]pyridin-1-yl}butanenitrile | LRMS (ESI) calc'd for $C_{19}H_{18}N_5O_2$ $[M + H]^+$: 348, found 348. |
| V-15 | 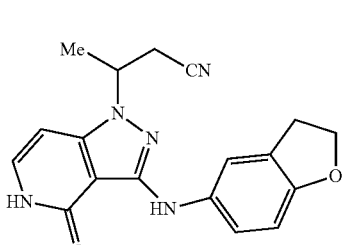 | (3R or S)-3-[3-(2,3-dihydro-1-benzofuran-5-ylamino)-4-oxo-4,5-dihydro-1H-pyrazolo[4,3-c]pyridin-1-yl]butanenitrile | LRMS (ESI) calc'd for $C_{18}H_{18}N_5O_2$ $[M + H]^+$: 336, found 336. |

TABLE 17-continued

| Example | Structure | Compound Name | MS |
|---|---|---|---|
| V-16 | 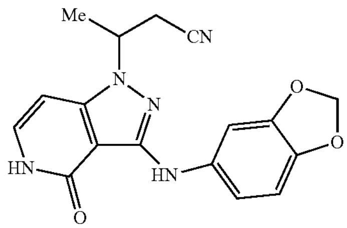 [SMILES: CC(CC#N)n1nc(Nc2ccc3c(c2)OCO3)c2c(=O)[nH]ccc21] | (3R or S)-3-[3-(1,3-benzodioxol-5-ylamino)-4-oxo-4,5-dihydro-1H-pyrazolo[4,3-c]pyridin-1-yl]butanenitrile | LRMS (ESI) calc'd for $C_{17}H_{16}N_5O_3$ [M + H]$^+$: 338, found 338. |
| V-17 | 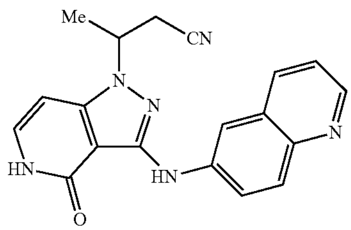 | (3R or S)-3-[4-oxo-3-(quinolin-6-ylamino)-4,5-dihydro-1H-pyrazolo[4,3-c]pyridin-1-yl]butanenitrile | LRMS (ESI) calc'd for $C_{19}H_{17}N_6O$ [M + H]$^+$: 345, found 345. |
| V-18 | 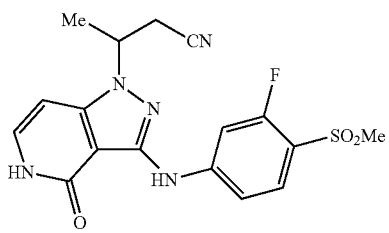 [SMILES: CC(CC#N)n1nc(Nc2ccc(S(C)(=O)=O)c(F)c2)c2c(=O)[nH]ccc21] | (3R or S)-3-(3-{[3-fluoro-4-(methylsulfonyl)phenyl]amino}-4-oxo-4,5-dihydro-1H-pyrazolo[4,3-c]pyridin-1-yl)butanenitrile | LRMS (ESI) calc'd for $C_{17}H_{17}FN_5O_3S$ [M + H]$^+$: 390, found 390. |
| V-19 | 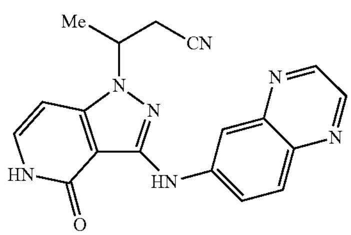 [SMILES: CC(CC#N)n1nc(Nc2ccc3nccnc3c2)c2c(=O)[nH]ccc21] | (3R or S)-3-[4-oxo-3-(quinoxalin-6-ylamino)-4,5-dihydro-1H-pyrazolo[4,3-c]pyridin-1-yl]butanenitrile | LRMS (ESI) calc'd for $C_{18}H_{16}N_7O$ [M + H]$^+$: 346, found 346. |
| V-20 | 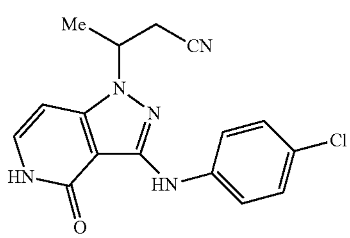 [SMILES: CC(CC#N)n1nc(Nc2ccc(Cl)cc2)c2c(=O)[nH]ccc21] | (3R or S)-3-{3-[(4-chlorophenyl)amino]-4-oxo-4,5-dihydro-1H-pyrazolo[4,3-c]pyridin-1-yl}butanenitrile | LRMS (ESI) calc'd for $C_{16}H_{15}ClN_5O$ [M + H]$^+$: 328, found 328. |
| V-21 | 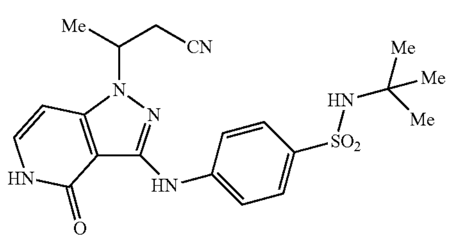 [SMILES: CC(CC#N)n1nc(Nc2ccc(S(=O)(=O)NC(C)(C)C)cc2)c2c(=O)[nH]ccc21] | N-tert-butyl-4-({1-[(1S or R)-2-cyano-1-methylethyl]-4-oxo-4,5-dihydro-1H-pyrazolo[4,3-c]pyridin-3-yl}amino)benzenesulfonamide | LRMS (ESI) calc'd for $C_{20}H_{25}N_6O_3S$ [M + H]$^+$: 429, found 429. |

TABLE 17-continued

| Example | Structure | Compound Name | MS |
|---|---|---|---|
| V-22 | 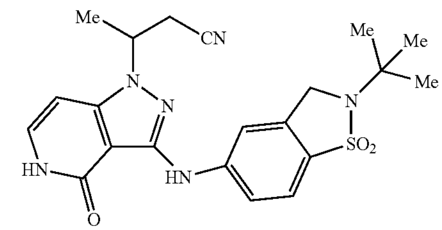 [SMILES: CC(CC#N)n1nc(Nc2ccc3c(c2)CN(C(C)(C)C)S3(=O)=O)c2c(=O)[nH]ccc21] | (3R or S)-3-{3-[(2-tert-butyl-1,1-dioxido-2,3-dihydro-1,2-benzisothiazol-5-yl)amino]-4-oxo-4,5-dihydro-1H-pyrazolo[4,3-c]pyridin-1-yl}butanenitrile | LRMS (ESI) calc'd for $C_{21}H_{25}N_6O_3S$ $[M + H]^+$: 441, found 441. |

Example VI-1

(S)-methyl 3-((4-(azetidin-1-ylsulfonyl)phenyl)amino)-1-(2-cyano-1-cyclopropylethyl)-4-oxo-4,5-dihydro-1H-pyrazolo[4,3-c]pyridine-7-carboxylate

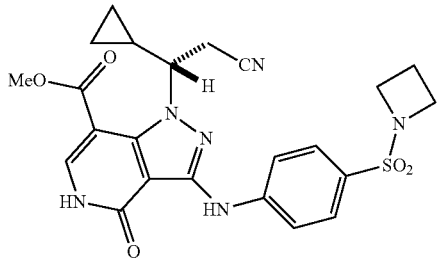

VI-1

Step 1: (S)-3-(3-((4-(azetidin-1-ylsulfonyl)phenyl)amino)-7-bromo-4-oxo-4,5-dihydro-1H-pyrazolo[4,3-c]pyridin-1-yl)-3-cyclopropylpropanenitrile

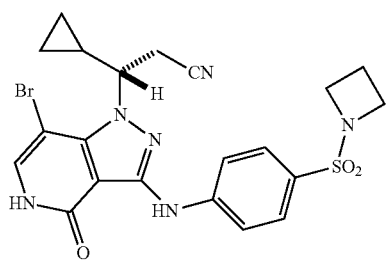

VI-1a

To (S)-3-(3-((4-(azetidin-1-ylsulfonyl)phenyl)amino)-4-oxo-4,5-dihydro-1H-pyrazolo[4,3-c]yridine-1-yl)-3-cyclopropylpropanenitrile (435 mg, 0.992 mmol) in acetonitrile (2 mL) was added NBS (194 mg, 1.091 mmol). The reaction mixture was stirred at room temperature for 6 hours. LC-MS show the formation of desired product, bis-brominated product and starting material. The reaction was quenched with aqueous sodium thiosulfate. After stirring for 20 min the reaction was diluted with EtOAc and brine. The reaction mixture was adjusted to pH=6.5 using aqueous NH₄Cl. The organics were separated, washed with brine, dried and concentrated. The crude mixture was purified by flash column (dry loaded on silica) and eluted with Ethyl acetate/DCM. Three fractions were collected and LC-MS showed the second fraction is the desired product (S)-3-(3-((4-(azetidin-1-ylsulfonyl)phenyl)amino)-7-bromo-4-oxo-4,5-dihydro-1H-pyrazolo[4,3-c]yridine-1-yl)-3-cyclopropylpropanenitrile. LRMS (ESI) calc'd for $C_{21}H_{22}BrN_6O_3S$ $[M+H]^+$: 517. found 517. ¹H NMR (400 MHz, DMSO-d₆): δ 8.12 (s, 1H), 7.62 (s, 1H), 7.52 (d, J=7.2 Hz, 2H), 7.28 (d, J=7.2 Hz, 2H), 4.02 (br, 1H), 3.60-3.5 (m, 5H), 3.10-3.02 (m, 2H), 2.14 (m, 2H), 0.90-0.52 (m, 5H).

Step 2: (S)-methyl 3-((4-(azetidin-1-ylsulfonyl)phenyl)amino)-1-(2-cyano-1-cyclopropylethyl) -4-oxo-4,5-dihydro-1H-pyrazolo[4,3-c]pyridine-7-carboxylate The reaction mixture containing (S)-3-(3-((4-(azetidin-1-ylsulfonyl)phenyl)amino)-7-bromo-4-oxo-4,5-dihydro-1H-pyrazolo[4,3-c]pyridin-1-yl)-3-cyclopropylpropanenitrile (120 mg, 0.232 mmol), PdCl2(dppf) (26 mg, 0.035 mmol), methanol (2 mL) in DMSO (2 mL) was placed in CO (25 psi) and heated to 70° C. for 22 hours. After the reaction is completed, the mixture was filtered and purified using prep-HPLC to give the dired product. LRMS (ESI) calc'd for $C_{23}H_{25}N_6O_5S$ $[M+H]^+$: 497. found 497. ¹H NMR (400 MHz, DMSO-d₆): δ 12.00 (s, 1H), 8.82 (s, 1H), 8.10 (d, J=7.2 Hz, 2H), 7.70 (d, J=7.2 Hz, 2H), 5.51 (br, 1H), 3.82 (s, 3H), 3.60 (m, 1H), 3.42-3.20 (m, 6H), 2.04 (m, 2H), 0.72-0.42 (m, 5H).

Example VI-2

(S)-3-(3-((4-(azetidin-1-ylsulfonyl)phenyl)amino)-7-(hydroxymethyl)-4-oxo-4,5-dihydro-1H-pyrazolo[4,3-c]pyridin-1-yl)-3-cyclopropylpropanenitrile

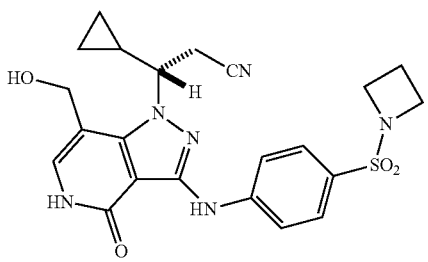

VI-2

To (S)-methyl 3-((4-(azetidin-1-ylsulfonyl)phenyl)amino)-1-(2-cyano-1-cyclopropylethyl)-4-oxo-4,5-dihydro-1H-pyrazolo[4,3-c]pyridine-7-carboxylate (25 mg, 0.050 mmol) in THF (2 mL) was added LiBH₄ (0.076 mL, 0.151 mmol). The formed mixture was stirred at 50° C. for overnight. The reaction mixture was filtered and purified using prep-HPLC to give the desired product (S)-3-(3-((4-(azetidin-1-ylsulfonyl)phenyl)amino)-7-(hydroxymethyl)-4-oxo-4,5-dihydro-1H-pyrazolo[4,3-c]pyridin-1-yl)-3-cyclopropylpropanenitrile. LRMS (ESI) calc'd for $C_{22}H_{25}N_6O_4S$ [M+H]$^+$: 469. found 469. $^1$H NMR (400 MHz, DMSO-d$_6$): δ 8.88 (s, 1H), 8.00 (d, J=7.2 Hz, 2H), 7.68 (d, J=7.2 Hz, 2H), 7.08 (s, 1H), 5.38 (br, 1H), 4.50-4.30 (m, 3H), 3.60-3.20 (m, 7H), 1.84 (m, 2H), 0.72-0.42 (m, 5H).

Example II-168

(S)-methyl 3-((4-(azetidin-1-ylsulfonyl)phenyl)amino)-1-(2-cyano-1-cyclopropylethyl)-4-oxo-4,5-dihydro-1H-pyrazolo[4,3-c]pyridine-7-carboxylate

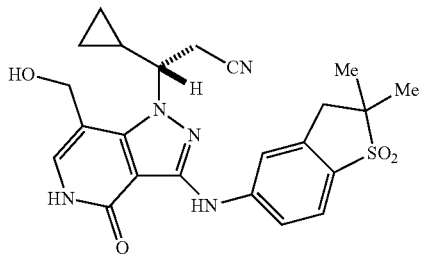

II-168

Step 1: 5-((4-(benzyloxy)-1-((S)-2-cyano-1-cyclopropylethyl)-1H-pyrazolo[4,3-c]pyridin-3-yl)amino)-2,2-dimethyl-1,1-dioxido-2,3-dihydrobenzo[b]thiophen-3-yl 1H-imidazole-1-carboxylate

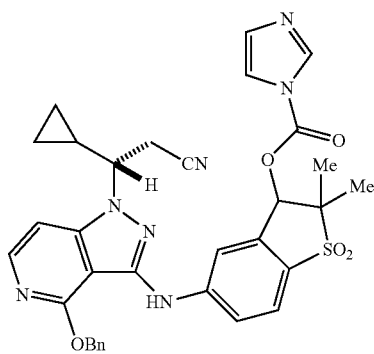

II-168a

To a 25 mL round bottom flask was place a solution of (3S)-3-(4-(benzyloxy)-3-((3-hydroxy-2,2-dimethyl-1,1-dioxido-2,3-dihydrobenzo[b]thiophen-5-yl)amino)-1H-pyrazolo[4,3-c]pyridin-1-yl)-3-cyclopropylpropanenitrile (100 mg, 0.18 mmol), 4-dimethylaminopyridine (5 mg, 0.04 mmol), di(1H-imidazol-1-yl) methane thione (48 mg, 0.27 mmol) and DCM (5 mL) was added, the mixture was stirred at ambient temperature for overnight. Water (10 mL) was added and the mixture was extracted with EtOAc (2×20 mL). The combined organic fractions was washed with brine (saturated, 2×20 mL), dried with Na2SO4 and filtered. The filtrate was concentrate in vacuo and the residue was purified by column chromatography on silica gel, eluting with EtOAc/petroleum ether (1/5) to to obtain O-(5-((4-(benzyloxy)-1-((R)-2-cyano-1-cyclopropylethyl)-1H-pyrazolo[4,3-c]pyridin-3-yl)amino)-2,2-dimethyl-1,1-dioxido-2,3-dihydrobenzo[b]thiophen-3-yl)1H-imidazole-1-carbothioate: MS (ESI) calc'd for $C_{33}H_{31}N_7O_4S_2$[M+H]$^+$: 654. found 654.

Step 2: (S)-3-(4-(benzyloxy)-3-((2,2-dimethyl-1,1-dioxido-2,3-dihydrobenzo[b]thiophen-5-yl)amino)-1H-pyrazolo[4,3-c]pyridin-1-yl)-3-cyclopropylpropanenitrile

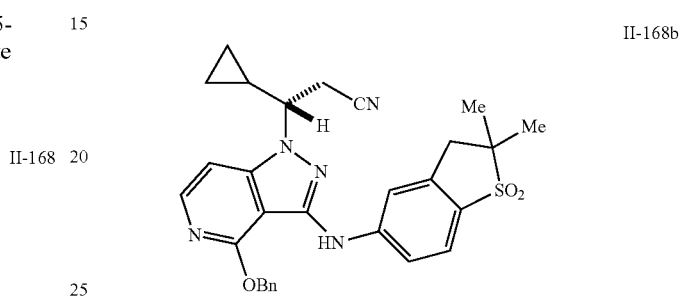

II-168b

To a 25 ml round-bottom flask was place a solution of O-(5-((4-(benzyloxy)-1-((R)-2-cyano-1-cyclopropylethyl)-1H-pyrazolo[4,3-c]pyridin-3-yl)amino)-2,2-dimethyl-1,1-dioxido-2,3-dihydrobenzo[b]thiophen-3-yl)1H-imidazole-1-carbothioate (97 mg, 0.15 mmol), dibutyl(pentyl)stannane (85 mg, 0.29 mmol), 2,2'-azobisisobutyronitrile (24 mg, 0.14 mmol) in toluene (10 mL). The mixture was degassed with nitrogen for 3 times and stirred for 2 h at 110° C. The mixture was concentrated in vacuo to give a residue. The residue was purified by column chromatography on silica gel, eluting with EtOAc/petroleum ether (1/5) to obtain (S)-3-(4-(benzyloxy)-3-((2,2-dimethyl-1,1-dioxido-2,3-dihydrobenzo[b]thiophen-5-yl)amino)-1H-pyrazolo[4,3-c]pyridin-1-yl)-3-cyclopropylpropanenitrile: MS (ESI) calc'd for $C_{29}H_{29}N_5O_5S$[M+H]$^+$: 528. found 528.

Step 3: (S)-3-cyclopropyl-3-(3-((2,2-dimethyl-1,1-dioxido-2,3-dihydrobenzo[b]thiophen-5-yl)amino)-4-oxo-4,5-dihydro-1H-pyrazolo[4,3-c]pyridin-1-yl)propanenitrile

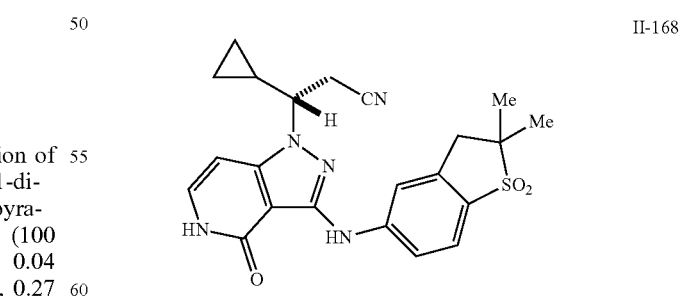

II-168

To a 50 mL three neck round-bottom flask was placed a mixture of (S)-3-(4-(benzyloxy)-3-((2,2-dimethyl-1,1-dioxido-2,3-dihydrobenzo[b]thiophen-5-yl)amino)-1H-pyrazolo[4,3-c]pyridin-1-yl)-3-cyclopropylpropanenitrile (50 mg, 0.09 mmol), wet palladium on carbon (30 mg, 10%) in MeOH (15 mL) under hydrogen (1.5 atm). The mixture was stirred for 12 h at ambient temperature. The reaction mixture was filtered. The filtrate was concentrated in vacuo to give (S)-3-cyclopropyl-3-(3-((2,2-dimethyl-1,1-dioxido-2,3-dihydrobenzo[b]thiophen-5-yl)amino)-4-oxo-4,5-dihydro-1H-pyrazolo[4,3-c]pyridin-1-yl)propanenitrile. MS (ESI) calc'd for $C_{22}H_{23}N_5O_5S$ [M+H]$^+$: 438. found 438; $^1$H NMR (300 MHz, DMSO-d6) d 11.16 (s, 1H), 8.63 (s, 1H), 7.92 (s, 1H), 7.73 (dd, J=8.4, 1.8 Hz, 1H), 7.58 (d, J=8.4 Hz, 1H), 7.23 (d, J=7.5 Hz, 1H), 6.63 (d, J=7.2 Hz, 1H), 4.25-4.23 (m, 1H), 3.39-3.31 (m, 4H), 1.47-1.46 (m, 1H), 1.36 (s, 6H), 0.69-0.31 (m, 4H).

The following Examples outlined in Table 18 were prepared by analogy using the general procedure outlined above for Compound II-168 above.

Step 1: (3S)-3-Cyclopropyl-3-(3-((2-methyl-1,1-dioxido-3-oxo-2,3-dihydrobenzo[b]thiophen-5-yl)amino)-4-oxo-4,5-dihydro-1H-pyrazolo[4,3-c]pyridin-1-yl)propanenitrile

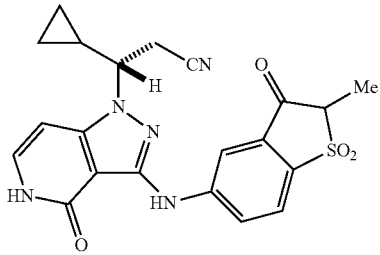

II-169a

| Example | Structure | Compound Name | MS |
|---|---|---|---|
| II-167 | 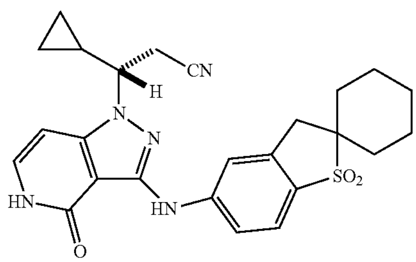 [SMILES: N#CC[C@@H](C1CC1)n1nc(Nc2ccc3c(c2)CC2(CCCCC2)S3(=O)=O)c2c(=O)[nH]ccc21] | (S)-3-cyclopropyl-3-(3-((1,1-dioxido-3H-spiro[benzo[b]thiophene-2,1'-cyclohexan]-5-yl)amino)-4-oxo-4,5-dihydro-1H-pyrazolo[4,3-c]pyridin-1-yl)propanenitrile | (ESI) calc'd for $C_{25}H_{27}N_5O_3S$ [M + H]$^+$: 478, found 478 |
| II-166 | 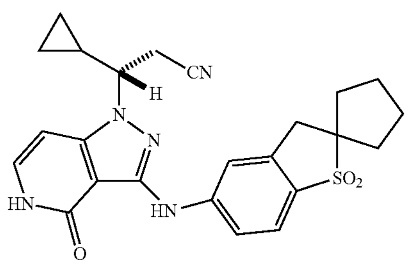 [SMILES: N#CC[C@@H](C1CC1)n1nc(Nc2ccc3c(c2)CC2(CCCC2)S3(=O)=O)c2c(=O)[nH]ccc21] | (S)-3-cyclopropyl-3-(3-((1,1-dioxido-3H-spiro[benzo[b]thiophene-2,1'-cyclopentan]-5-yl)amino)-4-oxo-4,5-dihydro-1H-pyrazolo[4,3-c]pyridin-1-yl)propanenitrile | (ESI) calc'd for $C_{25}H_{27}N_5O_3S$ [M + H]$^+$: 478, found 478 |

Examples II-169, II-170, II-171, and II-172

(S)-3-cyclopropyl-3-(3-(((2R,3S; 2R,3R; 2S,3S; and 2S,3R)-2,3-dimethyl-1,1-dioxido-2,3-dihydrobenzo[b]thiophen-5-yl)amino)-4-oxo-4,5-dihydro-1H-pyrazolo[4,3-c]pyridin-1-yl)propanenitrile

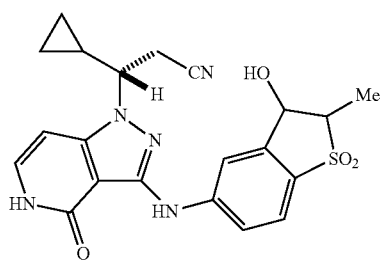

II-169, II-170, II-171, and II-172

5-Bromo-2-methylbenzo[b]thiophen-3(2H)-one 1,1-dioxide (0.17 g, 0.62 mmol), (S)-3-(3-amino-4-oxo-4,5-dihydro-H-pyrazolo[4,3-c]pyridin-1-yl)-3-cyclopropylpropanenitrile (0.10 g, 0.41 mmol), tris(dibenzylideneacetone)dipalladium (0)-chcloroform adduct (43 mg, 0.04 mmol), 2-di-tert-butylphosphino-2',4',6'-triisopropylbiphenyl (35 mg, 0.08 mmol), potassium acetate (81 mg, 0.82 mmol) in 2-propanol (30 mL) was degassed with nitrogen for 3 times and stirred under nitrogen for 16 h at 80° C. The reaction mixture was quenched with water (20 mL), diluted with water (20 mL) and extracted with EtOAc (3×50 mL). The combined organic layers was washed with water (1×20 mL) and brine (1×20 mL), dried over anhydrous Na2SO4 and filtered. The filtrate was concentrated under vacuum. The residue was purified by column chromatography on silica gel, eluting with EtOAc/petroleum ether (3/1) to obtain (3S)-3-cyclopropyl-3-(3-((2-methyl-1,1-dioxido-3-oxo-2,3-dihydrobenzo[b]thiophen-5-yl)amino)-4-oxo-4,5-dihydro-1H-pyrazolo[4,3-c]pyridin-1-yl)propanenitrile. MS (ESI) calc'd for $C_{21}H_{19}N_5O_4S$ [M+1]+438. found 438.

Step 2: (S)-3-Cyclopropyl-3-(3-(((2R,3S; 2R,3R; 2S,3S; and 2S,3R)-3-hydroxy-2-methyl-1,1-dioxido-2,3-dihydrobenzo[b]thiophen-5-yl)amino)-4-oxo-4,5-dihydro-1H-pyrazolo[4,3-c]pyridin-1-yl)propanenitrile

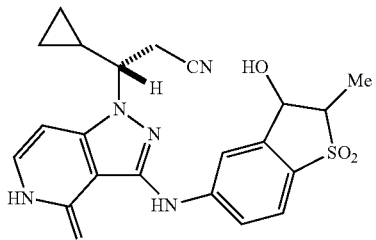

II-169, II-170, II-171, and II-172

Sodium borohydride (47 mg, 1.23 mmol) was added in portions to a stirred solution of (3S)-3-cyclopropyl-3-(3-((2-methyl-1,1-dioxido-3-oxo-2,3-dihydrobenzo[b]thiophen-5-yl)amino)-4-oxo-4,5-dihydro-H-pyrazolo[4,3-c]pyridin-1-yl)propanenitrile (0.18 g, 0.41 mmol) in MeOH (20 mL) at ambient temperature an stirred for 30 min at ambient temperature. The reaction mixture was quenched with water (20 mL), diluted with water (20 mL) and extracted with EtOAc (3×50 mL). The combined organic layers was washed with water (1×20 mL) and brine (1×20 mL), dried over anhydrous sodium sulfate and filtered. The filtrate was concentrated under vacuum to give the crude product. The crude product was purified by Flash-Prep-HPLC. Condition: Column Xbridge C18, 19*150 mm; Detector UV; Wave Length 254/220 nm; Mobile Phase and Gradient Phase A: water with 10 mmol NH4HCO3; Phase B: ACN. Gradient time: 0-12 min. B %: 22%~37%. trans (S)-3-cyclopropyl-3-(3-((-3-hydroxy-2-methyl-1,1-dioxido-2,3-dihydrobenzo[b]thiophen-5-yl)amino) -4-oxo-4,5-dihydro-1H-pyrazolo[4,3-c]pyridin-1-yl)propanenitrile was obtained at 5.63 min and cis (S)-3-cyclopropyl-3-(3-((-3-hydroxy-2-methyl-1,1-dioxido-2,3-dihydrobenzo[b]thiophen-5-yl)amino)-4-oxo-4,5-dihydro-1H-pyrazolo[4,3-c]pyridin-1-yl)propanenitrile was obtained at 6.25 min. Trans (S)-3-cyclopropyl-3-(3-((3-hydroxy-2-methyl-1,1-dioxido-2,3-dihydro benzo[b]thiophen-5-yl)amino)-4-oxo-4,5-dihydro-1H-pyrazolo[4,3-c]pyridin-1-yl)propanenitrile was purified by Chiral-Prep-HPLC with the following conditions: Column, Chiralpak IBO, 46*25 cm, 5 um; mobile phase: Hex:ethanol=50:50; Detector, UV 254 nm. 10 mg (5%) of 1-((S)-1-cyclopropylpropyl)-3-(((2R,3S or 2S,3R)-3-hydroxy-2-methyl-1,1-dioxido-2,3-dihydrobenzo[b]thiophen-5-yl)amino)-1H-pyrazolo[4,3-c]pyridin-4(5H)-one at 7.5 min; MS (ESI) calc'd for $C_{21}H_{21}N_5O_4S$ [M+1]+: 440. found 440; $^1$H NMR (400 MHz, DMSO-d6) d 11.16 (brs, 1H), 8.74 (s, 1H), 8.03 (s, 1H), 7.81 (d, J=8.4 Hz, 1H), 7.62 (d, J=8.4 Hz, 1H), 7.24 (t, J=6.4 Hz, 1H), 6.64 (t, J=6.8 Hz, 1H), 6.37 (d, J=7.2 Hz, 1H), 4.75 (t, J=7.6 Hz, 1H), 4.30-4.28 (m, 1H), 3.32-3.27 (m, 3H), 1.47-1.43 (m, 1H), 1.45 (d, J=6.8 Hz, 3H), 0.67-0.64 (m, 1H), 0.57-0.53 (m, 1H), 0.46-0.42 (m, 1H), 0.36-0.32 (m, 1H); and (S)-3-cyclopropyl-3-(3-(((2S,3R, or 2R,3S)-3-hydroxy-2-methyl-1,1-dioxido-2,3-dihydrobenzo[b]thiophen-5-yl)amino)-4-oxo-4,5-dihydro-1H-pyrazolo[4,3-c]pyridin-1-yl)propanenitrile at 15.5 min: MS (ESI) calc'd for $C_{21}H_{21}N_5O_4S$ [M+1]+: 440. found 440; $^1$H NMR (400 MHz, DMSO-d6) d 11.16 (brs, 1H), 8.74 (s, 1H), 8.04 (s, 1H), 7.81 (d, J=8.8 Hz, 1H), 7.62 (d, J=8.8 Hz, 1H), 7.24 (t, J=6.4 Hz, 1H), 6.64 (t, J=7.2 Hz, 1H), 6.38 (d, J=7.2 Hz, 1H), 4.75 (t, J=7.2 Hz, 1H), 4.31-4.26 (m, 1H), 3.36-3.27 (m, 3H), 1.47-1.43 (m, 1H), 1.44 (d, J=6.8 Hz, 3H), 0.67-0.65 (m, 1H), 0.55-0.53 (m, 1H), 0.45-0.42 (m, 1H), 0.35-0.32 (m, 1H).

Cis (S)-3-cyclopropyl-3-(3-((3-hydroxy-2-methyl-1,1-dioxido-2,3-dihydrobenzo[b]thiophen-5-yl)amino)-4-oxo-4,5-dihydro-1H-pyrazolo[4,3-c]pyridin-1-yl)propanenitrile was purified by Chiral-Prep-HPLC with the following conditions: Column, Chiralpak IBO, 46*25 cm, 5 um; mobile phase: Hex:ethanol=50:50; Detector, UV 254 nm. (S)-3-cyclopropyl-3-(3-(((2S,3S, or 2R,3R)-3-hydroxy-2-methyl-1,1-dioxido-2,3-dihydrobenzo[b]thiophen-5-yl)amino)-4-oxo-4,5-dihydro-1H-pyrazolo[4,3-c]pyridin-1-yl)propanenitrile was obtained at 7 min: MS (ESI) calc'd for $C_{21}H_{21}N_5O_4S$ [M+1]+: 440. found 440; $^1$H NMR (400 MHz, DMSO-d6) d 11.16 (brs, 1H), 8.70 (s, 1H), 8.00 (s, 1H), 7.82 (d, J=8.4 Hz, 1H), 7.60 (d, J=8.4 Hz, 1H), 7.23 (t, J=6.4 Hz, 1H), 6.64 (d, J=7.6 Hz, 1H), 6.05 (d, J=5.6 Hz, 1H), 5.22 (t, J=6.0 Hz, 1H), 4.29-4.27 (m, 1H), 3.67-3.64 (m, 1H), 3.37-3.28 (m, 2H), 1.47-1.45 (m, 1H), 1.25 (d, J=7.2 Hz, 3H), 0.69-0.66 (m, 1H), 0.57-0.54 (m, 1H), 0.46-0.43 (m, 1H), 0.36-0.33 (m, 1H); and (S)-3-cyclopropyl-3-(3-(((2R,3R, or 2S,3S)-3-hydroxy-2-methyl-1,1-dioxido-2,3-dihydrobenzo[b]thiophen-5-yl)amino)-4-oxo-4,5-dihydro-1H-pyrazolo[4,3-c]pyridin-1-yl)propanenitrile was obtained at 17 min: MS (ESI) calc'd for $C_{21}H_{21}N_5O_4S$ [M+1]+: 440. found 440; $^1$H NMR (400 MHz, DMSO-d6) d 11.16 (brs, 1H), 8.70 (s, 1H), 8.04 (s, 1H), 7.81 (d, J=8.8 Hz, 1H), 7.60 (d, J=8.8 Hz, 1H), 7.24 (t, J=6.4 Hz, 1H), 6.64 (d, J=7.2 Hz, 1H), 6.05 (d, J=6.0 Hz, 1H), 5.23 (t, J=6.0 Hz, 1H), 4.29-4.27 (m, 1H), 3.68-3.64 (m, 1H), 3.38-3.24 (m, 2H), 1.47-1.45 (m, 1H), 1.25 (d, J=7.2 Hz, 3H), 0.69-0.66 (m, 1H), 0.57-0.54 (m, 1H), 0.46-0.43 (m, 1H), 0.36-0.33 (m, 1H).

Biological Assays

Jak Biochemical HTRF Assay Protocol

The ability of compounds to inhibit the activity of JAK1, JAK2, JAK3, and Tyk2 was measured using a recombinant purified GST-tagged catalytic domain for each enzyme (Invitrogen JAK1 #M4290, JAK2 #M4290, JAK3 #M4290, Tyk2 #M4290) in an HTRF format biochemical assay. The reactions employed a common peptide substrate, LCB-EQEDEPEGDYFEWLW-NH$_2$ (in-house). The basic assay protocol is as follows: First, 250 nL of diluted compounds in DMSO were dispensed into the wells of a dry 384-well Black plate (Greiner #781076) using a Labcyte Echo 555 acoustic dispenser. Subsequent reagent additions employed an Agilent Bravo. Next, 18 µL of 1.11× enzyme and 1.11× substrate in 1× assay buffer (Invitrogen kinase buffer #PV3189, 2 mM DTT, 0.05% BSA) were added to the wells and shaken and then preincubated for 30 minutes at room temperature to allow compound binding to equilibrate. After equilibration, 2 µL of 10×ATP in 1× assay buffer was added to initiate the kinase reaction and the plates were shaken and then incubated at room temperature for 120 minutes. At the end of the incubation, 20 µL of 2× stop buffer (streptavidin-Dylight 650 (Thermo #84547B/100 mL), Eu-tagged pY20 antibody (Perkin Elmer #AD0067), EDTA, HEPES, and Triton) was added to quench the reaction. Plates were shaken and centrifuged and then incubated 60 minutes at room temperature and then read on a Perkin Elmer Envision (λex=337 nm, λem=665 and 615 nm, TRF delay time=20 µs). HTRF signal=10,000*665 nm reading/615 nm reading.

After normalization to untreated controls, the percent inhibition of the HTRF signal at each compound concentration was calculated. The plot of percent inhibition versus the log of compound concentration was fit with a 4-parameter dose response equation to calculate IC50 values.
Final reaction conditions were:

| Enzyme | [E] (nM) | [S] (µM) | [ATP] (µM) | [Eu-pY20] (nM) | [SA-Dylight] (nM) |
|---|---|---|---|---|---|
| JAK1 | 1.405 | 0.75 | 31.8 | 9 | 312.5 |
| JAK2 | 0.052 | 0.75 | 8.5 | 9 | 312.5 |
| JAK3 | 0.031 | 0.75 | 2.9 | 9 | 312.5 |
| Tyk2 | 2.612 | 0.75 | 6.9 | 9 | 312.5 |

Compound concentrations tested were 1496, 499, 175, 49.9, 18.7, 6.2, 2.1, 0.75, 0.24, 0.075, and 0.0125 nM, with 1.25% residual DMSO.

Biological Data

Examples of the instant invention were evaluated in JAK1 and JAK2 in vitro binding assays as described above. The following table tabulates the JAK1 IC50 values and JAK2 IC50 values disclosed for the instant invention.

| Example | JAK1 IC$_{50}$ | JAK2 IC$_{50}$ |
|---|---|---|
| II-1 | 3.09 | 3.46 |
| II-2 | 25.17 | 33 |
| II-3 | 0.23 | 0.51 |
| II-4 | 10.43 | 25.79 |
| II-5 | 6.86 | 9.85 |
| II-6 | 20.36 | 52.2 |
| II-7 | 0.14 | 0.28 |
| II-8 | 4.67 | 11.17 |
| II-9 | 18.53 | 4.54 |
| II-10 | 6.86 | 23.08 |
| II-11 | 64.92 | 16.92 |
| II-12 | 75.14 | 178.9 |
| II-13 | 4.42 | 4.51 |
| II-14 | 5.91 | 16.68 |
| II-15 | 10.03 | 4.95 |
| II-16 | 10.41 | 13.29 |
| II-17 | 0.35 | 2.2 |
| II-18 | 0.17 | 0.66 |
| II-19 | 0.08 | 0.44 |
| II-20 | 0.12 | 0.68 |
| II-21 | 0.12 | 0.33 |
| II-22 | 0.10 | 0.72 |
| II-23 | 0.04 | 0.28 |
| II-24 | 0.35 | 1.96 |
| II-25 | 0.78 | 4.92 |
| II-26 | 0.19 | 0.93 |
| II-27 | 3.39 | 13.63 |
| II-28 | 0.05 | 0.70 |
| II-29 | 1.47 | 9.90 |
| II-30 | 0.26 | 1.39 |
| II-31 | 0.37 | 1.86 |
| II-32 | 0.99 | 4.30 |
| II-33 | 0.11 | 1.32 |
| II-34 | 0.92 | 2.61 |
| II-35 | 1.12 | 5.57 |
| II-36 | 0.37 | 3.59 |
| II-37 | 0.12 | 0.42 |
| II-38 | 0.11 | 0.31 |
| II-39 | 0.14 | 0.34 |
| II-40 | 0.18 | 0.59 |
| II-41 | 0.22 | 0.65 |
| II-42 | 0.12 | 0.29 |
| II-43 | 0.27 | 0.30 |
| II-44 | 0.13 | 0.38 |
| II-45 | 0.10 | 0.40 |
| II-46 | 0.17 | 0.30 |
| II-47 | 0.15 | 0.32 |
| II-48 | 0.95 | 0.83 |
| II-49 | 0.57 | 1.32 |
| II-50 | 0.08 | 0.40 |
| II-51 | 0.08 | 0.55 |
| II-52 | 0.12 | 0.73 |
| II-53 | 0.62 | 1.07 |
| II-54 | 2.75 | 3.49 |
| II-55 | 0.40 | 0.67 |
| II-56 | 0.36 | 0.72 |
| II-57 | 0.57 | 1.22 |
| II-58 | 0.34 | 0.81 |
| II-59 | 0.69 | 1.14 |
| II-60 | 0.49 | 0.97 |
| II-61 | 0.61 | 0.73 |
| II-62 | 1.28 | 2.70 |
| II-63 | 1.15 | 2.80 |
| II-64 | 0.32 | 0.38 |
| II-65 | 0.34 | 0.52 |
| II-66 | 0.40 | 0.51 |
| II-67 | 0.20 | 0.54 |
| II-68 | 0.34 | 0.72 |
| II-69 | 1.03 | 2.18 |
| II-70 | 0.46 | 1.05 |
| II-71 | 0.25 | 0.50 |
| II-72 | 0.50 | 1.90 |
| II-73 | 0.33 | 0.79 |
| II-74 | 0.26 | 0.33 |
| II-75 | 0.46 | 0.91 |
| II-76 | 0.22 | 0.39 |
| II-77 | 0.27 | 0.49 |
| II-78 | 0.64 | 1.24 |
| II-79 | 0.62 | 1.30 |
| II-80 | 0.61 | 0.84 |
| II-81 | 0.42 | 0.46 |
| II-82 | 0.66 | 1.22 |
| II-83 | 1.86 | 1.91 |
| II-84 | 0.57 | 0.94 |
| II-85 | 0.46 | 1.17 |
| II-86 | 0.15 | 0.30 |
| II-87 | 0.31 | 0.36 |
| II-88 | 0.40 | 1.33 |
| II-89 | 0.29 | 0.80 |
| II-90 | 0.18 | 0.62 |
| II-91 | 0.50 | 1.07 |
| II-92 | 0.07 | 0.18 |
| II-93 | 0.48 | 1.96 |
| II-94 | 0.13 | 0.67 |
| II-95 | 0.39 | 0.80 |
| II-96 | 0.14 | 0.21 |
| II-97 | 0.20 | 0.50 |
| II-98 | 0.31 | 0.64 |
| II-99 | 0.29 | 0.83 |
| II-100 | 0.29 | 0.84 |
| II-101 | 0.22 | 0.70 |
| II-102 | 0.31 | 0.84 |
| II-103 | 0.09 | 0.23 |
| II-104 | 0.46 | 0.73 |
| II-105 | 0.32 | 0.43 |
| II-106 | 0.19 | 0.45 |
| II-107 | 0.40 | 0.72 |
| II-108 | 0.20 | 0.23 |
| II-109 | 0.16 | 0.19 |
| II-110 | 0.12 | 0.31 |
| II-111 | 0.20 | 0.46 |
| II-112 | 0.11 | 0.28 |
| II-113 | 0.16 | 0.27 |
| II-114 | 0.15 | 0.61 |
| II-115 | 0.24 | 1.00 |
| II-116 | 0.07 | 0.54 |
| II-117 | 1.50 | 3.64 |
| II-118 | 0.33 | 0.44 |
| II-119 | 4.33 | 10.02 |
| II-120 | 0.98 | 1.59 |
| II-121 | 0.10 | 0.14 |
| II-122 | 0.19 | 0.57 |
| II-123 | 1.04 | 5.31 |

| Example | JAK1 IC$_{50}$ | JAK2 IC$_{50}$ |
|---|---|---|
| II-124 | 0.12 | 2.47 |
| II-125 | 0.28 | 4.52 |
| II-126 | 0.08 | 1.22 |
| II-127 | 0.70 | 3.57 |
| II-128 | 0.16 | 1.93 |
| II-129 | 0.10 | 1.49 |
| II-130 | 0.24 | 2.71 |
| II-131 | 0.19 | 2.19 |
| II-132 | 0.10 | 0.24 |
| II-133 | 0.41 | 0.52 |
| II-134 | 0.13 | 2.92 |
| II-135 | 0.14 | 2.34 |
| II-136 | 0.12 | 1.53 |
| II-137 | 0.29 | 2.95 |
| II-138 | 0.29 | 3.01 |
| II-139 | 0.40 | 3.80 |
| II-140 | 0.22 | 0.63 |
| II-141 | 0.35 | 0.25 |
| II-142 | 0.40 | 0.27 |
| II-143 | 0.46 | 0.25 |
| II-144 | 0.43 | 0.35 |
| II-145 | 1.82 | 1.82 |
| II-146 | 0.43 | 0.58 |
| II-147 | 0.06 | 1.04 |
| II-148 | 0.07 | 0.34 |
| II-149 | 0.07 | 0.19 |
| II-150 | 0.22 | 2.07 |
| II-151 | 0.16 | 0.74 |
| II-152 | 5.50 | 2.73 |
| II-153 | 1.04 | 1.00 |
| II-154 | 0.41 | 1.03 |
| II-155 | 0.32 | 0.62 |
| II-156 | 0.10 | 0.89 |
| II-157 | 0.11 | 0.60 |
| II-158 | 0.59 | 1.42 |
| II-159 | 0.17 | 0.50 |
| II-160 | 0.61 | 0.65 |
| II-161 | 0.12 | 0.21 |
| II-162 | 0.17 | 0.16 |
| II-163 | 0.14 | 0.26 |
| II-164 | 1.31 | 2.65 |
| II-165 | 0.31 | 0.65 |
| II-166 | 0.13 | 0.41 |
| II-167 | 0.13 | 0.47 |
| II-168 | 0.10 | 0.37 |
| II-169 | 0.83 | 2.81 |
| II-170 | 0.19 | 0.42 |
| II-171 | 0.26 | 2.02 |
| II-172 | 0.27 | 0.82 |
| II-173 | 0.09 | 0.53 |
| II-174 | 0.68 | 0.46 |
| II-175 | 0.51 | 1.10 |
| II-176 | 1.13 | 0.59 |
| II-177 | 0.07 | 0.18 |
| II-178 | 0.35 | 0.71 |
| II-179 | 0.40 | 1.24 |
| II-180 | 0.64 | 0.55 |
| II-181 | 0.40 | 0.37 |
| II-182 | 0.62 | 0.58 |
| II-183 | 0.39 | 0.46 |
| II-184 | 0.25 | 0.48 |
| II-185 | 2.56 | 4.03 |
| II-186 | 2.05 | 1.92 |
| II-187 | 0.45 | 1.33 |
| II-188 | 0.82 | 1.30 |
| II-189 | 0.72 | 1.15 |
| II-190 | 0.88 | 1.48 |
| II-191 | 0.34 | 2.44 |
| II-192 | 0.20 | 1.38 |
| II-193 | 0.43 | 3.83 |
| II-194 | 0.43 | 3.16 |
| II-195 | 0.55 | 1.03 |
| II-196 | 0.55 | 0.96 |
| II-197 | 2.95 | 3.32 |
| II-198 | 3.62 | 10.01 |
| II-199 | 0.10 | 0.10 |
| II-200 | 0.07 | 0.06 |
| II-201 | 0.29 | 0.34 |
| II-202 | 1.17 | 0.94 |
| II-203 | 0.30 | 0.72 |
| II-204 | 0.13 | 0.41 |
| II-205 | 0.55 | 0.44 |
| II-206 | 0.20 | 0.33 |
| II-207 | 0.11 | 0.21 |
| II-208 | 1.55 | 1.71 |
| II-209 | 0.72 | 0.77 |
| III-1 | 0.38 | 0.93 |
| III-2 | 0.46 | 0.81 |
| III-3 | 2.21 | 2.52 |
| III-4 | 0.37 | 0.51 |
| III-5 | 1.23 | 1.20 |
| III-6 | 0.75 | 0.73 |
| III-7 | 2.37 | 2.72 |
| III-8 | 0.49 | 0.88 |
| III-9 | 0.45 | 0.61 |
| III-10 | 0.95 | 0.62 |
| III-11 | 0.61 | 0.79 |
| III-12 | 0.79 | 0.62 |
| III-13 | 0.81 | 0.52 |
| III-14 | 0.61 | 0.81 |
| III-15 | 0.47 | 0.86 |
| IV-1 | 0.45 | 0.39 |
| IV-2 | 0.60 | 0.59 |
| IV-3 | 0.52 | 0.71 |
| IV-4 | 0.68 | 0.88 |
| IV-5 | 0.58 | 0.70 |
| IV-6 | 0.28 | 0.53 |
| IV-7 | 0.82 | 2.24 |
| IV-8 | 0.48 | 0.53 |
| IV-9 | 0.23 | 1.10 |
| IV-10 | 0.20 | 1.07 |
| IV-11 | 0.54 | 0.52 |
| IV-12 | 1.05 | 1.07 |
| IV-13 | 0.91 | 0.64 |
| V-1 | 7.89 | 35.60 |
| V-2 | 2.67 | 8.30 |
| V-3 | 1.50 | 5.87 |
| V-4 | 0.94 | 6.06 |
| V-5 | 1.42 | 3.93 |
| V-6 | 1.60 | 9.69 |
| V-7 | 4.03 | 28.14 |
| V-8 | 5.49 | 24.25 |
| V-9 | 7.38 | 41.99 |
| V-10 | 4.05 | 14.84 |
| V-11 | 49.63 | 168.7 |
| V-12 | 0.88 | 8.53 |
| V-13 | 20.75 | 106.1 |
| V-14 | 6.99 | 27.86 |
| V-15 | 6.55 | 24.16 |
| V-16 | 15.82 | 50.25 |
| V-17 | 1.99 | 23.82 |
| V-18 | 14.46 | 32.48 |
| V-19 | 18.14 | 76.08 |
| V-20 | 6.07 | 39.73 |
| V-21 | 2.99 | 4.97 |
| V-22 | 1.75 | 3.30 |
| V-23 | 0.21 | 2.52 |
| VI-1 | 11.42 | 15.29 |
| VI-2 | 3.91 | 3.22 |

The invention claimed is:

1. A compound of formula I or a pharmaceutically acceptable salt, or a stereoisomer thereof:

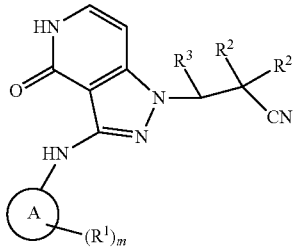

I

A is selected from phenyl, pyridinyl, 2,3-dihydrobenzo[d]thiazolyl, dihydroisoindolyl, dihydrobenzisothiazolyl, dihydroindenyl, 2,3-dihydrobenzofuranyl, 2,3-dihydro-IH-indenyl, dihydrobenzofuranyl, 1-oxo-2,3-dihydro-IH-indenyl, benzo[d]dioxolyl, quinolinyl, quinixalinyl, benzothiophenyl, 1,3-benzo[d]dioxolyl, isoindolyl, isoindolinyl, dihydro[b]thiophenyl,

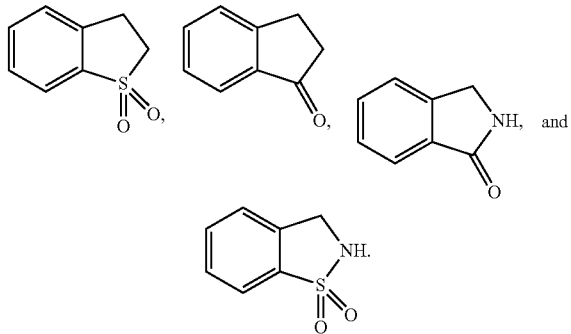

m is 0, 1, 2, 3, or 4;

$R^2$ is independently selected from hydrogen and $C_{1-6}$ alkyl;

$R^3$ is selected from: hydrogen, halogen, $C_{1-6}$ alkyl, $C_{3-6}$ cycloalkyl, and $(C_{3-8})$heterocycloalkyl;

wherein $R^2$ and $R^3$ are optionally, each independently substituted by 1, 2, or 3 $R^5$ substituents;

$R^5$ is independently selected from hydroxy, $(C_{1-6})$alkyl, $(C_{1-6})$alkoxy, $(C_{1-6}$ alkyl)OH, halogen, —$CO_2H$, —$(C_{0-4})$alkylCN, —O(C=O)$C_1$-$C_4$alkyl, $NO_2$, trifluoromethoxy, trifluoroethoxy, trifluoromethyl, trifluoroethyl, $C_{1-6}$ alkylsulfonyl, oxo (O=), aminosulfonyl, —$SO_2NH_2$, —$SO_2NH(C_{1-10}$ alkyl), —$SO_2N(C_{1-6}$ alkyl)$_2$, —$SO_2C_{1-6}$alkyl, —$SO_2CF_3$, —$SO_2CF_2H$, —$C_{1-6}$ alkylsulfinyl, —$O_{(0-1)}(C_{1-6})$haloalkyl, amino $(C_{1-6}$alkyl)$_{0-2}$ and $NH_2$;

$R^1$ is selected from:
halogen,
Oxo (=O),
$C_{1-10}$ alkyl(oxy)$_{0-1}$(carbonyl)$_{0-1}C_{0-10}$ alkyl,
$C_{1-10}$ heteroalkyl(oxy)$_{0-1}$(carbonyl)$_{0-1}C_{0-10}$ alkyl,
$C_{2-10}$ alkenyl(oxy)$_{0-1}$(carbonyl)$_{0-1}C_{0-10}$ alkyl,
aryl $C_{0-10}$ alkyl(oxy)$_{0-1}$(carbonyl)$_{0-1}C_{0-10}$ alkyl,
$C_{3-12}$ cycloalkyl $C_{0-10}$ alkyl(oxy)$_{0-1}$(carbonyl)$_{0-1}C_{0-10}$ alkyl,
heteroaryl $C_{0-10}$ alkyl(oxy)$_{0-1}$(carbonyl)$_{0-1}C_{0-10}$ alkyl,
$(C_{3-12})$heterocycloalkyl $C_{0-10}$ alkyl(oxy)$_{0-1}$(carbonyl)$_{0-1}C_{0-10}$ alkyl,
$C_{0-10}$ alkyl(oxy)$_{0-1}$(carbonyl)$_{0-1}$amino$C_{0-10}$ alkyl,
$(C_{1-10})$heteroalkyl(oxy)$_{0-1}$(carbonyl)$_{0-1}$amino$C_{0-10}$ alkyl,
$C_{3-12}$ cycloalkyl $C_{0-10}$ alkyl(oxy)$_{0-1}$(carbonyl)$_{0-1}$amino$C_{0-10}$ alkyl,
aryl $C_{0-10}$ alkyl(oxy)$_{0-1}$(carbonyl)$_{0-1}$amino$C_{0-10}$ alkyl,
heteroaryl $C_{0-10}$ alkyl(oxy)$_{0-1}$(carbonyl)$_{0-1}$amino$C_{0-10}$ alkyl,
$(C_{3-12})$heterocycloalkyl $C_{0-10}$ alkyl(carbonyl)$_{0-1}$amino$C_{0-10}$ alkyl,
$C_{0-10}$ alkylamino(carbonyl)$_{0-1}C_{0-10}$ alkyl,
$(C_{1-10})$heteroalkylamino(carbonyl)$_{0-1}C_{0-10}$ alkyl,
$C_{3-12}$ cycloalkylamino(carbonyl)$_{0-1}C_{0-10}$ alkyl,
aryl $C_{0-10}$ alkylaminoamino(carbonyl)$_{0-1}C_{0-10}$ alkyl,
heteroaryl $C_{0-10}$ alkylamino(carbonyl)$_{0-1}C_{0-10}$ alkyl,
$(C_{3-12})$heterocycloalkylamino(carbonyl)$_{0-1}C_{0-10}$ alkyl,
$C_{1-10}$ alkylsulfonyl$C_{0-10}$ alkyl,
$C_{1-10}$ heteroalkylsulfonyl$C_{0-10}$ alkyl,
$(C_{3-12})$cycloalkyl$C_{0-10}$alkylsulfonyl$C_{0-10}$ alkyl,
$(C_{3-12})$cycloheteroalkyl$C_{0-10}$alkylsulfonyl$C_{0-10}$ alkyl,
heteroaryl $C_{0-10}$ alkylsulfonyl$C_{0-10}$ alkyl,
aryl$C_{0-10}$ alkylsulfonyl$C_{0-10}$ alkyl,
$C_{1-10}$ alkylsulfamoyl$C_{0-10}$ alkyl,
$C_{1-10}$ heteroalkylsulfamoyl$C_{0-10}$ alkyl,
$(C_{3-12})$cycloalkyl$C_{0-10}$ alkylsulfamoyl$C_{0-10}$ alkyl,
$(C_{3-12})$cycloheteroalkyl$C_{0-10}$alkylsulfamoyl$C_{0-10}$ alkyl,
heteroaryl$C_{0-10}$ alkylsulfamoyl$C_{0-10}$ alkyl,
aryl$C_{0-10}$ alkylsulfamoyl$C_{0-10}$ alkyl,
$(C_{0-10}$ alkyl)$_{1-2}$ amino,
—$CO_2(C_{0-10}$ alkyl),
—$(C_{0-10}$ alkyl)$CO_2H$,
—$SO_2NH_2$,
—$SO_2NH(C_{1-10}$ alkyl),
—$SO_2N(C_{1-10}$ alkyl)$_2$,
—$SO_2CF_3$,
—$SO_2CF_2H$,
$C_{1-10}$ alkylsulfinyl$C_{0-10}$ alkyl,
$C_{1-4}$acylamino $C_{0-10}$ alkyl,
hydroxy,
—$(C_{1-10}$ alkyl)OH,
—$C_{0-10}$ alkylalkoxy,
cyano,
$(C_{1-6}$alkyl)cyano, and
$C_{1-6}$haloalkyl;

wherein $R^1$ is independently optionally substituted with 1, 2, 3, or 4 $R^4$ substituents and wherein two $R^1$ may optionally join together with the ring atoms to which they are attached to form a 3 to 6 membered ring; and $R^4$ is independently selected from hydroxy, $(C_{1-6})$alkyl, $(C_{1-6})$alkoxy, $(C_{1-10}$ alkyl)OH, halogen, —$(C_{1-10}$ alkyl)OH, —$(C_{0-10}$ alkyl)$CO_2H$, —$CO_2H$, $C_{1-10}$ alkyl(oxy)$_{0-1}$(carbonyl)$_{0-1}C_{0-10}$ alkyl, —$(C_{0-6})$alkylCN, —$C_{0-10}$ alkyl O(C=O)$C_1$-$C_6$ alkyl, $NO_2$, trifluoromethoxy, trifluoroethoxy, trifluoromethyl, trifluoroethyl, —N—C(O)O($C_{0-6}$)alkyl, —N($R^b$)—C(O)O($C_{0-6}$)alkyl, $C_{1-10}$ alkylsulfonyl, oxo (O=), aminosulfonyl, —$SO_2NH_2$, —$SO_2NH(C_{1-10}$ alkyl), —$SO_2N(C_{1-10}$ alkyl)$_2$, —$SO_2C_{1-6}$alkyl, —$SO_2CF_3$, —$SO_2CF_2H$, —$C_{1-10}$ alkylsulfinyl, —$O_{(0-1)}(C_{1-10})$haloalkyl, amino($C_{1-6}$alkyl)$_{0-2}$, $C_{3-12}$ cycloalkyl, $(C_{3-12})$cycloheteroalkyl, and $NH_2$, wherein $R^b$ is $C_{1-10}$ alkyl.

2. A compound according to claim 1, wherein $R^2$ is hydrogen.

3. A compound according to claim 2, wherein $R^3$ is selected from $R^3$ is selected from: hydrogen, halogen, methyl, ethyl, propyl, isopropyl, butyl, and tert-butyl, cyclopropyl, cyclobutyl and cyclopentyl, wherein $R^3$ is optionally substituted by 1, 2, or 3 $R^5$ substituents.

4. A compound of claim 1 or a pharmaceutically acceptable salt, or a stereoisomer thereof selected from:

- 4-((1-(1-cyanopropan-2-yl)-4-oxo-4,5-dihydro-1H-pyrazolo[4,3-c]pyridin-3-yl)amino)-N,N-dimethylbenzenesulfonamide;
- 4-((1-(2-cyano-1-cyclopropylethyl)-4-oxo-4,5-dihydro-1H-pyrazolo[4,3-c]pyridin-3-yl)amino)-N,N-dimethylbenzenesulfonamide;
- 4-(1-((-2-cyano-1-(2,2-difluorocyclopropyl)ethyl)-4-oxo-4,5-dihydro-1H-pyrazolo[4,3-c]pyridin-3-yl)amino)-N,N-dimethylbenzenesulfonamide;
- 4-((1-(2-cyano-1-(2,2-dimethylcyclopropyl)ethyl)-4-oxo-4,5-dihydro-1H-pyrazolo[4,3-c]pyridin-3-yl)amino)-N,N-dimethylbenzenesulfonamide;
- 4-((1-(2-cyano-1-cyclobutylethyl)-4-oxo-4,5-dihydro-1H-pyrazolo[4,3-c]pyridin-3-yl)amino)-N,N-dimethylbenzenesulfonamide;
- 3-cyclobutyl-3-(4-oxo-3-((4-(pyrrolidin-1-ylsulfonyl)phenyl)amino)-4,5-dihydro-1H-pyrazolo[4,3-c]pyridin-1-yl)propanenitrile;
- 3-cyclopropyl-3-{3-[(4-fluorophenyl)amino]-4-oxo-4,5-dihydro-1H-pyrazolo[4,3-c]pyridin-1-yl}propanenitrile;
- 3-cyclopropyl-3-[4-oxo-3-({4-[(2,2,2-trifluoro-1-hydroxy-1-methylethyl]phenyl}amino)-4,5-dihydro-1H-pyrazolo[4,3-c]pyridin-1-yl]propanenitrile;
- 3-cyclopropyl-3-(3-{[1-hydroxy-1-(trifluoromethyl)-2,3-dihydro-1H-inden-5-yl]amino}-4-oxo-4,5-dihydro-1H-pyrazolo[4,3-c]pyridin-1-yl)propanenitrile;
- 3-cyclopropyl-3-{3-[(1,1-dioxido-2,3-dihydro-1-benzothiophen-5-yl)amino]-4-oxo-4,5-dihydro-1H -pyrazolo[4,3-c]pyridin-1-yl}propanenitrile;
- 3-{3-[(2-tert-butyl-1,1-dioxido-2,3-dihydro-1,2-benzisothiazol-5-yl)amino]-4-oxo-4,5-dihydro-1H-pyrazolo[4,3-c]pyridin-1-yl}-3-cyclopropylpropanenitrile;
- 4-({1-[2-cyano-1-cyclopropylethyl]-4-oxo-4,5-dihydro-1H-pyrazolo[4,3-c]pyridin-3-yl}amino)benzonitrile;
- 3-cyclopropyl-3-(4-oxo-3-{[4-(trifluoromethyl)phenyl]amino}-4,5-dihydro-1H-pyrazolo[4,3-c]pyridin-1-yl)propanenitrile;
- 3-cyclopropyl-3-(3-{[4-(methylsulfonyl)phenyl]amino}-4-oxo-4,5-dihydro-1H-pyrazolo[4,3-c]pyridin -1-yl)propanenitrile;
- 3-cyclopropyl-3-{4-oxo-3-[(3,4,5-trifluorophenyl)amino]-4,5-dihydro-1H-pyrazolo[4,3-c]pyridin-1-yl}propanenitrile;
- 3-cyclopropyl-3-{3-[(2-methyl-1,1-dioxido-2,3-dihydro-1,2-benzisothiazol-5-yl)amino]-4-oxo-4,5-dihydro-1H-pyrazolo[4,3-c]pyridin-1-yl}propanenitrile;
- 3-cyclopropyl-3-{3-[(2-fluoropyridin-4-yl)amino]-4-oxo-4,5-dihydro-1H-pyrazolo[4,3-c]pyridin-1-yl}propanenitrile;
- 3-cyclopropyl-3-{4-oxo-3-[(1-oxo-2,3-dihydro-1H-inden-5-yl)amino]-4,5-dihydro-1H-pyrazolo[4,3-c]pyridin-1-yl}propanenitrile;
- 3-cyclopropyl-3-[3-(2,3-dihydro-1-benzofuran-5-ylamino)-4-oxo-4,5-dihydro-1H-pyrazolo[4,3-c]pyridin-1-yl]propanenitrile;
- 3-[3-(1,3-benzodioxol-5-ylamino)-4-oxo-4,5-dihydro-1H-pyrazolo[4,3-c]pyridin-1-yl]-3-cyclopropylpropanenitrile;
- 3-cyclopropyl-3-[4-oxo-3-(quinolin-6-ylamino)-4,5-dihydro-1H-pyrazolo[4,3-c]pyridin-1-yl]propanenitrile;
- 3-cyclopropyl-3-(3-{[3-fluoro-4-(methylsulfonyl)phenyl]amino}-4-oxo-4,5-dihydro-1H-pyrazolo[4,3-c]pyridin-1-yl)propanenitrile;
- 3-cyclopropyl-3-[4-oxo-3-(quinoxalin-6-ylamino)-4,5-dihydro-1H-pyrazolo[4,3-c]pyridin-1-yl]propanenitrile;
- 3-{3-[(4-chlorophenyl)amino]-4-oxo-4,5-dihydro-1H-pyrazolo[4,3-c]pyridin-1-yl}-3-cyclopropylpropanenitrile;
- cyclopropyl-3-[3-({4-[(1-methylethyl)sulfonyl]phenyl}amino)-4-oxo-4,5-dihydro-1H-pyrazolo[4,3-c]pyridin-1-yl]propanenitrile;
- (3-{[4-(tert-butylsulfonyl)phenyl]amino}-4-oxo-4,5-dihydro-1H-pyrazolo[4,3-c]pyridin-1-yl)-3-cyclopropylpropanenitrile;
- N-tert-butyl-4-{[(2-cyano-1-cyclopropylethyl)-4-oxo-4,5-dihydro-1H-pyrazolo[4,3-c]pyridin-3-yl]amino}benzenesulfonamide;
- 3-[3-({4-[1-amino-2,2,2-trifluoroethyl]phenyl}amino)-4-oxo-4,5-dihydro-1H-pyrazolo[4,3-c]pyridin-1-yl]-3-cyclopropylpropanenitrile;
- 4-({1-[2-cyano-1-cyclopropylethyl]-4-oxo-4,5-dihydro-1H-pyrazolo[4,3-c]pyridin-3-yl}amino)-N-ethyl-N-methylbenzenesulfonamide;
- 3-cyclopropyl-3-(4-oxo-3-{[4-(piperidin-1-ylsulfonyl)phenyl]amino}-4,5-dihydro-1H-pyrazolo[4,3-c]pyridin-1-yl)propanenitrile;
- 4-({1-[2-cyano-1-cyclopropylethyl]-4-oxo-4,5-dihydro-1H-pyrazolo[4,3-c]pyridin-3-yl}amino)-N-methyl-N-(1-methylethyl)benzenesulfonamide;
- 4-({1-[2-cyano-1-cyclopropylethyl]-4-oxo-4,5-dihydro-1H-pyrazolo[4,3-c]pyridin-3-yl}amino)-N-methylbenzenesulfonamide;
- 3-cyclopropyl-3-(4-oxo-3-{[4-(pyrrolidin-1-ylsulfonyl)phenyl]amino}-4,5-dihydro-1H-pyrazolo[4,3-c]pyridin-1-yl)propanenitrile;
- 4-({1-[2-cyano-1-cyclopropylethyl]-4-oxo-4,5-dihydro-1H-pyrazolo[4,3-c]pyridin-3-yl}amino)-N,N-diethylbenzenesulfonamide;
- 3-cyclopropyl-3-[3-({4-[(3,3-dimethylpiperidin-1-yl)sulfonyl]phenyl}amino)-4-oxo-4,5-dihydro-1H-pyrazolo[4,3-c]pyridin-1-yl]propanenitrile;
- 3-cyclopropyl-3-[3-({4-[(3,3-dimethylpyrrolidin-1yl)sulfonyl]phenyl}amino)-4-oxo-4,5-dihydro-1H-pyrazolo[4,3-c]pyridin-1-yl]propanenitrile;
- 3-{3-[(2-tert-butyl-1-oxo-2,3-dihydro-1H-isoindol-5-yl)amino]-4-oxo-4,5-dihydro-1H-pyrazolo[4,3-c]pyridin-1-yl}-3-cyclopropylpropanenitrile;
- 3-{3-[(2-cyclopentyl-1-oxo-2,3-dihydro-1H-isoindol-5-yl)amino]-4-oxo-4,5-dihydro-1H-pyrazolo[4,3-c]pyridin-1-yl}-3-cyclopropylpropanenitrile;
- 3-{3-[(2-cyclohexyl-1-oxo-2,3-dihydro-1H-isoindol-5-yl)amino]-4-oxo-4,5-dihydro-1H-pyrazolo[4,3-c]pyridin-1-yl}-3-cyclopropylpropanenitrile;
- 3-cyclopropyl-3-[3-({4-[(2,2-dimethylpiperidin-1-yl)sulfonyl]phenyl}amino)-4-oxo-4,5-dihydro-1H-pyrazolo[4,3-c]pyridin-1-yl]propanenitrile,
- tert-butyl 1-{[4-({1-[2-cyano-1-cyclopropylethyl]-4-oxo-4,5-dihydro-1H-pyrazolo[4,3-c]pyridin-3-yl}amino)phenyl]sulfonyl}piperidine-4-carboxylate,
- 3-cyclopropyl-3-{3-[(4-{[3-hydroxypyrrolidin-1-yl]sulfonyl}phenyl)amino]-4-oxo-4,5-dihydro-1H-pyrazolo[4,3-c]pyridin-1-yl}propanenitrile, tert-butyl 1-{[4-({1-[2-cyano-1-cyclopropylethyl]-4-oxo-4,5-dihydro-1H-pyrazolo[4,3-c]pyridin-3-yl}amino)phenyl]sulfonyl}-D-prolinate, 3-cyclopropyl-3-{4-oxo-3-[(4-{[3-(trifluoromethyl)pyrrolidin-1-yl]sulfonyl}phenyl)amino]-4,5-dihydro-1H-pyrazolo[4,3-c]pyridin-1-yl}propanenitrile;

3-cyclopropyl-3-{4-oxo-3-[(4-{[2-(trifluoromethyl)pyrrolidin-1-yl]sulfonyl}phenyl)amino]-4,5-dihydro-1H-pyrazolo[4,3-c]pyridin-1-yl}propanenitrile;

tert-butyl-1-{[4-({1-[2-cyano-1-cyclopropylethyl]-4-oxo-4,5-dihydro-1H-pyrazolo[4,3-c]pyridin-3-yl}amino)phenyl]sulfonyl}pyrrolidine-3-carboxylate;

3-cyclopropyl-3-[3-({4-[(2,2-dimethylpyrrolidin-1-yl)sulfonyl]phenyl}amino)-4-oxo-4,5-dihydro-1H-pyrazolo[4,3-c]pyridin-1-yl]propanenitrile;

3-cyclopropyl-3-{3-[(4-{[2-methylpyrrolidin-1-yl]sulfonyl}phenyl)amino]-4-oxo-4,5-dihydro-1H-pyrazolo[4,3-c]pyridin-1-yl}propanenitrile;

3-(3-{[4-(azetidin-1-ylsulfonyl)phenyl]amino}-4-oxo-4,5-dihydro-1H-pyrazolo[4,3-c]pyridin-1-yl)-3-cyclopropylpropanenitrile;

3-cyclopropyl-3-(3-{[4-(morpholin-4-ylsulfonyl)phenyl]amino}-4-oxo-4,5-dihydro-1H-pyrazolo[4,3-c]pyridin-1-yl)propanenitrile;

3-cyclopropyl-3-[3-({4-[(3,3-dimethylazetidin-1-yl)sulfonyl]phenyl}amino)-4-oxo-4,5-dihydro-1H-pyrazolo[4,3-c]pyridin-1-yl]propanenitrile;

3-cyclopropyl-3-[3-({4-[(3-methylazetidin-1-yl)sulfonyl]phenyl}amino)-4-oxo-4,5-dihydro-1H-pyrazolo[4,3-c]pyridin-1-yl]propanenitrile;

3-cyclopropyl-3-[3-({4-[(2,2-dimethylazetidin-1-yl)sulfonyl]phenyl}amino)-4-oxo-4,5-dihydro-1H-pyrazolo[4,3-c]pyridin-1-yl]propanenitrile;

3-cyclopropyl-3-[3-({4-[(3-hydroxy-3-methylazetidin-1-yl)sulfonyl]phenyl}amino)-4-oxo-4,5-dihydro-1H-pyrazolo[4,3-c]pyridin-1-yl]propanenitrile;

3-cyclopropyl-3-[3-({4-[(3-hydroxyazetidin-1-yl)sulfonyl]phenyl}amino)-4-oxo-4,5-dihydro-1H-pyrazolo[4,3-c]pyridin-1-yl]propanenitrile;

3-cyclopropyl-3-[3-({4-[(3,3-dimethylmorpholin-4-yl)sulfonyl]phenyl}amino)-4-oxo-4,5-dihydro-1H-pyrazolo[4,3-c]pyridin-1-yl]propanenitrile;

3-cyclopropyl-3-[3-({4-[(2,2-dimethylmorpholin-4-yl)sulfonyl]phenyl}amino)-4-oxo-4,5-dihydro-1H-pyrazolo[4,3-c]pyridin-1-yl]propanenitrile;

3-cyclopropyl-3-{3-[(4-{[3-methylmorpholin-4-yl]sulfonyl}phenyl)amino]-4-oxo-4,5-dihydro-1H-pyrazolo[4,3-c]pyridin-1-yl}propanenitrile;

3-cyclopropyl-3-{3-[(4-{[3-hydroxy-3-(trifluoromethyl)pyrrolidin-1-yl]sulfonyl}phenyl)amino]-4-oxo-4,5-dihydro-1H-pyrazolo[4,3-c]pyridin-1-yl}propanenitrile;

3-cyclopropyl-3-[3-({4-[hexahydrocyclopenta[b][1,4]oxazin-4(4aH)-ylsulfonyl]phenyl}amino)-4-oxo-4,5-dihydro-1H-pyrazolo[4,3-c]pyridin-1-yl]propanenitrile;

3-cyclopropyl-3-{3-[(4-{[2,6-dimethylmorpholin-4-yl]sulfonyl}phenyl)amino]-4-oxo-4,5-dihydro-1H-pyrazolo[4,3-c]pyridin-1-yl}propanenitrile;

3-cyclopropyl-3-{3-[(4-{[2-methylmorpholin-4-yl]sulfonyl}phenyl)amino]-4-oxo-4,5-dihydro-1H-pyrazolo[4,3-c]pyridin-1-yl}propanenitrile;

3-cyclopropyl-3-{3-[(4-{[2-methylazetidin-1-yl]sulfonyl}phenyl)amino]-4-oxo-4,5-dihydro-1H-pyrazolo[4,3-c]pyridin-1-yl}propanenitrile;

3-cyclopropyl-3-[3-({4-[(3-methoxyazetidin-1-yl)sulfonyl]phenyl}amino)-4-oxo-4,5-dihydro-1H-pyrazolo[4,3-c]pyridin-1-yl]propanenitrile;

3-cyclopropyl-3-[3-({4-[(3-fluoroazetidin-1-yl)sulfonyl]phenyl}amino)-4-oxo-4,5-dihydro-1H-pyrazolo[4,3-c]pyridin-1-yl]propanenitrile;

3-cyclopropyl-3-[3-({3-methyl-4-[2,2,2-trifluoro-1-hydroxy-1-methylethyl]phenyl}amino)-4-oxo-4,5-dihydro-1H-pyrazolo[4,3-c]pyridin-1-yl]propanenitrile;

3-cyclopropyl-3-[3-({4-[1-hydroxy-1(trifluoromethyl)propyl]phenyl}amino)-4-oxo-4,5-dihydro-1H-pyrazolo[4,3-c]pyridin-1-yl]propanenitrile;

tert-butyl 2-(4-((1-(2-cyano-1-cyclopropylethyl)-4-oxo-4,5-dihydro-1H-pyrazolo[4,3-c]pyridin-3-yl)amino)-N-methylphenylsulfonamido)-2-methylpropanoate;

3-cyclopropyl-3-(4-oxo-3-((1-oxo-2-(2,2,2-trifluoroethyl)isoindolin-5-yl)amino)-4,5-dihydro-1H-pyrazolo[4,3-c]pyridin-1-yl)propanenitrile;

ethyl 2-(4-((1-(2-cyano-1-cyclopropylethyl)-4-oxo-4,5-dihydro-1H-pyrazolo[4,3-c]pyridin-3-yl)amino)-N-methylphenylsulfonamido)-2-methylpropanoate;

tert-butyl 2-(5-((1-(2-cyano-1-cyclopropylethyl)-4-oxo-4,5-dihydro-1H-pyrazolo[4,3-c]pyridin-3-yl)amino)-1-oxoisoindolin-2-yl)-2-methylpropanoate;

4-({1-[2-cyano-1-cyclopropylethyl]-4-oxo-4,5-dihydro-1H-pyrazolo[4,3-c]pyridin-3-yl}amino)-N,N,2-trimethylbenzenesulfonamide;

3-cyclopropyl-3-(3-{[3-methyl-4-(pyrrolidin-1-ylsulfonyl)phenyl]amino}-4-oxo-4,5-dihydro-1H-pyrazolo[4,3-c]pyridin-1-yl)propanenitrile;

3-cyclopropyl-3-(3-{[4-(5,5-dimethyl-3-oxo-2-oxabicyclo[2.2.2]oct-1-yl)phenyl]amino}-4-oxo-4,5-dihydro-1H-pyrazolo[4,3-c]pyridin-1-yl)propanenitrile;

3-cyclopropyl-3-[3-({4-[-1-(dimethylamino)-2,2,2-trifluoroethyl]-3-methylphenyl}amino)-4-oxo-4,5-dihydro-1H-pyrazolo[4,3-c]pyridin-1-yl]propanenitrile;

3-cyclopropyl-3-[3-({4-[(1-methylcyclopropyl)sulfonyl]phenyl}amino)-4-oxo-4,5-dihydro-1H-pyrazolo[4,3-c]pyridin-1-yl]propanenitrile;

3-[3-({4-[1-(tert-butylamino)-2,2,2-trifluoroethyl]phenyl}amino)-4-oxo-4,5-dihydro-1H-pyrazolo[4,3-c]pyridin-1-yl]-3-cyclopropylpropanenitrile;

3-cyclopropyl-3-[4-oxo-3-({4-[2,2,2-trifluoro-1-pyrrolidin-1-ylethyl]phenyl}amino)-4,5-dihydro-1H-pyrazolo[4,3-c]pyridin-1-yl]propanenitrile;

3-cyclopropyl-3-{4-oxo-3-[(4-{2,2,2-trifluoro-1-[(1-methylethyl)amino]ethyl}phenyl)amino]-4,5-dihydro-1H-pyrazolo[4,3-c]pyridin-1-yl}propanenitrile;

3-[3-({4-[1-azetidin-1-yl-2,2,2-trifluoroethyl]phenyl}amino)-4-oxo-4,5-dihydro-1H-pyrazolo[4,3-c]pyridin-1-yl]-3-cyclopropylpropanenitrile;

3-cyclopropyl-3-[3-({4-[1-(ethylamino)-2,2,2-trifluoroethyl]phenyl}amino)-4-oxo-4,5-dihydro-1H-pyrazolo[4,3-c]pyridin-1-yl]propanenitrile;

tert-butyl 4-(5-((1-(2-cyano-1-cyclopropylethyl)-4-oxo-4,5-dihydro-1H-pyrazolo[4,3-c]pyridin-3-yl)amino)-1-oxoisoindolin-2-yl)cyclohexanecarboxylate;

2-(5-((1-(2-cyano-1-cyclopropylethyl)-4-oxo-4,5-dihydro-1H-pyrazolo[4,3-c]pyridin-3-yl)amino)-1-oxoisoindolin-2-yl)-2-methylpropanoic acid;

ethyl 3-(4-((1-(2-cyano-1-cyclopropylethyl)-4-oxo-4,5-dihydro-1H-pyrazolo[4,3-c]pyridin-3-yl)amino)phenyl)-4,4,4-trifluoro-3-hydroxy-2,2-dimethylbutanoate;

isopropyl 3-(4-((1-(2-cyano-1-cyclopropylethyl)-4-oxo-4,5-dihydro-1H-pyrazolo[4,3-c]pyridin-3-yl)amino)phenyl)-4,4,4-trifluoro-3-hydroxy-2,2-dimethylbutanoate;

3-cyclopropyl-3-(3-(1-hydroxy-2,2-dimethyl-1-(trifluoromethyl)-2,3-dihydro-1H-inden-5-yl)amino)-4-oxo-4,5-dihydro-1H-pyrazolo[4,3-c]pyridin-1-yl)propanenitrile;

3-cyclopropyl-3-(4-oxo-3-((4-(1-(trifluoromethyl)cyclopropyl)phenyl)amino)-4,5-dihydro-1H-pyrazolo[4,3-c]pyridin-1-yl)propanenitrile;

3-cyclopropyl-3-(3-((4-(1-(2-methoxyethyl)-1H-pyrazol-3-yl)phenyl)amino)-4-oxo-4,5-dihydro-1H-pyrazolo[4,3-c]pyridin-1-yl)propanenitrile;

3-(3-((3-chloro-4-(1-methyl-1H-pyrazol-3-yl)phenyl)amino)-4-oxo-4,5-dihydro-1H-pyrazolo[4,3-c]pyridin-1-yl)-3-cyclopropylpropanenitrile;

3-(3-((3-chloro-4-(1-(2-cyanoethyl)-1H-pyrazol-3-yl)phenyl)amino)-4-oxo-4,5-dihydro-1H-pyrazolo[4,3-c]pyridin-1-yl)-3-cyclopropylpropanenitrile;

ethyl 1-(4-((1-(2-cyano-1-cyclopropylethyl)-4-oxo-4,5-dihydro-1H-pyrazolo[4,3-c]pyridin-3-yl)amino)-2-methylphenyl)-1H-pyrazole-4-carboxylate;

isopropyl 6-((1-(2-cyano-1-cyclopropylethyl)-4-oxo-4,5-dihydro-1H-pyrazolo[4,3-c]pyridin-3-yl)amino)quinoline-2-carboxylate;

3-cyclopropyl-3-(3-((2-methylbenzo[d]thiazol-6-yl)amino)-4-oxo-4,5-dihydro-1H-pyrazolo[4,3-c]pyridin-1-yl)propanenitrile;

3-cyclopropyl-3-(3-((4-(oxazol-2-yl)phenyl)amino)-4-oxo-4,5-dihydro-1H-pyrazolo[4,3-c]pyridin-1-yl)propanenitrile;

3-cyclopropyl-3-(3-((3,3-dimethyl-2-oxoindolin-6-yl)amino)-4-oxo-4,5-dihydro-1H-pyrazolo[4,3-c]pyridin-1-yl)propanenitrile;

3-cyclopropyl-3-(3-((4-(1,1-dioxidothiomorpholine-4-carbonyl)-3-methylphenyl)amino)-4-oxo-4,5-dihydro-1H-pyrazolo[4,3-c]pyridin-1-yl)propanenitrile;

4-((1-(2-cyano-1-cyclopropylethyl)-4-oxo-4,5-dihydro-1H-pyrazolo[4,3-c]pyridin-3-yl)amino)benzoic acid;

4-((1-(2-cyano-1-cyclopropylethyl)-4-oxo-4,5-dihydro-1H-pyrazolo[4,3-c]pyridin-3-yl)amino)-N-(methylsulfonyl)benzamide;

3-cyclopropyl-3-(3-((2-morpholinoquinolin-6-yl)amino)-4-oxo-4,5-dihydro-1H-pyrazolo[4,3-c]pyridin-1-yl)propanenitrile;

3-cyclopropyl-3-(3-((2-(2,5-dimethylmorpholino)quinolin-6-yl)amino)-4-oxo-4,5-dihydro-1H-pyrazolo[4,3-c]pyridin-1-yl)propanenitrile;

3-cyclopropyl-3-(4-oxo-3-((4-1,1,1-trifluoro-2-methoxypropan-2-yl)phenyl)amino)-4,5-dihydro-1H-pyrazolo[4,3-c]pyridin-1-yl)propanenitrile;

3-cyclopropyl-3-(3-((4-(3-ethylmorpholine-4-carbonyl)-3-methylphenyl)amino)-4-oxo-4,5-dihydro-1H-pyrazolo[4,3-c]pyridin-1-yl)propanenitrile;

3-cyclopropyl-3-(3-((4-(3-isopropylmorpholine-4-carbonyl)-3-methylphenyl)amino)-4-oxo-4,5-dihydro-1H-pyrazolo[4,3-c]pyridin-1-yl)propanenitrile;

3-cyclopropyl-3-(3-((3-methyl-4-(2-methyl-1-(2H-1,2,3-triazol-2-yl)propyl)phenyl)amino)-4-oxo-4,5-dihydro-1H-pyrazolo[4,3-c]pyridin-1-yl)propanenitrile;

3-(3-((2-benzyl-1,1-dioxido-2,3-dihydrobenzo[d]isothiazol-5-yl)amino)-4-oxo-4,5-dihydro-1H-pyrazolo[4,3-c]pyridin-1-yl)-3-cyclopropylpropanenitrile;

3-Cyclopropyl-3-(3-((3-methyl-4-(2-methyl-1-(1H-1,2,3-triazol-1-yl)propyl)phenyl)amino)-4-oxo-4,5-dihydro-1H-pyrazolo[4,3-c]pyridin-1-yl)propanenitrile;

3-cyclopropyl-3-(3-((3-methyl-4-(2,2,2-trifluoro-1-hydroxyethyl)phenyl)amino)-4-oxo-4,5-dihydro-1H-pyrazolo[4,3-c]pyridin-1-yl)propanenitrile;

3-(3-((4-(cyclopentyl(2H-1,2,3-triazol-2-yl)methyl)-3-methylphenyl)amino)-4-oxo-4,5-dihydro-1H-pyrazolo[4,3-c]pyridin-1-yl)-3-cyclopropylpropanenitrile;

3-(3-((4-(1-amino-2,2,2-trifluoroethyl)-3-methylphenyl)amino)-4-oxo-4,5-dihydro-1H-pyrazolo[4,3-c]pyridin-1-yl)-3-cyclopropylpropanenitrile;

3-(3-((2-cyclohexyl-1,1-dioxido-2,3-dihydrobenzo[d]isothiazol-5-yl)amino)-4-oxo-4,5-dihydro-1H-pyrazolo[4,3-c]pyridin-1-yl)-3-cyclopropylpropanenitrile;

3-cyclopropyl-3-(3-((2-(1-methylcyclohexyl)-1,1-dioxido-2,3-dihydrobenzo[d]isothiazol-5-yl)amino)-4-oxo-4,5-dihydro-1H-pyrazolo[4,3-c]pyridin-1-yl)propanenitrile;

3-cyclopropyl-3-(3-((3-hydroxy-2,2-dimethyl-1,1-dioxido-2,3-dihydrobenzo[b]thiophen-5-yl)amino)-4-oxo-4,5-dihydro-1H-pyrazolo[4,3-c]pyridin-1-yl)propanenitrile;

3-cyclopropyl-3-(3-((3-hydroxy-1,1-dioxido-3H-spiro[benzo[b]thiophene-2,1'-cyclohexan]-5-yl)amino)-4-oxo-4,5-dihydro-1H-pyrazolo[4,3-c]pyridin-1-yl)propanenitrile;

3-cyclopropyl-3-(4-oxo-3-((4-(2-(trifluoromethyl)pyrrolidin-2-yl)phenyl)amino)-4,5-dihydro-1H-pyrazolo[4,3-c]pyridin-1-yl)propanenitrile;

3-(3-((4-(2-azaspiro[3.3]heptan-2-ylsulfonyl)-3-methylphenyl)amino)-4-oxo-4,5-dihydro-1H-pyrazolo[4,3-c]pyridin-1-yl)-3-cyclopropylpropanenitrile;

3-cyclopropyl-3-(3-((1,1-dioxido-3H-spiro[benzo[b]thiophene-2,1'-cyclopentan]-5-yl)amino)-4-oxo-4,5-dihydro-1H-pyrazolo[4,3-c]pyridin-1-yl)propanenitrile;

3-cyclopropyl-3-(3-((1,1-dioxido-3H-spiro[benzo[b]thiophene-2,1'-cyclohexan]-5-yl)amino)-4-oxo-4,5-dihydro-1H-pyrazolo[4,3-c]pyridin-1-yl)propanenitrile;

3-cyclopropyl-3-(3-((2,2-dimethyl-1,1-dioxido-2,3-dihydrobenzo[b]thiophen-5-yl)amino)-4-oxo-4,5-dihydro-1H-pyrazolo[4,3-c]pyridin-1-yl)propanenitrile;

3-cyclopropyl-3-(3-((3-hydroxy-2-methyl-1,1-dioxido-2,3-dihydrobenzo[b]thiophen-5-yl)amino)-4-oxo-4,5-dihydro-1H-pyrazolo[4,3-c]pyridin-1-yl)propanenitrile;

3-cyclopropyl-3-(3-((2-methyl-1,1-dioxido-2,3-dihydrobenzo[b]thiophen-5-yl)amino)-4-oxo-4,5-dihydro-1H-pyrazolo[4,3-c]pyridin-1-yl)propanenitrile;

3-cyclopropyl-3-(3-((3-methyl-4-(2-(trifluoromethyl)pyrrolidin-2-yl)phenyl)amino)-4-oxo-4,5-dihydro-1H-pyrazolo[4,3-c]pyridin-1-yl)propanenitrile;

3-cyclopropyl-3-(4-oxo-3-((1-oxo-2-(1-(trifluoromethyl)cyclohexyl)isoindolin-5-yl)amino)-4,5-dihydro-1H-pyrazolo[4,3-c]pyridin-1-yl)propanenitrile;

3-cyclopropyl-3-(3-((2-(4-methyltetrahydro-2H-pyran-4-yl)-1,1-dioxido-2,3-dihydrobenzo[d]isothiazol-5-yl)amino)-4-oxo-4,5-dihydro-1H-pyrazolo[4,3-c]pyridin-1-yl)propanenitrile;

3-cyclopropyl-3-(3-((4-(1-methyl-2-(trifluoromethyl)pyrrolidin-2-yl)phenyl)amino)-4-oxo-4,5-dihydro-1H-pyrazolo[4,3-c]pyridin-1-yl)propanenitrile;

4-((1-(2-cyano-1-cyclopropylethyl)-4-oxo-4,5-dihydro-1H-pyrazolo[4,3-c]pyridin-3-yl)amino)-N,2-dimethyl-N-(tetrahydro-2H-pyran-4-yl)benzamide;

3-cyclopropyl-3-(3-((3-fluoro-4-(2,2,2-trifluoro-1-(isopropylamino)ethyl)phenyl)amino)-4-oxo-4,5-dihydro-1H-pyrazolo[4,3-c]pyridin-1-yl)propanenitrile;

3-cyclopropyl-3-(3-((4-(1-(ethylamino)-2,2,2-trifluoroethyl)-3-fluorophenyl)amino)-4-oxo-4,5-dihydro-1H-pyrazolo[4,3-c]pyridin-1-yl)propanenitrile;

3-(3-((4-(1-(tert-butylamino)-2,2,2-trifluoroethyl)-3-fluorophenyl)amino)-4-oxo-4,5-dihydro-1H-pyrazolo[4,3-c]pyridin-1-yl)-3-cyclopropylpropanenitrile;

3-cyclopropyl-3-(4-oxo-3-((4-(2-(trifluoromethyl)tetrahydrofuran-2-yl)phenyl)amino)-4,5-dihydro-1H-pyrazolo[4,3-c]pyridin-1-yl)propanenitrile;

3-cyclopropyl-3-(3-((2-hydroxy-2-(trifluoromethyl)-2,3-dihydro-1H-inden-5-yl)amino)-4-oxo-4,5-dihydro-1H-pyrazolo[4,3-c]pyridin-1-yl)propanenitrile;

3-cyclopropyl-3-(3-((3-fluoro-4-(2,2,2-trifluoro-1-hydroxyethyl)phenyl)amino)-4-oxo-4,5-dihydro-1H-pyrazolo[4,3-c]pyridin-1-yl)propanenitrile;

3-(3-((3-chloro-4-(2,2,2-trifluoro-1-hydroxyethyl)phenyl)amino)-4-oxo-4,5-dihydro-1H-pyrazolo[4,3-c]pyridin-1-yl)-3-cyclopropylpropanenitrile;

3-cyclopropyl-3-(3-((2-hydroxy-2-methyl-2,3-dihydro-1H-inden-5-yl)amino)-4-oxo-4,5-dihydro-1H-pyrazolo[4,3-c]pyridin-1-yl)propanenitrile;

3-(3-((4-(1-(tert-butylamino)-2,2,2-trifluoroethyl)-3-chlorophenyl)amino)-4-oxo-4,5-dihydro-1H-pyrazolo[4,3-c]pyridin-1-yl)-3-cyclopropylpropanenitrile;

3-cyclopropyl-3-(4-oxo-3-((4-(2-(trifluoromethyl)piperidin-2-yl)phenyl)amino)-4,5-dihydro-1H-pyrazolo[4,3-c]pyridin-1-yl)propanenitrile;

methyl-2-(4-((1-(2-cyano-1-cyclopropylethyl)-4-oxo-4,5-dihydro-1H-pyrazolo[4,3-c]pyridin-3-yl)amino)phenyl)-2-(trifluoromethyl)pyrrolidine-1-carboxylate;

3-cyclopropyl-3-(3-((2-(4,4-difluoro-1-methylcyclohexyl)-1,1-dioxido-2,3-dihydrobenzo[d]isothiazol-5-yl)amino)-4-oxo-4,5-dihydro-1H-pyrazolo[4,3-c]pyridin-1-yl)propanenitrile;

3-cyclopropyl-3-(4-oxo-3-((4-(2,2,2-trifluoro-1-hydroxy-1-(pyridin-2-yl)ethyl)phenyl)amino)-4,5-dihydro-1H-pyrazolo[4,3-c]pyridin-1-yl)propanenitrile;

3-cyclopropyl-3-(4-oxo-3-((4-(2,2,2-trifluoro-1-hydroxy-1-(pyridin-4-yl)ethyl)phenyl)amino)-4,5-dihydro-1H-pyrazolo[4,3-c]pyridin-1-yl)propanenitrile;

3-cyclopropyl-3-(4-oxo-3-((4-(2,2,2-trifluoro-1-thiomorpholinoethyl)phenyl)amino)-4,5-dihydro-1H-pyrazolo[4,3-c]pyridin-1-yl)propanenitrile;

4-((1-(2-cyano-1-cyclopropylethyl)-4-oxo-4,5-dihydro-1H-pyrazolo[4,3-c]pyridin-3-yl)amino)-N,2-dimethyl-N-(2,2,2-trifluoroethyl)benzamide;

4-((1-(2-cyano-1-cyclopropylethyl)-4-oxo-4,5-dihydro-1H-pyrazolo[4,3-c]pyridin-3-yl)amino)-N-ethyl-2-methyl-N-(2,2,2-trifluoroethyl)benzamide;

4-((1-(2-cyano-1-cyclopropylethyl)-4-oxo-4,5-dihydro-1H-pyrazolo[4,3-c]pyridin-3-yl)amino)-N-(2-(dimethylamino)ethyl)-2-methyl-N-(2,2,2-trifluoroethyl)benzamide;

3-cyclopropyl-3-(3-((3-methyl-4-(thiomorpholine-4-carbonyl)phenyl)amino)-4-oxo-4,5-dihydro-1H-pyrazolo[4,3-c]pyridin-1-yl)propanenitrile;

3-cyclopropyl-3-(3-((3-methyl-4-(4-methylpiperazine-1-carbonyl)phenyl)amino)-4-oxo-4,5-dihydro-1H-pyrazolo[4,3-c]pyridin-1-yl)propanenitrile;

3-cyclopropyl-3-(3-((3-methyl-4-(2-(trifluoromethyl)pyrrolidine-1-carbonyl)phenyl)amino)-4-oxo-4,5-dihydro-1H-pyrazolo[4,3-c]pyridin-1-yl)propanenitrile;

4-((1-(2-cyano-1-cyclopropylethyl)-4-oxo-4,5-dihydro-1H-pyrazolo[4,3-c]pyridin-3-yl)amino)-N,2-dimethyl-N-(1-methylpiperidin-4-yl)benzamide;

4-((1-(2-cyano-1-cyclopropylethyl)-4-oxo-4,5-dihydro-1H-pyrazolo[4,3-c]pyridin-3-yl)amino)-N-ethyl-N,2-dimethylbenzamide;

3-cyclopropyl-3-(3-((3-methyl-4-(morpholine-4-carbonyl)phenyl)amino)-4-oxo-4,5-dihydro-1H-pyrazolo[4,3-c]pyridin-1-yl)propanenitrile;

3-cyclopropyl-3-(3-((4-(3,3-dimethylpyrrolidine-1-carbonyl)-3-methylphenyl)amino)-4-oxo-4,5-dihydro-1H-pyrazolo[4,3-c]pyridin-1-yl)propanenitrile;

3-cyclopropyl-3-(3-((4-(3,3-dimethylazetidine-1-carbonyl)-3-methylphenyl)amino)-4-oxo-4,5-dihydro-1H-pyrazolo[4,3-c]pyridin-1-yl)propanenitrile;

3-cyclopropyl-3-(3-((4-(2,2-dimethylmorpholine-4-carbonyl)-3-methylphenyl)amino)-4-oxo-4,5-dihydro-1H-pyrazolo[4,3-c]pyridin-1-yl)propanenitrile;

3-cyclopropyl-3-(3-((4-(2,5-dimethylpyrrolidine-1-carbonyl)-3-methylphenyl)amino)-4-oxo-4,5-dihydro-1H-pyrazolo[4,3-c]pyridin-1-yl)propanenitrile;

3-cyclopropyl-3-(3-((4-(3-fluoropyrrolidine-1-carbonyl)-3-methylphenyl)amino)-4-oxo-4,5-dihydro-1H-pyrazolo[4,3-c]pyridin-1-yl)propanenitrile;

3-cyclopropyl-3-(3-((3-methyl-4-(2-methylpiperidine-1-carbonyl)phenyl)amino)-4-oxo-4,5-dihydro-1H-pyrazolo[4,3-c]pyridin-1-yl)propanenitrile;

3-cyclopropyl-3-(3-((3-methyl-4-(2-methylpiperidine-1-carbonyl)phenyl)amino)-4-oxo-4,5-dihydro-1H-pyrazolo[4,3-c]pyridin-1-yl)propanenitrile;

3-cyclopropyl-3-(3-((4-(4,4-difluoropiperidine-1-carbonyl)-3-methylphenyl)amino)-4-oxo-4,5-dihydro-1H-pyrazolo[4,3-c]pyridin-1-yl)propanenitrile;

3-cyclopropyl-3-(3-((4-(4-hydroxy-4-methylpiperidine-1-carbonyl)-3-methylphenyl)amino)-4-oxo-4,5-dihydro-1H-pyrazolo[4,3-c]pyridin-1-yl)propanenitrile;

3-cyclopropyl-3-(3-((4-(4-methoxypiperidine-1-carbonyl)-3-methylphenyl)amino)-4-oxo-4,5-dihydro-1H-pyrazolo[4,3-c]pyridin-1-yl)propanenitrile;

3-cyclopropyl-3-(3-((4-(4-(2-hydroxypropan-2-yl)piperidine-1-carbonyl)-3-methylphenyl)amino)-4-oxo-4,5-dihydro-1H-pyrazolo[4,3-c]pyridin-1-yl)propanenitrile;

4-((1-(2-cyano-1-cyclopropylethyl)-4-oxo-4,5-dihydro-1H-pyrazolo[4,3-c]pyridin-3-yl)amino)-N-(3-hydroxy-3-methylbutyl)-N,2-dimethylbenzamide;

3-(3-((4-(azepane-1-carbonyl)-3-methylphenyl)amino)-4-oxo-4,5-dihydro-1H-pyrazolo[4,3-c]pyridin-1-yl)-3-cyclopropylpropanenitrile;

3-cyclopropyl-3-(3-((4-(3-fluoroazetidine-1-carbonyl)-3-methylphenyl)amino)-4-oxo-4,5-dihydro-1H-pyrazolo[4,3-c]pyridin-1-yl)propanenitrile;

3-cyclopropyl-3-(3-((4-(3-methoxyazetidine-1-carbonyl)-3-methylphenyl)amino)-4-oxo-4,5-dihydro-1H-pyrazolo[4,3-c]pyridin-1-yl)propanenitrile;

3-(3-((4-(8-oxa-3-azabicyclo[3.2.1]octane-3-carbonyl)-3-methylphenyl)amino)-4-oxo-4,5-dihydro-1H-pyrazolo[4,3-c]pyridin-1-yl)-3-cyclopropylpropanenitrile;

4-((1-(2-cyano-1-cyclopropylethyl)-4-oxo-4,5-dihydro-1H-pyrazolo[4,3-c]pyridin-3-yl)amino)-N-cyclohexyl-N,2-dimethylbenzamide;

tert-butyl(1-(4-((1-(2-cyano-1-cyclopropylethyl)-4-oxo-4,5-dihydro-1H-pyrazolo[4,3-c]pyridin-3-yl)amino)-2-methylbenzoyl)piperidin-4-yl)(methyl)carbamate;

3-(3-((4-fluorophenyl)amino)-4-oxo-4,5-dihydro-1H-pyrazolo[4,3-c]pyridine-1-yl)butanenitrile;

3-[4-oxo-3-({4-[(2,2,2-trifluoro-1-hydroxy-1-methylethyl]phenyl}amino)-4,5-dihydro-1H-pyrazolo[4,3-c]pyridin-1-yl]butanenitrile;

3-(3-{[1-hydroxy-1-(trifluoromethyl)-2,3-dihydro-1H-inden-5-yl]amino}-4-oxo-4,5-dihydro-1H-pyrazolo[4,3-c]pyridin-1-yl)butanenitrile;

3-{3-[(1,1-dioxido-2,3-dihydro-1-benzothiophen-5-yl)amino]-4-oxo-4,5-dihydro-1H-pyrazolo[4,3-c]pyridin-1-yl}butanenitrile;

4-({1-[2-cyano-1-methylethyl]-4-oxo-4,5-dihydro-1H-pyrazolo[4,3-c]pyridin-3-yl}amino)benzonitrile;
3-(4-oxo-3-{[4-(trifluoromethyl)phenyl]amino}-4,5-dihydro-1H-pyrazolo[4,3-c]pyridin-1-yl)butanenitrile;
3-(3-{[4-(methylsulfonyl)phenyl]amino}-4-oxo-4,5-dihydro-1H-pyrazolo[4,3-c]pyridin-1-yl)butanenitrile;
3-{4-oxo-3-[(3,4,5-trifluorophenyl)amino]-4,5-dihydro-1H-pyrazolo[4,3-c]pyridin-1-yl}butanenitrile;
3-{3-[(2-methyl-1,1-dioxido-2,3-dihydro-1,2-benzisothiazol-5-yl)amino]-4-oxo-4,5-dihydro-1H-pyrazolo[4,3-c]pyridin-1-yl}butanenitrile;
3-{3-[(2-fluoropyridin-4-yl)amino]-4-oxo-4,5-dihydro-1H-pyrazolo[4,3-c]pyridin-1-yl}butanenitrile;
3-{4-oxo-3-[(1-oxo-2,3-dihydro-1H-inden-5-yl)amino]-4,5-dihydro-1H-pyrazolo[4,3-c]pyridin-1-yl}butanenitrile;
3-[3-(2,3-dihydro-1-benzofuran-5-ylamino)-4-oxo-4,5-dihydro-1H-pyrazolo[4,3-c]pyridin-1-yl]butanenitrile;
3-[3-(1,3-benzodioxol-5-ylamino)-4-oxo-4,5-dihydro-1H-pyrazolo[4,3-c]pyridin-1-yl]butanenitrile;
3-[4-oxo-3-(quinolin-6-ylamino)-4,5-dihydro-1H-pyrazolo[4,3-c]pyridin-1-yl]butanenitrile;
3-(3-{[3-fluoro-4-(methylsulfonyl)phenyl]amino}-4-oxo-4,5-dihydro-1H-pyrazolo[4,3-c]pyridin-1-yl)butanenitrile;
3-[4-oxo-3-(quinoxalin-6-ylamino)-4,5-dihydro-1H-pyrazolo[4,3-c]pyridin-1-yl]butanenitrile;
3-{3-[(4-chlorophenyl)amino]-4-oxo-4,5-dihydro-1H-pyrazolo[4,3-c]pyridin-1-yl}butanenitrile;
N-tert-butyl-4-({1-[2-cyano-1-methylethyl]-4-oxo-4,5-dihydro-1H-pyrazolo[4,3-c]pyridin-3-yl}amino)benzenesulfonamide;
3-{3-[(2-tert-butyl-1,1-dioxido-2,3-dihydro-1,2-benzisothiazol-5-yl)amino]-4-oxo-4,5-dihydro-1H-pyrazolo[4,3-c]pyridin-1-yl}butanenitrile;
methyl 3-((4-(azetidin-1-ylsulfonyl)phenyl)amino)-1-(2-cyano-1-cyclopropylethyl)-4-oxo-4,5-dihydro-1H-pyrazolo[4,3-c]pyridine-7-carboxylate;
3-(3-((4-(azetidin-1-ylsulfonyl)phenyl)amino)-7-(hydroxymethyl)-4-oxo-4,5-dihydro-1H-pyrazolo[4,3-c]pyridin-1-yl)-3-cyclopropylpropanenitrile;
3-cyclopropyl-3-(3-(((1,1-dioxido-3H-spiro[benzo[b]thiophene-2,1'-cyclohexan]-5-yl)amino)-4-oxo-4,5-dihydro-1H-pyrazolo[4,3-c]pyridin-1-yl)propanenitrile;
3-cyclopropyl-3-(3-(((1,1-dioxido-3H-spiro[benzo[b]thiophene-2,1'-cyclopentan]-5-yl)amino)-4-oxo-4,5-dihydro-1H-pyrazolo[4,3-c]pyridin-1-yl)propanenitrile; and
3-cyclopropyl-3-(3-((2,3-dimethyl-1,1-dioxido-2,3-dihydrobenzo[b]thiophen-5-yl)amino)-4-oxo-4,5-dihydro-1H-pyrazolo[4,3-c]pyridin-1-yl)propanenitrile.

5. A method of treating rheumatoid arthritis in a mammal that can be ameliorated by the inhibition of Janus kinases JAK1 and JAK2 comprising administering to the mammal in need of such treatment, a therapeutically effective amount of a compound according to claim 1 or a pharmaceutically acceptable salt or a stereoisomer thereof.

6. A compound of claim 4 or a pharmaceutically acceptable salt thereof selected from:
(R)-4-((1-(1-cyanopropan-2-yl)-4-oxo-4,5-dihydro-1H-pyrazolo[4,3-c]pyridin-3-yl)amino)-N,N-dimethylbenzenesulfonamide;
(S)-4-((1-(1-cyanopropan-2-yl)-4-oxo-4,5-dihydro-1H-pyrazolo[4,3-c]pyridin-3-yl)amino)-N,N-dimethylbenzenesulfonamide;
(R)-4-((1-(1-cyanopropan-2-yl)-4-oxo-4,5-dihydro-1H-pyrazolo[4,3-c]pyridin-3-yl)amino)-N,N-dimethylbenzenesulfonamide;
(S)-4-((1-(1-cyanopropan-2-yl)-4-oxo-4,5-dihydro-1H-pyrazolo[4,3-c]pyridin-3-yl)amino)-N,N-dimethylbenzenesulfonamide;
(S)-4-((1-(2-cyano-1-cyclopropylethyl)-4-oxo-4,5-dihydro-1H-pyrazolo[4,3-c]pyridin-3-yl)amino)-N,N-dimethylbenzene-sulfonamide;
(R)-4-((1-(2-cyano-1-cyclopropylethyl)-4-oxo-4,5-dihydro-1H-pyrazolo[4,3-c]pyridin-3-yl)amino)-N,N-dimethylbenzenesulfonamide;
4-((1-((S)-2-cyano-1-((S)-2,2-difluorocyclopropyl)ethyl)-4-oxo-4,5-dihydro-1H-pyrazolo[4,3-c]pyridin-3-yl)amino)-N,N-dimethylbenzenesulfonamide;
4-((1-((S)-2-cyano-1-((R)-2,2-difluorocyclopropyl)ethyl)-4-oxo-4,5-dihydro-1H-pyrazolo[4,3-c]pyridin-3-yl)amino)-N,N-dimethylbenzenesulfonamide;
4-((1-((R)-2-cyano-1-((S)-2,2-difluorocyclopropyl)ethyl)-4-oxo-4,5-dihydro-1H-pyrazolo[4,3-c]pyridin-3-yl)amino)-N,N-dimethylbenzenesulfonamide;
4-((1-((R)-2-cyano-1(R)-2,2-difluorocyclopropyl)ethyl)-4-oxo-4,5-dihydro-1H-pyrazolo[4,3-c]pyridin-3-yl)amino)-N,N-dimethylbenzenesulfonamide;
4-((1-((S)-2-cyano-1-((S)-2,2-dimethylcyclopropyl)ethyl)-4-oxo-4,5-dihydro-1H-pyrazolo[4,3-c]pyridin-3-yl)amino)-N,N-dimethylbenzenesulfonamide;
4((1-((S)-2-cyano-1-((R)-2,2-dimethylcyclopropyl)ethyl)-4-oxo-4,5-dihydro-1H-pyrazolo[4,3-c]pyridin-3-yl)amino)-N,N-dimethylbenzenesulfonamide;
4-((1-((R)-2-cyano-1-((S)-2,2-dimethylcyclopropyl)ethyl)-4-oxo-4,5-dihydro-1H-pyrazolo[4,3-c]pyridin-3-yl)amino)-N,N-dimethylbenzenesulfonamide;
4-((1-((R)-2-cyano-1(R)-2,2-dimethylcyclopropyl)ethyl)-4-oxo-4,5-dihydro-1H-pyrazolo[4,3-c]pyridin-3-yl)amino)-N,N-dimethylbenzenesulfonamide;
(S)-4-((1-(2-cyano-l-cyclobutylethyl)-4-oxo-4,5-dihydro-1H-pyrazolo[4,3-c]pyridin-3-yl)amino)-N,N-dimethylbenzenesulfonamide;
(R)-4-((1-(2-cyano-1-cyclobutylethyl)-4-oxo-4,5-dihydro-1H-pyrazolo[4,3-c]pyridin-3-yl)amino)-N,N-dimethylbenzenesulfonamide;
(S)-3-cyclobutyl-3-(4-oxo-3-((4-(pyrrolidin-1-yl sulfonyl)phenyl)amino)-4,5-dihydro-1H-pyrazolo[4,3-c]pyridin-1-yl)propanenitrile;
(R)-3-cyclobutyl-3-(4-oxo-3-((4-(pyrrolidin-1-yl sulfonyl)phenyl)amino)-4,5-dihydro-1H-pyrazolo[4,3-c]pyridin-1-yl)propanenitrile;
(3S)-3-cyclopropyl-3-{3-[(4-fluorophenyl)amino]-4-oxo-4,5-dihydro-1H-pyrazolo[4,3-c]pyridin-1-yl}propanenitrile;
(3S)-3-cyclopropyl-3-[4-oxo-3-({4-[(1R)-2,2,2-trifluoro-1-hydroxy-1-methylethyl]phenyl}amino)-4,5-dihydro-1H-pyrazolo[4,3-c]pyridin-1-yl]propanenitrile;
(3S)-3-cyclopropyl-3[4-oxo-3-({4-[(1S)-2,2,2-trifluoro-1-hydroxy-1-methylethyl]phenyl}amino)-4,5-dihydro-1H-pyrazolo[4,3-c]pyridin-1-yl]propanenitrile;
(3S)-3-cyclopropyl-3-(3-{[(1R)-1-hydroxy-1-(trifluoromethyl)-2,3-dihydro-1H-inden-5-yl]amino}-4-oxo-4,5-dihydro-1H-pyrazolo[4,3-c]pyridin-1-yl)propanenitrile;
(3S)-3-cyclopropyl-3-(3-{[(1S)-1-hydroxy-1-(trifluoromethyl)-2,3-dihydro-1H-inden-5-yl]amino}4-oxo-4,5-dihydro-1H-pyrazolo[4,3-c]pyridin-1-yl)propanenitrile;

(3S)-3-cyclopropyl-3-{3-[(1,1-dioxido-2,3-dihydro-1-benzothiophen-5-yl)amino]-4-oxo-4,5-dihydro-1H-pyrazolo[4,3-c]pyridin-1-yl}propanenitrile;

(3S)-3-{3-[(2-tent-butyl-1,1-dioxido-2,3-dihydro-1,2-benzisothiazol-5-yl)amino]-4-oxo-4,5-dihydro-1H-pyrazolo[4,3-c]pyridin-1-yl}-3-cyclopropylpropanenitrile;

4-({1-[(1S)-2-cyano-1-cyclopropylethyl]-4-oxo-4,5-dihydro-1H-pyrazolo[4,3-c]pyridin-3-yl}amino)benzonitrile;

(3S)-3-cyclopropyl-3-(4-oxo-3-{[4-(trifluoromethyl)phenyl]amino}-4,5-dihydro-1H-pyrazolo[4,3-c]pyridin-1-yl)propanenitrile;

(3S)-3-cyclopropyl-3-(3-{[4-(methylsulfonyl)phenyl]amino}-4-oxo-4,5-dihydro-1H-pyrazolo[4,3-c]pyridin-1-yl)propanenitrile;

(3S)-3-cyclopropyl-3-{4-oxo-3-[(3,4,5-trifluorophenyl)amino]-4,5-dihydro-1H-pyrazolo[4,3-c]pyridin-1-yl}propanenitrile;

(3S)-3-cyclopropyl-3-{3-[(2-methyl-1,1-dioxido-2,3-dihydro-1,2-benzisothiazol-5-yl)amino]-4-oxo-4,5-dihydro-1H-pyrazolo[4,3-c]pyridin-1-yl}propanenitrile;

(3S)-3-cyclopropyl-3-{3-[(2-fluoropyridin-4-yl)amino]-4-oxo-4,5-dihydro-1H-pyrazolo[4,3-c]pyridin-1-yl}propanenitrile;

(3S)-3-cyclopropyl-3-{4-oxo-3-[(1-oxo-2,3-dihydro-1H-inden-5-yl)amino]-4,5-dihydro-1H-pyrazolo[4,3-c]pyridin-1-yl}propanenitrile;

(3S)-3-cyclopropyl-3-[3-(2,3-dihydro-1-b enzofuran-5-ylamino)-4-oxo-4,5-dihydro-1H-pyrazolo[4,3-c]pyridin-1-yl]propanenitrile;

(3S)-3-(1,3-benzodioxol-5-ylamino)-4-oxo-4,5-dihydro-1H-pyrazolo[4,3-c]pyridin-1-yl]-3-cyclopropylpropanenitrile;

(3S)-3-cyclopropyl-3[4-oxo-3-(quinolin-6-ylamino)-4,5-dihydro-1H-pyrazolo[4,3-c]pyridin-1-yl]propanenitrile;

(3S)-3-cyclopropyl-3-(3-{[3-fluoro-4-(methylsulfonyl)phenyl]amino}-4-oxo-4,5 -dihydro-1H-pyrazolo[4,3-c]pyridin-1-yl)propanenitrile;

(3S)-3-cyclopropyl-3-[4-oxo-3-(quinoxalin-6-ylamino)-4,5-dihydro-1H-pyrazolo[4,3-c]pyridin-1-yl]propanenitrile;

(3S)-3-{3-[(4-chlorophenyl)amino]-4-oxo-4,5-dihydro-1H-pyrazolo[4,3-c]pyridin-1-yl}-3-cyclopropylpropanenitrile;

(3S)-cyclopropyl-3-({4-[(1-methylethyl)sulfonyl]phenyl}amino)-4-oxo-4,5-dihydro-1H-pyrazolo[4,3-c]pyridin-1-yl)propanenitrile;

(3S)-(3-{[4-(tert-butylsulfonyl)phenyl]amino}-4-oxo-4,5-dihydro-1H-pyrazolo[4,3-c]pyridin-1-yl)-3-cyclopropylpropanenitrile;

N-tert-butyl-4-{[1S-(2-cyano-1-cyclopropylethyl)-4-oxo-4,5-dihydro-1H-pyrazolo[4,3-c]pyridin-3-yl]amino}benzenesulfonamide;

(3S)-3-({4-[(1R)-1-amino-2,2,2-trifluoroethyl]phenyl}amino)-4-oxo-4,5-dihydro-1H-pyrazolo[4,3-c]pyridin-1-yl]-3-cyclopropylpropanenitrile;

(3S)-3-({4-[(1S)-1-amino-2,2,2-trifluoroethyl]phenyl}amino)-4-oxo-4,5-dihydro-1H-pyrazolo[4,3-c]pyridin-1-yl]-3-cyclopropylpropanenitrile;

4-({1-[(1S)-2-cyano-1-cyclopropylethyl]-4-oxo-4,5-dihydro-1H-pyrazolo[4,3-c]pyridin-3-yl}amino)-N-ethyl-N-methylbenzenesulfonamide;

(3S)-3-cyclopropyl-3-(4-oxo-3-{[4-(piperidin-1-ylsulfonyl)phenyl]amino}-4,5-dihydro-1H-pyrazolo[4,3-c]pyridin-1-yl)propanenitrile;

4-({1-[(1S)-2-cyano-1-cyclopropylethyl]-4-oxo-4,5-dihydro-1H-pyrazolo[4,3-c]pyridin-3-yl}amino)-N-methyl-N-(1-methylethyl)benzenesulfonamide;

4-({1-[(1S)-2-cyano-1-cyclopropylethyl]-4-oxo-4,5-dihydro-1H-pyrazolo[4,3-c]pyridin-3-yl}amino)-N-methylbenzenesulfonamide;

(3S)-3-cyclopropyl-3-(4-oxo-3-{[4-(pyrrolidin-1-ylsulfonyl)phenyl]amino}-4,5-dihydro-1H-pyrazolo[4,3-c]pyridin-1-yl)propanenitrile;

4-({1-[(1S)-2-cyano-1-cyclopropylethyl]-4-oxo-4,5-dihydro-1H-pyrazolo[4,3-c]pyridin-3-yl}amino)-N,N-diethylbenzenesulfonamide;

(3S)-3-cyclopropyl-3-[3-({4-[(3,3-dimethylpiperidin-1-yl)sulfonyl]phenyl }amino)-4-oxo-4,5-dihydro-1H-pyrazolo[4,3-c]pyridin-1-yl]propanenitrile;

(3S)-3-cyclopropyl-3-({4-[(3,3-dimethylpyrrolidin-1-yl)sulfonyl]phenyl }amino)-4-oxo-4,5-dihydro-1H-pyrazolo[4,3-c]pyridin-1-yl]propanenitrile;

(3S)-3-{3-[(2-tert-butyl-1-oxo-2,3-dihydro-1H-isoindol-5-yl)amino]-4-oxo-4,5-dihydro-1H-pyrazolo[4,3-c]pyridin-1-yl}-3-cyclopropylpropanenitrile;

(3S)-3-{3-[(2-cyclopentyl-1-oxo-2,3-dihydro-1H-isoindol-5-yl)amino]-4-oxo-4,5-dihydro-1H-pyrazolo[4,3-c]pyridin-1-yl}-3-cyclopropylpropanenitrile;

(3S)-3-{3-[(2-cyclohexyl-1-oxo-2,3-dihydro-1H-isoindol-5-yl)amino]-4-oxo-4,5-dihydro-1H-pyrazolo[4,3-c]pyridin-1-yl}-3-cyclopropylpropanenitrile;

(3S)-3-cyclopropyl-3-({4-[(2,2-dimethylpiperidin-1-yl)sulfonyl]phenyl }amino)-4-oxo-4,5-dihydro-1H-pyrazolo[4,3-c]pyridin-1-yl]propanenitrile;

tert-butyl 1-{[4-({1-[(1S)-2-cyano-1-cyclopropylethyl]-4-oxo-4,5-dihydro-1H-pyrazolo[4,3-c]pyridin-3-yl}amino)phenyl]sulfonyl }piperidine-4-carboxylate;

(3S)-3-cyclopropyl-3-{3-[(4-{[(3S)-3-hydroxypyrrolidin-1-yl]sulfonyl }phenyl)amino]-4-oxo-4,5-dihydro-1H-pyrazolo[4,3-c]pyridin-1-yl}propanenitrile;

(3S)-3-cyclopropyl-3-{3-[(4-{[(3R)-3-hydroxypyrrolidin-1-yl]sulfonyl}phenyl)amino]-4-oxo-4,5-dihydro-1H-pyrazolo[4,3-c]pyridin-1-yl}propanenitrile;

tert-butyl 1-{[4-({1-[(1S)-2-cyano-1-cyclopropylethyl]-4-oxo-4,5-dihydro-1H-pyrazolo[4,3-c]pyridin-3-yl}amino)phenyl]sulfonyl }-D-prolinate;

(3S)-3-cyclopropyl-3-{4-oxo-3-[(4-{[(3R)-3-(trifluoromethyl)pyrrolidin-1-yl]sulfonyl }phenyl)amino]-4,5-dihydro-1H-pyrazolo[4,3-c]pyridin-1-yl}propanenitrile;

(3S)-3-cyclopropyl-3-{4-oxo-3-[(4-{[(3S)-3-(trifluoromethyl)pyrrolidin-1-yl]sulfonyl }phenyl)amino]-4,5-dihydro-1H-pyrazolo[4,3-c]pyridin-1-yl}propanenitrile;

(3S)-3-cyclopropyl-3-{4-oxo-3-[(4-{[(2R)-2-(trifluoromethyl)pyrrolidin-1-yl]sulfonyl }phenyl)amino]-4,5-dihydro-1H-pyrazolo[4,3-c]pyridin-1-yl}propanenitrile;

(3S)-3-cyclopropyl-3-{4-oxo-3-[(4-{[(2S)-2-(trifluoromethyl)pyrrolidin-1-yl]sulfonyl }phenyl)amino]-4,5-dihydro-1H-pyrazolo[4,3-c]pyridin-1-yl}propanenitrile;

tert-butyl(3S)-1-{[4-[(1R)-2-cyano-1-cyclopropylethyl]-4-oxo-4,5-dihydro-1H-pyrazolo[4,3-c]pyridin-3-yl}amino)phenyl]sulfonyl }pyrrolidine-3-carboxylate;

tert-butyl(3S)-1-{[4-({1-[(1S)-2-cyano-1-cyclopropylethyl]-4-oxo-4,5-dihydro-1H-pyrazolo[4,3-c]pyridin-3yl }amino)phenyl]sulfonyl }pyrrolidine-3-carboxylate;

(3S)-3-cyclopropyl-3-[3-({4-[(2,2-dimethylpyrrolidin-1-yl)sulfonyl]phenyl}amino)-4-oxo-4,5-dihydro-1H-pyrazolo[4,3-c]pyridin-1-yl]propanenitrile;

(3S)-3-cyclopropyl-3-{3-[(4-{[(2R)-2-methylpyrrolidin-1-yl]sulfonyl}phenyl)amino]-4-oxo-4,5-dihydro-1H-pyrazolo[4,3-c]pyridin-1-yl }propanenitrile;

(3S)-3-cyclopropyl-3-{3-[(4-{[(2S)-2-methylpyrrolidin-1-yl]sulfonyl}phenyl)amino]-4-oxo-4,5-dihydro-1H-pyrazolo[4,3-c]pyridin-1-yl}propanenitrile;

(3S)-3-(3-{[4-(azetidin-1-yl sulfonyl)phenyl]amino}-4-oxo-4,5-dihydro-1H-pyrazolo [4,3-c]pyridin-1-yl)-3-cyclopropylpropanenitrile;

(3S)-3-cyclopropyl-3-(3-{[4-(morpholin-4-yl sulfonyl)phenyl]amino}-4-oxo-4,5-dihydro-1H-pyrazolo[4,3-c]pyridin-1-yl)propanenitrile;

(3S)-3-cyclopropyl-3-[3-({4-[(3,3-dimethylazetidin-1-yl)sulfonyl]phenyl}amino)-4-oxo-4,5-dihydro-1H-pyrazolo[4,3-c]pyridin-1-yl]propanenitrile;

(3S)-3-cyclopropyl-3-[3-({4-[(3-methylazetidin-1-yl)sulfonyl]phenyl}amino)-4-oxo-4,5-dihydro-1H-pyrazolo[4,3-c]pyridin-1-yl]propanenitrile;

(3S)-3-cyclopropyl-3-[3-({4-[(2,2-dimethylazetidin-1-yl)sulfonyl]phenyl}amino)-4-oxo-4,5-dihydro-1H-pyrazolo[4,3-c]pyridin-1-yl]propanenitrile;

(3S)-3-cyclopropyl-3-[3-({4-[(3-hydroxy-3-methylazetidin-1-yl)sulfonyl]phenyl}amino)-4-oxo-4,5-dihydro-1H-pyrazolo[4,3-c]pyridin-1-yl]propanenitrile;

(3S)-3-cyclopropyl-3-[3-({4-[(3-hydroxyazetidin-1-yl)sulfonyl]phenyl}amino)-4-oxo-4,5-dihydro-1H-pyrazolo[4,3-c]pyridin-1-yl]propanenitrile;

(3S)-3-cyclopropyl-3-[3-({4-[(3,3-dimethylmorpholin-4-yl)sulfonyl]phenyl}amino)-4-oxo-4,5-dihydro-1H-pyrazolo[4,3-c]pyridin-1-yl]propanenitrile;

(3S)-3-cyclopropyl-3-[3-({4-[(2,2-dimethylmorpholin-4-yl)sulfonyl]phenyl}amino)-4-oxo-4,5-dihydro-1H-pyrazolo[4,3-c]pyridin-1-yl]propanenitrile;

(3S)-3-cyclopropyl-3-{3-[(4-[(3R)-3-methylmorpholin-4-yl]sulfonyl}phenyl)amino]-4-oxo-4,5-dihydro-1H-pyrazolo[4,3-c]pyridin-1-yl}propanenitrile;

(3S)-3-cyclopropyl-3-{3-[(4-{[(3S)-3-methylmorpholin-4-yl]sulfonyl}phenyl)amino]-4-oxo-4,5-dihydro-1H-pyrazolo[4,3-c]pyridin-1-yl}propanenitrile;

(3S)-3-cyclopropyl-3-{3-[(4-[(3R)-3-hydroxy-3-(trifluoromethyl)pyrrolidin-1-yl]sulfonyl}phenyl)amino]-4-oxo-4,5-dihydro-1H-pyrazolo[4,3-c]pyridin-1-yl}propanenitrile;

(3S)-3-cyclopropyl-3-{3-[(4-[(3S)-3-hydroxy-3-(trifluoromethyl)pyrrolidin-1-yl]sulfonyl}phenyl)amino]-4-oxo-4,5-dihydro-1H-pyrazolo[4,3-c]pyridin-1-yl}propanenitrile;

(3S)-3-cyclopropyl-3[3-({4-[(4aR,7aR)-hexahydrocyclopenta[b][1,4]oxazin-4(4aH)-ylsulfonyl]phenyl}amino)-4-oxo-4,5-dihydro-1H-pyrazolo[4,3-c]pyridin-1-yl]propanenitrile;

(3S)-3-cyclopropyl-3-[3-({4-[(4aS,7aS)-hexahydrocyclopenta[b][1,4]oxazin-4(4aH)-ylsulfonyl]phenyl}amino)-4-oxo-4,5-dihydro-1H-pyrazolo[4,3-c]pyridin-1-yl]propanenitrile;

(3S)-3-cyclopropyl-3-{3-[(4-{[(2S,6S)-2,6-dimethylmorpholin-4-yl]sulfonyl}phenyl)amino]-4-oxo-4,5-dihydro-1H-pyrazolo[4,3-c]pyridin-1-yl}propanenitrile;

(3S)-3-cyclopropyl-3-{3-[(4-{[(2R,6S)-2,6-dimethylmorpholin-4-yl]sulfonyl}phenyl)amino]-4-oxo-4,5-dihydro-1H-pyrazolo[4,3-c]pyridin-1-yl}propanenitrile;

(3S)-3-cyclopropyl-3-{3-[(4-[(2R)-2-methylmorpholin-4-yl]sulfonyl}phenyl)amino]-4-oxo-4,5-dihydro-1H-pyrazolo[4,3-c]pyridin-1-yl}propanenitrile;

(3S)-3-cyclopropyl-3-{3-[(4-[(2S)-2-methyl-morpholin-4-yl]sulfonyl}phenyl)amino]-4-oxo-4,5-dihydro-1H-pyrazolo[4,3-c]pyridin-1-yl}propanenitrile;

(3S)-3-cyclopropyl-3-{3-[(4-{[(2R)-2-methylazetidin-1-yl]sulfonyl}phenyl)amino]-4-oxo-4,5-dihydro-1H-pyrazolo[4,3-c]pyridin-1-yl}propanenitrile;

(3S)-3-cyclopropyl-3-{3-[(4-{[(2S)-2-methylazetidin-1-yl]sulfonyl}phenyl)amino]-4-oxo-4,5-dihydro-1H-pyrazolo[4,3-c]pyridin-1-yl}propanenitrile;

(3S)-3-cyclopropyl-3-[3-({4-[(3 -methoxyazetidin-1-yl)sulfonyl]phenyl}amino)-4-oxo-4,5-dihydro-1H-pyrazolo[4,3-c]pyridin-1-yl]propanenitrile;

(3S)-3-cyclopropyl-3-[3-({4-[(3-fluoroazetidin-1-yl)sulfonyl]phenyl}amino)-4-oxo-4,5-dihydro-1H-pyrazolo[4,3-c]pyridin-1-yl]propanenitrile;

(3S)-3-cyclopropyl-3-[3-({3-methyl-4-[(1R)-2,2,2-trifluoro-1-hydroxy-1-methylethyl]phenyl}amino)-4-oxo-4,5-dihydro-1H-pyrazolo[4,3-c]pyridin-1-yl]propanenitrile;

(3S)-3-cyclopropyl-3-[3-({3-methyl-4-[(1S)-2,2,2-trifluoro-1-hydroxy-1-methylethyl]phenyl}amino)-4-oxo-4,5-dihydro-1H-pyrazolo[4,3-c]pyridin-1-yl]propanenitrile (3S)-3-cyclopropyl-3-[3-({4-[(1R)-1-hydroxy-1-(trifluoromethyl)propyl]phenyl}amino)-4-oxo-4,5-dihydro-1H-pyrazolo[4,3 -c]pyridin-1-yl]propanenitrile;

(3S)-3-cyclopropyl-3-[3-({4-[(1S)-1-hydroxy-1-(trifluoromethyl)propyl]phenyl}amino)-4-oxo-4,5-dihydro-1H-pyrazolo[4,3-c]pyridin-1-yl]propanenitrile;

(S)-tert-butyl2-(4((1-(2-cyano-1-cyclopropylethyl)-4-oxo-4,5-dihydro 1H-pyrazolo[4, -c]pyridin-3-yl)amino)-N-methylphenylsulfonamido)-2-methylpropanoate;

(S)-3-cyclopropyl-3-(4-oxo-3-((1-oxo-2-(2,2,2-trifluoroethyl)isoindolin-5-yl)amino)-4,5-dihydro-1H-pyrazolo[4,3-c]pyridin-1-yl)propanenitrile;

(S)-ethyl2-(4-((1-(2-cyano-1-cyclopropyl ethyl)-4-oxo-4,5-dihydro-1H-pyrazolo[4,3-c]pyridin-3-yl)amino)-N-methylphenylsulfonamido)-2-methylpropanoate;

(S)-tert-butyl2-(5-((1-(2-cyano-1-cyclopropylethyl)-4-oxo-4,5-dihydro-1H-pyrazolo[4,3-c]pyridin-3-yl)amino)-1-oxoisoindolin-2-yl)-2-methylpropanoate;

4-({1-[(1S)-2-cyano-1-cyclopropylethyl]-4-oxo-4,5-dihydro-1H-pyrazolo[4,3-c]pyridin-3-yl}amino)-N,N,2-trimethylbenzenesulfonamide;

(3S)-3-cyclopropyl-3-(3-{[3-methyl-4-(pyrrolidin-1-ylsulfonyl)phenyl]amino}-4-oxo-4,5-dihydro-1H-pyrazolo[4,3-c]pyridin-1-yl)propanenitrile;

(3S)-3-cyclopropyl-3-(3-{[4-(5,5-dimethyl-3-oxo-2-oxabicyclo [2.2.2]oct-1-yl)phenyl]amino}-4-oxo-4,5-dihydro-1H-pyrazolo[4,3-c]pyridin-1-yl)propanenitrile;

(3S)-3-cyclopropyl-3-(3-{[4(5,5-dimethyl-3-oxo-2-oxabicyclo [2.2.2]oct-1-yl)phenyl]amino}-4-oxo-4,5-dihydro-1H-pyrazolo[4,3 -c]pyridin-1-yl)propanenitrile;

(3S)-3-cyclopropyl-3-[3-({4-[(1R)-1-(dimethylamino)-2,2,2-trifluoroethyl]-3-methylphenyl}amino)-4-oxo-4,5-dihydro-1H-pyrazolo[4,3-c]pyridin-1-yl]propanenitrile;

(3S)-3-cyclopropyl-3-[3-({4-[(1S)-1-(dimethylamino)-2,2,2-trifluoroethyl]-3-methylphenyl}amino)-4-oxo-4,5-dihydro-1H-pyrazolo[4,3-c]pyridin-1-yl]propanenitrile;

(3S)-3 -cyclopropyl-3-[3-({4-[(1-methylcyclopropyl)sulfonyl]phenyl}amino)-4-oxo-4,5-dihydro-1H-pyrazolo[4,3-c]pyridin-1-yl]propanenitrile;

(3S)-3-({4-[(1R)-1-(tert-butylamino)-2,2,2-trifluoroethyl]phenyl}amino)-4-oxo-4,5-dihydro-1H-pyrazolo[4,3-c]pyridin-1-yl]-3-cyclopropylpropanenitrile;

(3S)-3-({4-[(1S)-1-(tert-butylamino)-2,2,2-trifluoroethyl]phenyl}amino)-4-oxo-4,5-dihydro-1H-pyrazolo[4,3-c]pyridin-1-yl]-3-cyclopropylpropanenitrile);

(3S)-3-cyclopropyl-3-[4-oxo-3-({4-[(1R)-2,2,2-trifluoro-1-pyrrolidin-1-ylethyl]phenyl}amino)-4,5-dihydro-1H-pyrazolo [4,3-c]pyridin-1-yl]propanenitrile;

(3S)-3-cyclopropyl-3-[4-oxo-3-({4-[(1S)-2,2,2-trifluoro-1-pyrrolidin-1-ylethyl]phenyl}amino)-4,5-dihydro-1H-pyrazolo [4,3-c]pyridin-1-yl]propanenitrile;

(3S)-3-cyclopropyl-3-{4-oxo-3-[(4-{(1R)-2,2,2-trifluoro-1-[(1-methylethyl)amino]ethyl}phenyl)amino]-4,5-dihydro-1H-pyrazolo[4,3-c]pyridin-1-yl }propanenitrile;

(3S)-3-cyclopropyl-3-{4-oxo-3-[(4-{(1S)-2,2,2-trifluoro-1 -[(1-methylethyl)amino]ethyl}phenyl)amino]-4,5-dihydro-1H-pyrazolo[4,3-c]pyridin-1-yl}propanenitrile;

(3S)-3-({4-[(1R)-1-azetidin-1-yl-2,2,2-trifluoroethyl]phenyl}amino)-4-oxo-4,5-dihydro-1H-pyrazolo[4,3-c]pyridin-1-yl]-3-cyclopropylpropanenitrile;

(3S)-3-[3-({4-(1S)-1-azetidin-1-yl-2,2,2-trifluoroethyl]phenyl}amino)-4-oxo-4,5-dihydro-1H-pyrazolo[4,3-c]pyridin-1-yl]-3-cyclopropylpropanenitrile;

(3S)-3-cyclopropyl-3-[3-({4-[(1R)-1-(ethylamino)-2,2,2-trifluoroethyl]phenyl}amino)-4-oxo-4,5-dihydro-1H-pyrazolo[4,3-c]pyridin-1-yl]propanenitrile;

(3S)-3 -cyclopropyl-3-[3-({4-[(1S)-1-(ethylamino)-2,2,2-trifluoroethyl]phenyl}amino)-4-oxo-4,5-dihydro-1H-pyrazolo[4,3-c]pyridin-1-yl]propanenitrile;

(3S)-tert-butyl 4-(5-((1-(2-cyano-1-cyclopropylethyl)-4-oxo-4,5-dihydro-1H-pyrazolo[4,3-c]pyridin-3-yl) amino)-1 -oxoisoindolin-2-yl)cyclohexane-carboxylate;

(3S)-tert-butyl 4-(5-((1-(2-cyano-1-cyclopropylethyl)-4-oxo-4,5-dihydro-1H-pyrazolo[4,3-c]pyridin-3-yl) amino)-1-oxoisoindolin-2-yl)cyclohexane-carboxylate;

(S)-2-(5-((1-(2-cyano-1-cyclopropylethyl)-4-oxo-4,5-dihydro-1H-pyrazolo[4,3-c]pyridin-3-yl)amino)-1-oxoisoindolin-2-yl)-2-methylpropanoic acid;

ethyl 3-(4-((1-(S)-2-cyano-1-cyclopropylethyl)-4-oxo-4, 5-dihydro-1H-pyrazolo[4,3-c]pyridin-3-yl)amino)phenyl)-4,4,4-trifluoro-3-hydroxy-2,2-dimethylbutanoate;

ethyl 3-(4-((1-((S)-2-cyano-1-cyclopropylethyl)-4-oxo-4, 5-dihydro-1H-pyrazolo[4,3-c]pyridin-3-yl)amino)phenyl)-4,4,4-trifluoro-3-hydroxy-2,2-dimethylbutanoate;

isopropyl3-(4-((1-((S)-2-cyano-1-cyclopropylethyl)-4-oxo-4,5-dihydro-1H-pyrazolo[4,3-c]pyridin-3-yl) amino)phenyl)-4,4,4-trifluoro-3-hydroxy-2,2-dimethylbutanoate;

isopropyl3-(4-((1-((S)-2-cyano-1-cyclopropylethyl)-4-oxo-4,5-dihydro-1H-pyrazolo[4,3-c]pyridin-3-yl) amino)phenyl)-4,4,4-trifluoro-3-hydroxy-2,2-dimethylbutanoate;

(S)-3-cyclopropyl-3-(3-(((S)-1-hydroxy-2,2-dimethyl-1-(trifluoromethyl)-2,3-dihydro-1H-inden-5-yl)amino)-4-oxo-4,5-dihydro-1H-pyrazolo[4,3-c]pyridin-1-yl)propanenitrile;

(S)-3-cyclopropyl-3-(3-(((R)-1-hydroxy-2,2-dimethyl-1-(trifluoromethyl)-2,3-dihydro-1H-inden-5-yl)amino)-4-oxo-4,5-dihydro-1H-pyrazolo[4,3-c]pyridin-1-yl)propanenitrile;

(S)-3-cyclopropyl-3-(4-oxo-3((4-(1-(trifluoromethyl)cyclopropyl)phenyl)amino)-4,5-dihydro-1H-pyrazolo[4, 3-c]pyridin-1-yl)propanenitrile;

(S)-3-cyclopropyl-3-(3-((4-(1-(2-methoxyethyl)-1H-pyrazol-3 -yl)phenyl)amino)-4-oxo-4,5-dihydro-1H-pyrazolo[4,3-c]pyridin-1yl)propanenitrile;

(S)-3-(3-((3-chloro-4-(1-methyl-1H-pyrazol-3-yl)phenyl) amino)-4-oxo-4,5-dihydro-1H-pyrazolo[4,3-c]pyridin-1-yl)-3-cyclopropylpropanenitrile;

(S)-3-(3-((3-chloro-4-(1-(2-cyanoethyl)-1H-pyrazol-3-yl) phenyl)amino)-4-oxo-4,5-dihydro-1H-pyrazolo[4,3-c] pyridin-1-yl)-3-cyclopropylpropanenitrile;

(S)-ethyl 1-(4-((1-(2-cyano-1-cyclopropylethyl)-4-oxo-4, 5-dihydro-1H-pyrazolo[4,3-c]pyridin-3-yl)amino)-2-methylphenyl)-1H-pyrazole-4-carboxylate;

(S)-isopropyl 6-((1-(2-cyano-1-cyclopropylethyl)-4-oxo-4,5-dihydro-1H-pyrazolo[4,3-c]pyridin-3-yl)amino) quinoline-2-carboxylate;

(S)-3-cyclopropyl-3-(3((2-methylbenzo[d]thiazol-6-yl) amino)-4-oxo-4,5-dihydro-1H-pyrazolo[4,3-c]pyridin-1-yl)propanenitrile;

(S)-3-cyclopropyl-3-(3-((4-(oxazol-2-yl)phenyl)amino)-4-oxo-4,5-dihydro-1H-pyrazolo[4,3-c]pyridin-1-yl) propanenitrile;

(S)-3-cyclopropyl-3-(3-((4-(oxazol-5-yl)phenyl)amino)-4-oxo-4,5-dihydro-1H-pyrazolo[4,3-c]pyridin-1-yl) propanenitrile;

(S)-3-cyclopropyl-3-(3-((3,3-dimethyl-2-oxoindolin-6-yl)amino)-4-oxo-4,5-dihydro-1H-pyrazolo[4,3-c]pyridin-1-yl)propanenitrile;

(S)-3-cyclopropyl-3-(3-((4-(1,1-dioxidothiomorpholine-4-carbonyl)-3-methylphenyl)amino)-4-oxo-4,5-dihydro-1H-pyrazolo[4,3-c]pyridin-1-yl)propanenitrile;

(S)-4-((1-(2-cyano-1-cyclopropylethyl)-4-oxo-4,5-dihydro-1H-pyrazolo[4,3-c]pyridin-3-yl)amino)benzoic acid;

(S)-4-((1-(2-cyano-1-cyclopropylethyl)-4-oxo-4,5-dihydro-1H-pyrazolo[4,3-c]pyridin-3-yl)amino)-N-(methylsulfonyl)benzamide;

(S)-3-cyclopropyl-3-(3-((2-morpholinoquinolin-6-yl) amino)-4-oxo-4,5-dihydro-1H-pyrazolo[4,3-c]pyridin-1-yl)propanenitrile;

(S)-3-cyclopropyl-3-(3-((2-((2R,5S)-2,5-dimethylmorpholino)quinolin-6-yl)amino)-4-oxo-4,5-dihydro-1H-pyrazolo[4,3-c]pyridin-1-yl)propanenitrile;

(S)-3-cyclopropyl-3-(3-((2-((2S,5S)-2,5-dimethylmorpholino)quinolin-6-yl)amino)-4-oxo-4,5-dihydro-1H-pyrazolo[4,3-c]pyridin-1-yl)propanenitrile;

(S)-3-cyclopropyl-3-(3-((2-(2R,5R)-2,5-dimethylmorpholino)quinolin-6-yl)amino)-4-oxo-4,5-dihydro-1H-pyrazolo[4,3-c]pyridin-1-yl)propanenitrile;

(S)-3-cyclopropyl-3-(4-oxo-3-((4-((S or R)-1,1,1-trifluoro-2-methoxypropan-2-yl)phenyl)amino)-4,5-dihydro-1H-pyrazolo[4,3-c]pyridin-1yl)propanenitrile;

(S)-3-cyclopropyl-3-(3-((4-((S)-3-ethylmorpholine-4-carbonyl)-3-methylphenyl)amino)-4-oxo-4,5-dihydro-1H-pyrazolo[4,3-c]pyridin-1-yl)propanenitrile;

(S)-3-cyclopropyl-3-(3-((4-((R)-3-ethylmorpholine-4-carbonyl)-3-methylphenyl)amino)-4-oxo-4,5-dihydro-1H-pyrazolo[4,3-c]pyridin-1-yl)propanenitrile;

(S)-3-cyclopropyl-3-(3-((4-((S)-3-isopropylmorpholine-4-carbonyl)-3-methylphenyl)amino)-4-oxo-4,5-dihydro-1H-pyrazolo[4,3-c]pyridin-1-yl)propanenitrile;

(S)-3-cyclopropyl-3-(3-((4-((R)-3-isopropylmorpholine-4-carbonyl)-3-methylphenyl)amino)-4-oxo-4,5-dihydro-1H-pyrazolo[4,3-c]pyridin-1-yl)propanenitrile;

(S)-3-cyclopropyl-3-(3-((3-methyl-4-((S)-2-methyl-1-(2H-1,2,3-triazol-2-yl)propyl)phenyl)amino)-4-oxo-4, 5-dihydro-1H-pyrazolo [4,3-c]pyridin-1-yl)propanenitrile;

(S)-3-cyclopropyl-3-(3-((3-methyl-4-((R)-2-methyl-1-(2H-1,2,3-triazol-2-yl)propyl)phenyl)amino)-4-oxo-4, 5-dihydro-1H-pyrazolo [4,3-c]pyridin-1-yl)propanenitrile;

(S)-3-(3-((2-benzyl-1,1-dioxido-2,3-dihydrobenzo[d]isothiazol-5-yl)amino)-4-oxo-4,5-dihydro-1H-pyrazolo[4,3-c]pyridin-1-yl)-3-cyclopropylpropanenitrile;

(S)-3-Cyclopropyl-3-(3-((3-methyl-4-((S)-2-methyl-1-(1H-1,2,3-triazol-1-yl)propyl)phenyl)amino)-4-oxo-4,5-dihydro-1H-pyrazolo[4,3-c]pyridin-1-yl)propanenitrile;

(S)-3-Cyclopropyl-3-(3-((3-methyl-4-((R)-2-methyl-1-(1H-1,2,3-triazol-1-yl)propyl)phenyl)amino)-4-oxo-4,5-dihydro-1H-pyrazolo[4,3-c]pyridin-1-yl)propanenitrile;

(S)-3-cyclopropyl-3-(3-((3-methyl-4-((R)-2,2,2-trifluoro-1-hydroxyethyl)phenyl)amino)-4-oxo-4,5-dihydro-1H-pyrazolo[4,3-c]pyridin-1-yl)propanenitrile;

(S)-3-cyclopropyl-3-(3-((3-methyl-4-((S)-2,2,2-trifluoro-1-hydroxyethyl)phenyl)amino)-4-oxo-4,5-dihydro-1H-pyrazolo[4,3-c]pyridin-1-yl)propanenitrile;

(S)-3-(3-((4-((S)-cyclopentyl(2H-1,2,3-triazol-2-yl)methyl)-3-methylphenyl)amino)-4-oxo-4,5-dihydro-1H-pyrazolo[4,3-c]pyridin-1-yl)-3-cyclopropylpropanenitrile;

(S)-3-(3-((4-((S)-cyclopentyl (2H-1,2,3-triazol-2-yl)methyl)-3-methylphenyl)amino)-4-oxo-4,5-dihydro-1H-pyrazolo[4,3-c]pyridin-1-yl)-3-cyclopropyl-propanenitrile;

(S)-3-(3-((4-((R)-1-amino-2,2,2-trifluoroethyl)-3-methylphenyl)amino)-4-oxo-4,5-dihydro-1H-pyrazolo[4,3-c]pyridin-1-yl)-3-cyclopropyl-propanenitrile;

(S)-3-(3-((4-((S)-1-amino-2,2,2-trifluoroethyl)-3-methylphenyl)amino)-4-oxo-4,5-dihydro-1H-pyrazolo[4,3-c]pyridin-1-yl)-3-cyclopropyl-propanenitrile;

(S)-3-(3((2-cyclohexyl-1,1-dioxido-2,3-dihydrobenzo[d]isothiazol-5-yl)amino)-4-oxo-4,5-dihydro-1H-pyrazolo[4,3-c]pyridin-1-yl)-3-cyclopropylpropanenitrile;

(S)-3-cyclopropyl-3-(3-((2-(1-methylcyclohexyl)-1,1-dioxido-2,3-dihydrobenzo[d]isothiazol-5-yl)amino)-4-oxo-4,5-dihydro-1H-pyrazolo[4,3-c]pyridin-1-yl)propanenitrile;

(S)-3-cyclopropyl-3-(3-(((S)-3-hydroxy-2,2-dimethyl-1,1-dioxido-2,3-dihydrobenzo[b]thiophen-5-yl)amino)-4-oxo-4,5-dihydro-1H-pyrazolo[4,3-c]pyridin-1-yl)propanenitrile;

(S)-3-cyclopropyl-3-(3-(((R)-3-hydroxy-2,2-dimethyl-1,1-dioxido-2,3-dihydrobenzo[b]thiophen-5-yl)amino)-4-oxo-4,5-dihydro-1H-pyrazolo[4,3-c]pyridin-1-yl)propanenitrile;

(S)-3-cyclopropyl-3-(3-(((S)-3-hydroxy-1,1-dioxido-3H-spiro[benzo[b]thiophene-2,1'-cyclohexan]-5-yl)amino)-4-oxo-4,5-dihydro-1H-pyrazolo[4,3-c]pyridin-1-yl)propanenitrile;

(S)-3-cyclopropyl-3-(3-(((S)-3-hydroxy-1,1-dioxido-3H-spiro[benzo[b]thiophene-2,1'-cyclohexan]-5-yl)amino)-4-oxo-4,5-dihydro-1H-pyrazolo[4,3-c]pyridin-1-yl)propanenitrile;

(S)-3-cyclopropyl-3-(4-oxo-3-((44(R)-2-(trifluoromethyl)pyrrolidin-2-yl)phenyl)amino)-4,5-dihydro-1H-pyrazolo[4,3-c]pyridin-1-yl)propanenitrile;

(S)-3-cyclopropyl-3-(4-oxo-3-((44(S)-2-(trifluoromethyl)pyrrolidin-2-yl)phenyl)amino)-4,5-dihydro-1H-pyrazolo[4,3-c]pyridin-1-yl)propanenitrile;

(S)-3-(3-((4-(2-azaspiro[3.3] heptan-2-ylsulfonyl)-3-methylphenyl)amino)-4-oxo-4,5-dihydro-1H-pyrazolo[4,3-c]pyridin-1-yl)-3-cyclopropylpropanenitrile;

(S)-3-cyclopropyl-3-(3-((3-methyl-4-(2-azaspiro[3.3] heptane-2-carbonyl)phenyl)amino)-4-oxo-4,5-dihydro-1H-pyrazolo[4,3-c]pyridin-1-yl)propanenitrile;

(S)-3-cyclopropyl-3-(3-(((1,1-dioxido-3H-spiro[benzo[b]thiophene-2,1'-cyclopentan]-5-yl)amino)-4-oxo-4,5-dihydro-1H-pyrazolo[4,3-c]pyridin-1-yl)propanenitrile;

(S)-3-cyclopropyl-3-(3-(((1,1-dioxido-3H-spiro[benzo[b]thiophene-2,1'-cyclohexan]-5-yl)amino)-4-oxo-4,5-dihydro-1H-pyrazolo[4,3-c]pyridin-1-yl)propanenitrile;

(S)-3-cyclopropyl-3-(3-((2,2-dimethyl-1,1-dioxido-2,3-dihydrobenzo[b]thiophen-5-yl)amino)-4-oxo-4,5-dihydro-1H-pyrazolo[4,3-c]pyridin-1-yl)propanenitrile;

(S)-3 -cyclopropyl-3 -(3-(((2R,3S)-3-hydroxy-2-methyl-1,1-dioxido-2,3-dihydrobenzo[b]thiophen-5-yl)amino)-4-oxo-4,5-dihydro-1H-pyrazolo[4,3-c]pyridin-1-yl)propanenitrile;

(S)-3-cyclopropyl-3-(3-(((2S,3R)-3-hydroxy-2-methyl-1,1-dioxido-2,3-dihydrobenzo[b]thiophen-5-yl)amino)-4-oxo-4,5-dihydro-1H-pyrazolo[4,3-c]pyridin-1-yl)propanenitrile;

(S)-3-cyclopropyl-3-(3-(((2R,3R)-3-hydroxy-2-methyl-1,1-dioxido-2,3-dihydrobenzo[b]thiophen-5-yl)amino)-4-oxo-4,5-dihydro-1H-pyrazolo[4,3-c]pyridin-1-yl)propanenitrile;

(S)-3 -cyclopropyl-3-(3-(((2S,3S)-3-hydroxy-2-methyl-1,1-dioxido-2,3-dihydrobenzo[b]thiophen-5-yl)amino)-4-oxo-4,5-dihydro-1H-pyrazolo[4,3-c]pyridin-1-yl)propanenitrile;

(3S)-3-cyclopropyl-3-(3-((2-methyl-1, 1-dioxido-2,3-dihydrobenzo[b]thiophen-5-yl)amino)-4-oxo-4,5-dihydro-1H-pyrazolo[4,3-c]pyridin-1-yl)propanenitrile;

(S)-3-cyclopropyl-3-(3-((3-methyl-4-((R)-2-(trifluoromethyl)pyrrolidin-2-yl)phenyl)amino)-4-oxo-4,5-dihydro-1H-pyrazolo[4,3-c]pyridin-1-yl)propanenitrile;

(S)-3-cyclopropyl-3-(3-((3-methyl-4-((S)-2-(trifluoromethyl)pyrrolidin-2-yl)phenyl)amino)-4-oxo-4,5-dihydro-1H-pyrazolo[4,3-c]pyridin-1-yl)propanenitrile;

(S)-3-cyclopropyl-3-(4-oxo-3-((1-oxo-2-(1-(trifluoromethyl)cyclohexyl)isoindolin-5-yl)amino)-4,5-dihydro-1H-pyrazolo[4,3-c]pyridin-1-yl)propanenitrile;

(S)-3-cyclopropyl-3-(3-((2-(4-methyltetrahydro-2H-pyran-4-yl)-1,1-dioxido-2,3-dihydrobenzo[d]isothiazol-5-yl)amino)-4-oxo-4,5-dihydro-1H-pyrazolo[4,3-c]pyridin-1-yl)propanenitrile;

(S)-3-cyclopropyl-3-(3-((4-((R)-1 -methyl-2-(trifluoromethyl)pyrrolidin-2-yl)phenyl)amino)-4-oxo-4,5-dihydro-1H-pyrazolo[4,3-c]pyridin-1-yl)propanenitrile;

(S)-3-cyclopropyl-3-(3 -((4-((R)-1-methyl-2-(trifluoromethyl)pyrrolidin-2-yl)phenyl)amino)-4-oxo-4,5-dihydro-1H-pyrazolo[4,3 c]pyridin-1-yl)propanenitrile;

(S)-4-((1-(2-cyano-1-cyclopropylethyl)-4-oxo-4,5-dihydro-1H-pyrazolo[4,3-c]pyridin-3-yl)amino)-N,2,1-dimethyl-N-(tetrahydro-2H-pyran-4-yl)benzamide;

(S)-3-cyclopropyl-3-(3-((3-fluoro-4-((R)-2,2,2-trifluoro-1-(isopropylamino)ethyl)phenyl)amino)-4-oxo-4,5-dihydro-1H-pyrazolo[4,3-c]pyridin-1-yl)propanenitrile;

(S)-3-cyclopropyl-3-(3-((3-fluoro-4-((S)-2,2,2-trifluoro-1-(isopropylamino)ethyl)phenyl)amino)-4-oxo-4,5-dihydro-1H-pyrazolo[4,3-c]pyridin-1-yl)propanenitrile;

(S)-3-cyclopropyl-3-(3-((4-((R)-1-(ethylamino)-2,2,2-trifluoroethyl)-3-fluorophenyl)amino)-4-oxo-4,5-dihydro-1H-pyrazolo[4,3-c]pyridin-1-yl)propanenitrile;

(S)-3-cyclopropyl-3-(3-((4-((S)-1 -(ethylamino)-2,2,2-trifluoroethyl)-3-fluorophenyl)amino)-4-oxo-4,5-dihydro-1H-pyrazolo[4,3-c]pyridin-1-yl)propanenitrile;

(S)-3-(3-((4-((R)-1 -(tert-butylamino)-2,2,2-trifluoroethyl)-3-fluorophenyl)amino)-4-oxo-4,5-dihydro-1H-pyrazolo[4,3-c]pyridin-1-yl)-3 -cyclopropyl-propanenitrile;

(S)-3-(3-((4-((S)-1-(tert-butylamino)-2,2,2-trifluoro-ethyl)-3-fluorophenyl)amino)-4-oxo-4,5-dihydri-1H-pyrazolo[4,3 -c]pyridin-1 -yl)-3 -cyclopropyl-propanenitrile;

(S)-3-cyclopropyl-3-(4-oxo-3-((4((S)-2-(trifluoromethyl) tetrahydrofuran-2-yl)phenyl)amino)-4,5-dihydro-1H-pyrazolo[4,3-c]pyridin-1-yl)propanenitrile;

(S)-3-cyclopropyl-3-(4-oxo-3-((4-((R)-2-(trifluoromethyl)tetrahydrofuran-2-yl)phenyl)amino)-4,5-dihydro-1H-pyrazolo[4,3-c]pyridin-1-yl)propanenitrile;

(S)-3-cyclopropyl-3-(3-(((R)-2-hydroxy-2-(trifluoromethyl)-2,3-dihydro-1H-inden-5-yl)amino)-4-oxo-4,5-dihydro-1H-pyrazolo[4,3-c]pyridin-1-yl)propanenitrile;

(S)-3-cyclopropyl-3-(3-(((S)-2-hydroxy-2-(trifluoromethyl)-2,3-dihydro-1H-inden-5-yl)amino)-4-oxo-4,5-dihydro-1H-pyrazolo[4,3-c]pyridin-1-yl)propanenitrile;

(S)-3-cyclopropyl-3-(3-((3-fluoro-4-((R)-2,2,2-trifluoro-1-hydroxyethyl)phenyl)amino)-4-oxo-4,5-dihydro-1H-pyrazolo[4,3-c]pyridin-1-yl)propanenitrile;

(S)-3-cyclopropyl-3-(3-((3-fluoro-4-((S)-2,2,2-trifluoro-1-hydroxyethyl)phenyl)amino)-4-oxo-4,5-dihydro-1H-pyrazolo[4,3-c]pyridin-1-yl)propanenitrile;

(S)-3-(3-((3-chloro-4-((R)-2,2,2-trifluoro-1-hydroxyethyl)phenyl)amino)-4-oxo-4,5-dihydro-1H-pyrazolo[4,3-c]pyridin-1-yl)-3 -cyclopropylpropanenitrile;

(S)-3-(3-((3-chloro-4-((S)-2,2,2-trifluoro-1-hydroxyethyl)phenyl)amino)-4-oxo-4,5-dihydro-1H-pyrazolo[4,3-c]pyridin-1-yl)-3 -cyclopropylpropanenitrile;

(S)-3-cyclopropyl-3-(3-(((R)-2-hydroxy-2-methyl-2,3-dihydro-1H-inden-5-yl)amino)-4-oxo-4,5-dihydro-1H-pyrazolo[4,3-c]pyridin-1-yl)propanenitrile;

(S)-3-cyclopropyl-3-(3-(((S)-2-hydroxy-2-methyl-2,3-dihydro-1H-inden-5-yl)amino)-4-oxo-4,5-dihydro-1H-pyrazolo[4,3-c]pyridin-1-yl)propanenitrile;

(S)-3-(3-((4-((R)-1-(tert-butylamino)-2,2,2-trifluoro-ethyl)-3-chlorophenyl)amino)-4-oxo-4,5-dihydro-1H-pyrazolo[4,3-c]pyridin-1-yl)-3-cyclopropyl-propanenitrile;

(S)-3-(3-((4-((S)-1-(tert-butylamino)-2,2,2-trifluoro-ethyl)-3-chlorophenyl)amino)-4-oxo-4,5-dihydro-1H-pyrazolo[4,3-c]pyridin-1-yl)-3-cyclopropyl-propanenitrile;

(S)-3-cyclopropyl-3-(4-oxo-3-((4-((R)-2-(trifluoromethyl)piperidin-2-yl)phenyl)amino)-4,5-dihydro-1H-pyrazolo[4,3-c]pyridin-1-yl)propanenitrile;

(S)-3-cyclopropyl-3-(4-oxo-3-((4-((S)-2-(trifluoromethyl)piperidin-2-yl)phenyl)amino)-4,5-dihydro-1H-pyrazolo[4,3-c]pyridin-1-yl)propanenitrile;

(R)-methyl 2-(4-((1-((S)-2-cyano-1-cyclopropylethyl)-4-oxo-4,5-dihydro-1H-pyrazolo[4,3-c]pyridin-3-yl)amino)phenyl)-2-(trifluoromethyl)pyrrolidine-1-carboxylate;

(S)-methyl 2-(4-(((14(S)-2-cyano-1-cyclopropylethyl)-4-oxo-4,5-dihydro-1H-pyrazolo[4,3-c]pyridin-3-yl)amino)phenyl)-2-(trifluoromethyl)pyrrolidine-1-carboxylate;

(S)-3-cyclopropyl-3-(3-((2-(4,4-difluoro-1-methylcyclohexyl)-1,1-dioxido-2,3-dihydrobenzo[d]isothiazol-5-yl)amino)-4-oxo-4,5-dihydro-1H-pyrazolo[4,3-c]pyridin-1-yl)propanenitrile;

(S)-3-cyclopropyl-3-(4-oxo-3-((4-((S)-2,2,2-trifluoro-1-hydroxy-1-(pyridin-2-yl)ethyl)phenyl)amino)-4,5-dihydro-1H-pyrazolo[4,3-c]pyridin-1-yl)propanenitrile;

(S)-3-cyclopropyl-3-(4-oxo-3-((4-((R)-2,2,2-trifluoro-1-hydroxy-1-(pyridin-2-yl)ethyl)phenyl)amino)-4,5 -dihydro-1H-pyrazolo[4,3-c]pyridin-1-yl)propanenitrile;

(S)-3-cyclopropyl-3-(4-oxo-3-((4-((S)-2,2,2-trifluoro-1-hydroxy-1-(pyridin-4-yl)ethyl)phenyl)amino)-4,5-dihydro-1H-pyrazolo[4,3-c]pyridin-1-yl)propanenitrile;

(S)-3-cyclopropyl-3-(4-oxo-3-((4-((R)-2,2,2-trifluoro-1-hydroxy-1-(pyridin-4-yl)ethyl)phenyl)amino)-4,5-dihydro-1H-pyrazolo[4,3-c]pyridin-1-yl)propanenitrile;

(S)-3-cyclopropyl-3-(4-oxo-3-((4-((R)-2,2,2-trifluoro-1-thiomorpholinoethyl)phenyl)amino)-4,5-dihydro-1H-pyrazolo[4,3-c]pyridin-1-yl)propanenitrile;

(S)-3-cyclopropyl-3-(4-oxo-3-((4-((S)-2,2,2-trifluoro-1-thiomorpholinoethyl)phenyl)amino)-4,5-dihydro-1H-pyrazolo[4,3-c]pyridin-1-yl)propanenitrile;

(S) -4-((1-(2-cyano-1-cyclopropylethyl)-4-oxo-4,5-dihydro-1H-pyrazolo[4,3-c]pyridin-3-yl)amino)-N,2-dimethyl-N-(2,2,2-trifluoroethyl)benzamide;

(S)-4-((1-(2-cyano-1-cyclopropylethyl)-4-oxo-4,5-dihydro-1H-pyrazolo[4,3-c]pyridin-3-yl)amino)-N-ethyl-2-methyl-N-(2,2,2-trifluoroethyl)benzamide;

(S)-4-((1-(2-cyano-1-cyclopropylethyl)-4-oxo-4,5-dihydro-1H-pyrazolo[4,3-c]pyridin-3-yl)amino)-N-(2-(dimethylamino)ethyl)-2-methyl-N-(2,2,2-trifluoroethyl)benzamide;

(S)-3-cyclopropyl-3-(3-((3-methyl-4-(thiomorpholine-4-carbonyl)phenyl)amino)-4-oxo-4,5-dihydro-1H-pyrazolo[4,3-c]pyridin-1-yl)propanenitrile;

(S)-3-cyclopropyl-3-(3-((3-methyl-4-(4-methylpiperazine-1-carbonyl)phenyl)amino)-4-oxo-4,5-dihydro-1H-pyrazolo[4,3-c]pyridin-1-yl)propanenitrile;

(S)-3-cyclopropyl-3-(3-((3-methyl-4-((S)-2-(trifluoromethyl)pyrrolidine-1-carbonyl)phenyl)amino)-4-oxo-4, 5-dihydro-1H-pyrazolo [4,3-c]pyridin-1-yl)propanenitrile;

(S)-4-((1-(2-cyano-1-cyclopropylethyl)-4-oxo-4,5-dihydro-1H-pyrazolo[4,3-c]pyridin-3-yl)amino)-N,2-dimethyl-N-(1-methylpiperidin-4-yl)benzamide;

(S)-4-((1-(2-cyano-1-cyclopropylethyl)-4-oxo-4,5-dihydro-1H-pyrazolo[4,3-c]pyridin-3-yl)amino)-N-ethyl-N,2-dimethylbenzamide;

(S)-3-cyclopropyl-3-(3-((3-methyl-4-(morpholine-4-carbonyl)phenyl)amino)-4-oxo-4,5-dihydro-1H-pyrazolo[4,3-c]pyridin-1-yl)propanenitrile;

(S)-3-cyclopropyl-3-(3-((4-(3,3-dimethylpyrrolidine-1-carbonyl)-3-methylphenyl)amino)-4-oxo-4,5-dihydro-1H-pyrazolo[4,3-c]pyridin-1-yl)propanenitrile;

(S)-3-cyclopropyl-3-(3-((4-(3,3-dimethylazetidine-1-carbonyl)-3-methylphenyl)amino)-4-oxo-4,5-dihydro-1H-pyrazolo[4,3-c]pyridin-1-yl)propanenitrile;

(S)-3-cyclopropyl-3-(3-((4-(2,2-dimethylmorpholine-4-carbonyl)-3-methylphenyl)amino)-4-oxo-4,5-dihydro-1H-pyrazolo[4,3-c]pyridin-1-yl)propanenitrile;

(S)-3-cyclopropyl-3-(3-((4-((2R,5R)-2,5-dimethylpyrrolidine-1-carbonyl)-3-methylphenyl)amino)-4-oxo-4,5-dihydro-1H-pyrazolo[4,3-c]pyridin-1-yl)propanenitrile;

(S)-3-cyclopropyl-3-(3-((4-((R)-3-fluoropyrrolidine-1-carbonyl)-3-methylphenyl)amino)-4-oxo-4,5-dihydro-1H-pyrazolo[4,3-c]pyridin-1-yl)propanenitrile;

(S)-3-cyclopropyl-3-(3-((4-((S)-3-fluoropyrrolidine-1-carbonyl)-3-methylphenyl)amino)-4-oxo-4,5-dihydro-1H-pyrazolo[4,3-c]pyridin-1-yl)propanenitrile;

(S)-3-cyclopropyl-3-(3-((3-methyl-4-((S)-2-methylpiperidine-1-carbonyl)phenyl)amino)-4-oxo-4,5-dihydro-1H-pyrazolo[4,3-c]pyridin-1-yl)propanenitrile;

(S)-3-cyclopropyl-3-(3-((3-methyl-4-((R)-2-methylpiperidine-1-carbonyl)phenyl)amino)-4-oxo-4,5-dihydro-1H-pyrazolo[4,3-c]pyridin-1-yl)propanenitrile;

(S)-3-cyclopropyl-3-(3-((4-(4,4-difluoropiperidine-1-carbonyl)-3-methylphenyl)amino)-4-oxo-4,5-dihydro-1H-pyrazolo[4,3-c]pyridin-1-yl)propanenitrile;

(S)-3-cyclopropyl-3-(3-((4-(4-hydroxy-4-methyl piperidine-1-carbonyl)-3-methylphenyl)amino)-4-oxo-4,5-dihydro-1H-pyrazolo[4,3-c]pyridin-1-yl)propanenitrile;

(S)-3-cyclopropyl-3-(3-((4-(4-methoxypiperidine-1-carbonyl)-3-methylphenyl)amino)-4-oxo-4,5-dihydro-1H-pyrazolo[4,3-c]pyridin-1-yl)propanenitrile;

(S) 3-cyclopropyl-3-(3-((4-(4-(2-hydroxypropan-2-yl)piperidine-1-carbonyl)-3-methylphenyl)amino)-4-oxo-4,5-dihydro-1H-pyrazolo[4,3-c]pyridin-1-yl)propanenitrile;

(S)-4-((1-(2-cyano-1-cyclopropylethyl)-4-oxo-4,5-dihydro-1H-pyrazolo[4,3-c]pyridin-3-yl)amino)-N-(3-hydroxy-3-methylbutyl)-N,2-dimethylbenzamide;

(S)-3-(3-((4-(azepane-1-carbonyl)-3-methyl phenyl)amino)-4-oxo-4,5-dihydro-1H-pyrazolo[4,3-c]pyridin-1-yl)-3-cyclopropylpropanenitrile;

(S)-3-cyclopropyl-3-(3-((4-(3-fluoroazetidine-1-carbonyl)-3-methylphenyl)amino)-4-oxo-4,5-dihydro-1H-pyrazolo[4,3-c]pyridin-1-yl)propanenitrile;

(S)-3-cyclopropyl-3-(3-((4-(3-methoxyazetidine-1-carbonyl)-3-methylphenyl)amino)-4-oxo-4,5-dihydro-1H-pyrazolo[4,3-c]pyridin-1-yl)propanenitrile;

(S)-3-(3-((4-((1R,5S)-8-oxa-3-azabicyclo [3.2.1]octane-3-carbonyl)-3-methylphenyl)amino)-4-oxo-4,5-dihydro-1H-pyrazolo[4,3-c]pyridin-1-yl)-3-cyclopropylpropanenitrile;

(S)-4-((1-(2-cyano-1-cyclopropylethyl)-4-oxo-4,5-dihydro-1H-pyrazolo[4,3-c]pyridin-3-yl)amino)-N-cyclohexyl-N,2-dimethylbenzamide;

(S)-tert-butyl(1-(4-(((1-(2-cyano-1-cyclopropylethyl)-4-oxo-4,5-dihydro-1H-pyrazolo[4,3-c]pyridin-3-yl)amino)-2-methylbenzoyl)piperidin-4-yl)(methyl)carbamate;

(R)-3-(3-((4-fluorophenyl)amino)-4-oxo-4,5-dihydro-1H-pyrazolo[4,3-c]pyridine-1-yl)butanenitrile;

(S)-3-(3-((4-fluorophenyl)amino)-4-oxo-4,5-dihydro-1H-pyrazolo[4,3-c]pyridine-1-yl)butanenitrile;

(3R)-3-[4-oxo-3-({4-[(1S or R)-2,2,2-trifluoro-1-hydroxy-1-methylethyl]phenyl}amino)-4,5-dihydro-1H-pyrazolo[4,3-c]pyridin-1-yl]butanenitrile;

(3S)-3-[4-oxo-3-({4-[(1S or R)-2,2,2-trifluoro-1-hydroxy-1-methylethyl]phenyl}amino)-4,5-dihydro-1H-pyrazolo[4,3-c]pyridin-1-yl]butanenitrile;

(3R)-3-(3-{[(1S or R)-1-hydroxy-1-(trifluoro-methyl)-2,3-dihydro-1H-inden-5-yl]amino}-4-oxo-4,5-dihydro-1H -pyrazolo [4,3-c]pyridin-1-yl)butanenitrile;

(3S)-3-(3-[(1S or R)-1 -hydroxy-1-(trifluoro-methyl)-2,3-dihydro-1H-inden-5-yl]amino}-4-oxo-4,5-dihydro-1H-pyrazolo [4,3-c]pyridin-1-yl)butanenitrile;

(3S)-3-{3-[(1,1-dioxido-2,3-dihydro-1-benzothiophen-5-yl)amino]-4-oxo-4,5-dihydro-1H-pyrazolo[4,3-c]pyridin-1-yl}butanenitrile;

(3R)-3-{3-[(1,1-dioxido-1-benzothiophen-5-yl)amino]-4-oxo-4,5-dihydro-1H-pyrazolo[4,3-c]pyridin-1-yl}butanenitrile;

4-({1-[(1S)-2-cyano-1-methylethyl]-4-oxo-4,5-dihydro-1H-pyrazolo[4,3-c]pyridin-3-yl}amino)benzonitrile;

4-({1-[(1R)-2-cyano-1-methylethyl]-4-oxo-4,5-dihydro-1H-pyrazolo[4,3-c]pyridin-3-yl}amino)benzonitrile;

(3R)-3-(4-oxo-3-{[4-(trifluoromethyl)phenyl]amino}-4,5-dihydro-1H-pyrazolo[4,3-c]pyridin-1-yl)butanenitrile;

(3S)-3-(3-{[4-(methyl-sulfonyl)phenyl]amino}-4-oxo-4,5-dihydro-1H-pyrazolo[4,3-c]pyridin-1-yl)butanenitrile;

(3R)-3-{4-oxo-3-[(3,4,5-trifluorophenyl)amino]-4,5-dihydro-1H-pyrazolo[4,3-c]pyridin-1-yl}butanenitrile;

(3R)-3-{4-oxo-3-[(3,4,5-trifluorophenyl)amino]-4,5-dihydro-1H-pyrazolo[4,3-c]pyridin-1-yl}butanenitrile;

(3S)-3-{4-oxo-3-[(3,4,5-trifluorophenyl)amino]-4,5-dihydro-1H-pyrazolo[4,3-c]pyridin-1-yl}butanenitrile;

(3R)-3-{3-[(2-methyl-1,1-dioxido-2,3-dihydro-1,2-benzisothiazol-5-yl)amino]-4-oxo-4,5-dihydro-1H-pyrazolo[4,3-c]pyridin-1-yl}butanenitrile;

(3S)-3-{3-[(2-methyl-1,1-dioxido-2,3-dihydro-1,2-benzisothiazol-5-yl)amino]-4-oxo-4,5-dihydro-1H-pyrazolo[4,3-c]pyridin-1-yl}butanenitrile;

(3R)-3-{3-[(2-fluoro-pyridin-4-yl)amino]-4-oxo-4,5-dihydro-1H-pyrazolo[4,3-c]pyridin-1-yl}butanenitrile;

(3S)-3-{3-[(2-fluoro-pyridin-4-yl)amino]-4-oxo-4,5-dihydro-1H-pyrazolo[4,3-c]pyridin-1-yl}butanenitrile;

(3R)-3-{4-oxo-3-[(1-oxo-2,3-dihydro-1H-inden-5-yl)amino]-4,5-dihydro-1H-pyrazolo[4,3-c]pyridin-1-yl}butanenitrile;

(3S)-3-{4-oxo-3-[(1-oxo-2,3-dihydro-1H-inden-5-yl)amino]-4,5-dihydro-1H-pyrazolo[4,3-c]pyridin-1-yl}butanenitrile;

(3R)-3-[3-(2,3-dihydro-1-b enzofuran-5-ylamino)-4-oxo-4,5-dihydro-1H-pyrazolo[4,3-c]pyridin-1-yl]butanenitrile;

(3S)-3-[3-(2,3-dihydro-1-benzofuran-5-ylamino)-4-oxo-4,5-dihydro-1H-pyrazolo[4,3-c]pyridin-1-yl]butanenitrile;

(3R)-3-[3-(1,3-benzodioxol-5-ylamino)-4-oxo-4,5-dihydro-1H-pyrazolo[4,3-c]pyridin-1-yl]butanenitrile;

(3S)-3-[3-(1,3-benzodioxol-5-ylamino)-4-oxo-4,5-dihydro-1H-pyrazolo[4,3-c]pyridin-1-yl]butanenitrile;

(3R)-3-[4-oxo-3-(quinolin-6-ylamino)-4,5-dihydro-1H-pyrazolo[4,3-c]pyridin-1-yl]butanenitrile;

(3S)-3-[4-oxo-3-(quinolin-6-ylamino)-4,5-dihydro-1H-pyrazolo[4,3-c]pyridin-1-yl]butanenitrile;

(3R)-3-(3-{[3-fluoro-4-(methylsulfonyl)phenyl]amino}-4-oxo-4,5-dihydro-1H-pyrazolo[4,3-c]pyridin-1-yl)butanenitrile;

(3S)-3-(3-{[3-fluoro-4-(methyl sulfonyl)phenyl]amino}-4-oxo-4,5-dihydro-1H-pyrazolo[4,3-c]pyridin-1-yl)butanenitrile;

(3R)-3-[4-oxo-3-(quinoxalin-6-ylamino)-4,5-dihydro-1H-pyrazolo[4,3-c]pyridin-1-yl]butanenitrile;

(3S)-3-[4-oxo-3-(quinoxalin-6-ylamino)-4,5-dihydro-1H-pyrazolo[4,3-c]pyridin-1-yl]butanenitrile;

(3R)-3-{3-[(4-chlorophenyl)amino]-4-oxo-4,5-dihydro-1H-pyrazolo[4,3-c]pyridin-1-yl}butanenitrile;

(3S)-3-{3-[(4-chlorophenyl)amino]-4-oxo-4,5-dihydro-1H-pyrazolo[4,3-c]pyridin-1-yl}butanenitrile;

N-tert-butyl-4-({1-[(1S)-2-cyano-1-methylethyl]-4-oxo-4,5-dihydro-1H-pyrazolo[4,3-c]pyridin-3-yl}amino)benzenesulfonamide;

N-tert-butyl-4-({1-[(1R)-2-cyano-1-methylethyl]-4-oxo-4,5-dihydro-1H-pyrazolo[4,3-c]pyridin-3-yl}amino)benzenesulfonamide;

(3R)-3-{3-[(2-tert-butyl-1,1-dioxido-2,3-dihydro-1,2-benzisothiazol-5-yl)amino]-4-oxo-4,5-dihydro-1H-pyrazolo[4,3-c]pyridin-1-yl}butanenitrile;

(3S)-3-{3-[(2-tent-butyl-1,1-dioxido-2,3-dihydro-1,2-benzisothiazol-5-yl)amino]-4-oxo-4,5-dihydro-1H-pyrazolo[4,3-c]pyridin-1-yl}butanenitrile;

(S)-methyl 3-((4-(azetidin-1-ylsulfonyl)phenyl)amino)-1-(2-cyano-1-cyclopropylethyl)-4-oxo-4,5-dihydro-1H-pyrazolo[4,3-c]pyridine-7-carboxylate;

(S)-3-(3-((4-(azetidin-1-ylsulfonyl)phenyl)amino)-7-(hydroxymethyl)-4-oxo-4,5-dihydro-1H-pyrazolo[4,3-c]pyridin-1-yl)-3-cyclopropylpropanenitrile (S)-methyl 3-((4-(azetidin-1-ylsulfonyl)phenyl)amino)-1-(2-cyano-1-cyclopropylethyl)-4-oxo-4,5-dihydro-1H-pyrazolo[4,3-c]pyridine-7-carboxylate;

(S)-3-cyclopropyl-3-(3((1,1-dioxido-3H-spiro[benzo[b]thiophene-2,1'-cyclohexan]-5-yl)amino)-4-oxo-4,5-dihydro-1H-pyrazolo[4,3-c]pyridin-1-yl)propanenitrile;

(S)-3-cyclopropyl-3-(3-((1,1-dioxido-3H-spiro[benzo[b]thiophene-2,1'-cyclopentan]-5-yl)amino)-4-oxo-4,5-dihydro-1H-pyrazolo[4,3-c]pyridin-1-yl)propanenitrile;

(S)-3-cyclopropyl-3-(3-(((2R,3S)-2,3-dimethyl-1,1-dioxido-2,3-dihydrobenzo[b]thiophen-5-yl)amino)-4-oxo-4,5-dihydro-1H-pyrazolo[4,3-c]pyridin-1-yl)propanenitrile;

(S)-3-cyclopropyl-3-(3-(((2R,3R)-2,3-dimethyl-1,1-dioxido-2,3-dihydrobenzo[b]thiophen-5-yl)amino)-4-oxo-4,5-dihydro-1H-pyrazolo[4,3-c]pyridin-1-yl)propanenitrile;

(S)-3-cyclopropyl-3-(3-(((2S,3S)-2,3-dimethyl-1,1-dioxido-2,3-dihydrobenzo[b]thiophen-5-yl)amino)-4-oxo-4,5-dihydro-1H-pyrazolo[4,3-c]pyridin-1-yl)propanenitrile; or (S)-3-cyclopropyl-3-(3-(((2S,3R)-2,3-dimethyl-1,1-dioxido-2,3-dihydrobenzo[b]thiophen-5-yl)amino)-4-oxo-4,5-dihydro-1H-pyrazolo[4,3-c]pyridin-1-yl)propanenitrile.

7. A pharmaceutical composition comprising a comnpound of claim 1 or a pharmaceutically acceptable salt thereof and a pharmaceutically acceptable carrier.

* * * * *